United States Patent [19]

Suzuki

[11] Patent Number: 5,891,706
[45] Date of Patent: Apr. 6, 1999

[54] HUMAN PROTOCADHERIN-43 ANTIBODIES

[75] Inventor: Shintaro Suzuki, Torrance, Calif.

[73] Assignee: Doheny Eye Institute, Los Angeles, Calif.

[21] Appl. No.: 453,702

[22] Filed: May 30, 1995

Related U.S. Application Data

[60] Division of Ser. No. 268,161, Jun. 27, 1994, which is a continuation-in-part of PCT/US93/12588, Dec. 23, 1993, which is a continuation-in-part of Ser. No. 998,003, Dec. 29, 1992.

[51] Int. Cl.⁶ .............................. C12N 5/12; C07K 16/28
[52] U.S. Cl. .............................. 435/240.27; 530/387.22; 530/388.85; 530/387.9
[58] Field of Search ........................... 530/387.9, 388.22, 530/388.85; 435/240.27

[56] References Cited

FOREIGN PATENT DOCUMENTS

| | | |
|---|---|---|
| WO 91/04745 | 4/1991 | WIPO . |
| WO 92/08731 | 5/1992 | WIPO . |

OTHER PUBLICATIONS

Shimoyama, Yutaka Journal of the Keio Medical Society 68:189–205, 1991.
Geiger J.Cell Science 97:607–614, 1990.
Laqunowich, Biochem Biophy Res Comm 172:313–320, 1990.
Angres, Development 111:829–844, May 8, 1991.
Amagai et al., "Autoantibodies against a Novel Epithelial Cadherin in Pemphigus Vulgaris, a Disease of Cell Adhesion", *Cell,* 67: 869–877 (Nov. 29, 1991).
Angerer et al., "Demonstration of Tissue–Specific Gene Expression by in Situ Hybridization", *Methods in Enzymology,* 152: 649–660, (1987).
Ausubel et al., Eds., *Current Protocols in Molecular Biology,* Sections 6.1.1 to 6.1.4 and 6.2.1 to 6.2.3, John Wiley & Sons, New York (1987).
Burt, "Morphologic Abnormalities in the Postnatal Differentiation of CA1 Pyramidal Cells and Granule Cells in the Hippocampal Formation of the Ataxic Mouse", *Anat. Rec.* 196: 61–69 (1980).
Chen et al., Cell–Cell Contacts Mediated by E–Cadherin (Uvomorulin) Restrict Invasive Behavior of L–Cells:, *J. Cell, Biol.,* 114(2): 319–327 (Jul. 1991).
Civitelli et al., "Connexin43 Mediates Direct Intercellular Communication in Human Osteoblastic Cell Networks", *J. Clin. Invest.,* 91: 1888–1896 (1993).
Detrick et al., "The Effects of N–Cadherin Misexpression on Morphogenesis in Xenopus Embryos", *Neuron,* 4: 493–506 (Apr. 1990).
Donalies et al., "Expression of M–cadherin, a Member of the Cadherin Multigene Family, Correlates with Differentiation of Skeletal Muscle Cells", *Proc. Natl. Acad. Sci. USA,* 88: 8024–8028 (Sep. 1991).
Frixen et al., "E–Cadherin–Miedated Cell–Cell Adhesion Prevents Invasiveness of Human Carcinoma Cells" *J. Cell. Biol.,* 113(1): 173–185 (Apr. 1991).
Fujimori et al., "Ectopic Expression of N–cadherin Perturbs Histogenesis in Xenopus Embryos", *Development,* 110: 97–104 (1990).
Gallin et al., "Sequence Analysis of a cDNA Clone Encoding the Liver Cell Adhesion Molecule, L–CAM", *Proc. Natl. Acad. Sci. USA,* 84: 2808–2812 (May 1987).
Goodwin et al., "Desmoglein Shows Extensive Homology to the Cadherin Family of Cell Adhesion Molecules", *Biochem. Biophsy. Res. Commun.,* 173(3): 1224–1230 (Dec. 31, 1990).
Hatta et al., "Cloning and Expression of cDNA Encoding a Neural Calcium–dependent Cell Adhesion Molecule: Its Identity in the Cadherin Gene Family", *J. Cell. Biol.,* 106: 873–881 (Mar. 1988).
Holton et al., "Desmosomal Glycoproteins 2 and 3 (desmocollins) Show N–terminal Similarity to Calcium–Dependent Cell–Cell Adhesion Molecules", *J. Cell. Science,* 97: 239–246 (1990).
Hynes et al., "Contact and Adhesive Specificities in the Associations, Migrations, and Targeting of Cells and Axons", *Cell,* 68: 303–322, (Jan. 24, 1992).
Inuzuka et al., "R–Cadherin: A Novel $Ca^{2+}$–Dependent Cell–Cell Adhesion Molecule Expressed in the Retina", *Neruron,* 7: 69–79 (1991).
Kennett, "Cell Fusion", *Methods in Enzymol.,* 58: 345–359 (1979).
Kikuchi et al., "The Defective Organ of Corti in Shaker–1 Mice", *Acta Oto–Laryng.,* 60: 287–303 (1965).
Kintner, "Regulation of Embryonic Cell Adhesion by the Cadherin Cytoplasmic Domain", *Cell,* 69: 225–236 (Apr. 17, 1992).
Koch et al., "Identification of Desmoglein, a Constitutive Desmosomal Glycoprotein, as a Member of the Cadherin Family of Cell Adhesion Molecules", *Eur. J. Cell Biol.,* 53: 1–12 (1990).
Liaw et al., "Identification and Cloning of Two Species of Cadherins in Bovine Endothelial Cells", *EMBO J.,* 9(9): 2701–2708 (1990).
Lord et al., Shaker, A New Mutation of the House Mouse (*Mus Muscukus*) *Am. Nat.,* 63: 453–442 (1929).
Lyon, M., "Twirler: A Mutant Affecting the Inner Ear of the House Mouse", *J. Embryol. Exp. Morphol.,* 6: 105–116 (1958).
Lyon, M., "Ataxia—A New Recessive Mutant of the House Mouse", *J. Hered.,* 46: 77–80 (1955).

(List continued on next page.)

*Primary Examiner*—Lila Feisee
*Assistant Examiner*—Nancy A. Johnson
*Attorney, Agent, or Firm*—Marshall, O'Toole, Gerstein, Murray & Borun

[57] ABSTRACT

Polynucleotide sequences encoding novel cadherin-like polypeptides, designated protocadherins, and variants thereof are provided by the invention as well as methods and materials for the recombinant production of the same. Antibody substances specific for human protocadherin-43 are also disclosed as useful for modulating the natural binding and/or regulatory activities of the protocadherins.

2 Claims, 3 Drawing Sheets

OTHER PUBLICATIONS

Mahoney et al., "The fat Tumor Suppressor Gene in Drosophila Encodes a Novel Member of the Cadherin Gene Superfamily", *Cell*, 67: 853–868 (Nov. 29, 1991).

Maniatis et al., pp. 196 in *Molecular Cloning: A Laboratory Manual*, Cold Spring Harbor, New York: Cold Spring Harbor Laboratory (1982).

Maruyama et al., "Detection of Calcium Binding Proteins by $^{45}$Ca Autoradiography on Nitrocellulose Membrane after Sodium Dodecyl Sulfate Gel Electrophoresis[1]", *J. Biochem.*, 95: 511–519 (1984).

Matsunaga et al., "Guidance of Optic Nerve Fibers by N–cadherin Adhesion Molecules", *Nature*, 334: 62–64 (Jul. 1988).

Miyatani et al., "Neural Cadherin: Role in Selective Cell–Cell Adhesion", *Science*, 245: 631–635 (Aug. 1989).

Nagafuchi et al., "Transformation of Cell Adhesion Properties by Exogenously Introduced E–cadherin cDNA", *Nature*, 329: 341–343 (Sep. 1987).

Napolitano, et al., "Molecular Cloning and Characterization of B–Cadherin, a Novel Chick Cadherin", *Cell. Biol.*, 113(4): 893–905 (May 1991).

Nose et al., "Isolation of Placental Cadherin cDNA: Identification of a Novel gene Family of Cell–Cell Adhesion Molecules", *EMBO J.*, 6(12): 3655–3661 (1987).

Porter et al., "Dystrophin Colocalizes with β–Spectrin in Distinct Subsarcolemmal Domains in Mammalian Sketal Muscle", *J. Cell. Biol.*, 117(5): 997–1005 (Jun. 1992).

Pytela et al., "Polymerase Chain Reaction Cloning with Degenerate Primers: Homology–Based Identifiction of Adhesion Molecules", *Methods in Enzymology*, Erkki Ruoslahti and Eva Engvall, Eds., 245:420–451, Acedemic Press, (1994).

Ranscht et al., "T–Cadherin, A Novel Cadherin Cell Adhesion Mol. in the Nervous System Lacks the Conserved Cytoplasmic region", *Neuron*, 7: 391–402 (Sep. 1991).

Ringwald et al., "The Structure of Cell Adhesion Molecule Uvomorulin. Insights into the Molecular Mechanism of $Ca^{2+}$–Dependent Cell Adhesion", *EMBO J.*, 3647–3653 (1987).

Sano et al. "Protocadherins: A Large Family of Cadherin–Related Molecules in Central Nervous System", *The EMBO Journal*, 12(6): 2249–2256 (1993).

Seldon et al., "Genetic Analysis of Autoimmune gld Mice", *J. Exp. Med.*, 167: 688–693 (1988).

Shimoyama et al., "Molecular Cloning of a Human $Ca^{2+}$–Dependent Cell–Cell Adhesion Molecule Homologous to Mouse Placental Cadherin: Its Low Expression in Human Placental Tissues", *J. Cell. Biol.*, 109: 1787–1794 (Oct. 1989).

Suzuki et al., "Diversity of the Cadherin Family: Evidence for Eight New Cadherins in Nervous Tissue", *Cell Regulation*, 2: 261–270 (Apr. 1991).

Suzuki et al., "Evidence for Cadherin Superfamily" *Cell Struc. Func.*, 16: 605 (Nov. 23, 1991).

Suzuki et al., "Evidence for Cadherin Superfamily" *J. Cell. Biol.*, 115: 72(a) (Abstract 416) (Dec. 9, 1991).

Takeichi, Cadherin Cell Adhesion Receptors as a Morphogenetic Regulator:, *Science*, 251: 1451–1455 (Mar. 1991).

Takeichi, Cadherins: A Molecular Family Important in Selective Cell–Cell Adhesion:, *Annu. Rev. Biochem.*, 59: 237–252 (1990).

Thomas, "Hybridization of Denatured RNA and Small DNA Fragments Transferred to Nitrocellulose", *Proc. Natl. Acad. Sci. USA*, 77(9): 5201–5205 (Sep. 1980).

Towbin et al., Electrophoretic Transfer of Proteins from Polyacrylamide Gels to Nitrocellulose Sheets: Procedure and Some Applications:, *PNAS* 76: 4350–4354, (Sep. 1979).

Urushihara et al., "Immunological Detection of Cell Surface Components Related with Aggregation of Chinese Hamster and Chick Embryonic Cells", *Dev. Biol.*, 70: 206–216 (1979).

Vandenbark et al., "Experimental Allergic Encephalomyelitis and Cellular Immunity in the Lewis Rat", *Cell. Immunol.*, 12: 85–93 (1974).

Vleminckx et al., "Genetic Manipulation of E–Cadherin Expression by Epithelial Tumor Cells Reveals an Invasion Suppressor Role", *Cell*, 66: 107–119 (Jul. 12, 1991).

| | | | | |
|---|---|---|---|---|
| PC43 | EC 1 | (29) | ASTVIHYEIPEEREK-----GFAVGNVVANL--GLDLGSLSA-- | (63) |
| | EC 2 | (136) | PTQEMKLEISEAVAP-----GTRFPLESAH---DPDLGSNSL-- | (169) |
| | EC 3 | (245) | NQSLYRARVPGGCTS-----GTRVVQVLAT---DLDEGPNGE-- | (278) |
| | EC 4 | (353) | TVTSVYSPVPEDAS------GTVIALLSVT---DLDAGENGL-- | (385) |
| | EC 5 | (457) | SQSSYDVYIEENNLP-----GAPILNLSVW---DPDAPQNAR-- | (490) |
| | EC 6 | (567) | LYPRPGGSSVEMLPRGTSA-GHLVSRVVGW---DADAGHNAW-- | (604) |
| PC42 | EC 1 | (42) | VPEEQPPNTLI--------GSL---------AADYGFPDVG-- | (65) |
| | EC 2 | (147) | ASPVITLAIPENTNI-----GSLFPIPLAS---DRDAGPNGV-- | (180) |
| | EC 3 | (247) | ERPSYEAELSENSPI-----GHSVIQVKAN---DSDQGANAE-- | (280) |
| | EC 4 | (354) | EIRGIGLVTHQDGMANISEDVAEETAVALVQVSDRDEGENAA-- | (395) |
| | EC 5 | (473) | TQSVTEVAFPENNKP-----GEVIAEITAS---DADSGSNAE-- | (506) |
| | EC 6 | (579) | MLSGYNFSVMENMPA-----LSPVGMTVTI---DGDKGENAQ-- | (612) |
| | EC 7 | (682) | TAPSNTSHKLLTPQTRL---GETVSQVAAE---DFDSGVNAE-- | (717) |
| FAT | EC18 | (1) | EDTVYSFDIPENAQR------GYQVGQIVAR---DADLGQNAQ-- | (34) |
| N-CAD | EC 1 | (1) | DWVIPPINLPENSRG-----PFPQELVRIRS--DRDKNLSLRYS | (37) |
| | EC 2 | (109) | LHQVWNGSVPEGSKP-----GTYVMTVTAI---DADDPNALNGM | (144) |
| | EC 3 | (224) | TAMTFYGEVPENRVD-----VIVANLTVT----DKDQPHTPAWN | (258) |
| | EC 4 | (339) | APNPKIIRQEEGLHA-----GTMLTTLTAQ---DPDRYMQQN-- | (372) |
| | EC 5 | (447) | LPQEAETCETPEPNSINIAAL----------DYDIDPNAGP-- | (477) |
| MOTIF | | | **o**v*En*****-----Gt*v***v*A*----D*D*G*N**-- | |

FIGURE 1A

```
PC43  EC 1   (64)  RRFPVVSGASRR----------FFEVNRET----GEMFVNDR------------    (91)
      EC 2  (170)  QTYELSRNEY------------FALRVQTREDSTKYAELVLERA----        (201)
      EC 3  (279)  IIYSFGSHNRAGVRQL------FALDLVT----GMLTIKGR------         (309)
      EC 4  (386)  VTCEVPPGLP------------FSLTSSLKNYFTLKTSAD-------         (413)
      EC 5  (491)  LSFFLLEQGAETGLVGRYFTINRDN----GIVSSLVP----               (523)
      EC 6  (605)  LSYSLFGSPNQSL---------FAIGLHT----GQISTARPV----          (633)

PC42  EC 1   (66)  HLYKLEVGAP------------YLRVDGKT----GDIFTTETS----          (92)
      EC 2  (181)  ASYELQVAED------------QEEKQPQLIVMGN--------             (203)
      EC 3  (281)  IEYTFHQAPEVVRRL-------LRLDRNT----GLITVQGP----           (310)
      EC 4  (396)  VTCVVAGDVP------------FQLRQASETGSDSKKKYFLQTTTP          (429)
      EC 5  (507)  LVYSLEPEPAAKGL--------FTISPET----GEIQVKTS----           (535)
      EC 6  (613)  VQLSVEQDNGD-----------FVIQNGT----GTILSSLS----           (638)
      EC 7  (718)  LIYSIAGGNPYGL---------FQIGSHS----GAITLEKE----           (745)

FAT   EC18   (35)  LSYGVVSDWANDV---------FSLNPQT----GMLTLTAR----           (62)

N-CAD EC 1   (38)  VTGPGADQPPTGI---------FIINPIS----GQLSVTKP----           (65)
      EC 2  (145)  LRYRILSQAPSTPSPNM-FTINNET----GDIITVAAG----              (177)
      EC 3  (259)  AAYRISGGDPTGR---------FAILTDPNSND-GLVTVVKP----          (290)
      EC 4  (373)  IRYTKLSDPAN-----------WLKIDPVN----GQITTIAV----          (399)
      EC 5  (478)  FAFDLPLSPVTIKRN-------WTINRLN-----GDFAQLNLK----         (508)

MOTIF              I*O*I**************O*I***T-----G*I*T***-----
```

FIGURE 1B

```
PC43  EC 1   (92)  LDRLELCGTLPSCTVTLELVVENP--------------------LELFSVEVVIQDINDNNPAF  (135)
      EC 2  (202)  LDREREPSLQLVLTALDGGTPAL---------------------SASLPIHIKVLDANDNAPVF  (244)
      EC 3  (310)  LDFEDTKLHEIYIQAKDKGANPE---------------------GAHCKVLVEVDVNDNAPEI  (352)
      EC 4  (414)  LDRETVPEYNLSITARDAGTPSL---------------------SALTIVRVQVSDINDNPPQS  (456)
      EC 5  (524)  LDYEDRREFELTAHISDGGTPVL---------------------ATNISVNIFVTDRNDNAPQV  (566)
      EC 6  (634)  QDTDSPRQTLTVL-IKDNGEPSLSTTATLTVSVTEDSPEARAEFPSGSAPREQKKN       (688)

PC42  EC 1   (93)  IDREGLRECQNQLPGDPCILEFEVSITDLVQNAS--PRLLEGQIEVQDINDNTPNF        (146)
      EC 2  (204)  LDRERWDSYDLTIKVQDGGSPPR---------------------ATSALLRVTVLDTNDNAPKF  (246)
      EC 3  (311)  VDREDLSTLRFSVLAKDRGTNPK---------------------SARAQVVTVKDMNDNAPTI  (353)
      EC 4  (430)  LDYEKVKDYTIEIVAVDSGNPPL---------------------SSTNSLKVQVVDVNDNAPVF  (472)
      EC 5  (536)  LDREQRESYELKVVAADRGSPSL---------------------QGTATVLVNVLDCNDNDPKF  (578)
      EC 6  (639)  FDREQQSTYTFQLKAVDGGVPPR---------------------SAYVGVTINVLDENDNAPYI  (681)
      EC 7  (746)  IERRHHGLHRLVVKVSDRGKPPRYGTALVHLYVNETLANRTLLETLLGHSLDTPLD        (801)
                                    (802) IDIAGDPEYERSKQRGN  (818)

FAT   EC18  (63)   LDYEEVQHYILIVQAQDNGQPSL---------------------STTITVYCNVLDLNDNAPIF  (105)

N-CAD EC 1   (66)  LDRELIARFHLRAHAVDINGNQV---------------------ENPIDIVINVIDMNDNRPEF  (108)
      EC 2  (178)  LDREKVQQYTLIIQATDMEGNPTYGL------------------SNTATAVITVTDVNDNPPEF  (223)
      EC 3  (291)  IDFETNRMFVLTVAAENQVPLAKGIQHPP---------------QSTATVSVTVIDVNE-NPYF  (338)
      EC 4  (400)  LDRESPYVQNNIYNATFLASDNGIPPM-----------------SGTGTLQIYLLDINDNAPQV  (446)
      EC 5  (509)  IKFLEAGIYEVPIIITDSGNPPKSNIS-----------------ILRVKVCQCDSNGDCTDVDR  (555)

MOTIF              LDRE*****o*L*v*A*D*G*P**-------------------**T*TV*v*V*D*NDNAP*F

FIGURE 1C
```

HUMAN PROTOCADHERIN-43 ANTIBODIES

This is a Rule 60 Divisional of U.S. patent application Ser. No. 08/268,161, filed Jun. 27, 1994, which in turn is a continuation-in-part of International Patent Application No. PCT/US93/12588, filed Dec. 23, 1993, which in turn is a continuation-in-part of U.S. patent application Ser. No. 07/998,003, filed Dec. 29, 1992.

FIELD OF THE INVENTION

The present invention relates, in general, to materials and methods relevant to cell-cell adhesion. More particularly, the invention relates to novel adhesion proteins, designated protocadherins, and to polynucleotide sequences encoding the protocadherins. The invention also relates to methods for inhibiting binding of the protocadherins to their natural ligands/antiligands.

BACKGROUND

In vivo, intercellular adhesion plays an important role in a wide range of events including morphogenesis and organ formation, leukocyte extravasation, tumor metastasis and invasion, and the formation of cell junctions. Additionally, cell-cell adhesion is crucial for the maintenance of tissue integrity.

Intercellular adhesion is mediated by specific cell surface adhesion molecules. Cell adhesion molecules have been classified into at least four families including the immunoglobulin superfamily, the integrin superfamily, the selectin family and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain (the N-terminal 113 amino acids of the domain appear to be directly involved in binding) consisting of five subdomains characterized by sequences unique to cadherins, a hydrophobic membrane-spanning domain and a C-terminal cytoplasmic domain that interacts with the cytoskeleton through catenins and other cytoskeleton-associated proteins. Some cadherins lack a cytoplasmic domain, however, and appear to function in cell-cell adhesion by a different mechanism than cadherins having a cytoplasmic domain. The cytoplasmic domain is required for the adhesive function of the extracellular domain in cadherins that do have an cytoplasmic domain. Binding between members of the cadherin family expressed on different cells is homophilic (i.e., a member of the cadherin family binds to cadherins of its own or a closely related subclass) and $Ca^{2+}$-dependent. For recent reviews on cadherins, see Takeichi, *Annu. Rev. Biochem.*, 59: 237–252 (1990) and Takeichi, *Science,* 251: 1451–1455 (1991).

The first cadherins to be described (E-cadherin in mouse epithelial cells, L-CAM in avian liver, uvomorulin in the mouse blastocyst, and CAM 120/80 in human epithelial cells) were identified by their involvement in $Ca^{2+}$-dependent cell adhesion and their unique immunological characteristics and tissue localization. With the later immunological identification of N-cadherin, which was found to have a different tissue distribution than E-cadherin, it became apparent that a new family of $Ca^{2+}$-dependent cell-cell adhesion molecules had been discovered.

The molecular cloning of the genes encoding E-cadherin [see Nagafuchi et al., *Nature,* 329: 341–343 (1987)], N-cadherin [Hatta et al., *J. Cell. Biol.,* 106: 873–881 (1988)], and P-cadherin [Nose et al, *EMBO J.,* 6: 3655–3661 (1987)] provided structural evidence that the cadherins comprised a family of cell adhesion molecules. Cloning of L-CAM [Gallin et al., *Proc. Natl. Acad. Sci. USA,* 84: 2808–2812 (1987)] and uvomorulin [Ringwald et al., *EMBO J.,* 6: 3647–3653 (1986)] revealed that they were identical to E-cadherin. Comparisons of the amino acid sequences of E-, N-, and P-cadherins showed a level of amino acid similarity of about 45%–58% among the three subclasses. Liaw et al, *EMBO J.,* 9: 2701–2708 (1990) describes the use of PCR with degenerate oligonucleotides based on conserved regions of the E-, N- and P-cadherins to amplify N- and P-cadherin from a bovine microvascular endothelial cell cDNA.

The isolation by PCR of eight additional cadherins was reported in Suzuki et al., *Cell Regulation,* 2: 261–270 (1991). Subsequently, several other cadherins were described including R-cadherin [Inuzuka et al, *Neuron,* 7: 69–79 (1991)], M-cadherin [Donalies, *Proc. Natl. Acad. Sci. USA,* 88: 8024–8028 (1991)], B-cadherin [Napolitano, *J. Cell. Biol.,* 113: 893–905 (1991)] and T-cadherin [Ranscht, *Neuron,* 7: 391–402 (1991)].

Additionally, proteins distantly related to cadherins such as desmoglein [Goodwin et al., *Biochem. Biophys. Res. Commun.,* 173: 1224–1230 (1990) and Koch et al, *Eur. J. Cell Biol,* 53: 1–12 (1990)] and the desmocollins [Holton et al., *J. Cell Science,* 97: 239–246 (1990)] have been described. The extracellular domains of these molecules are structurally related to the extracellular domains of typical cadherins, but each has a unique cytoplasmic domain. Mahoney et al., *Cell,* 67: 853–868 (1991) describes a tumor suppressor gene of Drosophila, called fat, that also encodes a cadherin-related protein. The fat tumor suppressor comprises 34 cadherin-like subdomains followed by four EGF-like repeats, a transmembrane domain, and a novel cytoplasmic domain. The identification of these cadherin-related proteins is evidence that a large superfamily characterized by a cadherin extracellular domain motif exists.

Studies of the tissue expression of the various cadherin-related proteins reveal that each subclass of molecule has a unique tissue distribution pattern. For example, E-cadherin is found in epithelial cells while N-cadherin is found in neural and muscle cells. Expression of cadherin-related proteins also appears to be spatially and temporally regulated during development because individual proteins appear to be expressed by specific cells and tissues at specific developmental stages [for review see Takeichi (1991), supra]. Both the ectopic expression of cadherin-related proteins and the inhibition of native expression of cadherin-related proteins hinders the formation of normal tissue structure [Detrick et al., *Neuron,* 4: 493–506 (1990); Fujimori et al, *Development,* 110: 97–104 (1990); Kintner, *Cell,* 69: 225–236 (1992)].

The unique temporal and tissue expression pattern of the different cadherins and cadherin-related proteins is particularly significant when the role each subclass of proteins may play in vivo in normal events (e.g., the maintenance of the intestinal epithelial barrier) and in abnormal events (e.g., tumor metastasis or inflammation) is considered. Different subclasses or combinations of subclasses of cadherin-related proteins are likely to be responsible for different cell-cell adhesion events in which therapeutic detection and/or intervention may be desirable. For example, auto-antibodies from patients with pemphigus vulgaris, an autoimmune skin disease characterized by blister formation caused by loss of cell adhesion, react with a cadherin-related protein offering direct support for adhesion function of cadherins in vivo

[Amagai et al., *Cell*, 67: 869–877 (1991)]. Studies have also suggested that cadherins and cadherin-related proteins may have regulatory functions in addition to adhesive activity. Matsunaga et al., *Nature*, 334: 62–64 (1988) reports that N-cadherin has neurite outgrowth promoting activity. The Drosophila fat tumor supressor gene appears to regulate cell growth and supress tumor invasion as does mammalian E-cadherin [see Mahoney et al., supra; Frixen et al., *J. Cell. Biol.*, 113:173–185 (1991); Chen et al, *J. Cell, Biol.*, 114:319–327 (1991); and Vleminckx et al., *Cell*, 66:107–119 (1991)]. Thus, therapeutic intervention in the regulatory activities of cadherin-related proteins expressed in specific tissues may be desirable.

There thus continues to exist a need in the art for the identification and characterization of additional cadherin-related proteins which participate in cell-cell adhesion and/or regulatory events. Moreover, to the extent that cadherin-related proteins might form the basis for the development of therapeutic and diagnostic agents, it is essential that the genes encoding the proteins be cloned. Information about the DNA sequences and amino acid sequences encoding the cadherin-related proteins would provide for the large scale production of the proteins by recombinant techniques and for the identification of the tissues/cells naturally producing the proteins. Such sequence information would also permit the preparation of antibody substances or other novel binding molecules specifically reactive with the cadherin-related proteins that may be useful in modulating the natural ligand/antiligand binding reactions in which the proteins are involved.

SUMMARY OF THE INVENTION

The present invention provides cadherin-related materials and methods that are relevant to cell-cell adhesion. In one of its aspects, the present invention provides purified and isolated polynucleotides (e.g., DNA and RNA, both sense and antisense strands) encoding the novel cell adhesion molecules designated herein as protocadherins, including protocadherin-42, protocadherin-43, protocadherin pc3, protocadherin pc4 and protocadherin pc5. Preferred polynucleotide sequences of the invention include genomic and cDNA sequences as well as wholly or partially synthesized DNA sequences, and biological replicas thereof (i.e., copies of the sequences made in vitro). Biologically active vectors comprising the polynucleotide sequences are also contemplated.

Specifically illustrating protocadherin polynucleotide sequences of the present invention are the inserts in the plasmids pRC/RSV-pc42 and pRC/RSV-pc43 which were deposited with the American Type Culture Collection (ATCC), 12301 Parklawn Drive, Rockville, Md. 20852 on Dec. 16, 1992 and were assigned ATCC Accession Nos. 69162 and 69163, respectively.

The scientific value of the information contributed through the disclosures of the DNA and amino acid sequences of the present invention is manifest. For example, knowledge of the sequence of a partial or complete DNA encoding a protocadherin makes possible the isolation by standard DNA/DNA hybridization or PCR techniques of full length cDNA or genomic DNA sequences that encode the protein (or variants thereof) and, in the case of genomic DNA sequences, that specify protocadherin-specific regulatory sequences such as promoters, enhancers and the like. Alternatively, DNA sequences of the present invention may be chemically synthesized by conventional techniques. Hybridization and PCR techniques also allow the isolation of DNAs encoding heterologous species proteins homologous to the protocadherins specifically illustrated herein.

According to another aspect of the invention, host cells, especially eucaryotic and procaryotic cells, are stably transformed or transfected with the polynucleotide sequences of the invention in a manner allowing the expression of protocadherin polypeptides in the cells. Host cells expressing protocadherin polypeptide products, when grown in a suitable culture medium, are particularly useful for the large scale production of protocadherin polypeptides, fragments and variants thereby enabling the isolation of the desired polypeptide products from the cells or from the medium in which the cells are grown.

The novel protocadherin protein products of the invention may be obtained as isolates from natural tissue sources, but are preferably produced by recombinant procedures involving the host cells of the invention. The products may be obtained in fully or partially glycosylated, partially or wholly de-glycosylated, or non-glycosylated forms depending on the host cell selected or recombinant production and/or post-isolation processing.

Protocadherin variants according to the invention may comprise polypeptide analogs wherein one or more of the specified amino acids is deleted or replaced or wherein one or more non-naturally encoded amino acids are added: (1) without loss, and preferably with enhancement, of one or more of the biological activities or immunological characteristics specific for a protocadherin; or (2) with specific disablement of a particular ligand/antiligand binding function. Also contemplated by the present invention are antibody substances (e.g., monoclonal and polyclonal antibodies, chimeric and humanized antibodies, antibody domains including Fab, Fab', F(ab')$_2$, Fv or single variable domains, and single chain antibodies) which are specific for the protocadherins of the invention. Antibody substances can be developed using isolated natural, recombinant or synthetic protocadherin polypeptide products or host cells expressing such products on their surfaces. The antibody substances may be utilized for purifying protocadherin polypeptides of the invention, for determining tissue expression of polypeptides and as antagonists of the ligand/antiligand binding activities of the protocadherins. Specifically illustrating monoclonal antibodies of the present invention are the protocadherin-43 specific monoclonal antibodies produced by the hybridoma cell line designated 38I2C which was deposited with the ATCC on Dec. 2, 1992 and was assigned ATCC Accession No. HB 11207.

Numerous other aspects and advantages of the present invention will be apparent upon consideration of the following detailed description, reference being made to the drawing wherein FIGS. 1A–C is an alignment of protocadherin amino acid sequences of the invention with the amino acid sequences of N-cadherin and of the Drosophila fat tumor suppressor.

BRIEF DESCRIPTION OF THE DRAWING

FIGS. 1A–1C presents an alignment of the amino acid sequences of the deduced extracellular subdomains of PC42 (EC-1 through EC-7), PC43 (EC-1 through EC-6), mouse N-cadherin (EC-1 through EC-5) and drosophila fat EC-18. A sequence on a line in FIG. 1A continues on the same line in FIGS. 1B and 1C.

DETAILED DESCRIPTION

The present invention is illustrated by the following examples wherein Examples 1, 2 and 3 describe the isolation by PCR of protocadherin polynucleotide sequences. Example 3 also describes the chromosome localization of several protocadherin genes of the invention. Example 4 describes the isolation by DNA/DNA hybridization of additional protocadherin polynucleotide sequences of the present invention. Example 5 presents the construction of expression plasmids including polynucleotides encoding protocadherin-42 or protocadherin-43 and the transfection of L cells with the plasmids. The generation of antibodies to protocadherin-42 and protocadherin-43 is described in Example 6. Example 7 presents the results of immunoassays of transfected L cells for the expression of protocadherin-42 or protocadherin-43. Example 8 describes the cell aggregation properties of L cells transfected with protocadherin-42, protocadherin-43 or a chimeric protocadherin-43/E-cadherin molecule. The calcium-binding properties of pc43 are described in Example 9. The results of assays of various tissues and cell lines for the expression of protocadherin-42 and protocadherin-43 by Northern blot, Western blot and in situ hybridization are respectively presented in Examples 10, 11 and 12. Example 13 describes immunoprecipitation experiments identifying a 120 kDa protein that coprecipitates with protocadherin-43.

EXAMPLE 1

The polymerase chain reaction (PCR) was used to isolate novel rat cDNA fragments encoding cadherin-related polypeptides.
Design of PCR Primers Two regions of conserved amino acid sequence, one from the middle of the third cadherin extracellular subdomain (EC-3) and the other from the C-terminus of the fourth extracellular subdomain (EC-4), were identified by comparison of the published amino acid sequences for L-CAM (Gallin et al., supra), E-cadherin (Nagafuchi et al., supra), mouse P-cadherin (Nose et al., supra), uvomorulin (Ringwald et al., supra), chicken N-cadherin (Hatta et al., supra), mouse N-cadherin [Miyatani et al., Science, 245:631–635 (1989)] and human P-cadherin [Shimoyama et al., J. Cell. Biol., 109:1787–1794 (1989)], and the corresponding degenerate oligonucleotides respectively set out below in IUPAC-IUB Biochemical nomenclature were designed for use as PCR primers.

Primer 1 (SEQ ID NO: 1)
5' AARSSNNTNGAYTRYGA 3'
Primer 2 (SEQ ID NO: 2)
3' TTRCTRTIRCGNGGNNN 5'

The degenerate oligonucleotides were synthesized using an Applied Biosystems model 380B DNA synthesizer (Foster City, Calif.).
Cloning of cDNA Sequences by PCR PCR was carried out in a manner similar to that described in Suzuki et al., Cell Regulation, 2: 261–270 (1991) on a rat brain cDNA preparation. Total RNA was prepared from rat brain by the guanidium isothiocyanate/cesium chloride method described in Maniatis et al, pp. 196 in Molecular Cloning: A Laboratory Manual, Cold Spring Harbor, N.Y.: Cold Spring Harbor Laboratory (1982). Brain poly(A)⁺ RNAs were then isolated using a FastTrack® kit (Invitrogen, San Diego, Calif.) and cDNA was prepared using a cDNA synthesis kit (Boehringer Mannheim Biochemicals, Indianapolis, Ind.). The PCR reaction was initiated by adding 2.5 units of Taq DNA polymerase (Boehringer Mannheim Biochemicals) to 100 ng template cDNA and 10 µg of each primer, after which 35 reaction cycles of denaturation at 94° C. for 1.5 minutes, annealing at 45° C. for 2 minutes, and polymerization at 72° C. for 3 minutes were carried out. Two major bands of about 450 base pairs (bp) and 130 bp in size were found when the products of the PCR reaction were subjected to agarose gel electrophoresis. The 450 bp band corresponded to the expected length between the two primer sites corresponding to the middle of the third cadherin extracellular subdomain (EC-3) and the carboxyl terminus of the fourth cadherin extracellular subdomain (EC-4), but the 130 bp band could not be predicted from any of the previously identified cadherin sequences. The 450 bp and 130 bp bands were extracted by a freezing and thawing method. The resulting fragments were phosphorylated at the 5' end with T4 polynucleotide kinase and subcloned by a blunt-end ligation into the Sma I site of M13mp18 (Boehringer Mannheim Biochemicals) in a blunt end ligation for sequence analysis. Sequencing of the fragments was carried out by the dideoxynucleotide chain termination method using a Sequenase kit (United States Biochemicals, Cleveland, Ohio). DNA and amino acid sequence were analyzed using the Beckman Microgenie program (Fullerton, Calif.).
Analysis of cDNA Sequences Nineteen novel partial cDNA clones were isolated. The DNA and deduced amino acid sequences of the clones (including sequences corresponding to the PCR primers) are set out as follows: RAT-123 (SEQ ID NOs: 3 and 4, respectively), RAT-212 (SEQ ID NOs: 5 and 6), RAT-214 (SEQ ID NOs: 7 and 8), RAT-216 (SEQ ID NOs: 9 and 10), RAT-218 (SEQ ID NOs: 11 and 12), RAT-224 (SEQ ID NOs: 13 and 14), RAT-312 (SEQ ID NOs: 15 and 16), RAT-313 (SEQ ID NOs: 17 and 18), RAT-314 (SEQ ID NOs: 19 and 20), RAT-315 (SEQ ID NOs: 21 and 22), RAT-316 (SEQ ID NOs: 23 and 24), RAT-317 (SEQ ID NOs: 25 and 26), RAT-321 (SEQ ID NOs: 27 and 28), RAT-323 (SEQ ID NOs: 29 and 30), RAT-336 (SEQ ID NOs: 31 and 32), RAT-352 (SEQ ID NOs: 33 and 34), RAT-411 (SEQ ID NOs: 35 and 36), RAT-413 (SEQ ID NOs: 37 and 38), and RAT-551 (SEQ ID NOs: 39 and 40).

The deduced amino acid sequences of the cDNA clones are homologous to, but distinct from the known cadherins. The cadherins described thus far have highly conserved, short amino acid sequences in the third extracellular subdomain (EC-3) including the consensus sequence D-Y-E or D-F-E located at the middle region of the subdomain and the consensus sequence D-X-N-E-X-P-X-F (SEQ ID NO: 41) or D-X-D-E-X-P-X-F (SEQ ID NO: 42) at its end (Hatta et al., supra), while the corresponding sequences of other subdomains, except for the fifth extracellular subdomain (EC-5), are D-R-E and D-X-N-D-N-X-P-X-F (SEQ ID NO: 43), respectively. In contrast, the deduced amino acid sequences of the new clones that correspond to cadherin extracellular subdomains include the sequence D-Y-E or D-F-E at one end, but have the sequence D-X-N-D-N-X-P-X-F instead of D-X-N-E-X-P-X-F or D-X-D-E-X-P-X-F, at the other end. The polypeptides encoded by the partial clones are homologous to previously identified cadherins but did not show significant homology to any other sequences in Genbank. Therefore, the partial cDNAs appear to comprise a new subclass of cadherin-related molecules.

EXAMPLE 2

Various cDNA fragments structurally similar to the rat cDNAs described in Example 1 were isolated from human, mouse, and Xenopus brain cDNA preparations and from Drosophila and C. elegans whole body cDNA preparations by PCR using Primers 1 and 2 as described in Example 1. The DNA and deduced amino acid sequences of the resulting PCR fragments (including sequences corresponding to the PCR primers) are set out as follows: MOUSE-321 (SEQ ID NOs: 44 and 45), MOUSE-322 (SEQ ID NOs: 46 and 47), MOUSE-324 (SEQ ID NOs: 48 and 49), MOUSE-326 (SEQ ID NOs: 50 and 51), HUMAN-11 (SEQ ID NOs: 52 and 53), HUMAN-13 (SEQ ID NOs: 54 and 55), HUMAN-21 (SEQ ID NOs: 56 and 57), HUMAN-24 (SEQ ID NOs: 58 and 59), HUMAN-32 (SEQ ID NOs: 60 and 61), HUMAN42 (SEQ ID NOs: 62 and 63), HUMAN-43 (SEQ ID NOs: 64 and 65), HUMAN-212 (SEQ ID NOs: 66 and 67), HUMAN-213 (SEQ ID NOs: 68 and 69), HUMAN-215 (SEQ ID NOs: 70 and 71), HUMAN-223 (SEQ ID NOs: 72 and 73), HUMAN-410 (SEQ ID NOs: 74 and 75), HUMAN-443 (SEQ ID NOs: 76 and 77), XENOPUS-21 (SEQ ID NOs: 78 and 79), XENOPUS-23 (SEQ ID NOs: 80 and 81), XENOPUS-25 (SEQ ID NOs: 82 and 83), XENOPUS-31 (SEQ ID NOs: 84 and 85), DROSOPHILA-12 (SEQ ID NOs: 86 and 87), DROSOPHILA-13 (SEQ ID NOs: 88 and 89), DROSOPHILA-14 (SEQ ID NOs: 90 and 91) and *C. elegans*-41 SEQ ID NOs: 92 and 93). Comparison of the deduced amino acid sequences indicates significant similarity between sets of these clones. In particular, there are three sets of clones that appear to be cross-species homologues: RAT-218, MOUSE-322 and HUMAN-43; RAT-314, MOUSE-321 and HUMAN-11; and MOUSE-326 and HUMAN-42.

EXAMPLE 3

To ascertain the complete structure of the new proteins defined by the PCR products, two full length human cDNAs corresponding to the partial cDNAs HUMAN-42 and HUMAN-43 were isolated.

Isolation of Full-length Human cDNAs

A human fetal brain cDNA library (Stratagene, La Jolla, Calif.) in the λZapII vector was screened by the plaque hybridization method [described in Ausubel et al., Eds., *Current Protocols in Molecular Biology*, Sections 6.1.1 to 6.1.4 and 6.2.1 to 6.2.3, John Wiley & Sons, New York (1987)] with $^{32}$P-labelled HUMAN-42 and HUMAN-43 DNA fragments. The positive clones were plaque-purified and, using a helper virus, the inserts were cut out by an in vivo excision method in the form of a Bluescript SK(+) plasmid. The insert sequences were then subcloned into the M13 vector (Boehringer Mannheim, Biochemicals) for sequencing. Several overlapping cDNA clones were isolated with each probe including two cDNAs which contained the putative entire coding sequences of two novel proteins designated protocadherin-42 (pc42) and protocadherin-43 (pc43). The DNA and deduced amino acid sequences of pc42 are set out in SEQ ID NOs: 94 and 95, respectively, while the DNA and deduced amino acid sequences of pc43 are set out in SEQ ID NOs: 96 and 97, respectively.

A description of the cloning of protocadherin sequences of the invention was published in Sano et al, *The EMBO Journal*, 12(6): 2249–2256 (1993) after filing of the priority application hereto. The deduced amino acid sequence of pc43 was previously presented at the Dec. 9, 1991 meeting of the American Society for Cell Biology. An abstract of the presentation is published as Suzuki et al, *J. Cell. Biol.*, 115: 72a (Abstract 416) (Dec. 9, 1991).

Analysis of Full-length Human Clones

Comparison of the full length cDNA sequences of pc42 and pc43 to the sequences of the various DNA fragments originally obtained by PCR reveals that MOUSE-326 and HUMAN-42 correspond to a portion of the fourth extracellular subdomain (EC-4) of pc42, and RAT-314, MOUSE-321, and HUMAN-II correspond to a portion of the third extracellular subdomain (EC-3) of pc43 and RAT-218, MOUSE-322 and HUMAN-43 correspond to a portion of the fifth extracellular domain (EC-5) of pc43.

The overall structures of pc42 and pc43 are similar to that of typical cadherins but the new molecules also have distinct features. Both protocadherin cDNA sequences contain putative translation initiation sites and translated amino acid sequences start with typical signal sequences, but the clones lack the prosequences that are present in all known cadherin precursors. The cDNAs encode proteins having a large N-terminal extracellular domain and a relatively short C-terminal cytoplasmic domain connected by a transmembrane sequence. The extracellular domains of pc42 and pc43 are different in length and pc42 contains seven subdomains that closely resemble the typical cadherin extracellular subdomain while pc43 has six such subdomains. The sizes of the protocadherin cytoplasmic domains are similar to those of typical cadherins, but the sequences do not show any significant homology with those of known cadherins or cadherin-related proteins.

Amino acid identity determinations between extracellular subdomains of human pc42 and pc43, and of mouse N-cadherin (SEQ ID NO: 98) (presented as an example of a "typical" cadherin) and the eighteenth extracellular subdomain of Drosophila fat tumor suppressor (EC-18, SEQ ID NO: 99) (the eighteenth extracellular subdomain of fat is a prototypical fat subdomain) are presented in Table 1 below, wherein, for example, "N-EC-1×pc42" indicates that the first extracellular subdomain of N-cadherin was compared to the extracellular subdomain of pc42 indicated on the horizontal axis.

TABLE 1

|  | EC-1 | EC-2 | EC-3 | EC-4 | EC-5 | EC-6 | EC-7 |
|---|---|---|---|---|---|---|---|
| N-EC-1 x pc42 | 20 | 27 | 26 | 26 | 31 | 29 | 17 |
| N-EC-1 x pc43 | 31 | 23 | 23 | 26 | 31 | 24 |  |
| N-EC-2 x pc42 | 28 | 30 | 32 | 30 | 37 | 31 | 19 |
| N-EC-2 x pc43 | 30 | 28 | 30 | 36 | 29 | 30 |  |
| N-EC-3 x pc42 | 21 | 26 | 30 | 29 | 31 | 30 | 22 |
| N-EC-3 x pc43 | 25 | 18 | 26 | 28 | 28 | 25 |  |
| N-EC-4 x pc42 | 28 | 28 | 26 | 25 | 29 | 27 | 17 |
| N-EC-4 x pc43 | 21 | 25 | 28 | 28 | 29 | 24 |  |
| N-EC-5 x pc42 | 24 | 21 | 25 | 24 | 24 | 19 | 12 |
| N-EC-5 x pc43 | 15 | 21 | 20 | 20 | 25 | 16 |  |
| fat EC-18 x pc42 | 22 | 35 | 32 | 34 | 42 | 35 | 19 |
| fat EC-18 x pc43 | 32 | 30 | 36 | 36 | 33 | 29 |  |

The amino acid identity values between the extracellular subdomains of pc42 and pc43, and N-cadherin EC-1 through EC-5 and Drosophila fat EC-18 are mostly less than 40%. These identity values are comparable to the values between the subdomains of other cadherin subclasses. However, higher identity values indicate that pc42 and pc43 are more closely related to fat than to N-cadherin.

Amino acid identity determinations between extracellular subdomains of human pc42 and pc43 are presented in Table 2 below.

TABLE 2

|  | pc42 | | | | | | |
|---|---|---|---|---|---|---|---|
| pc43 | EC-1 | EC-2 | EC-3 | EC-4 | EC-5 | EC-6 | EC-7 |
| EC-1 | 33 | 27 | 29 | 26 | 25 | 26 | 25 |
| EC-2 | 26 | 38 | 29 | 33 | 34 | 28 | 21 |
| EC-3 | 26 | 32 | 41 | 30 | 32 | 31 | 22 |
| EC-4 | 25 | 34 | 30 | 41 | 39 | 31 | 18 |
| EC-5 | 23 | 32 | 29 | 27 | 36 | 34 | 16 |
| EC-6 | 25 | 25 | 26 | 25 | 28 | 23 | 26 |

The identity values between respective EC-1, EC-2, EC-3, EC-4, EC-5 subdomains and the last subdomains of pc42 and pc43 are generally higher values than values obtained for comparisons of the protocadherins to N-cadherin. These results suggest that pc42 and pc43 are more closely related to one another than they are to classic cadherins.

FIGS. 1A–C presents an alignment of the deduced amino acid sequences of the extracellular subdomains of pc42 (EC-1 through EC-7), (amino acids 42–818 of SEQ ID NO: 95), pc43 (EC-1 through EC-6) (amino acids 29–688 of SEQ ID NO: 97), mouse N-cadherin (EC-1 through EC-5) (amino acids 1–557 of SEQ ID NO: 98) and Drosophila fat EC-18 (SEQ ID No: 99). A sequence on a line in FIG. 1A continues on the same line in FIGS. 1B and 1C. Gaps were introduced to maximize homology.

In FIGS. 1A–1C, the position at which an amino acid appears in a SEQ ID NO: is indicated in parenthesis. For example, in FIG. 1A the first amino acid of EC1 of protocadherin-43 is an alanine which appears at position 29 in SEQ ID NO: 97 and the last amino acid of the protocadherin-43 EC1 appearing in FIG. 1A is an alanine which appears at position 63 in SEQ ID NO: 97.

The amino acid residues described by capital letters in the "motif" line are present in more than half of the subdomains of N-cadherin, pc42, pc43 and Drosophila fat. The amino acid residues described by small letters in the motif line are less well conserved in human pc42, pc43, and Drosophila fat. FIGS. 1A–1C shows that many amino acids characteristic of other cadherin extracellular domain repeats are conserved in the pc42 and pc43 sequences, including the cadherin sequence motifs DXD, DRE and DXNDNXPXF (SEQ ID NO: 43), two glycine residues, and one glutamic acid residue. Additionally, pc42 and pc43 share unique features in comparison to N-cadherin. More amino acids at specific sites are conserved between pc42 and pc43, such as the DXDXGXN (SEQ ID NO: 100) protocadherin sequence motif near the amino terminus of the pc42 and pc43 subdomains and the AXDXGXP (SEQ ID NO: 101) sequence motif near the carboxyl terminus of the subdomains. Additionally, both protocadherins share regions that do not show significant homology with the typical cadherin motif (of N-cadherin) near the carboxyl terminus of EC-1, in the middle of EC-2 and EC-4, and at the carboxyl terminus of the last repeat. A cysteine residue is located at a similar position in the middle of EC-4 of pc42 and pc43. In general, the extracellular subdomains of pc42 and pc43 are more similar to EC-18 of fat than the extracellular subdomains of N-cadherin.

Possible Alternative Splicing

Sequence analysis of various overlapping protocadherin cDNA clones revealed that some clones contained unique sequences at the 3' end, although the 5' end sequences were identical to other clones. The sequences forming the boundaries of the 3' end regions are consistent with the consensus sequence of mRNA splicing, suggesting that these clones may correspond to alternatively spliced mRNAs. The DNA and deduced amino acid sequences of one possible product of alternative splicing of pc42 mRNA are set out in SEQ ID NOs: 102 and 103. The DNA and deduced amino acid sequences of two possible products of alternative splicing of pc43 mRNA are respectively presented in SEQ ID NO: 104 and 105, and SEQ ID NOs: 106 and 107.

Chromosome Localization

The chromosomal location of the protocadherin 413 gene (SEQ ID NO: 37) and of the pc42 and pc43 genes was determined by conventional methods.

Briefly, C3H/HeJ-gld and *Mus spretus* (Spain) mice and [(C3H/HeJ-gld×*Mus spretus*) F₁×C3H/HeJ-gld] interspecies backcross mice were bred and maintained as previously described in Seldin, et al., *J. Exp. Med.*, 167: 688–693 (1988). *Mus spretus* was chosen as the second parent in the cross because of the relative ease of detection of informative restriction fragment length variants (RFLVs) in comparison with crosses using conventional inbred laboratory strains. Gene linkage was determined by segregation analysis.

Genomic DNA isolated from mouse organs by standard techniques was digested with restriction endonucleases and 10 μg samples were electrophoresed in 0.9% agarose gels. DNA was transferred to Nytran membranes (Schleicher & Schull, Inc., Keene, N.H.), hybridized with the appropriate probe at 65° C. and washed under stringent conditions, all as previously described in Maniatis et al., supra). To localize the pc42 gene, a mouse sequence probe corresponding to nucleotides 1419 to 1906 of SEQ ID NO: 94 was used and for pc43 a rat sequence probe corresponding to nucleotides 1060 to 1811 of SEQ ID NO: 96 was used. To localize the procadherin 413 gene, a probe including the sequence set out in SEQ ID NO: 37 was used. Other clones used as probes in the current study and RFLVs used to detect anonymous DNA loci were all previously described [Chromosome 7, DNA segment, Washington 12 (D7Was12); the parathyroid hormone (Pth); calcitonin (Calc); hemoglobin, β chain (Hbb); metallothionein-I (Mt-1); adenine phosphoribosyltransferase (Aprt); growth hormone receptor (Ghr); prostaglandin E receptor EP2 subtype (Ptgerep2); dihydrofolate reductase-2 (Dhfr2); fibroblast growth factor a (Fgfa); and glucocorticoid receptor-1 (Grl-1)].

Comparison of the haplotype distribution of protocadherin genes with those determined for loci throughout the mouse genome allowed each to be mapped to specific regions of mouse chromosomes. The probability for linkage was >99% and indicated assignment of both the pc42 gene and the pc43 gene was chromosome 18. The assignment of the protocadherin 413 gene was chromosome 7. The region of chromosome 18 to which the pc42 and pc43 genes were mapped corresponds to the ataxia (ax) loci [Burt, *Anat. Rec.*, 196: 61–69 (1980) and Lyon, *J. Hered.*, 46: 77–80 (1955)] and twirler (Tw) loci [Lyon, *J. Embryol. Exp. Morphol.*, 6: 105–116 (1958)], while the region of chromosome 7 to which the protocadherin 413 gene was mapped corresponds to the shaker (sh-1) locus [Kikuchi et al, *Acta Oto-Laryngol.*, 60: 287–303 (1965) and Lord et al, *Am. Nat.*, 63: 453–442 (1929)]. These loci have been implicated as involved in hereditary neural disease in the mouse. This result is consistent with in situ hybridization results (see Example 12) showing that pc42 and pc43 are strongly expressed in the brain and particularly in the cerebellum.

EXAMPLE 4

Two additional novel human protocadherin cDNAs and one additional novel rat protocadherin cDNA were isolated using rat protocadherin fragments described in Example 1 as probes.

Initially, the rat clone RAT-214 (SEQ ID NO: 7) was used as a probe to screen a rat brain cDNA library (Stratagene, La Jolla, Calif.). The final washing step was performed twice at 50° C. in 0.1× SSC with 0.1% SDS for 15 minutes. Various clones were identified which contained partial cDNA inserts encoding related protocadherin amino acid sequences. The nucleotide sequence of one novel rat clone designated #6-2 is set out in SEQ ID NO: 108. The first fifteen nucleotides of SEQ ID NO: 108 are the sequence of a linker and are not part of the rat #6-2 clone.

A human fetal brain cDNA library obtained from Stratagene was screened with the 0.7 kbp PstI fragment of clone #6-2. The fragment appears to encode the EC-2 and EC-3 of the rat protocadherin. After screening about 2×10⁶ phages, eleven positive clones were isolated. Sequencing of the clones identified a novel full length human protocadherin cDNA designated human pc3. The nucleotide and deduced amino acid sequence of human pc3 are set out in SEQ ID NOs: 109 and 110.

The 0.7 kbp PstI fragment of rat clone #6-2 was also used to rescreen the Stratagene rat brain cDNA library for full length rat cDNA clones. A clone containing an insert encoding a full length novel protocadherin cDNA was isolated. The DNA and deduced amino acid sequence of the insert are set out in SEQ ID NO: 111 and 112. The full length rat cDNA was named pc5 because it does not appear to be the homolog of the human pc3 clone based upon a comparison of the sequences.

Concurrently, the 0.8 kbp Eco RI-Pst I fragment of partial rat cDNA designated #43 (SEQ ID NO: 113), which was obtained by screening the Stratagene rat brain cDNA library with a probe corresponding to the human pc43 cytoplasmic domain, was used to probe the Stratagene human cDNA library for full length human protocadherin cDNAs. The fragment appears to encode EC-3 through the beginning of EC-6 of clone #43. One partial clone identified encodes a novel human protocadherin named human pc4. The nucleotide sequence and deduced amino acid sequences of the human pc4 clone are set out in SEQ ID NOs: 114 and 115. The amino acid sequence encoded by the pc4 clone appears to begin in the middle of EC-2 of pc4 and continues through the cytoplasmic tail of the protocadherin.

EXAMPLE 5

The full length human cDNAs encoding pc42 and pc43 were expressed in L cells (ATCC CCL 1) using the pRC/RSV expression vector (Invitrogen, San Diego, Calif.). The cDNAs were isolated from the Bluescript SK(+) clones described in Example 2 by digestion with SspI followed by blunt-ending with DNA polymerase and digestion with XbaI (for pc42), or by double digestion with SpeI and EcoRV (for pc43). The pRC/RSV expression vector was digested with HindIII, followed by blunt-ending and re-digestion with XbaI for insertion of pc42 sequences, or by digested with XbaI followed by blunt-ending and re-digestion with SpeI for insertion of pc43 sequences. The isolated protocadherin DNAs were ligated into the linearized pRC/RSV vector. The resulting pc42 expression plasmid designated pRC/RSV-pc42 (ATCC 69162) and pc43 expression plasmid designated pRC/RSV-pc43 (ATCC 69163) were purified by CsCl gradient centrifugation and transfected into L cells by a Ca-phosphate method.

The pc42 and pc43 transfectants were morphologically similar to the parental cells. Northern blot analysis of L cells transfected with pc42 or pc43 DNA sequences showed that the transfected cells expressed mRNAs of a size expected to encode the particular protocadherin.

EXAMPLE 6

Rabbit polyclonal antibodies specific for pc42 and pc43 were generated as well as a mouse monoclonal antibody specific for pc43.
Preparation of Polyclonal Antibodies Specific for pc42 and ps43

DNA sequences encoding portions of the extracellular domain of pc42 and pc43 were each fused to a maltose binding protein-encoding sequence and expressed in bacteria. Specifically, DNAs corresponding to EC-4 through EC-7 of pc42 and EC-3 through EC-5 of pc43 were prepared by PCR and subcloned in the correct reading frame into the multicloning site of the pMAL expression vector (New England Biolabs, Beverly, Mass.) which contains sequences encoding maltose binding protein immediately upstream of the multicloning site. The resulting plasmids were then introduced into *E. coli* NM522 cells (Invitrogen, San Diego, Calif.) by a single step transformation method. Expression of the fusion proteins was induced by the addition of IPTG and the fusion proteins were purified from cell extracts by amylose resin affinity chromatography (New England Biolabs) as described by the manufacturer. The fusion proteins were used for the immunization of rabbits without further purification.

Polyclonal antibodies were prepared in rabbits by immunization at four subcutaneous sites with 500 μg of purified fusion protein in Freund's complete adjuvant. Subsequent immunizations with 100 μg of the fusion protein were in Freund's incomplete adjuvant. Immune sera was passed through sepharose coupled to maltose binding protein (New England Biolabs) and polyclonal antibodies were purified from immune sera using Sepharose affinity columns prepared by reaction of the purified fusion protein with CNBr Sepharose (Pharmacia). Reactivity of the polyclonal sera with purified pc42 fusion protein and pc42 transfected cell extracts (described in Example 5) was confirmed.
Preparation of Monoclonal Antibodies Specific for pc43

The pc43 fusion protein (containing the EC-3 through EC-5 subdomains of pc43) was used to generate monoclonal antibodies in mice according to the method of Kennett, *Methods in Enzymol*, 58:345–359 (1978). Briefly, mice were immunized with the pc43 fusion protein (100 μg) at two subcutaneous sites. The spleen from the highest titer mouse was fused to the NS1 myeloma cell line. The resulting hybridoma supernatants were screened in a ELISA assay for reactivity with the pc43 fusion protein and with maltose binding protein. The fusion wells with the highest reactivity to the pc43 extracellular domains were subcloned. The hybridoma cell line designated 38I2C (ATCC HB 11207) produced a IgG₁ subtype monoclonal antibody specific for pc43. Reactivity of the monoclonal antibody produced by hybridoma cell line 38I2C to pc43 was confirmed by immunoblotting the pc43 L cell transfectants described in Example 5. The 38I2C monoclonal antibody is specific for human pc43.

EXAMPLE 7

L cells transfected with DNA sequences encoding pc42 and pc43 as prepared in Example 5 were assayed for expression of the protocadherins by immunoblot and by immunofluorescence microscopy.
Immunoblot Analysis Cell extracts of pc42 and pc43 transfectants were subjected to SDS-PAGE and then blotted electrophoretically onto a PVDF membrane (Millipore, Bedford, Mass.). The membranes were incubated with 5% skim milk in Tris-buffered saline (TBS) for two hours and then respectively with either pc42 polyclonal sera or pc43 monoclonal antibody for one hour. The membranes were washed three times (for 5 minutes each wash) with TBS containing 0.05% Tween 20 and respectively incubated with alkaline phosphatase-conjugated anti-rabbit IgG antibody or anti-mouse IgG antibody (Promega, Madison, Wis.) in the same buffer for one hour. After washing the membranes with TBS containing 0.05% Tween 20, reactive bands were visualized by using Western Blue solution (Promega).

Anti-pc42 polyclonal antibodies stained a band of about 170 kDa molecular weight in pc42 transfected cells, but not parental L cells. The pc43-specific monoclonal antibody (38I2C) and polyclonal antibodies stained two adjacent bands of about 150 kDa molecular weight in pc43 transfected cells. The pc43 antibodies did not stain bands in parental L-cells. The molecular weights indicated by the staining of bands by the pc42 and pc43 antibodies are significantly larger than the molecular weights predicted from the deduced amino acid sequences. This discrepancy in molecular weight is common among various cadherin-related proteins and may be attributable to the glycosylation and/or cadherin specific structural properties. The pc42 antibody also stained smaller bands, which may be proteolytic degradation products.

When transfected cells were trypsinized and cell extracts were prepared, run on SDS/PAGE and immunoblotted with the appropriate antibody, the pc42 and pc43 polypeptides expressed by the transfected cells were found to be highly sensitive to proteolysis and were easily digested by 0.01% trypsin treatment. In contrast to the classic cadherins, however, these proteins were not protected from the digestion in the presence of 1–5 mM $Ca^{2+}$.

Immunofluorescence Microscopy

Transfected cells were grown on a cover slip precoated with fibronectin and were fixed with 4% paraformaldehyde for 5 minutes at room temperature or with cold methanol on ice for 10 minutes followed by 4% paraformaldehyde fixation. After washing with TBS, the cells were incubated with TBS containing 1% BSA for 30 minutes and then with anti-pc42 polyclonal antibody or anti-pc43 monoclonal antibody in TBS containing 1% BSA for 1 hour at room temperature. Cover slips were then washed with TBS containing 0.01% BSA and respectively incubated with FITC-conjugated anti-rabbit antibody or anti-mouse antibody (Cappel, Durham, N.C.) for 60 minutes at room temperature. The cells were washed again with TBS containing 0.01% BSA and subjected to fluorescence microscopy. Both pc42-specific and pc43-specific polyclonal antibodies stained the cell periphery of transfected cells expressing the protocadherin proteins, mainly at the cell-cell contact sites. The antibodies did not stain the parent L cells, nor did rabbit preimmune sera stain the pc42 and pc43 transfectants.

EXAMPLE 8

The cell aggregation properties of the transfected L cells expressing protocadherin proteins were examined. Transfected L cells were cultured in Dulbecco's Modified Eagles Medium (DMEM) (Gibco, Grand Island, N.Y.) supplemented with 10% fetal bovine serum at 37° C. in 5% $CO_2$. Cells grown near confluence were treated with 0.01% trypsin in the presence of 1 mM EGTA for 25 minutes on a rotary shaker at 37° C. and collected by centrifugation. The cells were washed three times with $Ca^{2+}$ free HEPES-buffered saline (HBS) after adding soybean trypsin inhibitor, and were resuspended in HBS containing 1% BSA. The cell aggregation assay [Urushihara et al., *Dev. Biol.,* 70: 206–216 (1979)] was performed by incubating the resuspended cells in a 1:1 mixture of DMEM and HBS containing 1% BSA, 2 mM $CaCl_2$ and 20 µg/ml of deoxyribonucelease on a rotary shaker at 37° C. for 30 minutes to 6 hours.

The pc42 and pc43 transfectants did not show any significant cell aggregation activity during periods of incubation less than 1 hour. This is in contrast to the cell aggregation that occurs with classic cadherins in similar experiments (Nagafuchi et al., supra, and Hatta et al., supra). However, prolonged incubation of transfected cells (more than 1–2 hours) resulted in gradual re-aggregation of the cells into small aggregates. Similar results were obtained when single cell suspensions of transfected cells were prepared by trypsin treatment in the presence of $Ca^{2+}$. No re-aggregation was observed under the same conditions when untransfected L cells or L cells transfected with pRC/RSV vector alone were tested. When pc43 transfectants labelled with DiO (Molecular Probes, Eugene, Oreg.) were incubated with unlabelled pc42 transfectants in the cell aggregation assay, aggregation of labelled and unlabelled cells was almost mutually exclusive indicating that protocadherin binding is homophilic.

In view of the fact that the protocadherin cytoplasmic domains exhibit no apparent homology to cadherin domains, experiments were performed to determine if the difference in cytoplasmic domains could account for the difference in cell aggregation activity observed in cadherin and protocadherin transfectants. The cytoplasmic domain of pc43 was replaced with the cytoplasmic domain of E-cadherin and aggregation of cells transfected with the chimeric construct was analyzed.

The Bluescript SK(+) clone described in Example 2 which contained the entire coding sequence for pc43 was digested with EcoRV and then partially digested with XbaI to remove the sequence corresponding to the cytoplasmic domain, and the plasmid DNA was purified by agarose gel electrophoresis. The cDNA corresponding to the cytoplasmic domain of mouse E-cadherin was synthesized by PCR using mouse cDNA made from mouse lung mRNA as a template and specific primers corresponding to a region near the N-terminus of the cytoplasmic domain sequence or the region containing the stop codon of mouse E-cadherin (Nagafuchi et al., supra). A XbaI sequence was included to the 5' end of the upstream primer. The E-cadherin cytoplasmic domain cDNA was then subcloned into the linearized pc43 Bluescript clone. The DNA containing the entire resulting chimeric sequence was cut out with SpeI and EcoRV and was subcloned into the SpeI-blunted XbaI site of the expression vector pRc/RSV vector. Finally, L cells were transfected with the resultant construct by a calcium phosphate method. After screening with G418 for about 10 days, the transfectants were stained with FITC-labeled 38I2C anti-pc43 antibody and subjected to FACS analysis. A portion of highly labeled cells were isolated and cloned. Transfectants showed a morphology similar to that of parental L cells and the expressed protein was localized at the cell periphery using pc43 antibody for immunofluorescence microscopy.

Cell aggregation activity of the chimeric transfectants was analyzed as follows. The chimeric pc43 transfectants were labeled with DiO for 20 minutes at room temperature. The resultant cells were trypsinized in the presence of 1 mM EGTA and single cell suspension was made. Then, the cells were mixed with unlabeled other type of transfectants and incubated on a rotary shaker for two hours. The results were examined with a fluorescence and a phase contrast microscope apparatus. Antibody inhibition of cell aggregation was examined by incubation of the transfectants in the presence of polyclonal anti-pc43 antibody (100 ng/ml) in the standard assay medium.

In the cell aggregation assay, the chimeric pc43 transfectants showed clear $Ca^{2+}$-dependent cell aggregation within forty minutes of incubation. Cell aggregation was inhibited by the addition of pc43-specific polyclonal antibody.

EXAMPLE 9

The procedures of Maruyama et al, *J. Biochem.,* 95: 511–519 (1984) were used to determine the calcium binding properties of pc43 by Western blot analysis in the presence or absence of calcium-45. The pc43 fusion protein described in Example 6 containing pc43 subdomains EC-3 through EC-5 was compared to the calcium binding protein calmodulin. Samples of purified pc43 fusion protein were run on SDS/PAGE and electrophoretically transferred to PVDF membrane. Binding of the $^{45}Ca^{2+}$ to the pc43 fusion protein was detected by autoradiography and was determined to be nearly as efficient as binding of $^{45}Ca^{2+}$ to calmodulin. In contrast, there was no binding of calcium to purified maltose binding protein lacking the pc43 extracellular domain. The pc43 subdomains EC-3 through EC-5 contain sequences highly homologous to the putative $Ca^{2+}$ binding motifs found in E-cadherin. [See, Ringwald et al, EMBO J., 6: 3647–3653 (1987).]

EXAMPLE 10

The expression of mRNA encoding pc42 and pc43 was assayed in various tissues and cell lines by Northern blot.

Total RNAs were prepared by the guanidium isothiocyanate method and poly(A)+ RNAs were isolated using a FastTrack kit (Invitrogen). RNA preparations were electrophoresed in a 0.8% agarose gel under denaturing conditions and transferred onto a nitrocellulose filter using a capillary method. Northern blot analyses were performed according to the method of Thomas, Proc. Natl. Acad. Sci. USA, 77: 5201–5205 (1980). The final wash was in 0.2× standard saline citrate containing 0.1% sodium dodecyl sulfate at 65° C. for 10 minutes.

Protocadherin mRNA Expression in Adult Rat Tissues

Total mRNA preparations of rat tissues including brain, heart, liver, lung, skin, kidney and muscle were separated electrophoretically under denaturing conditions (10 µg mRNA/lane) and transferred onto nitrocellulose filters. The filters were hybridized with $^{32}P$-labelled cDNA fragments MOUSE-326 (which corresponds to EC-4 of human pc42) and RAT-218 (which corresponds to EC-5 of human pc43). The mRNAs of both protocadherins were highly expressed in brain. The pc42 probe detected a major band of 7 kb and a minor band of 4 kb in size, possibly representing the products of alternative splicing. The pc43 probe hybridized to a major band of 5 kb in size and with minor bands of smaller sizes.

Developmental Expression of Protocadherin mRNA in Rat Brain

To examine the developmental regulation of mRNA expression of the protocadherins, brain mRNA from rats at embryonic days 17 and 20, neonatal days 5 and 11 and from adult rats was prepared and subjected to Northern blot analysis as described above for other rat tissues. β-actin was used as an internal standard. mRNA levels for pc42 and pc43 proteins increased during embryonic development of the brain as compared with β-actin expression.

Protocadherin mRNA Expression in Human Cell Lines

Several neuronal and glial cell lines (including human SK-N-SH neuroblastoma, human U251 glioma, and mouse Neuro-2a neuroblastoma cell lines) were assayed by Northern blot using $^{32}P$-labelled for expression of pc42 and pc43 mRNA. Human cell lines were probed with HUMAN-42 (which corresponds to EC-4 of human pc42) and HUMAN-43 (which corresponds to EC-5 of human pc43) cDNA fragments while the mouse cell line was probed with MOUSE-326 (which corresponds to EC-4 of human pc42) and RAT-322 (which corresponds to EC-5 of human pc43) cDNA fragments. SK-N-SH human neuroblastoma cells and U251 human glioma cells were found to express pc43 mRNA and Neuro-2a mouse neuroblastoma cells were found to express pc42 mRNA.

EXAMPLE 11

Expression of pc43 protein in various tissues, extracts and cells was assayed by Western blot and immunofluorescence microscopy.

Expression in Rat Cardiac Muscle Extracts

A rat heart non-ionic detergent extract was prepared by freezing a heart in liquid nitrogen after removal, powdering in a mortar and pestle, grinding briefly in a polytron in 0.5% Nonidet P40 in [10 mM PIPES (pH 6.8), 50 mM NaCl, 250 mM $NH_4SO_4$, 300 mM sucrose, 3 mM $MgCl_2$] and microfuging for 15 minutes. Samples were separated by SDS/PAGE and electrophoretically transferred to nitrocellulose (Towbin et al., PNAS 76:4350–4354, 1979). Two pc43 protein bands with molecular weights of 150 KDa and 140 KDa were detected with rabbit polyclonal antibodies to pc43 by the immunoblot method described in Example 7.

Expression in Tissue Sections and Cells

To determine the localization of the protocadherins in various tissues, human and rat adult tissues were removed, incubated in 30% sucrose in PBS for 30 minutes at 4° C., embedded in OCT compound (Tissue-Tek, Elkhart, Ind.) in cryomolds and quickly frozen. Six micron sections were cut and placed on glass slides. The slides were washed with PBS and fixed in 3% p-formaldehyde for 5 minutes. To permeablize the tissue sections, the slides were immersed in −20° C. acetone for 10 minutes and air dried. The sections were blocked with 2% goat serum and 1% BSA in PBS for 30 minutes and then incubated with the rabbit anti-pc43 polyclonal antisera for 1 hour at room temperature. The sections were rinsed 3 times in PBS containing 0.1% BSA and incubated with a biotinylated anti-rabbit (Vector Laboratories, Burlingame, Calif.) in 1% BSA in PBS for 30 minutes. After rinsing 3 times, strepavidin-conjugated with FITC (Vector Laboratories) was added for 30 minutes and again washed 3 times. For co-localization studies, an appropriate primary antibody was used with a TRITC-conjugated secondary antibody.

A. Muscle

Immunolocalization of pc43 in rat cardiac muscle shows that pc43 is localized in a repeating pattern which is consistent with pc43 being associated with the sarcomeres. Sarcomeres are repetitive contractile units between the fascia adherens in skeletal and cardiac muscle. Co-localization with cytoskeletal proteins shows that pc43 is present at the ends of the sarcomeres in the Z lines which are associated with desmin and the actin-binding protein vinculin, and alpha-actinin. The thin microfilaments of F-actin are associated with the thick myosin filaments between the Z lines. In contrast, N-cadherin is localized at the ends of cardiac myocytes at the fascia adherens junctions at sites of myocyte:myocyte contact. The localization of pc43 in cardiac muscle suggests that pc43 may play a role in muscle contraction in the anchoring of the contractile apparatus to the plasma membrane.

Similar localization for pc43 was observed in rat skeletal muscle. Ultrastructural studies have shown that dystrophin, the gene product lacking in Duchenne muscular dystrophy, is a component of the sarcolemma [Porter et al., J. Cell. Biol., 117:997–1005 (1992)]. The sarcolemma is connected to the contractile apparatus at the M and Z lines where pc43 is localized.

B. Brain

Reactivity of anti-pc43 polyclonal antibody and monoclonal antibody 38I2C on frozen sections of rat and human cerebellum, respectively, shows that the major sites of pc43 expression are located in Purkinje cells and the granule cell layer which contains numerous small neurons.

C. Placenta

Strong reactivity of monoclonal antibody 38I2C with human syncytiotrophoblasts was also observed in development of the placenta at an early state (5–7 weeks of gestation). Expression appeared to gradually decrease as the stage progressed indicating that pc43 may be involved in the implantation of fertilized eggs into the placenta.

D. Neuroblastoma and Astrocytoma Cells

Immunocytochemical localization of pc43 in Sk-N-SH neuroblastoma cells and UW28 astrocytoma cells using anti-pc43 antibodies reveals a punctate cell surface distribution of pc43 and in some cells there is a localization at the tips of extensions of neuronal foot processes. At sites of cell-cell contact of UW28 astrocytoma cells, pc43 is organized in a series of parallel lines. The lines start at the contact site and extend approximately 5 micron. F-actin microfilaments were identified with rhodamine-phalloidin (Molecular Probes, Eugene, Oreg., as described by the manufacturer) showing that the microfilaments in the cell appear to end in the pc43 linear structures which extend from the edge of the cell at sites of cell contact.

Immunoblotting studies with pc43 specific antibodies show that a protein with a molecular weight of 140 kDa is recognized in human Sk-N-SH neuroblastoma cells and in UW28 astrocytoma cells.

E. Osteoblasts

Immunocytochemical localization of pc43 using monoclonal antibody 38I2C in tow human ostogenic sarcoma cell lines [SaOS (ATCC HTB 85) and MG-63 (ATCC CRL 1427)] and in cultures of normal human trabecular osteoblasts [culture system described in Civitelli et al, *J. Clin. Invest.*, 91: 1888–1896 (1993)] showed that pc43 is expressed in osteoblasts in a pattern similar to that seen in UW28 astrocytoma cells. At sites of cell-cell contact, pc43 is organized in a series of parallel lines that appear to correspond to the actin stress fibers. In addition, in some cells, pc43 appears to localize at the tips of contacting cell processes. Northern blot analysis provides additional evidence that pc43 is expressed in normal human trabecular osteoblasts. A pc43 specific DNA probe hybridized to a major band of 5 kb in samples of poly-A mRNA isolated from normal human trabecular osteoblasts.

EXAMPLE 12

In situ hybridization experiments using protocadherin specific RNA probes were performed on cryosections of rat tissue.

Sense and antisense $^{35}$S-riboprobes were made using the standard procedure described by Promega (Madison, Wis.). An approximately 400 bp EcoRI-XbaI fragment of the MOUSE-326 cDNA clone was used as a pc42 specific probe. This fragment encodes the middle of EC-3 to the end of EC-4 of pc42. An approximately 700 bp SmaI fragment of the RAT-218 cDNA clone was used as a pc43 specific probe. The fragment encodes the end of EC-3 to the end of EC-5 of pc43.

Rat adult tissues were harvested and immediately embedded with OCT Compound (Tissue-Tek) in cryomolds and quickly frozen in a bath of 95% ethanol/dry ice. The frozen blocks were stored at −80° C. until cut. Six micron tissue sections were cut using a cryostat (Reichert-Jung, Model #2800 Frigocut N, Leica, Inc., Gilroy, Calif.). Cut tissue sections were stored at −80° C.

The in situ protocol used was a variation of that described by Angerer et al., *Methods in Enzmology*, 152: 649–660, (1987). All solutions were treated with diethylpyrocarbonate (DEPC, Sigma, St. Louis, Mo.) to remove RNase contamination. The tissue sections were first fixed in 4% paraformaldehyde at 4° C. for 20 minutes. To remove excess paraformaldehyde and stop the tissue fixation, the slides were washed in PBS (phosphate buffered saline), denatured in a graded series of alcohols (70, 95, 100%) and then dried. To prevent the tissue from detaching from the glass slide during the in situ procedure, the tissue sections were treated in a poly-L-lysine solution (Sigma) at room temperature for 10 minutes. To denature all RNA in the tissue, the sections were placed in a solution of 70% formamide/2× SSC (0.15M NaCl/0.3M Na citrate, pH 7.0) at 70° C. for 2 minutes after which they were rinsed in chilled 2× SSC, dehydrated in a graded series of alcohols and then dried. Once dried, the sections were prehybridized in hybridization buffer [50% formamide/50 mM DTT (dithiothrietol)/0.3M NaCl/20 mM Tris, pH 8.0/5 mM EDTA/1× Denhardt's (0.02% Ficoll Type 400/0.02% polyvinylpyrrolidone/0.02% BSA)/10% Dextran Sulfate] at the final hybridization temperature for approximately 4 hours. After prehybridization, approximately $1\times10^6$ cpm of the appropriate riboprobe was added to each section. The sections were generally hybridized at 45° C. overnight (12–16 hours). To insure that the hybridization seen was specific, in some experiments the hybridization stringency was increased by raising the hybridization temperature to 50° C. As both the 45° C. and 50° C. experiments gave comparable results, the standard hybridization temperature used was 45° C.

To remove excess, nonhybridized probe, the sections were put through a series of washes. The sections were first rinsed in 4× SSC to remove the bulk of the hybridization solution and probe. Next a 15 minute wash in 4× SSC/50 mM DTT was carried out at room temperature. Washes at increased stringencies were also utilized. A 40 minute wash in 50% formamide/2× SSC/50 mM DTT was performed at 60° C. Four final room temperature washes were carried out for 10 minutes each: two in 2× SSC and two in 0.1× SSC. The washed slides were dehydrated in a graded series of alcohols and dried.

To visualize the hybridized probe, the slides were dipped in Kodak NTB2 nuclear emulsion (International Biotechnology, New Haven, Conn.) which had been diluted 1:1 in dH$_2$O. Once dry, the slides were stored at 4° C. in light-tight boxes for the appropriate exposure time. The in situ slides were independently viewed by two persons and scored positive or negative for hybridization signal.

All in situ hybridization studies were performed on rat tissue. Because results from Northern blot experiments (see Example 9) indicated that both pc42 and pc43 are expressed in adult brain, in situ hybridization studies were carried out to localize the expression of these molecules to specific brain cell types. Hybridization seen in the normal adult rat brain was specific (no background hybridization was seen with the sense probes) and was localized to specific regions in the brain. The overall pattern of expression seen for pc42 and pc43 was very similar, with the major difference being in the level of expression. pc43 appears to be expressed at a lower level than pc42. Both molecules are expressed in the germinal and pyramidal cells of the hippocampus, Purkinje cells of the cerebellum and neurons in grey matter. In addition, pc42 is expressed in glial cells in the white matter but, in contrast to the expression of pc43 in glioma cell lines (as described in Example 9), expression of pc43 in normal glial cells was not observed. In the spinal chord, both protocadherins are expressed in the motor neurons in the gray matter and pc42 is expressed in the glial cells in the white matter.

When expression of both protocadherin molecules was analyzed in brains and spinal chords from rats having EAE (experimental allergic encephalomyelitis) [Vandenbark et al., *Cell. Immunol.*, 12: 85–93 (1974)], the same structures as described above were found to be positive. In addition, expression of pc42 was observed in the leukocytic infiltrates in the EAE tissues. Expression of pc42 in leukocytes was confirmed by in situ hybridization analysis of two leukocytic cell lines, RBL-1 and y3.

Expression of both protocadherin-42 and -43 was observed in the developing brain of rat embryos at all embryological days tested (E15–E19). In addition protocadherin-43 was observed in the developing rat heart at all embryological days tested (E13–E19). This finding is consistent with the immunohistochemistry results showing protocadherin-43 expression in adult heart.

To determine possible roles of protocadherins in the development of the nervous system, expression profiles of protocadherin members in developing rat brain and adult rat brain were also examined by in situ hybridization. A series of coronal, sagittal and horizontal sections of rat brains at postnatal days 0, 6, 14, 30 (P0 through P30) and at 3 months (young adult) were hybridized with labelled cRNA probes corresponding to various protocadherins of the invention including pc42, pc43, RAT-212, RAT-411, and RAT-418. In developing brain, RAT-411 was expressed at high levels in neurons of the olfactory bulb, i.e., mitral cells and periglomerular cells. The expression of RAT-411 mRNA was transient; expression appeared at P0, peaked at P6, diminished by P14, and was undetectable at P30 and in adult brain. In the adult, pc43 mRNA was found to be expressed predominantly in Purkinje cells in the cerebellum. The expression of pc43 mRNA in Purkinje cells was observed from the beginning of Purkinje cell differentiation at around P6. Other protocadherin members were expressed at very low levels in various areas of developing and adult brains. These results indicate that protocadherin members are differentially expressed during the development of the central nervous system, and suggest that RAT-411 and pc43 have specific roles during the development of olfactory bulb neurons and Purkinje cells, respectively.

EXAMPLE 13

Conventional immunoprecipitations using pc43-specific polyclonal antibodies and monoclonal antibody 38I2C were performed to identify proteins that interacted with pc43 in L cell transfectants.

The pc43 and chimeric pc43 transfectants were metabolically labeled by incubating the cells in Dulbecco's modified Eagle's medium containing [$^{35}$S]methionine (50 uCi/ml) overnight. After washing, the transfectants were lysed with PBS containing Triton×100 and incubated with anti-pc43 antibody. The immunocomplexes were then collected using protein A-Sepharose beads. The resulting beads were washed five times with a washing buffer (50 mM Tris-HCl, pH 8.0, containing 0.5M NaCl, 0.1% ovalbumin, 0.5% NP-40, 0.5% Triton×100 and 1 mM EDTA) at room temperature. Protein was separated by SDS-PAGE and subjected to autoradiography.

The chimeric pc43 co-precipitated with 105 kDa and a 95 kDa bands that are likely to correspond to α- and β-catenins, respectively, because anti-α-catenin and anti-β-catenin antibodies stained comparable bands. Pc43, on the other hand, co-precipitated with a 120 kDa band.

While the present invention has been described in terms of specific methods and compositions, it is understood that variations and modifications will occur to those skilled in the art. Therefore, only such limitations as appear in the claims should be placed on the invention.

---

What is claimed is:

1. The hybridoma cell line designated 38I2C (ATCC HB 11207).

2. An antibody produced by the hybridoma cell line of claim 1.

* * * * *

UNITED STATES PATENT AND TRADEMARK OFFICE
CERTIFICATE OF CORRECTION

PATENT NO. : 5,891,706
DATED : April 6, 1999
INVENTOR(S) : Shintaro Suzuki

It is certified that error appears in the above-identified patent and that said Letters Patent is hereby corrected as shown below:

On the title page, item [56]

Under References cited, under Other Publications, Frixen *et al,.* replace "E-Cadherin-Miedated" with --E-Cadherin-Mediated--.

Under References cited, Other Publications, Porter *et al.*, replace "Sketal" with --Skeletal--.

Under References cited, Other Publications, Pytela *et al.*, replace "Identifiction" with --Identification--.

Under References cited, Other Publications, Pytela *et al.*, replace "Acedemic" with --Academic--.

Under References cited, Other Publications, Ringwald *et al.*, after "EMBO J.," and before "3647-3653" insert --6(12):--.

Under References cited, Other Publications, replace "Laqunowich" with --Lagunowich--.

Under References cited, Other Publications, Lagunowich, replace "Biochem Biophy Res Comm" with --Biochem. Biophys. Res. Comm.--.

UNITED STATES PATENT AND TRADEMARK OFFICE
CERTIFICATE OF CORRECTION

PATENT NO. : 5,891,706
DATED : April 6, 1999
INVENTOR(S) : Shintaro Suzuki

It is certified that error appears in the above-identified patent and that said Letters Patent is hereby corrected as shown below:

Column 1, line 48, replace "an" with --a--.

Column 3, line 6, replace "supressor" with --suppressor--.

Column 3, line 7, replace "supress" with --suppress--.

Column 5 lines 46, replace "3'TTRCTRTIRCGNGGNNN 5'" with --3' TTRCTRTTRCGNGGNNN 5'--.

Column 7, line 64, replace "HUMAN-II" with --HUMAN-11--.

Column 9, line 59, replace "NO" with --NOs--.

Column 10, line 18, replace "procadherin" with --protocadherin--.

Column 11, line 62, replace "ps43" with --pc43--.

Column 20, line 29, replace "Pc43" with --pc43--.

Signed and Sealed this

Eleventh Day of January, 2000

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 115

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

A A R S S N N T N G  A Y T R Y G A                                1 7

( 2 ) INFORMATION FOR SEQ ID NO:2:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
TTRCTRTTRC GNGGNNN                                                                                      17
```

(2) INFORMATION FOR SEQ ID NO:3:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
AAGGGAGTGG ACTTTGAGGA GCAGCCTGAG CTTAGTCTCA TCCTCACGGC TTTGGATGGA      60
GGGACTCCAT CCAGGTCTGG GACTGCATTG GTTCAAGTGG AAGTCATAGA TGCCAATGAC     120
AACGCACCGT A                                                          131
```

(2) INFORMATION FOR SEQ ID NO:4:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Lys Gly Val Asp Phe Glu Glu Gln Pro Glu Leu Ser Leu Ile Leu Thr
 1               5                  10                  15
Ala Leu Asp Gly Gly Thr Pro Ser Arg Ser Gly Thr Ala Leu Val Gln
                20                  25                  30
Val Glu Val Ile Asp Ala Asn Asp Asn Ala Pro
                35                  40
```

(2) INFORMATION FOR SEQ ID NO:5:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
AAACGCATGG ATTTCGAGGA GTCTTCCTCC TACCAGATCT ATGTGCAAGC TACTGACCGG      60
GGACCAGTAC CCATGGCGGG TCATTGCAAG GTGTTGGTGG ACATTATAGA TGTGAACGAC     120
AACGCACCTA A                                                          131
```

(2) INFORMATION FOR SEQ ID NO:6:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Lys Ala Met Asp Phe Glu Glu Ser Ser Ser Tyr Gln Ile Tyr Val Gln
 1               5                  10                  15
Ala Thr Asp Arg Gly Pro Val Pro Met Ala Gly His Cys Lys Val Leu
                20                  25                  30
```

```
Val Asp Ile Ile Asp Val Asn Asp Asn Ala Pro
            35                  40
```

(2) INFORMATION FOR SEQ ID NO:7:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
AAGCGACTGG ACTTTGAGAC CCTGCAGACC TTCGAGTTCA GCGTGGGTGC CACAGACCAT        60
GGCTCCCCCT CGCTCCGCAG TCAGGCTCTG GTGCGCGTGG TGGTGCTGGA CCACAATGAC       120
AATGCCCCCA A                                                            131
```

(2) INFORMATION FOR SEQ ID NO:8:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Lys Arg Leu Asp Phe Glu Thr Leu Gln Thr Phe Glu Phe Ser Val Gly
 1               5                  10                  15
Ala Thr Asp His Gly Ser Pro Ser Leu Arg Ser Gln Ala Leu Val Arg
            20                  25                  30
Val Val Val Leu Asp His Asn Asp Asn Ala Pro
            35                  40
```

(2) INFORMATION FOR SEQ ID NO:9:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
AAGGGCCTGG ATTACGAGGC ACTGCAGTCC TTCGAGTTCT ACGTGGGCGC TACAGATGGA        60
GGCTCACCCG CGCTCAGCAG CCAGACTCTG GTGCGGATGG TGGTGCTGGA TGACAACGAC       120
AACGCCCCTA A                                                            131
```

(2) INFORMATION FOR SEQ ID NO:10:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

```
Lys Gly Leu Asp Tyr Glu Ala Leu Gln Ser Phe Glu Phe Tyr Val Gly
 1               5                  10                  15
```

Ala Thr Asp Gly Gly Ser Pro Ala Leu Ser Ser Gln Thr Leu Val Arg
                20                      25                      30

Met Val Val Leu Asp Asp Asn Asp Asn Ala Pro
            35                  40

( 2 ) INFORMATION FOR SEQ ID NO:11:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

AAGGCGTTTG ATTTTGAGGA TCAGAGAGAG TTCCAGCTAA CCGCTCATAT AAACGACGGA        60

GGTACCCCGG TTTTGGCCAC CAACATCAGC GTGAACATAT TTGTTACTGA CCGCAATGAC       120

AACGCCCCGC A                                                            131

( 2 ) INFORMATION FOR SEQ ID NO:12:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

Lys Ala Phe Asp Phe Glu Asp Gln Arg Glu Phe Gln Leu Thr Ala His
1               5                   10                      15

Ile Asn Asp Gly Gly Thr Pro Val Leu Ala Thr Asn Ile Ser Val Asn
                20                      25                      30

Ile Phe Val Thr Asp Arg Asn Asp Asn Ala Pro
            35                  40

( 2 ) INFORMATION FOR SEQ ID NO:13:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

AAGGCGGTGG ATTACGAAAT CACCAAGTCC TATGAGATAG ATGTTCAAGC CCAAGATCTG        60

GGTCCCAATT CTATTCCTGC TCATTGCAAA ATTATAATTA AGGTCGTGGA TGTCAACGAC       120

AACGCTCCCA A                                                            131

( 2 ) INFORMATION FOR SEQ ID NO:14:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

Lys Ala Val Asp Tyr Glu Ile Thr Lys Ser Tyr Glu Ile Asp Val Gln

```
           1               5                    10                   15
Ala Gln Asp Leu Gly Pro Asn Ser Ile Pro Ala His Cys Lys Ile Ile
                20                   25                   30

Ile Lys Val Val Asp Val Asn Asp Asn Ala Pro
        35                  40
```

(2) INFORMATION FOR SEQ ID NO:15:

(i) SEQUENCE CHARACTERISTICS:
        (A) LENGTH: 135 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

```
TATGACCATG ATTACGAGAC AACCAAAGAA TATACACTGC GGATCCGGGC CCAGGATGGT      60

GGCCGGACTC CACTTTCCAA CGTCTCCGGT CTAGTAACCG TGCAGGTCCT AGACATCAAC     120

GACAATGCCC CCCCA                                                     135
```

(2) INFORMATION FOR SEQ ID NO:16:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Tyr Asp His Asp Tyr Glu Thr Thr Lys Glu Tyr Thr Leu Arg Ile Arg
1               5                   10                  15

Ala Gln Asp Gly Gly Arg Thr Pro Leu Ser Asn Val Ser Gly Leu Val
                20                  25                  30

Thr Val Gln Val Leu Asp Ile Asn Asp Asn Ala Pro
            35                  40
```

(2) INFORMATION FOR SEQ ID NO:17:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
GGGGGGTCGA TTACGAGGAG AACGGCATGT TAGAGATCGA CGTGCAGGCC AGAGACCTAG      60

GACCTAACCC AATTCCAGCC CATTGCAAGG TCACAGTCAA GCTCATCGAC CGCAATGATA     120

ACGCCCCCA                                                             129
```

(2) INFORMATION FOR SEQ ID NO:18:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

Arg Gly Val Asp Tyr Glu Glu Asn Gly Met Leu Glu Ile Asp Val Gln
1               5                       10                      15

Ala Arg Asp Leu Gly Pro Asn Pro Ile Pro Ala His Cys Lys Val Thr
                20              25                  30

Val Lys Leu Ile Asp Arg Asn Asp Asn Ala Pro
            35              40

(2) INFORMATION FOR SEQ ID NO:19:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

AAGGGGTTGG ACTACGAAGA CACCAAACTC CATGAGATTT ACATCCAGGC CAAAGACAAA 60

GGTGCCAATC CGGAAGGAGC GCATTGCAAA GTACTGGTAG AGGTTGTGGA CGTTAACGAC 120

AATGCCCCTC A 131

(2) INFORMATION FOR SEQ ID NO:20:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Lys Gly Leu Asp Tyr Glu Asp Thr Lys Leu His Glu Ile Tyr Ile Gln
1               5                       10                      15

Ala Lys Asp Lys Gly Ala Asn Pro Glu Gly Ala His Cys Lys Val Leu
                20              25                  30

Val Glu Val Val Asp Val Asn Asp Asn Ala Pro
            35              40

(2) INFORMATION FOR SEQ ID NO:21:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

AAGGGTTTGG ACTTTGAGCA AGTAGATGTC TACAAAATCC GCGTTGACGC GACGGACAAA 60

GGACACCCTC CGATGGCAGG CCATTGCACT GTTTTAGTGA GGGTATTGGA TGAAAACGAC 120

AATGCGCCTC T 131

(2) INFORMATION FOR SEQ ID NO:22:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein ( x i ) SEQUENCE DESCRIPTION: SEQ ID NO:22:

| Lys | Gly | Leu | Asp | Phe | Glu | Gln | Val | Asp | Val | Tyr | Lys | Ile | Arg | Val | Asp |
|---|---|---|---|---|---|---|---|---|---|---|---|---|---|---|---|
| 1 | | | | 5 | | | | | 10 | | | | | 15 | |

| Ala | Thr | Asp | Lys | Gly | His | Pro | Pro | Met | Ala | Gly | His | Cys | Thr | Val | Leu |
|---|---|---|---|---|---|---|---|---|---|---|---|---|---|---|---|
| | | | 20 | | | | | 25 | | | | | 30 | | |

| Val | Arg | Val | Leu | Asp | Glu | Asn | Asp | Asn | Ala | Pro |
|---|---|---|---|---|---|---|---|---|---|---|
| | | 35 | | | | 40 | | | | |

( 2 ) INFORMATION FOR SEQ ID NO:23:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
AAGGGTATAG ACTTCGAGCA GATCAAGGAC TTCAGCTTTC AAGTGGAAGC CCGGGACGCC      60
GGCAGTCCCC AGGCGCTGTC CGGCAACTGC ACTGTCAACA TCTTGATAGT GGATCAGAAC     120
GACAACGCCC CTAA                                                       134
```

( 2 ) INFORMATION FOR SEQ ID NO:24:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

| Lys | Gly | Ile | Asp | Phe | Glu | Gln | Ile | Lys | Asp | Phe | Ser | Phe | Gln | Val | Glu |
|---|---|---|---|---|---|---|---|---|---|---|---|---|---|---|---|
| 1 | | | | 5 | | | | | 10 | | | | | 15 | |

| Ala | Arg | Asp | Ala | Gly | Ser | Pro | Gln | Ala | Leu | Ala | Gly | Asn | Thr | Thr | Val |
|---|---|---|---|---|---|---|---|---|---|---|---|---|---|---|---|
| | | | 20 | | | | | 25 | | | | | 30 | | |

| Asn | Ile | Leu | Ile | Val | Asp | Gln | Asn | Asp | Asn | Ala | Pro |
|---|---|---|---|---|---|---|---|---|---|---|---|
| | | | 35 | | | | 40 | | | | |

( 2 ) INFORMATION FOR SEQ ID NO:25:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
AAGCCGTTCG ACTATGAGCA AACCGCCAAC ACGCTGGCAC AGATTGACGC CGTGCTGGAA      60
AAACAGGGCA GCAATAAATC GAGCATTCTG GATGCCACCA TTTTCCTGGC CGATAAAAAC     120
GACAATGCGC CAGA                                                       134
```

( 2 ) INFORMATION FOR SEQ ID NO:26:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:26:

| Lys | Pro | Phe | Asp | Tyr | Glu | Gln | Thr | Ala | Asn | Thr | Leu | Ala | Gln | Ile | Asp |
|---|---|---|---|---|---|---|---|---|---|---|---|---|---|---|---|
| 1 |  |  |  | 5 |  |  |  |  | 10 |  |  |  |  | 15 |  |

| Ala | Val | Leu | Glu | Lys | Gln | Gly | Ser | Asn | Lys | Ser | Ser | Ile | Leu | Asp | Ala |
|---|---|---|---|---|---|---|---|---|---|---|---|---|---|---|---|
|  |  |  | 20 |  |  |  |  | 25 |  |  |  |  | 30 |  |  |

| Thr | Ile | Phe | Leu | Ala | Asp | Lys | Asn | Asp | Asn | Ala | Pro |
|---|---|---|---|---|---|---|---|---|---|---|---|
|  |  | 35 |  |  |  |  | 40 |  |  |  |  |

( 2 ) INFORMATION FOR SEQ ID NO:27:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

```
AAGCGGCTGG ATTTCGAACA GTTCCAGCAG CACAAGCTGC TCGTAAGGGC TGTTGATGGA      60
GGAATGCCGC CACTGAGCAG CGATGTGGTC GTCACTGTGG ATGTCACCGA CCTCAACGAT     120
AACGCGCCCT A                                                          131
```

( 2 ) INFORMATION FOR SEQ ID NO:28:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:28:

| Lys | Arg | Leu | Asp | Phe | Glu | Gln | Phe | Gln | Gln | His | Lys | Leu | Leu | Val | Arg |
|---|---|---|---|---|---|---|---|---|---|---|---|---|---|---|---|
| 1 |  |  |  | 5 |  |  |  |  | 10 |  |  |  |  | 15 |  |

| Ala | Val | Asp | Gly | Gly | Met | Pro | Pro | Leu | Ser | Ser | Asp | Val | Val | Val | Thr |
|---|---|---|---|---|---|---|---|---|---|---|---|---|---|---|---|
|  |  |  | 20 |  |  |  |  | 25 |  |  |  |  | 30 |  |  |

| Val | Asp | Val | Thr | Asp | Leu | Asn | Asp | Asn | Ala | Pro |
|---|---|---|---|---|---|---|---|---|---|---|
|  |  |  | 35 |  |  |  |  | 40 |  |  |

( 2 ) INFORMATION FOR SEQ ID NO:29:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

```
AAGGGGATAG ACTTTGAGAG TGAGAATTAC TATGAATTTG ATGTGCGGGC TCGCGATGGG      60
GGTTCTCCAG CCATGGAGCA ACATTGCAGC CTTCGAGTGG ATCTGCTGGA CGTAAATGAC     120
AACGCCCCAC T                                                          131
```

( 2 ) INFORMATION FOR SEQ ID NO:30:

( i ) SEQUENCE CHARACTERISTICS:
        ( A ) LENGTH: 43 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:30:

| Lys | Gly | Ile | Asp | Phe | Glu | Ser | Glu | Asn | Tyr | Tyr | Glu | Phe | Asp | Val | Arg |
|---|---|---|---|---|---|---|---|---|---|---|---|---|---|---|---|
| 1 | | | | 5 | | | | | 10 | | | | | 15 | |

| Ala | Arg | Asp | Gly | Gly | Ser | Pro | Ala | Met | Glu | Gln | His | Cys | Ser | Leu | Arg |
|---|---|---|---|---|---|---|---|---|---|---|---|---|---|---|---|
| | | | 20 | | | | | 25 | | | | | 30 | | |

| Val | Asp | Leu | Leu | Asp | Val | Asn | Asp | Asn | Ala | Pro |
|---|---|---|---|---|---|---|---|---|---|---|
| | | 35 | | | | 40 | | | | |

(2) INFORMATION FOR SEQ ID NO:31:

(i) SEQUENCE CHARACTERISTICS:
(A) LENGTH: 131 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:31:

```
AAGGCATTGG ACTTTGAGGC CCGGCGACTG TATTCGCTGA CAGTTCAGGC CACGGACCGA      60
GGCGTGCCCT CGCTCACCGG GCGTGCCGAA GCGCTTATCC AGCTGCTAGA TGTCAACGAC     120
AACGCACCCA T                                                          131
```

(2) INFORMATION FOR SEQ ID NO:32:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:32:

| Lys | Ala | Leu | Asp | Phe | Glu | Ala | Arg | Arg | Leu | Tyr | Ser | Leu | Thr | Val | Gln |
|---|---|---|---|---|---|---|---|---|---|---|---|---|---|---|---|
| 1 | | | | 5 | | | | | 10 | | | | | 15 | |

| Ala | Thr | Asp | Arg | Gly | Val | Pro | Ser | Leu | Thr | Gly | Arg | Ala | Glu | Ala | Leu |
|---|---|---|---|---|---|---|---|---|---|---|---|---|---|---|---|
| | | | 20 | | | | | 25 | | | | | 30 | | |

| Ile | Gln | Leu | Leu | Asp | Val | Asn | Asp | Asn | Ala | Pro |
|---|---|---|---|---|---|---|---|---|---|---|
| | | 35 | | | | 40 | | | | |

(2) INFORMATION FOR SEQ ID NO:33:

(i) SEQUENCE CHARACTERISTICS:
(A) LENGTH: 125 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:33:

```
AAGCCAATTG ATTACGAGGC AACTCCATAC TATAACATGG AAATTGTAGC CACAGACAGC      60
GGAGGTCTTT CGGGAAAATG CACTGTGTCT ATACAGGTGG TGGATGTGAA CGACAACGCC     120
CCCAA                                                                 125
```

(2) INFORMATION FOR SEQ ID NO:34:

(i) SEQUENCE CHARACTERISTICS:

(A) LENGTH: 41 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:34:

| Lys | Pro | Ile | Asp | Tyr | Glu | Ala | Thr | Pro | Tyr | Tyr | Asn | Met | Glu | Ile | Val |
|---|---|---|---|---|---|---|---|---|---|---|---|---|---|---|---|
| 1 | | | | 5 | | | | | 10 | | | | | 15 | |

| Ala | Thr | Asp | Ser | Gly | Gly | Leu | Ser | Gly | Lys | Cys | Thr | Val | Ser | Ile | Gln |
|---|---|---|---|---|---|---|---|---|---|---|---|---|---|---|---|
| | | | 20 | | | | | 25 | | | | | 30 | | |

| Val | Val | Asp | Val | Asn | Asp | Asn | Ala | Pro |
|---|---|---|---|---|---|---|---|---|
| | | | 35 | | | | 40 | |

(2) INFORMATION FOR SEQ ID NO:35:

(i) SEQUENCE CHARACTERISTICS:
(A) LENGTH: 446 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:35:

```
AAGCGGGTAG ACTTCGAAAT GTGCAAAAGA TTTTACCTTG TGGTGGAAGC TAAAGACGGA      60
GGCACCCCAG CCCTCAGCAC GGCAGCCACT GTCAGCATCG ACCTCACAGA TGTGAATGAT     120
AACCCTCCTC GGTTCAGCCA AGATGTCTAC AGTGCTGTCA TCAGTGAGGA TGCCTTAGAG     180
GGGGACTCTG TCATTCTGCT GATAGCAGAA GATGTGGATA GCAAGCCTAA TGGACAGATT     240
CGGTTTTCCA TCGTGGGTGG AGATAGGGAC AATGAATTTG CTGTCGATCC AATCTTGGGA     300
CTTGTGAAAG TTAAGAAGAA ACTGGACCGG GAGCGGGTGT CAGGATACTC CCTGCTCATC     360
CAGGCAGTAG ATAGTGGCAT TCCTGCAATG TCCTCAACGA CAACTGTCAA CATTGATATT     420
TCTGATGTGA ACGACAACGC CCCCCT                                          446
```

(2) INFORMATION FOR SEQ ID NO:36:

(i) SEQUENCE CHARACTERISTICS:
(A) LENGTH: 148 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:36:

| Lys | Arg | Val | Asp | Phe | Glu | Met | Cys | Lys | Arg | Phe | Tyr | Leu | Val | Val | Glu |
|---|---|---|---|---|---|---|---|---|---|---|---|---|---|---|---|
| 1 | | | | 5 | | | | | 10 | | | | | 15 | |

| Ala | Lys | Asp | Gly | Gly | Thr | Pro | Ala | Leu | Ser | Thr | Ala | Ala | Thr | Val | Ser |
|---|---|---|---|---|---|---|---|---|---|---|---|---|---|---|---|
| | | | 20 | | | | | 25 | | | | | 30 | | |

| Ile | Asp | Leu | Thr | Asp | Val | Asn | Asp | Asn | Pro | Pro | Arg | Phe | Ser | Gln | Asp |
|---|---|---|---|---|---|---|---|---|---|---|---|---|---|---|---|
| | | | 35 | | | | | 40 | | | | | 45 | | |

| Val | Tyr | Asp | Ala | Val | Ile | Ser | Glu | Asp | Ala | Leu | Glu | Gly | Asp | Ser | Val |
|---|---|---|---|---|---|---|---|---|---|---|---|---|---|---|---|
| | | 50 | | | | | 55 | | | | | 60 | | | |

| Ile | Leu | Leu | Ile | Ala | Glu | Asp | Val | Asp | Ser | Lys | Pro | Asn | Gly | Gln | Ile |
|---|---|---|---|---|---|---|---|---|---|---|---|---|---|---|---|
| 65 | | | | | 70 | | | | | 75 | | | | | 80 |

| Arg | Phe | Ser | Ile | Val | Gly | Gly | Asp | Arg | Asp | Asn | Glu | Phe | Ala | Val | Asp |
|---|---|---|---|---|---|---|---|---|---|---|---|---|---|---|---|
| | | | | 85 | | | | | 90 | | | | | 95 | |

| Pro | Ile | Leu | Gly | Leu | Val | Lys | Val | Lys | Lys | Lys | Leu | Asp | Arg | Glu | Arg |
|---|---|---|---|---|---|---|---|---|---|---|---|---|---|---|---|
| | | | 100 | | | | | 105 | | | | | 110 | | |

```
Val  Ser  Gly  Tyr  Ser  Leu  Leu  Ile  Gln  Ala  Val  Asp  Ser  Gly  Ile  Pro
          115                 120                           125

Ala  Met  Ser  Ser  Thr  Thr  Thr  Val  Asn  Ile  Asp  Ile  Ser  Asp  Val  Asn
     130                 135                 140

Asp  Asn  Ala  Pro
145
```

( 2 ) INFORMATION FOR SEQ ID NO:37:

( i ) SEQUENCE CHARACTERISTICS:
        ( A ) LENGTH: 440 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

```
AAGGGGGTTG  ATTATGAGAC  AAACCCACGG  CTACGACTGG  TGCTACAGGC  AGAGAGTGGA        60
GGAGCCTTTG  CTTTCTCGGT  GCTGACCCTG  ACCCTTCAAG  ATGCCAATGA  CAATGCTCCC       120
CGTTTCCTGC  AGCCTCACTA  CGTGGCTTTC  CTGCCAGAGT  CCCGACCCTT  GGAAGGGCCC       180
CTGCTGCAGG  TGGAAGCAGA  CGACCTGGAT  CAAGGCTCTG  GAGGACAGAT  CTCCTACAGT       240
CTGGCTGCAT  CCCAGCCAGC  ACGGGGCTTG  TTCCATGTAG  ACCCAGCCAC  AGGCACTATC       300
ACTACCACAG  CCATCCTGGA  CCGGGAAATC  TGGGCTGAAA  CACGGCTGGT  ACTGATGGCC       360
ACAGACAGAG  GAAGCCCAGC  ATTGGTGGGC  TCAGCTACCC  TGACAGTGAT  GGTCATCGAT       420
ACCAACGACA  ATGCTCCCCT                                                      440
```

( 2 ) INFORMATION FOR SEQ ID NO:38:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:38:

```
Lys  Gly  Val  Asp  Tyr  Glu  Thr  Asn  Pro  Arg  Leu  Arg  Leu  Val  Leu  Gln
1                   5                        10                      15

Ala  Glu  Ser  Gly  Gly  Ala  Phe  Ala  Phe  Ser  Val  Leu  Thr  Leu  Thr  Leu
               20                 25                           30

Gln  Asp  Ala  Asn  Asp  Asn  Ala  Pro  Arg  Phe  Leu  Gln  Pro  His  Tyr  Val
          35                      40                      45

Ala  Phe  Leu  Pro  Glu  Ser  Arg  Pro  Leu  Glu  Gly  Pro  Leu  Leu  Gln  Val
     50                      55                      60

Glu  Ala  Asn  Asp  Leu  Asp  Gln  Gly  Ser  Gly  Gln  Ile  Ser  Tyr  Ser
65                       70                      75                      80

Leu  Ala  Ala  Ser  Gln  Pro  Ala  Arg  Gly  Leu  Phe  His  Val  Asp  Pro  Ala
               85                      90                      95

Thr  Gly  Thr  Ile  Thr  Thr  Thr  Ala  Ile  Leu  Asp  Arg  Glu  Ile  Trp  Ala
               100                     105                     110

Glu  Thr  Arg  Leu  Val  Leu  Met  Ala  Thr  Asp  Arg  Gly  Ser  Pro  Ala  Leu
          115                     120                     125

Val  Gly  Ser  Ala  Thr  Leu  Thr  Val  Met  Val  Ile  Asp  Thr  Asn  Asp  Asn
     130                     135                     140

Ala  Pro
```

( 2 ) INFORMATION FOR SEQ ID NO:39:

( i ) SEQUENCE CHARACTERISTICS:
        ( A ) LENGTH: 124 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

```
AAGGTCTCGA TTATGAGGCA ACTCCATATT ATAACGTGGA AATTGTAGCC ACAGATGGTG      60
GGGGCCTTTC AGGAAAATGC ACTGTGGCTA TAGAAGTGGT GGATGTGAAC GACGGCGCTC     120
CAAT                                                                  124
```

( 2 ) INFORMATION FOR SEQ ID NO:40:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

```
Lys Gly Leu Asp Tyr Glu Ala Thr Pro Tyr Tyr Asn Val Glu Ile Val
 1               5                  10                  15
Ala Thr Asp Gly Gly Ala Phe Asp Glu Asn Cys Thr Val Ala Ile Glu
                20                  25                  30
Val Val Asp Val Asn Asp Asn Ala Pro
                35                  40
```

( 2 ) INFORMATION FOR SEQ ID NO:41:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:41:

```
Asp Xaa Asn Glu Xaa Pro Xaa Phe
 1               5
```

( 2 ) INFORMATION FOR SEQ ID NO:42:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA ( x i ) SEQUENCE DESCRIPTION: SEQ ID NO:42:

```
Asp Xaa Asp Glu Xaa Pro Xaa Phe
 1               5
```

( 2 ) INFORMATION FOR SEQ ID NO:43:

( i ) SEQUENCE CHARACTERISTICS:
        ( A ) LENGTH: 9 amino acids ( B ) TYPE: amino acid
( C ) STRANDEDNESS: single
( D ) TOPOLOGY: linear ( i i ) MOLECULE TYPE: DNA ( x i ) SEQUENCE DESCRIPTION: SEQ ID NO:43:

```
Asp  Xaa  Asn  Asp  Asn  Xaa  Pro  Xaa  Phe
1                 5
```

( 2 ) INFORMATION FOR SEQ ID NO:44:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

```
AAGCGGATGG ATTTTGAAGA CACCAAACTC CATGAGATTT ACATCCAGGC CAAAGACAAA      60
GGTGCCAATC CCGAAGGAGC GCATTGCAAA GTACTTGTAG AGGTTGTAGA CGTAAACGAC     120
AACGCCCCAG T                                                          131
```

( 2 ) INFORMATION FOR SEQ ID NO:45:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:45:

```
Leu  Arg  Met  Asp  Phe  Glu  Asp  Thr  Lys  Leu  His  Glu  Ile  Tyr  Ile  Gln
1                   5                  10                             15

Ala  Lys  Asp  Lys  Gly  Ala  Asn  Pro  Glu  Gly  Ala  His  Cys  Lys  Val  Leu
                    20                  25                       30

Val  Glu  Val  Val  Asp  Val  Asn  Asp  Asn  Ala  Pro
                    35                  40
```

( 2 ) INFORMATION FOR SEQ ID NO:46:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

```
AAGGCTTTGG ATTACGAGGA TCAGAGAGAG TTCCAACTAA CAGCTCATAT AAACGACGGA      60
GGTACCCCAG TCTTAGCCAC CAACATCAGC GTGAACGTAT TTGTTACTGA CCGCAATGAT     120
AACGCCCCCT A                                                          131
```

( 2 ) INFORMATION FOR SEQ ID NO:47:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear (ii) MOLECULE TYPE: protein (xi) SEQUENCE DESCRIPTION: SEQ ID NO:47:

| Lys | Ala | Leu | Asp | Tyr | Glu | Asp | Gln | Arg | Glu | Phe | Gln | Leu | Thr | Ala | His |
|---|---|---|---|---|---|---|---|---|---|---|---|---|---|---|---|
| 1 | | | | 5 | | | | | 10 | | | | | 15 | |

| Ile | Asn | Asp | Gly | Gly | Thr | Pro | Val | Leu | Ala | Thr | Asn | Ile | Ser | Val | Asn |
|---|---|---|---|---|---|---|---|---|---|---|---|---|---|---|---|
| | | | 20 | | | | | 25 | | | | | 30 | | |

| Val | Phe | Val | Thr | Asp | Arg | Asn | Asp | Asn | Ala | Pro |
|---|---|---|---|---|---|---|---|---|---|---|
| | | 35 | | | | | 40 | | | |

(2) INFORMATION FOR SEQ ID NO:48:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

```
AAGCGCTTGG ACTACGAGGA GAGTAACAAT TATGAAATTC ACGTGGATGC TACAGATAAA      60
GGATACCCAC CTATGGTTGC TCACTGCACC GTACTCGTGG GAATCTTGGA TGAAAATGAC     120
AACGCACCCA T                                                          131
```

(2) INFORMATION FOR SEQ ID NO:49:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

| Lys | Arg | Leu | Asp | Tyr | Glu | Glu | Ser | Asn | Asn | Tyr | Glu | Ile | His | Val | Asp |
|---|---|---|---|---|---|---|---|---|---|---|---|---|---|---|---|
| 1 | | | | 5 | | | | | 10 | | | | | 15 | |

| Ala | Thr | Asp | Lys | Gly | Tyr | Pro | Pro | Met | Val | Ala | His | Cys | Thr | Val | Leu |
|---|---|---|---|---|---|---|---|---|---|---|---|---|---|---|---|
| | | | 20 | | | | | 25 | | | | | 30 | | |

| Val | Gly | Ile | Leu | Asp | Glu | Asn | Asp | Asn | Ala | Pro |
|---|---|---|---|---|---|---|---|---|---|---|
| | | | 35 | | | | | 40 | | |

(2) INFORMATION FOR SEQ ID NO:50:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

```
AAACCGGTGG ACTACGAGAA AGTCAAAGAC TATACCATCG AGATCGTGGC TGTGGATTCC      60
GGCAACCCTC CACTCTCTAG CACCAACTCC CTCAAGGTGC AGGTGGTAGA CGTCAACGAT     120
AACGCCCCTC T                                                          131
```

(2) INFORMATION FOR SEQ ID NO:51:

(i) SEQUENCE CHARACTERISTICS:
        (A) LENGTH: 43 amino acids
        (B) TYPE: amino acid
        (C) STRANDEDNESS: single (D) TOPOLOGY: linear (i i) MOLECULE TYPE: protein (x i) SEQUENCE DESCRIPTION: SEQ ID NO:51:

| Lys | Pro | Val | Asp | Tyr | Glu | Lys | Val | Lys | Asp | Tyr | Thr | Ile | Glu | Ile | Val |
|---|---|---|---|---|---|---|---|---|---|---|---|---|---|---|---|
| 1 | | | | 5 | | | | | 10 | | | | | 15 | |

| Ala | Val | Asp | Ser | Gly | Asn | Pro | Pro | Leu | Ser | Ser | Thr | Asn | Ser | Leu | Lys |
|---|---|---|---|---|---|---|---|---|---|---|---|---|---|---|---|
| | | | 20 | | | | | 25 | | | | | 30 | | |

| Val | Gln | Val | Val | Asp | Val | Asn | Asp | Asn | Ala | Pro |
|---|---|---|---|---|---|---|---|---|---|---|
| | | 35 | | | | | 40 | | | |

(2) INFORMATION FOR SEQ ID NO:52:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:52:

```
AAGCCTTTTG ATTTCGAGGA CACCAAACTC CATGAGATTT ACATCCAGGC CAAAGACAAG        60
GGCGCCAATC CCGAAGGAGC ACATTGCAAA GTGTTGGTGG AGGTTGTGGA TGTGAACGAC       120
AATGCCCCTC A                                                           131
```

(2) INFORMATION FOR SEQ ID NO:53:

(i) SEQUENCE CHARACTERISTICS:
        (A) LENGTH: 43 amino acids
        (B) TYPE: amino acid
        (C) STRANDEDNESS: single
        (D) TOPOLOGY: linear (i i) MOLECULE TYPE: protein (x i) SEQUENCE DESCRIPTION: SEQ ID NO:53:

| Lys | Pro | Phe | Asp | Phe | Glu | Asp | Thr | Lys | Leu | His | Glu | Ile | Tyr | Ile | Gln |
|---|---|---|---|---|---|---|---|---|---|---|---|---|---|---|---|
| 1 | | | | 5 | | | | | 10 | | | | | 15 | |

| Ala | Lys | Asp | Lys | Gly | Ala | Asn | Pro | Glu | Gly | Ala | His | Cys | Lys | Val | Leu |
|---|---|---|---|---|---|---|---|---|---|---|---|---|---|---|---|
| | | | 20 | | | | | 25 | | | | | 30 | | |

| Val | Glu | Val | Val | Asp | Val | Asn | Asp | Asn | Ala | Pro |
|---|---|---|---|---|---|---|---|---|---|---|
| | | 35 | | | | | 40 | | | |

(2) INFORMATION FOR SEQ ID NO:54:

(i) SEQUENCE CHARACTERISTICS:
        (A) LENGTH: 122 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:54:

```
AAAGGTGTCG ATTACGAGGT GAGTCCACGG CTGCGACTGG TGCTGCAGGC AGAGAGTCGA        60
GGAGCCTTTG CCTTCACTGT GCTGACCCTG ACCCTGCAAG ATGCCAACGA CAACGCCCCG       120
AG                                                                     122
```

(2) INFORMATION FOR SEQ ID NO:55:

(i) SEQUENCE CHARACTERISTICS:
        (A) LENGTH: 40 amino acids ( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:55:

| Lys | Gly | Val | Asp | Tyr | Glu | Val | Ser | Pro | Arg | Leu | Arg | Leu | Val | Leu | Gln |
|---|---|---|---|---|---|---|---|---|---|---|---|---|---|---|---|
| 1 | | | | 5 | | | | | 10 | | | | | 15 | |
| Ala | Glu | Ser | Arg | Gly | Ala | Phe | Ala | Phe | Thr | Val | Leu | Thr | Leu | Thr | Leu |
| | | | 20 | | | | | 25 | | | | | 30 | | |
| Gln | Asp | Ala | Asn | Asp | Asn | Ala | Pro | | | | | | | | |
| | | | 35 | | | | 40 | | | | | | | | |

( 2 ) INFORMATION FOR SEQ ID NO:56:

( i ) SEQUENCE CHARACTERISTICS:
( A ) LENGTH: 131 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:56:

```
AAAGGGATTG  ATTACGAGCA  GTTGAGAGAC  CTACAGCTGT  GGGTGACAGC  CAGCGACAGC        60
GGGGACCCGC  CTCTTAGCAG  CAACGTGTCA  CTGAGCCTGT  TTGTGCTGGA  CCAGAACGAC       120
AACGCCCCCC  T                                                                131
```

( 2 ) INFORMATION FOR SEQ ID NO:57:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:57:

| Lys | Gly | Ile | Asp | Tyr | Glu | Gln | Leu | Arg | Asp | Leu | Gln | Leu | Trp | Val | Thr |
|---|---|---|---|---|---|---|---|---|---|---|---|---|---|---|---|
| 1 | | | | 5 | | | | | 10 | | | | | 15 | |
| Ala | Ser | Asp | Ser | Gly | Asp | Pro | Pro | Leu | Ser | Ser | Asn | Val | Ser | Leu | Ser |
| | | | 20 | | | | | 25 | | | | | 30 | | |
| Leu | Phe | Val | Leu | Asp | Gln | Asn | Asp | Asn | Ala | Pro | | | | | |
| | | | 35 | | | | 40 | | | | | | | | |

( 2 ) INFORMATION FOR SEQ ID NO:58:

( i ) SEQUENCE CHARACTERISTICS:
( A ) LENGTH: 125 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:58:

```
AAGGCGGTCG  ATTTTGAGCG  CACATCCTCT  TATCAACTCA  TCATTCAGGC  CACCAATATG        60
GCAGGAATGG  CTTCCAATGC  TACAGTCAAT  ATTCAGATTG  TTGATGAAAA  CGACAACGCC       120
CCCCA                                                                        125
```

( 2 ) INFORMATION FOR SEQ ID NO:59:

( i ) SEQUENCE CHARACTERISTICS:
   ( A ) LENGTH: 41 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:59:

| Lys | Ala | Val | Asp | Phe | Glu | Arg | Thr | Ser | Ser | Tyr | Gln | Leu | Ile | Ile | Gln |
|---|---|---|---|---|---|---|---|---|---|---|---|---|---|---|---|
| 1 | | | | 5 | | | | | 10 | | | | | 15 | |

| Ala | Thr | Asn | Met | Ala | Gly | Met | Ala | Ser | Asn | Ala | Thr | Val | Asn | Ile | Gln |
|---|---|---|---|---|---|---|---|---|---|---|---|---|---|---|---|
| | | | 20 | | | | | 25 | | | | | 30 | | |

| Ile | Val | Asp | Glu | Asn | Asp | Asn | Ala | Pro |
|---|---|---|---|---|---|---|---|---|
| | | 35 | | | | | 40 | |

( 2 ) INFORMATION FOR SEQ ID NO:60:

( i ) SEQUENCE CHARACTERISTICS:
      ( A ) LENGTH: 131 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:60:

| AAACGGCTAG | ACTTTGAAAA | GATACAAAAA | TATGTTGTAT | GGATAGAGGC | CAGAGATGGT | 60 |
| GGTTTCCCTC | CTTTCTCCTC | TTACGAGAAA | CTTGATATAA | CAGTATTAGA | TGTCAACGAT | 120 |
| AACGCGCCTA | A | | | | | 131 |

( 2 ) INFORMATION FOR SEQ ID NO:61:

( i ) SEQUENCE CHARACTERISTICS:
      ( A ) LENGTH: 43 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:61:

| Lys | Arg | Leu | Asp | Phe | Glu | Lys | Ile | Gln | Lys | Tyr | Val | Val | Trp | Ile | Glu |
|---|---|---|---|---|---|---|---|---|---|---|---|---|---|---|---|
| 1 | | | | 5 | | | | | 10 | | | | | 15 | |

| Ala | Arg | Asp | Gly | Gly | Phe | Pro | Pro | Phe | Ser | Ser | Tyr | Glu | Lys | Leu | Asp |
|---|---|---|---|---|---|---|---|---|---|---|---|---|---|---|---|
| | | | 20 | | | | | 25 | | | | | 30 | | |

| Ile | Thr | Val | Leu | Asp | Val | Asn | Asp | Asn | Ala | Pro |
|---|---|---|---|---|---|---|---|---|---|---|
| | | | 35 | | | | | 40 | | |

( 2 ) INFORMATION FOR SEQ ID NO:62:

( i ) SEQUENCE CHARACTERISTICS:
      ( A ) LENGTH: 131 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:62:

| AAGGGGATCG | ATTATGAGAA | GGTCAAAGAC | TACACCATTG | AGATTGTGGC | TGTGGACTCT | 60 |
| GGCAACCCCC | CACTCTCCAG | CACTAACTCC | CTCAAGGTGC | AGGTGGTGGA | CGTCAATGAC | 120 |
| AACGCACCGT | G | | | | | 131 |

(2) INFORMATION FOR SEQ ID NO:63:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:63:

```
Lys Gly Ile Asp Tyr Glu Lys Val Lys Asp Tyr Thr Ile Glu Ile Val
 1               5                  10                  15
Ala Val Asp Ser Gly Asn Pro Pro Leu Ser Ser Thr Asn Ser Leu Lys
                20                  25                  30
Val Gln Val Val Asp Val Asn Asp Asn Ala Pro
                35                  40
```

(2) INFORMATION FOR SEQ ID NO:64:

(i) SEQUENCE CHARACTERISTICS:
(A) LENGTH: 131 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:64:

```
AAGGGACTCG ACTACGAGGA TCGGCGGGAA TTTGAATTAA CAGCTCATAT CAGCGATGGG      60
GGCACCCCGG TCCTAGCCAC CAACATCAGC GTGAACATAT TTGTCACTGA TCGCAACGAT     120
AATGCCCCCG T                                                          131
```

(2) INFORMATION FOR SEQ ID NO:65:

(i) SEQUENCE CHARACTERISTICS:
(A) LENGTH: 43 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:65:

```
Lys Gly Leu Asp Tyr Glu Asp Arg Arg Glu Phe Glu Leu Thr Ala His
 1               5                  10                  15
Ile Ser Asp Gly Gly Thr Pro Val Leu Ala Thr Asn Ile Ser Val Asn
                20                  25                  30
Ile Phe Val Thr Asp Arg Asn Asp Asn Ala Pro
                35                  40
```

(2) INFORMATION FOR SEQ ID NO:66:

(i) SEQUENCE CHARACTERISTICS:
(A) LENGTH: 470 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:66:

```
AAGGGTTTGG ACTACGAGAC CACACAGGCC TACCAGCTCA CGGTCAACGC CACAGATCAA      60
GACAACACCA GGCCTCTGTC CACCCTGGCC AACTTGGCCA TCATCATCAC AGATGTCCAG     120
GACATGGACC CCATCTTCAT CAACCTGCCT TACAGCACCA ACATCTACGA GCATTCTCCT     180
```

```
CCGGGCACGA  CGGTGCGCAT  CATCACCGCC  ATAGACCAGG  ATCAAGGACG  TCCCCGGGGC    240

ATTGGCTACA  CCATCGTTTC  AGGGAATACC  AACAGCATCT  TTGCCCTGGA  CTACATCAGC    300

GGAGTGCTGA  CCTTGAATGG  CCTGCTGGAC  CGGGAGAACC  CCCTGTACAG  CCATGGCTTC    360

ATCCTGACTG  TGAAGGGCAC  GGAGCTGAAC  GATGACCGCA  CCCCATCTGA  CGCTACAGTC    420

ACCACGACCT  TCAATATCCT  GGTTATTGAC  ATCAACGACA  ACGCCCACT                 470
```

( 2 ) INFORMATION FOR SEQ ID NO:67:

( i ) SEQUENCE CHARACTERISTICS:
        ( A ) LENGTH: 156 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:67:

```
Lys  Gly  Leu  Asp  Tyr  Glu  Thr  Thr  Gln  Ala  Tyr  Gln  Leu  Thr  Val  Asn
1              5                        10                       15

Ala  Thr  Asp  Gln  Asp  Asn  Thr  Arg  Pro  Leu  Ser  Thr  Leu  Ala  Asn  Leu
              20                       25                       30

Ala  Ile  Ile  Ile  Thr  Asp  Val  Gln  Asp  Met  Asp  Pro  Ile  Phe  Ile  Asn
         35                       40                       45

Leu  Pro  Tyr  Ser  Thr  Asn  Ile  Tyr  Glu  His  Ser  Pro  Pro  Gly  Thr  Thr
    50                       55                       60

Val  Arg  Ile  Ile  Thr  Ala  Ile  Asp  Gln  Asp  Gln  Gly  Arg  Pro  Arg  Gly
65                       70                       75                       80

Ile  Gly  Tyr  Thr  Ile  Val  Ser  Gly  Asn  Thr  Asn  Ser  Ile  Phe  Ala  Leu
              85                       90                       95

Asp  Tyr  Ile  Ser  Gly  Val  Leu  Thr  Leu  Asn  Gly  Leu  Leu  Asp  Arg  Glu
              100                      105                      110

Asn  Pro  Leu  Tyr  Ser  Gly  Gly  Phe  Ile  Leu  Thr  Val  Lys  Gly  Thr  Glu
         115                      120                      125

Leu  Asn  Asp  Asp  Arg  Thr  Pro  Ser  Asp  Ala  Thr  Val  Thr  Thr  Thr  Phe
    130                      135                      140

Asn  Ile  Leu  Val  Ile  Asp  Ile  Asn  Asp  Asn  Ala  Pro
145                      150                      155
```

( 2 ) INFORMATION FOR SEQ ID NO:68:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:68:

```
AAGGGGGTCG  ATTACGAGGT  ACTACAGGCC  TTTGAGTTCC  ACGTGAGCGC  CACAGACCGA    60

GGCTCACCGG  GGCTCAGCAG  CCAGGCTCTG  GTGCGCGTGG  TGGTGCTGGA  CGACAATGAC   120

AACGCTCCCG  T                                                           131
```

( 2 ) INFORMATION FOR SEQ ID NO:69:

( i ) SEQUENCE CHARACTERISTICS:
        ( A ) LENGTH: 43 amino acids
        ( B ) TYPE: amino acid
        ( C ) STRANDEDNESS: single (D) TOPOLOGY: linear (ii) MOLECULE TYPE: protein (xi) SEQUENCE DESCRIPTION: SEQ ID NO:69:

| Lys | Gly | Val | Asp | Tyr | Glu | Val | Leu | Gln | Ala | Phe | Glu | Phe | His | Val | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Thr | Asp | Arg | Gly | Ser | Pro | Gly | Leu | Ser | Ser | Gln | Ala | Leu | Val | Arg |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Val | Val | Val | Leu | Asp | Asp | Asn | Asp | Asn | Ala | Pro |
|-----|-----|-----|-----|-----|-----|-----|-----|-----|-----|-----|
|     |     | 35  |     |     |     | 40  |     |     |     |     |

(2) INFORMATION FOR SEQ ID NO:70:

(i) SEQUENCE CHARACTERISTICS:
    (A) LENGTH: 131 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:70:

| AAGGGGCTGG | ATTATGAGCA | GTTCCAGACC | CTACAACTGG | GAGTGACCGC | TAGTGACAGT | 60 |
| GGAAACCCAC | CATTAAGAAG | CAATATTTCA | CTGACCCTTT | TCGTGCTGGA | CCAGAATGAT | 120 |
| AACGCCCCAA | A | | | | | 131 |

(2) INFORMATION FOR SEQ ID NO:71:

(i) SEQUENCE CHARACTERISTICS:
    (A) LENGTH: 43 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:71:

| Lys | Gly | Leu | Asp | Tyr | Glu | Gln | Phe | Gln | Thr | Leu | Gln | Leu | Gly | Val | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ala | Ser | Asp | Ser | Gly | Asn | Pro | Pro | Leu | Arg | Ser | Asn | Ile | Ser | Leu | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Leu | Phe | Val | Leu | Asp | Gln | Asn | Asp | Asn | Ala | Pro |
|-----|-----|-----|-----|-----|-----|-----|-----|-----|-----|-----|
|     |     | 35  |     |     |     | 40  |     |     |     |     |

(2) INFORMATION FOR SEQ ID NO:72:

(i) SEQUENCE CHARACTERISTICS:
    (A) LENGTH: 131 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:72:

| AAGCGGGTTG | ATTACGAGGA | TGTCCAGAAA | TACTCGCTGA | GCATTAAGGC | CCAGGATGGG | 60 |
| CGGCCCCCGC | TCATCAATTC | TTCAGGGGTG | GTGTCTGTGC | AGGTGCTGGA | TGTCAACGAC | 120 |
| AATGCCCCGG | A | | | | | 131 |

(2) INFORMATION FOR SEQ ID NO:73:

(i) SEQUENCE CHARACTERISTICS:
    (A) LENGTH: 43 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:73:

| Lys | Arg | Val | Asp | Tyr | Glu | Asp | Val | Gln | Lys | Tyr | Ser | Leu | Ser | Ile | Lys |
|---|---|---|---|---|---|---|---|---|---|---|---|---|---|---|---|
| 1 | | | | 5 | | | | | 10 | | | | | 15 | |
| Ala | Gln | Asp | Gly | Arg | Pro | Pro | Leu | Ile | Asn | Ser | Ser | Gly | Val | Val | Ser |
| | | | 20 | | | | 25 | | | | | 30 | | | |
| Val | Gln | Val | Leu | Asp | Val | Asn | Asp | Asn | Ala | Pro | | | | | |
| | | 35 | | | | 40 | | | | | | | | | |

(2) INFORMATION FOR SEQ ID NO:74:

(i) SEQUENCE CHARACTERISTICS:
(A) LENGTH: 125 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:74:

AAACCGGTAG ACTTTGAGCT ACAGCAGTTC TATGAAGTAG CTGTGGTGGC TTGGAACTCT      60
GAGGGATTTC ATGTCAAAAG GGTCATTAAA GTGCAACTTT TAGATGACAA CGACAATGCC     120
CCGAT                                                                 125

(2) INFORMATION FOR SEQ ID NO:75:

(i) SEQUENCE CHARACTERISTICS:
(A) LENGTH: 41 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:75:

| Lys | Pro | Val | Asp | Phe | Glu | Leu | Gln | Gln | Phe | Tyr | Glu | Val | Ala | Val | Val |
|---|---|---|---|---|---|---|---|---|---|---|---|---|---|---|---|
| 1 | | | | 5 | | | | | 10 | | | | | 15 | |
| Ala | Trp | Asn | Ser | Glu | Gly | Phe | His | Val | Lys | Arg | Val | Ile | Lys | Val | Gln |
| | | | 20 | | | | 25 | | | | | 30 | | | |
| Leu | Leu | Asp | Asp | Asn | Asp | Asn | Ala | Pro | | | | | | | |
| | | 35 | | | | 40 | | | | | | | | | |

(2) INFORMATION FOR SEQ ID NO:76:

(i) SEQUENCE CHARACTERISTICS:
(A) LENGTH: 125 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:76:

AAGGGATTAG ATTTTGAAAC TTTGCCCATT TACACATTGA TAATACAAGG AACTAACATG      60
GCTGGTTTGT CCACTAATAC AACGGTTCTA GTTCACTTGC AGGATGAGAA TGATAACGCC     120
CCAAA                                                                 125

(2) INFORMATION FOR SEQ ID NO:77:

( i ) SEQUENCE CHARACTERISTICS:
            ( A ) LENGTH: 41 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO:77:

| Lys | Gly | Leu | Asp | Phe | Glu | Thr | Leu | Pro | Ile | Tyr | Thr | Leu | Ile | Ile | Gln |
|---|---|---|---|---|---|---|---|---|---|---|---|---|---|---|---|
| 1 | | | | 5 | | | | | 10 | | | | | 15 | |
| Gly | Thr | Asn | Met | Ala | Gly | Leu | Ser | Thr | Asn | Thr | Thr | Val | Leu | Val | His |
| | | | 20 | | | | | 25 | | | | | 30 | | |
| Leu | Gln | Asp | Glu | Asn | Asp | Asn | Ala | Pro | | | | | | | |
| | | | 35 | | | | 40 | | | | | | | | |

( 2 ) INFORMATION FOR SEQ ID NO:78:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:78:

AAGCGGGCGG ATTTCGAGGC GATCCGGGAG TACAGTCTGA GGATCAAAGC GCAGGACGGG      60
GGGCGGCCTC CCCTCAGCAA CACCACGGGC ATGGTCACAG TGCAGGTCGT GGACGTCAAT      120
GACAACGCAC CCCT      134

( 2 ) INFORMATION FOR SEQ ID NO:79:

( i ) SEQUENCE CHARACTERISTICS:
        ( A ) LENGTH: 44 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:79:

| Lys | Arg | Ala | Asp | Phe | Glu | Ala | Ile | Arg | Glu | Tyr | Ser | Leu | Arg | Ile | Lys |
|---|---|---|---|---|---|---|---|---|---|---|---|---|---|---|---|
| 1 | | | | 5 | | | | | 10 | | | | | 15 | |
| Ala | Gln | Asp | Gly | Gly | Arg | Pro | Pro | Leu | Ser | Asn | Thr | Thr | Gly | Met | Val |
| | | | 20 | | | | | 25 | | | | | 30 | | |
| Thr | Val | Gln | Val | Val | Asp | Val | Asn | Asp | Asn | Ala | Pro | | | | |
| | | | 35 | | | | 40 | | | | | | | | |

( 2 ) INFORMATION FOR SEQ ID NO:80:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:80:

AAGCGGTTGG ATTACGAAAA GGCATCGGAA TATGAAATCT ATGTTCAAGC CGCTGACAAA      60
GGCGCTGTCC CTATGGCTGG CCATTGCAAA GTGTTGCTGG AGATCGTGGA TGTCAACGAC      120
AACGCCCCT T      131

( 2 ) INFORMATION FOR SEQ ID NO:81:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:81:

```
Lys Arg Leu Asp Tyr Glu Lys Ala Ser Glu Tyr Glu Ile Tyr Val Gln
1               5                   10                  15
Ala Ala Asp Lys Gly Ala Val Pro Met Ala Gly His Cys Lys Val Leu
            20                  25                  30
Leu Glu Ile Val Asp Val Asn Asp Asn Ala Pro
            35                  40
```

( 2 ) INFORMATION FOR SEQ ID NO:82:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:82:

```
AAGGGGATCG ATTATGAGGA TCAGGTCTCT TACACATTAG CAGTAACAGC ACATGACTAT        60
GGCATCCCTC AAAAATCAGA CACTACCTAT TTGGAAATCT TAGTAATTGA TGTTAACGAC       120
AACGCGCCCC A                                                            131
```

( 2 ) INFORMATION FOR SEQ ID NO:83:

( i ) SEQUENCE CHARACTERISTICS:
    ( A ) LENGTH: 43 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:83:

```
Lys Gly Ile Asp Tyr Glu Asp Gln Val Ser Tyr Thr Leu Ala Val Thr
1               5                   10                  15
Ala His Asp Tyr Gly Ile Pro Gln Lys Ser Asp Thr Thr Tyr Leu Glu
            20                  25                  30
Ile Leu Val Ile Asp Val Asn Asp Asn Ala Pro
            35                  40
```

( 2 ) INFORMATION FOR SEQ ID NO:84:

( i ) SEQUENCE CHARACTERISTICS:
    ( A ) LENGTH: 131 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:84:

```
AAAGGGTTAG ATTTCGAGGG CACTAAAGAT TCAGCGTTTA AAATAGTGGC AGCTGACACA        60
GGGAAGCCCA GCCTCAACCA GACAGCCCTG GTGAGAGTAG AGCTGGAGGA TGAGAACGAC       120
AACGCCCCAA T                                                            131
```

( 2 ) INFORMATION FOR SEQ ID NO:85:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:85:

```
Lys Gly Leu Asp Phe Glu Gly Thr Lys Asp Ser Ala Phe Lys Ile Val
1               5                   10                  15
Ala Ala Asp Thr Gly Lys Pro Ser Leu Asn Gln Thr Ala Leu Val Arg
            20                  25                  30
Val Glu Leu Glu Asp Glu Asn Asp Asn Ala Pro
            35              40
```

( 2 ) INFORMATION FOR SEQ ID NO:86:

( i ) SEQUENCE CHARACTERISTICS:
        ( A ) LENGTH: 130 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

```
AAGGGTGTGG ATTTTGAAAG TGTGCGTAGC TACAGGCTGG TTATTCGTGC TCAAGATGGA        60
GGCAGCCCCT CCAGAAGTAA CACCACCCAG CTCTTGGTCA ACGTCATCGA TCGAATGACA       120
ATGCGCCGCT                                                              130
```

( 2 ) INFORMATION FOR SEQ ID NO:87:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:87:

```
Lys Gly Val Asp Phe Glu Ser Val Arg Ser Tyr Arg Leu Val Ile Arg
1               5                   10                  15
Ala Gln Asp Gly Gly Ser Pro Ser Arg Ser Asn Thr Thr Gln Leu Leu
            20                  25                  30
Val Asn Val Ile Asp Val Asn Asp Asn Ala Pro
            35              40
```

( 2 ) INFORMATION FOR SEQ ID NO:88:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:88:

```
AAGGGTGTGG ACTTCGAGCT GACACATCTG TATGAGATTT GGATTGAGGC TGCCGATGGA        60
GACACGCCAA GTCTGCGTAG TGTAACTCTT ATAACGCTCA ACGTAACGGA TGCCAATGAC       120
```

```
AATGCTCCCA A                                                                                               131
```

( 2 ) INFORMATION FOR SEQ ID NO:89:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:89:

```
Lys  Gly  Val  Asp  Phe  Glu  Leu  Thr  His  Leu  Tyr  Glu  Ile  Trp  Ile  Glu
1                   5                        10                       15

Ala  Ala  Asp  Gly  Asp  Thr  Pro  Ser  Leu  Arg  Ser  Val  Thr  Leu  Ile  Thr
               20                       25                       30

Leu  Asn  Val  Thr  Asp  Ala  Asn  Asp  Asn  Ala  Pro
               35                       40
```

( 2 ) INFORMATION FOR SEQ ID NO:90:

( i ) SEQUENCE CHARACTERISTICS:
        ( A ) LENGTH: 441 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:90:

```
CAAGGCGTTT  GATTTGAAG   AGACAAGTAG  ATATGTGTTG  AGTGTGGAAG  CTAAGGATGG       60
AGGAGTACAC  ACAGCTCACT  GTAATGTTCA  AATAGAAATT  GTTGACGAGA  ATGACAATGC      120
CCCAGAGGTG  ACATTCATGT  CCTTCTCTAA  CCAGATTCCA  GAGGATTCAG  ACCTTGGAAC      180
TGTAATAGCC  CTCATAAAAG  TGCGAGACAA  GGATTCTGGG  CAAAATGGCA  TGGTGACATG      240
CTATACTCAG  GAAGAAGTTC  CTTTCAAATT  AGAATCCACC  TCGAAGAATT  ATTACAAGCT      300
GGTGATTGCT  GGAGCCCTAA  ACCGGGAGCA  GACAGCAGAC  TACAACGTCA  CAATCATAGC      360
CACCGACAAG  GGCAAACCAG  CCCTTTCCTC  CAGGACAAGC  ATCACCCTGC  ACATCTCCGA      420
CATCAACGAT  AATGCCCCCG  T                                                   441
```

( 2 ) INFORMATION FOR SEQ ID NO:91:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:91:

```
Lys  Ala  Phe  Asp  Phe  Glu  Glu  Thr  Ser  Arg  Tyr  Val  Leu  Ser  Val  Glu
1                   5                        10                       15

Ala  Lys  Asp  Gly  Gly  Val  His  Thr  Ala  His  Cys  Asn  Val  Gln  Ile  Glu
               20                       25                       30

Ile  Val  Asp  Glu  Asn  Asp  Asn  Ala  Pro  Glu  Val  Thr  Phe  Met  Ser  Phe
               35                       40                       45

Ser  Asn  Gln  Ile  Pro  Glu  Asp  Ser  Asp  Leu  Gly  Thr  Val  Ile  Ala  Leu
               50                       55                       60

Ile  Lys  Val  Arg  Asp  Lys  Asp  Ser  Gly  Gln  Asn  Gly  Met  Val  Thr  Cys
```

| | | | | 65 | | | | | 70 | | | | | 75 | | | | | 80 |
|---|---|---|---|---|---|---|---|---|---|---|---|---|---|---|---|---|---|---|---|

Tyr Thr Gln Glu Glu Val Pro Phe Lys Leu Glu Ser Thr Ser Lys Asn
                85                      90                      95

Tyr Tyr Lys Leu Val Ile Ala Gly Ala Leu Asn Arg Glu Gln Thr Ala
            100                     105                     110

Asp Tyr Asn Val Thr Ile Ile Ala Thr Asp Lys Gly Lys Pro Ala Leu
            115                     120                     125

Ser Ser Arg Thr Ser Ile Thr Leu His Ile Ser Asp Ile Asn Asp Asn
    130                     135                     140

Ala Pro
145

(2) INFORMATION FOR SEQ ID NO:92:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:92:

AAGCGAGTGG ATTACGAGGC CACTCGGAAT TATAAGCTGA GAGTTAAGGC TACTGATCTT    60

GGGATTCCAC CGAGATCTTC TAACATGACA CTGTTCATTC ATGTCCTTGA TGTTAACGAC    120

AACGCTCCCT T    131

(2) INFORMATION FOR SEQ ID NO:93:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:93:

Lys Arg Val Asp Tyr Glu Ala Thr Arg Asn Tyr Lys Leu Arg Val Lys
1               5                   10                  15

Ala Thr Asp Leu Gly Ile Pro Pro Arg Ser Ser Asn Met Thr Leu Phe
            20                  25                  30

Ile His Val Leu Asp Val Asn Asp Asn Ala Pro
            35                  40

(2) INFORMATION FOR SEQ ID NO:94:

(i) SEQUENCE CHARACTERISTICS:
        (A) LENGTH: 4104 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 495..3572

(xi) SEQUENCE DESCRIPTION: SEQ ID NO:94:

CCTCTATTCG ACATTCTCTT TGGATTGTTT TGCTATAACT TGAAATTTGG GATGTCACAA    60

ACGAAACTGT CATCTGTTTC CGCCAAACTG TGGTTCTGCT AATCTCCCAG GCTGGCAGCA    120

TTGGAGACTT GCTGACTTCT TTCATCCCCC ACTCTTTTCA CCTGAAATTC CTTTCCTTGG    180

```
TTTTGCTCTA AGTCCTATGC TTCAGTCAGG GGCCAACCAA ATCTCACTGC CTCCTTTTTA              240

TCATGAAGCC TTTGATCACT GATAGTTCTT TTTATATCTT GAAAAATCAC CCTTCCCAGT              300

ACAGTTAATA TTTAGTATCT CTACTCATCT TGGCACTTAC TCACAGCTCC ATAATTCAGT              360

CGTTTTCGTA CCTCTTCATG GTGATGGGGA GCCCTTTGGA GGTGGTGACT GTGCTTTATA              420

CTCCTCATGA TGCTTCACAT GTGGCAGGCG TGGAGTGCCC GGAGGCGGCC CTCCTGATTC              480

TGGGGCCTCC CAGG ATG GAG CCC CTG AGG CAC AGC CCA GGC CCT GGG GGG                530
              Met Glu Pro Leu Arg His Ser Pro Gly Pro Gly Gly
               1           5                    10

CAA CGG CTA CTG CTG CCC TCC ATG CTG CTA GCA CTG CTG CTC CTG CTG                578
Gln Arg Leu Leu Leu Pro Ser Met Leu Leu Ala Leu Leu Leu Leu Leu
         15              20                  25

GCT CCA TCC CCA GGC CAC GCC ACT CGG GTA GTG TAC AAG GTG CCG GAG                626
Ala Pro Ser Pro Gly His Ala Thr Arg Val Val Tyr Lys Val Pro Glu
         30              35                  40

GAA CAG CCA CCC AAC ACC CTC ATT GGG AGC CTC GCA GCC GAC TAT GGT                674
Glu Gln Pro Pro Asn Thr Leu Ile Gly Ser Leu Ala Ala Asp Tyr Gly
 45              50                  55                      60

TTT CCA GAT GTG GGG CAC CTG TAC AAG CTA GAG GTG GGT GCC CCG TAC                722
Phe Pro Asp Val Gly His Leu Tyr Lys Leu Glu Val Gly Ala Pro Tyr
                 65                  70                  75

CTT CGC GTG GAT GGC AAG ACA GGT GAC ATT TTC ACC ACC GAG ACC TCC                770
Leu Arg Val Asp Gly Lys Thr Gly Asp Ile Phe Thr Thr Glu Thr Ser
                 80              85                  90

ATC GAC CGT GAG GGG CTC CGT GAA TGC CAG AAC CAG CTC CCT GGT GAT                818
Ile Asp Arg Glu Gly Leu Arg Glu Cys Gln Asn Gln Leu Pro Gly Asp
             95              100                 105

CCC TGC ATC CTG GAG TTT GAG GTA TCT ATC ACA GAC CTC GTG CAG AAT                866
Pro Cys Ile Leu Glu Phe Glu Val Ser Ile Thr Asp Leu Val Gln Asn
    110                 115                 120

GCG AGC CCC CGG CTG CTA GAG GGC CAG ATA GAA GTA CAA GAC ATC AAT                914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT                962
Asp Asn Thr Pro Asn Phe Ala Ser Pro Val Ile Thr Leu Ala Ile Pro
                145                 150                 155

GAG AAC ACC AAC ATC GGC TCA CTC TTC CCC ATC CCG CTG GCT TCA GAC                1010
Glu Asn Thr Asn Ile Gly Ser Leu Phe Pro Ile Pro Leu Ala Ser Asp
                160                 165                 170

CGT GAT GCT GGT CCC AAC GGT GTG GCA TCC TAT GAG CTG CAG GTG GCA                1058
Arg Asp Ala Gly Pro Asn Gly Val Ala Ser Tyr Glu Leu Gln Val Ala
            175                 180                 185

GAG GAC CAG GAG GAG AAG CAA CCA CAG CTC ATT GTG ATG GGC AAC CTG                1106
Glu Asp Gln Glu Glu Lys Gln Pro Gln Leu Ile Val Met Gly Asn Leu
        190                 195                 200

GAC CGT GAG CGC TGG GAC TCC TAT GAC CTC ACC ATC AAG GTG CAG GAT                1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG                1202
Gly Gly Ser Pro Pro Arg Ala Thr Ser Ala Leu Leu Arg Val Thr Val
                225                 230                 235

CTT GAC ACC AAT GAC AAC GCC CCC AAG TTT GAG CGG CCC TCC TAT GAG                1250
Leu Asp Thr Asn Asp Asn Ala Pro Lys Phe Glu Arg Pro Ser Tyr Glu
                240                 245                 250

GCC GAA CTA TCT GAG AAT AGC CCC ATA GGC CAC TCG GTC ATC CAG GTG                1298
Ala Glu Leu Ser Glu Asn Ser Pro Ile Gly His Ser Val Ile Gln Val
            255                 260                 265

AAG GCC AAT GAC TCA GAC CAA GGT GCC AAT GCA GAA ATC GAA TAC ACA                1346
```

| Lys | Ala | Asn | Asp | Ser | Asp | Gln | Gly | Ala | Asn | Ala | Glu | Ile | Glu | Tyr | Thr | |
|---|---|---|---|---|---|---|---|---|---|---|---|---|---|---|---|---|
| | 270 | | | | 275 | | | | | 280 | | | | | | |

| TTC | CAC | CAG | GCG | CCC | GAA | GTT | GTG | AGG | CGT | CTT | CTT | CGA | CTG | GAC | AGG | 1394 |
|---|---|---|---|---|---|---|---|---|---|---|---|---|---|---|---|---|
| Phe | His | Gln | Ala | Pro | Glu | Val | Val | Arg | Arg | Leu | Leu | Arg | Leu | Asp | Arg | |
| 285 | | | | 290 | | | | | 295 | | | | | 300 | | |

| AAC | ACT | GGA | CTT | ATC | ACT | GTT | CAG | GGC | CCG | GTG | GAC | CGT | GAG | GAC | CTA | 1442 |
|---|---|---|---|---|---|---|---|---|---|---|---|---|---|---|---|---|
| Asn | Thr | Gly | Leu | Ile | Thr | Val | Gln | Gly | Pro | Val | Asp | Arg | Glu | Asp | Leu | |
| | | | | 305 | | | | | 310 | | | | | 315 | | |

| AGC | ACC | CTG | CGC | TTC | TCA | GTG | CTT | GCT | AAG | GAC | CGA | GGC | ACC | AAC | CCC | 1490 |
|---|---|---|---|---|---|---|---|---|---|---|---|---|---|---|---|---|
| Ser | Thr | Leu | Arg | Phe | Ser | Val | Leu | Ala | Lys | Asp | Arg | Gly | Thr | Asn | Pro | |
| | | | 320 | | | | | 325 | | | | | 330 | | | |

| AAG | AGT | GCC | CGT | GCC | CAG | GTG | GTT | GTG | ACC | GTG | AAG | GAC | ATG | AAT | GAC | 1538 |
|---|---|---|---|---|---|---|---|---|---|---|---|---|---|---|---|---|
| Lys | Ser | Ala | Arg | Ala | Gln | Val | Val | Val | Thr | Val | Lys | Asp | Met | Asn | Asp | |
| | | 335 | | | | | 340 | | | | | 345 | | | | |

| AAT | GCC | CCC | ACC | ATT | GAG | ATC | CGG | GGC | ATA | GGG | CTA | GTG | ACT | CAT | CAA | 1586 |
|---|---|---|---|---|---|---|---|---|---|---|---|---|---|---|---|---|
| Asn | Ala | Pro | Thr | Ile | Glu | Ile | Arg | Gly | Ile | Gly | Leu | Val | Thr | His | Gln | |
| | 350 | | | | | 355 | | | | | 360 | | | | | |

| GAT | GGG | ATG | GCT | AAC | ATC | TCA | GAG | GAT | GTG | GCA | GAG | GAG | ACA | GCT | GTG | 1634 |
|---|---|---|---|---|---|---|---|---|---|---|---|---|---|---|---|---|
| Asp | Gly | Met | Ala | Asn | Ile | Ser | Glu | Asp | Val | Ala | Glu | Glu | Thr | Ala | Val | |
| 365 | | | | 370 | | | | | 375 | | | | | 380 | | |

| GCC | CTG | GTG | CAG | GTG | TCT | GAC | CGA | GAT | GAG | GGA | GAG | AAT | GCA | GCT | GTC | 1682 |
|---|---|---|---|---|---|---|---|---|---|---|---|---|---|---|---|---|
| Ala | Leu | Val | Gln | Val | Ser | Asp | Arg | Asp | Glu | Gly | Glu | Asn | Ala | Ala | Val | |
| | | | | 385 | | | | | 390 | | | | | 395 | | |

| ACC | TGT | GTG | GTG | GCA | GGT | GAT | GTG | CCC | TTC | CAG | CTG | CGC | CAG | GCC | AGT | 1730 |
|---|---|---|---|---|---|---|---|---|---|---|---|---|---|---|---|---|
| Thr | Cys | Val | Val | Ala | Gly | Asp | Val | Pro | Phe | Gln | Leu | Arg | Gln | Ala | Ser | |
| | | | 400 | | | | | 405 | | | | | 410 | | | |

| GAG | ACA | GGC | AGT | GAC | AGC | AAG | AAG | TAT | TTC | CTG | CAG | ACT | ACC | ACC | | 1778 |
|---|---|---|---|---|---|---|---|---|---|---|---|---|---|---|---|---|
| Glu | Thr | Gly | Ser | Asp | Ser | Lys | Lys | Tyr | Phe | Leu | Gln | Thr | Thr | Thr | | |
| | | 415 | | | | | 420 | | | | | 425 | | | | |

| CCG | CTA | GAC | TAC | GAG | AAG | GTC | AAA | GAC | TAC | ACC | ATT | GAG | ATT | GTG | GCT | 1826 |
|---|---|---|---|---|---|---|---|---|---|---|---|---|---|---|---|---|
| Pro | Leu | Asp | Tyr | Glu | Lys | Val | Lys | Asp | Tyr | Thr | Ile | Glu | Ile | Val | Ala | |
| | 430 | | | | | 435 | | | | | 440 | | | | | |

| GTG | GAC | TCT | GGC | AAC | CCC | CCA | CTC | TCC | AGC | ACT | AAC | TCC | CTC | AAG | GTG | 1874 |
|---|---|---|---|---|---|---|---|---|---|---|---|---|---|---|---|---|
| Val | Asp | Ser | Gly | Asn | Pro | Pro | Leu | Ser | Ser | Thr | Asn | Ser | Leu | Lys | Val | |
| 445 | | | | | 450 | | | | | 455 | | | | | 460 | |

| CAG | GTG | GTG | GAC | GTC | AAT | GAC | AAC | GCA | CCT | GTC | TTC | ACT | CAG | AGT | GTC | 1922 |
|---|---|---|---|---|---|---|---|---|---|---|---|---|---|---|---|---|
| Gln | Val | Val | Asp | Val | Asn | Asp | Asn | Ala | Pro | Val | Phe | Thr | Gln | Ser | Val | |
| | | | | 465 | | | | | 470 | | | | | 475 | | |

| ACT | GAG | GTC | GCC | TTC | CCG | GAA | AAC | AAC | AAG | CCT | GGT | GAA | GTG | ATT | GCT | 1970 |
|---|---|---|---|---|---|---|---|---|---|---|---|---|---|---|---|---|
| Thr | Glu | Val | Ala | Phe | Pro | Glu | Asn | Asn | Lys | Pro | Gly | Glu | Val | Ile | Ala | |
| | | | 480 | | | | | 485 | | | | | 490 | | | |

| GAG | ATC | ACT | GCC | AGT | GAT | GCT | GAC | TCT | GGC | TCT | AAT | GCT | GAG | CTG | GTT | 2018 |
|---|---|---|---|---|---|---|---|---|---|---|---|---|---|---|---|---|
| Glu | Ile | Thr | Ala | Ser | Asp | Ala | Asp | Ser | Gly | Ser | Asn | Ala | Glu | Leu | Val | |
| | | 495 | | | | | 500 | | | | | 505 | | | | |

| TAC | TCT | CTG | GAG | CCT | GAG | CCG | GCT | GCT | AAG | GGC | CTC | TTC | ACC | ATC | TCA | 2066 |
|---|---|---|---|---|---|---|---|---|---|---|---|---|---|---|---|---|
| Tyr | Ser | Leu | Glu | Pro | Glu | Pro | Ala | Ala | Lys | Gly | Leu | Phe | Thr | Ile | Ser | |
| | 510 | | | | | 515 | | | | | 520 | | | | | |

| CCC | GAG | ACT | GGA | GAG | ATC | CAG | GTG | AAG | ACA | TCT | CTG | GAT | CGG | GAA | CAG | 2114 |
|---|---|---|---|---|---|---|---|---|---|---|---|---|---|---|---|---|
| Pro | Glu | Thr | Gly | Glu | Ile | Gln | Val | Lys | Thr | Ser | Leu | Asp | Arg | Glu | Gln | |
| 525 | | | | | 530 | | | | | 535 | | | | | 540 | |

| CGG | GAG | AGC | TAT | GAG | TTG | AAG | GTG | GTG | GCA | GCT | GAC | CGG | GGC | AGT | CCT | 2162 |
|---|---|---|---|---|---|---|---|---|---|---|---|---|---|---|---|---|
| Arg | Glu | Ser | Tyr | Glu | Leu | Lys | Val | Val | Ala | Ala | Asp | Arg | Gly | Ser | Pro | |
| | | | | 545 | | | | | 550 | | | | | 555 | | |

| AGC | CTC | CAG | GGC | ACA | GCC | ACT | GTC | CTT | GTC | AAT | GTG | CTG | GAC | TGC | AAT | 2210 |
|---|---|---|---|---|---|---|---|---|---|---|---|---|---|---|---|---|
| Ser | Leu | Gln | Gly | Thr | Ala | Thr | Val | Leu | Val | Asn | Val | Leu | Asp | Cys | Asn | |
| | | | 560 | | | | | 565 | | | | | 570 | | | |

| GAC | AAT | GAC | CCC | AAA | TTT | ATG | CTG | AGT | GGC | TAC | AAC | TTC | TCA | GTG | ATG | 2258 |
|---|---|---|---|---|---|---|---|---|---|---|---|---|---|---|---|---|
| Asp | Asn | Asp | Pro | Lys | Phe | Met | Leu | Ser | Gly | Tyr | Asn | Phe | Ser | Val | Met | |
| | | 575 | | | | | 580 | | | | | 585 | | | | |

| GAG | AAC | ATG | CCA | GCA | CTG | AGT | CCA | GTG | GGC | ATG | GTG | ACT | GTC | ATT | GAT | 2306 |

```
                Glu Asn Met Pro Ala Leu Ser Pro Val Gly Met Val Thr Val Ile Asp
                    590             595             600

GGA GAC AAG GGG GAG AAT GCC CAG GTG CAG CTC TCA GTG GAG CAG GAC        2354
Gly Asp Lys Gly Glu Asn Ala Gln Val Gln Leu Ser Val Glu Gln Asp
605             610             615             620

AAC GGT GAC TTT GTT ATC CAG AAT GGC ACA GGC ACC ATC CTA TCC AGC        2402
Asn Gly Asp Phe Val Ile Gln Asn Gly Thr Gly Thr Ile Leu Ser Ser
                625             630             635

CTG AGC TTT GAT CGA GAG CAA CAA AGC ACC TAC ACC TTC CAG CTG AAG        2450
Leu Ser Phe Asp Arg Glu Gln Gln Ser Thr Tyr Thr Phe Gln Leu Lys
            640             645             650

GCA GTG GAT GGT GGC GTC CCA CCT CGC TCA GCT TAC GTT GGT GTC ACC        2498
Ala Val Asp Gly Gly Val Pro Pro Arg Ser Ala Tyr Val Gly Val Thr
        655             660             665

ATC AAT GTG CTG GAC GAG AAT GAC AAC GCA CCC TAT ATC ACT GCC CCT        2546
Ile Asn Val Leu Asp Glu Asn Asp Asn Ala Pro Tyr Ile Thr Ala Pro
    670             675             680

TCT AAC ACC TCT CAC AAG CTG CTG ACC CCC CAG ACA CGT CTT GGT GAG        2594
Ser Asn Thr Ser His Lys Leu Leu Thr Pro Gln Thr Arg Leu Gly Glu
685             690             695             700

ACG GTC AGC CAG GTG GCA GCC GAG GAC TTT GAC TCT GGT GTC AAT GCC        2642
Thr Val Ser Gln Val Ala Ala Glu Asp Phe Asp Ser Gly Val Asn Ala
                705             710             715

GAG CTG ATC TAC AGC ATT GCA GGT GGC AAC CCT TAT GGA CTC TTC CAG        2690
Glu Leu Ile Tyr Ser Ile Ala Gly Gly Asn Pro Tyr Gly Leu Phe Gln
            720             725             730

ATT GGG TCA CAT TCA GGT GCC ATC ACC CTG GAG AAG GAG ATT GAG CGG        2738
Ile Gly Ser His Ser Gly Ala Ile Thr Leu Glu Lys Glu Ile Glu Arg
        735             740             745

CGC CAC CAT GGG CTA CAC CGC CTG GTG GTG AAG GTC AGT GAC CGC GGC        2786
Arg His His Gly Leu His Arg Leu Val Val Lys Val Ser Asp Arg Gly
    750             755             760

AAG CCC CCA CGC TAT GGC ACA GCC TTG GTC CAT CTT TAT GTC AAT GAG        2834
Lys Pro Pro Arg Tyr Gly Thr Ala Leu Val His Leu Tyr Val Asn Glu
765             770             775             780

ACT CTG GCC AAC CGC ACG CTG CTG GAG ACC CTC CTG GGC CAC AGC CTG        2882
Thr Leu Ala Asn Arg Thr Leu Leu Glu Thr Leu Leu Gly His Ser Leu
                785             790             795

GAC ACG CCG CTG GAT ATT GAC ATT GCT GGG GAT CCA GAA TAT GAG CGC        2930
Asp Thr Pro Leu Asp Ile Asp Ile Ala Gly Asp Pro Glu Tyr Glu Arg
            800             805             810

TCC AAG CAG CGT GGC AAC ATT CTC TTT GGT GTG GTG GCT GGT GTG GTG        2978
Ser Lys Gln Arg Gly Asn Ile Leu Phe Gly Val Val Ala Gly Val Val
        815             820             825

GCC GTG GCC TTG CTC ATC GCC CTG GCG GTT CTT GTG CGC TAC TGC AGA        3026
Ala Val Ala Leu Leu Ile Ala Leu Ala Val Leu Val Arg Tyr Cys Arg
    830             835             840

CAG CGG GAG GCC AAA AGT GGT TAC CAG GCT GGT AAG AAG GAG ACC AAG        3074
Gln Arg Glu Ala Lys Ser Gly Tyr Gln Ala Gly Lys Lys Glu Thr Lys
845             850             855             860

GAC CTG TAT GCC CCC AAG CCC AGT GGC AAG GCC TCC AAG GGA AAC AAA        3122
Asp Leu Tyr Ala Pro Lys Pro Ser Gly Lys Ala Ser Lys Gly Asn Lys
                865             870             875

AGC AAA GGC AAG AAG AGC AAG TCC CCA AAG CCC GTG AAG CCA GTG GAG        3170
Ser Lys Gly Lys Lys Ser Lys Ser Pro Lys Pro Val Lys Pro Val Glu
            880             885             890

GAC GAG GAT GAG GCC GGG CTG CAG AAG TCC CTC AAG TTC AAC CTG ATG        3218
Asp Glu Asp Glu Ala Gly Leu Gln Lys Ser Leu Lys Phe Asn Leu Met
        895             900             905

AGC GAT GCC CCT GGG GAC AGT CCC CGC ATC CAC CTG CCC CTC AAC TAC        3266
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Ser | Asp | Ala | Pro | Gly | Asp | Ser | Pro | Arg | Ile | His | Leu | Pro | Leu | Asn | Tyr |      |
|     | 910 |     |     |     | 915 |     |     |     |     | 920 |     |     |     |     |     |      |
| CCA | CCA | GGC | AGC | CCT | GAC | CTG | GGC | CGC | CAC | TAT | CGC | TCT | AAC | TCC | CCA | 3314 |
| Pro | Pro | Gly | Ser | Pro | Asp | Leu | Gly | Arg | His | Tyr | Arg | Ser | Asn | Ser | Pro |      |
| 925 |     |     |     |     | 930 |     |     |     |     | 935 |     |     |     |     | 940 |      |
| CTG | CCT | TCC | ATC | CAG | CTG | CAG | CCC | CAG | TCA | CCC | TCA | GCC | TCC | AAG | AAG | 3362 |
| Leu | Pro | Ser | Ile | Gln | Leu | Gln | Pro | Gln | Ser | Pro | Ser | Ala | Ser | Lys | Lys |      |
|     |     |     |     | 945 |     |     |     |     | 950 |     |     |     |     | 955 |     |      |
| CAC | CAG | GTG | GTA | CAG | GAC | CTG | CCA | CCT | GCA | AAC | ACA | TTC | GTG | GGC | ACC | 3410 |
| His | Gln | Val | Val | Gln | Asp | Leu | Pro | Pro | Ala | Asn | Thr | Phe | Val | Gly | Thr |      |
|     |     |     | 960 |     |     |     |     | 965 |     |     |     |     | 970 |     |     |      |
| GGG | GAC | ACC | ACG | TCC | ACG | GGC | TCT | GAG | CAG | TAC | TCC | GAC | TAC | AGC | TAC | 3458 |
| Gly | Asp | Thr | Thr | Ser | Thr | Gly | Ser | Glu | Gln | Tyr | Ser | Asp | Tyr | Ser | Tyr |      |
|     |     | 975 |     |     |     |     | 980 |     |     |     |     | 985 |     |     |     |      |
| CGC | ACC | AAC | CCC | CCC | AAA | TAC | CCC | AGC | AAG | CAG | GTA | GGC | CAG | CCC | TTT | 3506 |
| Arg | Thr | Asn | Pro | Pro | Lys | Tyr | Pro | Ser | Lys | Gln | Val | Gly | Gln | Pro | Phe |      |
|     | 990 |     |     |     |     | 995 |     |     |     |     | 1000|     |     |     |     |      |
| CAG | CTC | AGC | ACA | CCC | CAG | CCC | CTA | CCC | CAC | CCC | TAC | CAC | GGA | GCC | ATC | 3554 |
| Gln | Leu | Ser | Thr | Pro | Gln | Pro | Leu | Pro | His | Pro | Tyr | His | Gly | Ala | Ile |      |
| 1005|     |     |     |     | 1010|     |     |     |     | 1015|     |     |     |     | 1020|      |
| TGG | ACC | GAG | GTG | TGG | GAG | TGATGGAGCA | GGTTTACTGT | GCCTGCCCGT |     |     |     |     |     |     |     | 3602 |
| Trp | Thr | Glu | Val | Trp | Glu |     |     |     |     |     |     |     |     |     |     |      |
|     |     |     |     | 1025|     |     |     |     |     |     |     |     |     |     |     |      |

|             |             |             |             |             |      |
| ----------- | ----------- | ----------- | ----------- | ----------- | ---- |
| GTTGGGGGCC  | AGCCTGAGCC  | AGCAGTGGGA  | GGTGGGGCCT  | TAGTGCCTCA  | CCGGGCACAC | 3662 |
| GGATTAGGCT  | GAGTGAAGAT  | TAAGGGAGGG  | TGTGCTCTGT  | GGTCTCCTCC  | CTGCCCTCTC | 3722 |
| CCCACTGGGG  | AGAGACCTGT  | GATTTGCCAA  | GTCCCTGGAC  | CCTGGACCAG  | CTACTGGGCC | 3782 |
| TTATGGGTTG  | GGGGTGGTAG  | GCAGGTGAGC  | GTAAGTGGGG  | AGGGAAATGG  | GTAAGAAGTC | 3842 |
| TACTCCAAAC  | CTAGGTCTCT  | ATGTCAGACC  | AGACCTAGGT  | GCTTCTCTAG  | GAGGGAAACA | 3902 |
| GGGAGACCTG  | GGGTCCTGTG  | GATAACTGAG  | TGGGGAGTCT  | GCCAGGGGAG  | GGCACCTTCC | 3962 |
| CATTGTGCCT  | TCTGTGTGTA  | TTGTGCATTA  | ACCTCTTCCT  | CACCACTAGG  | CTTCTGGGGC | 4022 |
| TGGGTCCCAC  | ATGCCCTTGA  | CCCTGACAAT  | AAAGTTCTCT  | ATTTTGGAA   | AAAAAAAAA  | 4082 |
| AAAAAAAAA   | AAAAAAAAA   | AA          |             |             |            | 4104 |

( 2 ) INFORMATION FOR SEQ ID NO:95:

( i ) SEQUENCE CHARACTERISTICS:
        ( A ) LENGTH: 1026 amino acids
        ( B ) TYPE: amino acid
        ( D ) TOPOLOGY: linear ( i i ) MOLECULE TYPE: protein ( x i ) SEQUENCE DESCRIPTION: SEQ ID NO:95:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Glu | Pro | Leu | Arg | His | Ser | Pro | Gly | Pro | Gly | Gly | Gln | Arg | Leu | Leu |
| 1   |     |     |     | 5   |     |     |     |     | 10  |     |     |     |     | 15  |     |
| Leu | Pro | Ser | Met | Leu | Leu | Ala | Leu | Leu | Leu | Leu | Ala | Pro | Ser | Pro |     |
|     |     |     | 20  |     |     |     | 25  |     |     |     |     | 30  |     |     |     |
| Gly | His | Ala | Thr | Arg | Val | Val | Tyr | Lys | Val | Pro | Glu | Glu | Gln | Pro | Pro |
|     |     | 35  |     |     |     |     | 40  |     |     |     |     | 45  |     |     |     |
| Asn | Thr | Leu | Ile | Gly | Ser | Leu | Ala | Ala | Asp | Tyr | Gly | Phe | Pro | Asp | Val |
|     | 50  |     |     |     |     | 55  |     |     |     |     | 60  |     |     |     |     |
| Gly | His | Leu | Tyr | Lys | Leu | Glu | Val | Gly | Ala | Pro | Tyr | Leu | Arg | Val | Asp |
| 65  |     |     |     |     | 70  |     |     |     |     | 75  |     |     |     |     | 80  |
| Gly | Lys | Thr | Gly | Asp | Ile | Phe | Thr | Thr | Glu | Thr | Ser | Ile | Asp | Arg | Glu |
|     |     |     |     | 85  |     |     |     |     | 90  |     |     |     |     | 95  |     |
| Gly | Leu | Arg | Glu | Cys | Gln | Asn | Gln | Leu | Pro | Gly | Asp | Pro | Cys | Ile | Leu |

|  |  |  | 100 |  |  |  | 105 |  |  |  | 110 |  |  |
|---|---|---|---|---|---|---|---|---|---|---|---|---|---|

Glu Phe Glu Val Ser Ile Thr Asp Leu Val Gln Asn Ala Ser Pro Arg
          115                    120                    125

Leu Leu Glu Gly Gln Ile Glu Val Gln Asp Ile Asn Asp Asn Thr Pro
    130                    135                    140

Asn Phe Ala Ser Pro Val Ile Thr Leu Ala Ile Pro Glu Asn Thr Asn
145                 150                    155                    160

Ile Gly Ser Leu Phe Pro Ile Pro Leu Ala Ser Asp Arg Asp Ala Gly
                165                    170                    175

Pro Asn Gly Val Ala Ser Tyr Glu Leu Gln Val Ala Glu Asp Gln Glu
            180                    185                    190

Glu Lys Gln Pro Gln Leu Ile Val Met Gly Asn Leu Asp Arg Glu Arg
        195                    200                    205

Trp Asp Ser Tyr Asp Leu Thr Ile Lys Val Gln Asp Gly Gly Ser Pro
    210                    215                    220

Pro Arg Ala Thr Ser Ala Leu Leu Arg Val Thr Val Leu Asp Thr Asn
225                    230                    235                    240

Asp Asn Ala Pro Lys Phe Glu Arg Pro Ser Tyr Glu Ala Glu Leu Ser
                245                    250                    255

Glu Asn Ser Pro Ile Gly His Ser Val Ile Gln Val Lys Ala Asn Asp
            260                    265                    270

Ser Asp Gln Gly Ala Asn Ala Glu Ile Glu Tyr Thr Phe His Gln Ala
        275                    280                    285

Pro Glu Val Val Arg Arg Leu Leu Arg Leu Asp Arg Asn Thr Gly Leu
    290                    295                    300

Ile Thr Val Gln Gly Pro Val Asp Arg Glu Asp Leu Ser Thr Leu Arg
305                    310                    315                    320

Phe Ser Val Leu Ala Lys Asp Arg Gly Thr Asn Pro Lys Ser Ala Arg
                325                    330                    335

Ala Gln Val Val Val Thr Val Lys Asp Met Asn Asp Asn Ala Pro Thr
            340                    345                    350

Ile Glu Ile Arg Gly Ile Gly Leu Val Thr His Gln Asp Gly Met Ala
        355                    360                    365

Asn Ile Ser Glu Asp Val Ala Glu Glu Thr Ala Val Ala Leu Val Gln
370                    375                    380

Val Ser Asp Arg Asp Glu Gly Glu Asn Ala Ala Val Thr Cys Val Val
385                    390                    395                    400

Ala Gly Asp Val Pro Phe Gln Leu Arg Gln Ala Ser Glu Thr Gly Ser
                405                    410                    415

Asp Ser Lys Lys Lys Tyr Phe Leu Gln Thr Thr Thr Pro Leu Asp Tyr
            420                    425                    430

Glu Lys Val Lys Asp Tyr Thr Ile Glu Ile Val Ala Val Asp Ser Gly
        435                    440                    445

Asn Pro Pro Leu Ser Ser Thr Asn Ser Leu Lys Val Gln Val Val Asp
    450                    455                    460

Val Asn Asp Asn Ala Pro Val Phe Thr Gln Ser Val Thr Glu Val Ala
465                    470                    475                    480

Phe Pro Glu Asn Asn Lys Pro Gly Glu Val Ile Ala Glu Ile Thr Ala
                485                    490                    495

Ser Asp Ala Asp Ser Gly Ser Asn Ala Glu Leu Val Tyr Ser Leu Glu
            500                    505                    510

Pro Glu Pro Ala Ala Lys Gly Leu Phe Thr Ile Ser Pro Glu Thr Gly
        515                    520                    525

```
Glu Ile Gln Val Lys Thr Ser Leu Asp Arg Glu Gln Arg Glu Ser Tyr
    530             535                 540
Glu Leu Lys Val Val Ala Ala Asp Arg Gly Ser Pro Ser Leu Gln Gly
545             550                 555                 560
Thr Ala Thr Val Leu Asn Val Leu Asp Cys Asn Asp Asn Asp Pro
            565             570                 575
Lys Phe Met Leu Ser Gly Tyr Asn Phe Ser Val Met Glu Asn Met Pro
            580             585             590
Ala Leu Ser Pro Val Gly Met Val Thr Val Ile Asp Gly Asp Lys Gly
        595             600                 605
Glu Asn Ala Gln Val Gln Leu Ser Val Glu Gln Asp Asn Gly Asp Phe
    610             615             620
Val Ile Gln Asn Gly Thr Gly Thr Ile Leu Ser Ser Leu Ser Phe Asp
625             630             635                 640
Arg Glu Gln Gln Ser Thr Tyr Thr Phe Gln Leu Lys Ala Val Asp Gly
            645             650             655
Gly Val Pro Pro Arg Ser Ala Tyr Val Gly Val Thr Ile Asn Val Leu
        660             665             670
Asp Glu Asn Asp Asn Ala Pro Tyr Ile Thr Ala Pro Ser Asn Thr Ser
        675             680             685
His Lys Leu Leu Thr Pro Gln Thr Arg Leu Gly Glu Thr Val Ser Gln
    690             695             700
Val Ala Ala Glu Asp Phe Asp Ser Gly Val Asn Ala Glu Leu Ile Tyr
705             710             715                 720
Ser Ile Ala Gly Gly Asn Pro Tyr Gly Leu Phe Gln Ile Gly Ser His
            725             730             735
Ser Gly Ala Ile Thr Leu Glu Lys Glu Ile Glu Arg Arg His His Gly
        740             745             750
Leu His Arg Leu Val Val Lys Val Ser Asp Arg Gly Lys Pro Pro Arg
    755             760             765
Tyr Gly Thr Ala Leu Val His Leu Tyr Val Asn Glu Thr Leu Ala Asn
    770             775             780
Arg Thr Leu Leu Glu Thr Leu Leu Gly His Ser Leu Asp Thr Pro Leu
785             790             795                 800
Asp Ile Asp Ile Ala Gly Asp Pro Glu Tyr Glu Arg Ser Lys Gln Arg
            805             810             815
Gly Asn Ile Leu Phe Gly Val Val Ala Gly Val Val Ala Val Ala Leu
        820             825             830
Leu Ile Ala Leu Ala Val Leu Val Arg Tyr Cys Arg Gln Arg Glu Ala
        835             840             845
Lys Ser Gly Tyr Gln Ala Gly Lys Lys Glu Thr Lys Asp Leu Tyr Ala
    850             855             860
Pro Lys Pro Ser Gly Lys Ala Ser Lys Gly Asn Lys Ser Lys Gly Lys
865             870             875             880
Lys Ser Lys Ser Pro Lys Pro Val Lys Pro Val Glu Asp Glu Asp Glu
            885             890             895
Ala Gly Leu Gln Lys Ser Leu Lys Phe Asn Leu Met Ser Asp Ala Pro
        900             905             910
Gly Asp Ser Pro Arg Ile His Leu Pro Leu Asn Tyr Pro Pro Gly Ser
        915             920             925
Pro Asp Leu Gly Arg His Tyr Arg Ser Asn Ser Pro Leu Pro Ser Ile
        930             935             940
Gln Leu Gln Pro Gln Ser Pro Ser Ala Ser Lys Lys His Gln Val Val
945             950             955             960
```

| Gln | Asp | Leu | Pro | Pro<br>965 | Ala | Asn | Thr | Phe | Val<br>970 | Gly | Thr | Gly | Asp<br>975 | Thr | Thr |
|---|---|---|---|---|---|---|---|---|---|---|---|---|---|---|---|
| Ser | Thr | Gly | Ser<br>980 | Glu | Gln | Tyr | Ser | Asp<br>985 | Tyr | Ser | Tyr | Arg | Thr<br>990 | Asn | Pro |
| Pro | Lys | Tyr<br>995 | Pro | Ser | Lys | Gln | Val<br>1000 | Gly | Gln | Pro | Phe | Gln<br>1005 | Leu | Ser | Thr |
| Pro | Gln<br>1010 | Pro | Leu | Pro | His | Pro<br>1015 | Tyr | His | Gly | Ala | Ile<br>1020 | Trp | Thr | Glu | Val |
| Trp<br>1025 | Glu | | | | | | | | | | | | | | |

( 2 ) INFORMATION FOR SEQ ID NO:96:

( i ) SEQUENCE CHARACTERISTICS:
        ( A ) LENGTH: 4705 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2827

( x i ) SEQUENCE DESCRIPTION: SEQ ID NO:96:

CGAAAGCCAT GTCGGACTCG TCGCCCAGCG CCCAAGCGCT AACCCGCTGA AAGTTTCTCA     60

GCGAAATCTC AGGGACGATC TGGACCCCGC TGAGAGGAAC TGCTTTTGAG TGAG ATG     117
                                                                                                    Met
                                                                                                    1

| GTC | CCA | GAG | GCC | TGG | AGG | AGC | GGA | CTG | GTA | AGC | ACC | GGG | AGG | GTA | GTG | 165 |
|---|---|---|---|---|---|---|---|---|---|---|---|---|---|---|---|---|
| Val | Pro | Glu | Ala | Trp<br>5 | Arg | Ser | Gly | Leu | Val<br>10 | Ser | Thr | Gly | Arg | Val<br>15 | Val | |
| GGA | GTT | TTG | CTT | CTG | CTT | GGT | GCC | TTG | AAC | AAG | GCT | TCC | ACG | GTC | ATT | 213 |
| Gly | Val | Leu | Leu<br>20 | Leu | Leu | Gly | Ala | Leu<br>25 | Asn | Lys | Ala | Ser | Thr<br>30 | Val | Ile | |
| CAC | TAT | GAG | ATC | CCG | GAG | GAA | AGA | GAG | AAG | GGT | TTC | GCT | GTG | GGC | AAC | 261 |
| His | Tyr<br>35 | Glu | Ile | Pro | Glu | Glu<br>40 | Arg | Glu | Lys | Gly | Phe<br>45 | Ala | Val | Gly | Asn | |
| GTG | GTC | GCG | AAC | CTT | GGT | TTG | GAT | CTC | GGT | AGC | CTC | TCA | GCC | CGC | AGG | 309 |
| Val<br>50 | Val | Ala | Asn | Leu | Gly<br>55 | Leu | Asp | Leu | Gly | Ser<br>60 | Leu | Ser | Ala | Arg | Arg<br>65 | |
| TTC | CCG | GTG | GTG | TCT | GGA | GCT | AGC | CGA | AGA | TTC | TTT | GAG | GTG | AAC | CGG | 357 |
| Phe | Pro | Val | Val | Ser<br>70 | Gly | Ala | Ser | Arg | Arg<br>75 | Phe | Phe | Glu | Val | Asn<br>80 | Arg | |
| GAG | ACC | GGA | GAG | ATG | TTT | GTG | AAC | GAC | CGT | CTG | GAT | CGA | GAG | GAG | CTG | 405 |
| Glu | Thr | Gly | Glu | Met<br>85 | Phe | Val | Asn | Asp | Arg<br>90 | Leu | Asp | Arg | Glu | Glu<br>95 | Leu | |
| TGT | GGG | ACA | CTG | CCC | TCT | TGC | ACT | GTA | ACT | CTG | GAG | TTG | GTA | GTG | GAG | 453 |
| Cys | Gly | Thr<br>100 | Leu | Pro | Ser | Cys | Thr<br>105 | Val | Thr | Leu | Glu | Leu<br>110 | Val | Val | Glu | |
| AAC | CCG | CTG | GAG | CTG | TTC | AGC | GTG | GAA | GTG | GTG | ATC | CAG | GAC | ATC | AAC | 501 |
| Asn | Pro<br>115 | Leu | Glu | Leu | Phe | Ser<br>120 | Val | Glu | Val | Val | Ile<br>125 | Gln | Asp | Ile | Asn | |
| GAC | AAC | AAT | CCT | GCT | TTC | CCT | ACC | CAG | GAA | ATG | AAA | TTG | GAG | ATT | AGC | 549 |
| Asp | Asn | Asn<br>130 | Pro | Ala | Phe | Pro<br>135 | Thr | Gln | Glu | Met | Lys<br>140 | Leu | Glu | Ile | Ser<br>145 | |
| GAG | GCC | GTG | GCT | CCG | GGG | ACG | CGC | TTT | CCG | CTC | GAG | AGC | GCG | CAC | GAT | 597 |
| Glu | Ala | Val | Ala | Pro<br>150 | Gly | Thr | Arg | Phe | Pro<br>155 | Leu | Glu | Ser | Ala | His<br>160 | Asp | |
| CCC | GAT | CTG | GGA | AGC | AAC | TCT | TTA | CAA | ACC | TAT | GAG | CTG | AGC | CGA | AAT | 645 |

```
          Pro  Asp  Leu  Gly  Ser  Asn  Ser  Leu  Gln  Thr  Tyr  Glu  Leu  Ser  Arg  Asn
                         165                      170                     175

GAA  TAC  TTT  GCG  CTT  CGC  GTG  CAG  ACG  CGG  GAG  GAC  AGC  ACC  AAG  TAC                693
Glu  Tyr  Phe  Ala  Leu  Arg  Val  Gln  Thr  Arg  Glu  Asp  Ser  Thr  Lys  Tyr
          180                      185                     190

GCG  GAG  CTG  GTG  TTG  GAG  CGC  GCC  CTG  GAC  CGA  GAA  CGG  GAG  CCT  AGT                741
Ala  Glu  Leu  Val  Leu  Glu  Arg  Ala  Leu  Asp  Arg  Glu  Arg  Glu  Pro  Ser
          195                      200                     205

CTC  CAG  TTA  GTG  CTG  ACG  GCG  TTG  GAC  GGA  GGG  ACC  CCA  GCT  CTC  TCC                789
Leu  Gln  Leu  Val  Leu  Thr  Ala  Leu  Asp  Gly  Gly  Thr  Pro  Ala  Leu  Ser
210                      215                     220                     225

GCC  AGC  CTG  CCT  ATT  CAC  ATC  AAG  GTG  CTG  GAC  GCG  AAT  GAC  AAT  GCG                837
Ala  Ser  Leu  Pro  Ile  His  Ile  Lys  Val  Leu  Asp  Ala  Asn  Asp  Asn  Ala
                         230                     235                     240

CCT  GTC  TTC  AAC  CAG  TCC  TTG  TAC  CGG  GCG  CGC  GTT  CCT  GGA  GGA  TGC                885
Pro  Val  Phe  Asn  Gln  Ser  Leu  Tyr  Arg  Ala  Arg  Val  Pro  Gly  Gly  Cys
               245                      250                     255

ACC  TCC  GGC  ACG  CGC  GTG  GTA  CAA  GTC  CTT  GCA  ACG  GAT  CTG  GAT  GAA                933
Thr  Ser  Gly  Thr  Arg  Val  Val  Gln  Val  Leu  Ala  Thr  Asp  Leu  Asp  Glu
               260                      265                     270

GGC  CCC  AAC  GGT  GAA  ATT  ATT  TAC  TCC  TTC  GGC  AGC  CAC  AAC  CGC  GCC                981
Gly  Pro  Asn  Gly  Glu  Ile  Ile  Tyr  Ser  Phe  Gly  Ser  His  Asn  Arg  Ala
          275                      280                     285

GGC  GTG  CGG  CAA  CTA  TTC  GCC  TTA  GAC  CTT  GTA  ACC  GGG  ATG  CTG  ACA               1029
Gly  Val  Arg  Gln  Leu  Phe  Ala  Leu  Asp  Leu  Val  Thr  Gly  Met  Leu  Thr
290                      295                     300                     305

ATC  AAG  GGT  CGG  CTG  GAC  TTC  GAG  GAC  ACC  AAA  CTC  CAT  GAG  ATT  TAC               1077
Ile  Lys  Gly  Arg  Leu  Asp  Phe  Glu  Asp  Thr  Lys  Leu  His  Glu  Ile  Tyr
                         310                     315                     320

ATC  CAG  GCC  AAA  GAC  AAG  GGC  GCC  AAT  CCC  GAA  GGA  GCA  CAT  TGC  AAA               1125
Ile  Gln  Ala  Lys  Asp  Lys  Gly  Ala  Asn  Pro  Glu  Gly  Ala  His  Cys  Lys
               325                      330                     335

GTG  TTG  GTG  GAG  GTT  GTG  GAT  GTG  AAT  GAC  AAC  GCC  CCG  GAG  ATC  ACA               1173
Val  Leu  Val  Glu  Val  Val  Asp  Val  Asn  Asp  Asn  Ala  Pro  Glu  Ile  Thr
               340                      345                     350

GTC  ACC  TCC  GTG  TAC  AGC  CCA  GTA  CCC  GAG  GAT  GCC  TCT  GGG  ACT  GTC               1221
Val  Thr  Ser  Val  Tyr  Ser  Pro  Val  Pro  Glu  Asp  Ala  Ser  Gly  Thr  Val
     355                      360                     365

ATC  GCT  TTG  CTC  AGT  GTG  ACT  GAC  CTG  GAT  GCT  GGC  GAG  AAC  GGG  CTG               1269
Ile  Ala  Leu  Leu  Ser  Val  Thr  Asp  Leu  Asp  Ala  Gly  Glu  Asn  Gly  Leu
370                      375                     380                     385

GTG  ACC  TGC  GAA  GTT  CCA  CCG  GGT  CTC  CCT  TTC  AGC  CTT  ACT  TCT  TCC               1317
Val  Thr  Cys  Glu  Val  Pro  Pro  Gly  Leu  Pro  Phe  Ser  Leu  Thr  Ser  Ser
                         390                     395                     400

CTC  AAG  AAT  TAC  TTC  ACT  TTG  AAA  ACC  AGT  GCA  GAC  CTG  GAT  CGG  GAG               1365
Leu  Lys  Asn  Tyr  Phe  Thr  Leu  Lys  Thr  Ser  Ala  Asp  Leu  Asp  Arg  Glu
               405                      410                     415

ACT  GTG  CCA  GAA  TAC  AAC  CTC  AGC  ATC  ACC  GCC  CGA  GAC  GCC  GGA  ACC               1413
Thr  Val  Pro  Glu  Tyr  Asn  Leu  Ser  Ile  Thr  Ala  Arg  Asp  Ala  Gly  Thr
               420                      425                     430

CCT  TCC  CTC  TCA  GCC  CTT  ACA  ATA  GTG  CGT  GTT  CAA  GTG  TCC  GAC  ATC               1461
Pro  Ser  Leu  Ser  Ala  Leu  Thr  Ile  Val  Arg  Val  Gln  Val  Ser  Asp  Ile
               435                      440                     445

AAT  GAC  AAC  CCT  CCA  CAA  TCT  TCT  CAA  TCT  TCC  TAC  GAC  GTT  TAC  ATT               1509
Asn  Asp  Asn  Pro  Pro  Gln  Ser  Ser  Gln  Ser  Ser  Tyr  Asp  Val  Tyr  Ile
450                      455                     460                     465

GAA  GAA  AAC  AAC  CTC  CCC  GGG  GCT  CCA  ATA  CTA  AAC  CTA  AGT  GTC  TGG               1557
Glu  Glu  Asn  Asn  Leu  Pro  Gly  Ala  Pro  Ile  Leu  Asn  Leu  Ser  Val  Trp
                         470                     475                     480

GAC  CCC  GAC  GCC  CCG  CAG  AAT  GCT  CGG  CTT  TCT  TTC  TTT  CTC  TTG  GAG               1605
```

-continued

| | | | | | | | | | | | | | | | | |
|---|---|---|---|---|---|---|---|---|---|---|---|---|---|---|---|---|
| Asp | Pro | Asp | Ala | Pro | Gln | Asn | Ala | Arg | Leu | Ser | Phe | Phe | Leu | Leu | Glu | |
| | | | 485 | | | | 490 | | | | | | 495 | | | |
| CAA | GGA | GCT | GAA | ACC | GGG | CTA | GTG | GGT | CGC | TAT | TTC | ACA | ATA | AAT | CGT | 1653 |
| Gln | Gly | Ala | Glu | Thr | Gly | Leu | Val | Gly | Arg | Tyr | Phe | Thr | Ile | Asn | Arg | |
| | | 500 | | | | 505 | | | | | | 510 | | | | |
| GAC | AAT | GGC | ATA | GTG | TCA | TCC | TTA | GTG | CCC | CTA | GAC | TAT | GAG | GAT | CGG | 1701 |
| Asp | Asn | Gly | Ile | Val | Ser | Ser | Leu | Val | Pro | Leu | Asp | Tyr | Glu | Asp | Arg | |
| | 515 | | | | | 520 | | | | | 525 | | | | | |
| CGG | GAA | TTT | GAA | TTA | ACA | GCT | CAT | ATC | AGC | GAT | GGG | GGC | ACC | CCG | GTC | 1749 |
| Arg | Glu | Phe | Glu | Leu | Thr | Ala | His | Ile | Ser | Asp | Gly | Gly | Thr | Pro | Val | |
| 530 | | | | | 535 | | | | | 540 | | | | | 545 | |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile | Ser | Val | Asn | Ile | Phe | Val | Thr | Asp | Arg | Asn | Asp | |
| | | | | 550 | | | | | 555 | | | | | 560 | | |
| AAT | GCC | CCC | CAG | GTC | CTA | TAT | CCT | CGG | CCA | GGT | GGG | AGC | TCG | GTG | GAG | 1845 |
| Asn | Ala | Pro | Gln | Val | Leu | Tyr | Pro | Arg | Pro | Gly | Gly | Ser | Ser | Val | Glu | |
| | | | 565 | | | | | 570 | | | | | 575 | | | |
| ATG | CTG | CCT | CGA | GGT | ACC | TCA | GCT | GGC | CAC | CTA | GTG | TCA | CGG | GTG | GTA | 1893 |
| Met | Leu | Pro | Arg | Gly | Thr | Ser | Ala | Gly | His | Leu | Val | Ser | Arg | Val | Val | |
| | | 580 | | | | | 585 | | | | | 590 | | | | |
| GGC | TGG | GAC | GCG | GAT | GCA | GGG | CAC | AAT | GCC | TGG | CTC | TCC | TAC | AGT | CTC | 1941 |
| Gly | Trp | Asp | Ala | Asp | Ala | Gly | His | Asn | Ala | Trp | Leu | Ser | Tyr | Ser | Leu | |
| | 595 | | | | | 600 | | | | | 605 | | | | | |
| TTT | GGA | TCC | CCT | AAC | CAG | AGC | CTT | TTT | GCC | ATA | GGG | CTG | CAC | ACT | GGT | 1989 |
| Phe | Gly | Ser | Pro | Asn | Gln | Ser | Leu | Phe | Ala | Ile | Gly | Leu | His | Thr | Gly | |
| 610 | | | | | 615 | | | | | 620 | | | | | 625 | |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala | Arg | Pro | Val | Gln | Asp | Thr | Asp | Ser | Pro | Arg | Gln | |
| | | | | 630 | | | | | 635 | | | | | 640 | | |
| ACT | CTC | ACT | GTC | TTG | ATC | AAA | GAC | AAT | GGG | GAG | CCT | TCG | CTC | TCC | ACC | 2085 |
| Thr | Leu | Thr | Val | Leu | Ile | Lys | Asp | Asn | Gly | Glu | Pro | Ser | Leu | Ser | Thr | |
| | | | 645 | | | | | 650 | | | | | 655 | | | |
| ACT | GCT | ACC | CTC | ACT | GTG | TCA | GTA | ACC | GAG | GAC | TCT | CCT | GAA | GCC | CGA | 2133 |
| Thr | Ala | Thr | Leu | Thr | Val | Ser | Val | Thr | Glu | Asp | Ser | Pro | Glu | Ala | Arg | |
| | | 660 | | | | | 665 | | | | | 670 | | | | |
| GCC | GAG | TTC | CCC | TCT | GGC | TCT | GCC | CCC | CGG | GAG | CAG | AAA | AAA | AAT | CTC | 2181 |
| Ala | Glu | Phe | Pro | Ser | Gly | Ser | Ala | Pro | Arg | Glu | Gln | Lys | Lys | Asn | Leu | |
| | 675 | | | | | 680 | | | | | 685 | | | | | |
| ACC | TTT | TAT | CTA | CTT | CTT | TCT | CTA | ATC | CTG | GTT | TCT | GTG | GGC | TTC | GTG | 2229 |
| Thr | Phe | Tyr | Leu | Leu | Leu | Ser | Leu | Ile | Leu | Val | Ser | Val | Gly | Phe | Val | |
| 690 | | | | | 695 | | | | | 700 | | | | | 705 | |
| GTC | ACA | GTG | TTC | GGA | GTA | ATC | ATA | TTC | AAA | GTT | TAC | AAG | TGG | AAG | CAG | 2277 |
| Val | Thr | Val | Phe | Gly | Val | Ile | Ile | Phe | Lys | Val | Tyr | Lys | Trp | Lys | Gln | |
| | | | | 710 | | | | | 715 | | | | | 720 | | |
| TCT | AGA | GAC | CTA | TAC | CGA | GCC | CCG | GTG | AGC | TCA | CTG | TAC | CGA | ACA | CCA | 2325 |
| Ser | Arg | Asp | Leu | Tyr | Arg | Ala | Pro | Val | Ser | Ser | Leu | Tyr | Arg | Thr | Pro | |
| | | | 725 | | | | | 730 | | | | | 735 | | | |
| GGG | CCC | TCC | TTG | CAC | GCG | GAC | GCC | GTG | CGG | GGA | GGC | CTG | ATG | TCG | CCG | 2373 |
| Gly | Pro | Ser | Leu | His | Ala | Asp | Ala | Val | Arg | Gly | Gly | Leu | Met | Ser | Pro | |
| | | 740 | | | | | 745 | | | | | 750 | | | | |
| CAC | CTT | TAC | CAT | CAG | GTG | TAT | CTC | ACC | ACG | GAC | TCC | CGC | CGC | AGC | GAC | 2421 |
| His | Leu | Tyr | His | Gln | Val | Tyr | Leu | Thr | Thr | Asp | Ser | Arg | Arg | Ser | Asp | |
| | 755 | | | | | 760 | | | | | 765 | | | | | |
| CCG | CTG | CTG | AAG | AAA | CCT | GGT | GCA | GCC | AGT | CCA | CTG | GCC | AGC | CGC | CAG | 2469 |
| Pro | Leu | Leu | Lys | Lys | Pro | Gly | Ala | Ala | Ser | Pro | Leu | Ala | Ser | Arg | Gln | |
| 770 | | | | | 775 | | | | | 780 | | | | | 785 | |
| AAC | ACG | CTG | CGG | AGC | TGT | GAT | CCG | GTG | TTC | TAT | AGG | CAG | GTG | TTG | GGT | 2517 |
| Asn | Thr | Leu | Arg | Ser | Cys | Asp | Pro | Val | Phe | Tyr | Arg | Gln | Val | Leu | Gly | |
| | | | | 790 | | | | | 795 | | | | | 800 | | |
| GCA | GAG | AGC | GCC | CCT | CCC | GGA | CAG | CAA | GCC | CCG | CCC | AAC | ACG | GAC | TGG | 2565 |

| | | | | | | | | | | | | | | |
|---|---|---|---|---|---|---|---|---|---|---|---|---|---|---|
| Ala | Glu | Ser | Ala | Pro | Pro | Gly | Gln | Gln | Ala | Pro | Pro | Asn | Thr | Asp | Trp |
| | | | 805 | | | | | 810 | | | | 815 | | | |

```
CGT TTC TCT CAG GCC CAG AGA CCC GGC ACC AGC GGC TCC CAA AAT GGC    2613
Arg Phe Ser Gln Ala Gln Arg Pro Gly Thr Ser Gly Ser Gln Asn Gly
        820                 825                 830

GAT GAC ACC GGC ACC TGG CCC AAC AAC CAG TTT GAC ACA GAG ATG CTG    2661
Asp Asp Thr Gly Thr Trp Pro Asn Asn Gln Phe Asp Thr Glu Met Leu
    835                 840                 845

CAA GCC ATG ATC TTG GCG TCC GCC AGT GAA GCT GCT GAT GGG AGC TCC    2709
Gln Ala Met Ile Leu Ala Ser Ala Ser Glu Ala Ala Asp Gly Ser Ser
850                 855                 860                 865

ACC CTG GGA GGG GGT GCC GGC ACC ATG GGA TTG AGC GCC CGC TAC GGA    2757
Thr Leu Gly Gly Gly Ala Gly Thr Met Gly Leu Ser Ala Arg Tyr Gly
                870                 875                 880

CCC CAG TTC ACC CTG CAG CAC GTG CCC GAC TAC CGC CAG AAT GTC TAC    2805
Pro Gln Phe Thr Leu Gln His Val Pro Asp Tyr Arg Gln Asn Val Tyr
            885                 890                 895

ATC CCA GGC AGC AAT GCA CAC T GACCAACGCA GCTGGCAAGC GGATGGCAAG     2857
Ile Pro Gly Ser Asn Ala His
            900
```

| | | |
|---|---|---|
| GCCCAGCAGG TGGCAATGGC AACAAGAAGA AGTCGGCAAG AAGGAGAAGA AGTAACATGG | 2917 |
| AGGCCAGGCC AAGAGCCACA GGGCAGCCTC TCCCCGAACC AGCCCAGCTT CTCCTTACCT | 2977 |
| GCACCCAGGC CTCAGAGTTT CAGGGCTAAC CCCCAGAATA CTGGTAGGGG CCAAGGCATC | 3037 |
| TCCCTTGGAA ACAGAAACAA GTGCCATCAC ACCATCCCTT CCCCAGGTGT AATATCCAAA | 3097 |
| GCAGTTCCGC TGGGAACCCC ATCCAATCAG TGGCTGTACC CATTTGGGTA GTGGGGTTCA | 3157 |
| TGTAGACACC AAGAACCATT TGCCACACCC CGTTTAGTTA CAGCTGAACC CTCCATCTTC | 3217 |
| CAAATCAATC AGGCCCATCC ATCCCATGCC TCCCTCCTCC CCACCCCACT CCAACAGTTC | 3277 |
| CTCTTTCCCG AGTAAGGTGG TTGGGGTGTT GAAGTACCAA GTAACCTACA AGCCTCCTAG | 3337 |
| TTCTGAAAAG TTGGAAGGGC ATCATGACCT CTTGGCCTCT CCTTTGATTC TCAATCTTCC | 3397 |
| CCCAAAGCAT GGTTTGGTGC CAGCCCCTTC ACCTCCTTCC AGAGCCCAAG ATCAATGCTC | 3457 |
| AAGTTTTGGA GGACATGATC ACCATCCCCA TGGTACTGAT GCTTGCTGGA TTTAGGGAGG | 3517 |
| GCATTTTGCT ACCAAGCCTC TTCCCAACGC CCTGGGACCA GTCTTCTGTT TTGTTTTTCA | 3577 |
| TTGTTTGAGC TTTCCACTGC ATGCCTTGAC TTCCCCCACC TCCTCCTCAA ACAAGAGACT | 3637 |
| CCACTGCATG TTCCAAGACA GTATGGGGTG GTAAGATAAG GAAGGGAAGT GTGTGGATGT | 3697 |
| GGATGGTGGG GGCATGGACA AAGCTTGACA CATCAAGTTA TCAAGGCCTT GGAGGAGGCT | 3757 |
| CTGTATGTCC TCAGGGACT GACAACATCC TCCAGATTCC AGCCATAAAC CAATAACTAG | 3817 |
| GCTGGACCCT TCCCACTACA TAATAGGGCT CAGCCAGGCA GCCAGCTTTG GCTGAGCTA | 3877 |
| ACAGGACCAA TGGATTAACT GGCATTTCAG TCCAAGGAAG CTCGAAGCAG GTTAGGACC | 3937 |
| AGGTCCCCTT GAGAGGTCAG AGGGGCCTCT GTGGGTGCTG GGTACTCCAG AGGTGCCACT | 3997 |
| GGTGGAAGGG TCAGCGGAGC CCCAGCAGGA AGGGTGGGCC AGCCAGGCCA TTCTTAGTCC | 4057 |
| CTGGGTTGGG GAGGCAGGGA GCTAGGGCAG GGACCAAATG AACAGAAAGT CTCAGCCCAG | 4117 |
| GATGGGCTT CTTCAACAGG CCCCTGCCCT CCTGAAGCCT CAGTCCTTCA CCTTGCCAGG | 4177 |
| TGCCGTTTCT CTTCCGTGAA GGCCACTGCC CAGGTCCCCA GTGCGCCCCC TAGTGGCCAT | 4237 |
| AGCCTGGTTA AAGTTCCCCA GTGCCTCCTT GTGATAGACC TTCTTCTCCC ACCCCCTTCT | 4297 |
| GCCCCTGGGT CCCCGGCCAT CCAGCGGGGC TGCCAGAGAA CCCCAGACCT GCCCTTACAG | 4357 |
| TAGTGTAGCG CCCCCTCCCT CTTTCGGCTG GTGTAGAATA GCCAGTAGTG TAGTGCGGTG | 4417 |
| TGCTTTTACG TGATGGCGGG TGGGCAGCGG GCGGCGGCGT CCGCGCAGCC GTCTGTCCTT | 4477 |

```
GATCTGCCCG    CGGCGGCCCG    TGTTGTGTTT    TGTGCTGTGT    CCAGCGCTAA    GGCGACCCCC        4537

TCCCCCGTAC    TGACTTCTCC    TATAAGCGCT    TCTCTTCGCA    TAGTCACGTA    GCTCCCACCC        4597

CACCCTCTTC    CTGTGTCTCA    CGCAAGTTTT    ATACTCTAAT    ATTTATATGG    CTTTTTTTCT        4657

TCGACAAAAA    AATAATAAAA    CGTTTCTTCT    GAAAAAAAAA    AAAAAAA                         4705
```

( 2 ) INFORMATION FOR SEQ ID NO:97:

( i ) SEQUENCE CHARACTERISTICS:
        ( A ) LENGTH: 904 amino acids
        ( B ) TYPE: amino acid
        ( D ) TOPOLOGY: linear ( i i ) MOLECULE TYPE: protein ( x i ) SEQUENCE DESCRIPTION: SEQ ID NO:97:

```
Met    Val    Pro    Glu    Ala    Trp    Arg    Ser    Gly    Leu    Val    Ser    Thr    Gly    Arg    Val
  1                           5                                        10                                  15

Val    Gly    Val    Leu    Leu    Leu    Leu    Gly    Ala    Leu    Asn    Lys    Ala    Ser    Thr    Val
                              20                                        25                       30

Ile    His    Tyr    Glu    Ile    Pro    Glu    Glu    Arg    Glu    Lys    Gly    Phe    Ala    Val    Gly
                 35                                    40                              45

Asn    Val    Val    Ala    Asn    Leu    Gly    Leu    Asp    Leu    Gly    Ser    Leu    Ser    Ala    Arg
        50                                    55                              60

Arg    Phe    Pro    Val    Val    Ser    Gly    Ala    Ser    Arg    Arg    Phe    Phe    Glu    Val    Asn
 65                                    70                    75                                          80

Arg    Glu    Thr    Gly    Glu    Met    Phe    Val    Asn    Asp    Arg    Leu    Asp    Arg    Glu    Glu
                              85                             90                             95

Leu    Cys    Gly    Thr    Leu    Pro    Ser    Cys    Thr    Val    Thr    Leu    Glu    Leu    Val    Val
                             100                           105                          110

Glu    Asn    Pro    Leu    Glu    Leu    Phe    Ser    Val    Glu    Val    Val    Ile    Gln    Asp    Ile
                    115                           120                          125

Asn    Asp    Asn    Asn    Pro    Ala    Phe    Pro    Thr    Gln    Glu    Met    Lys    Leu    Glu    Ile
       130                           135                          140

Ser    Glu    Ala    Val    Ala    Pro    Gly    Thr    Arg    Phe    Pro    Leu    Glu    Ser    Ala    His
145                                  150                          155                                 160

Asp    Pro    Asp    Leu    Gly    Ser    Asn    Ser    Leu    Gln    Thr    Tyr    Glu    Leu    Ser    Arg
                             165                           170                          175

Asn    Glu    Tyr    Phe    Ala    Leu    Arg    Val    Gln    Thr    Arg    Glu    Asp    Ser    Thr    Lys
                    180                           185                          190

Tyr    Ala    Glu    Leu    Val    Leu    Glu    Arg    Ala    Leu    Asp    Arg    Glu    Arg    Glu    Pro
              195                           200                          205

Ser    Leu    Gln    Leu    Val    Leu    Thr    Ala    Leu    Asp    Gly    Gly    Thr    Pro    Ala    Leu
210                                  215                          220

Ser    Ala    Ser    Leu    Pro    Ile    His    Ile    Lys    Val    Leu    Asp    Ala    Asn    Asp    Asn
225                                  230                          235                                 240

Ala    Pro    Val    Phe    Asn    Gln    Ser    Leu    Tyr    Arg    Ala    Arg    Val    Pro    Gly    Gly
                             245                           250                          255

Cys    Thr    Ser    Gly    Thr    Arg    Val    Val    Gln    Val    Leu    Ala    Thr    Asp    Leu    Asp
                     260                           265                          270

Glu    Gly    Pro    Asn    Gly    Glu    Ile    Ile    Tyr    Ser    Phe    Gly    Ser    His    Asn    Arg
              275                           280                          285

Ala    Gly    Val    Arg    Gln    Leu    Phe    Ala    Leu    Asp    Leu    Val    Thr    Gly    Met    Leu
       290                           295                          300

Thr    Ile    Lys    Gly    Arg    Leu    Asp    Phe    Glu    Asp    Thr    Lys    Leu    His    Glu    Ile
305                                  310                          315                                 320
```

| | | | | | | | | | | | | | | |
|---|---|---|---|---|---|---|---|---|---|---|---|---|---|---|
| Tyr | Ile | Gln | Ala | Lys<br>325 | Asp | Lys | Gly | Ala | Asn<br>330 | Pro | Glu | Gly | Ala | His<br>335 | Cys |
| Lys | Val | Leu | Val<br>340 | Glu | Val | Val | Asp<br>345 | Val | Asn | Asp | Asn | Ala<br>350 | Pro | Glu | Ile |
| Thr | Val | Thr<br>355 | Ser | Val | Tyr | Ser | Pro<br>360 | Val | Pro | Glu | Asp | Ala<br>365 | Ser | Gly | Thr |
| Val | Ile<br>370 | Ala | Leu | Leu | Ser | Val<br>375 | Thr | Asp | Leu | Asp | Ala<br>380 | Gly | Glu | Asn | Gly |
| Leu<br>385 | Val | Thr | Cys | Glu | Val<br>390 | Pro | Pro | Gly | Leu | Pro<br>395 | Phe | Ser | Leu | Thr | Ser<br>400 |
| Ser | Leu | Lys | Asn | Tyr<br>405 | Phe | Thr | Leu | Lys | Thr<br>410 | Ser | Ala | Asp | Leu | Asp<br>415 | Arg |
| Glu | Thr | Val | Pro<br>420 | Glu | Tyr | Asn | Leu | Ser<br>425 | Ile | Thr | Ala | Arg | Asp<br>430 | Ala | Gly |
| Thr | Pro | Ser<br>435 | Leu | Ser | Ala | Leu | Thr<br>440 | Ile | Val | Arg | Val | Gln<br>445 | Val | Ser | Asp |
| Ile | Asn<br>450 | Asp | Asn | Pro | Pro | Gln<br>455 | Ser | Ser | Gln | Ser | Ser<br>460 | Tyr | Asp | Val | Tyr |
| Ile<br>465 | Glu | Glu | Asn | Asn | Leu<br>470 | Pro | Gly | Ala | Pro | Ile<br>475 | Leu | Asn | Leu | Ser | Val<br>480 |
| Trp | Asp | Pro | Asp | Ala<br>485 | Pro | Gln | Asn | Ala | Arg<br>490 | Leu | Ser | Phe | Phe | Leu<br>495 | Leu |
| Glu | Gln | Gly | Ala<br>500 | Glu | Thr | Gly | Leu | Val<br>505 | Gly | Arg | Tyr | Phe | Thr<br>510 | Ile | Asn |
| Arg | Asp | Asn<br>515 | Gly | Ile | Val | Ser | Ser<br>520 | Leu | Val | Pro | Leu | Asp<br>525 | Tyr | Glu | Asp |
| Arg | Arg<br>530 | Glu | Phe | Glu | Leu | Thr<br>535 | Ala | His | Ile | Ser | Asp<br>540 | Gly | Gly | Thr | Pro |
| Val<br>545 | Leu | Ala | Thr | Asn | Ile<br>550 | Ser | Val | Asn | Ile | Phe<br>555 | Val | Thr | Asp | Arg | Asn<br>560 |
| Asp | Asn | Ala | Pro | Gln<br>565 | Val | Leu | Tyr | Pro | Arg<br>570 | Pro | Gly | Gly | Ser | Ser<br>575 | Val |
| Glu | Met | Leu | Pro<br>580 | Arg | Gly | Thr | Ser | Ala<br>585 | Gly | His | Leu | Val | Ser<br>590 | Arg | Val |
| Val | Gly | Trp<br>595 | Asp | Ala | Asp | Ala | Gly<br>600 | His | Asn | Ala | Trp | Leu<br>605 | Ser | Tyr | Ser |
| Leu | Phe<br>610 | Gly | Ser | Pro | Asn | Gln<br>615 | Ser | Leu | Phe | Ala | Ile<br>620 | Gly | Leu | His | Thr |
| Gly<br>625 | Gln | Ile | Ser | Thr | Ala<br>630 | Arg | Pro | Val | Gln | Asp<br>635 | Thr | Asp | Ser | Pro | Arg<br>640 |
| Gln | Thr | Leu | Thr | Val<br>645 | Leu | Ile | Lys | Asp | Asn<br>650 | Gly | Glu | Pro | Ser | Leu<br>655 | Ser |
| Thr | Thr | Ala | Thr<br>660 | Leu | Thr | Val | Ser | Val<br>665 | Thr | Glu | Asp | Ser | Pro<br>670 | Glu | Ala |
| Arg | Ala | Glu<br>675 | Phe | Pro | Ser | Gly | Ser<br>680 | Ala | Pro | Arg | Glu | Gln<br>685 | Lys | Lys | Asn |
| Leu | Thr<br>690 | Phe | Tyr | Leu | Leu | Leu<br>695 | Ser | Leu | Ile | Leu | Val<br>700 | Ser | Val | Gly | Phe |
| Val<br>705 | Val | Thr | Val | Phe | Gly<br>710 | Val | Ile | Ile | Phe | Lys<br>715 | Val | Tyr | Lys | Trp | Lys<br>720 |
| Gln | Ser | Arg | Asp | Leu<br>725 | Tyr | Arg | Ala | Pro | Val<br>730 | Ser | Ser | Leu | Tyr | Arg<br>735 | Thr |
| Pro | Gly | Pro | Ser | Leu | His | Ala | Asp | Ala | Val | Arg | Gly | Gly | Leu | Met | Ser |

|   |   |   |   |   | 740 |   |   |   |   | 745 |   |   |   |   | 750 |   |   |
|---|---|---|---|---|---|---|---|---|---|---|---|---|---|---|---|---|---|

Pro His Leu Tyr His Gln Val Tyr Leu Thr Thr Asp Ser Arg Arg Ser
            755             760             765

Asp Pro Leu Leu Lys Lys Pro Gly Ala Ala Ser Pro Leu Ala Ser Arg
    770             775             780

Gln Asn Thr Leu Arg Ser Cys Asp Pro Val Phe Tyr Arg Gln Val Leu
785             790             795             800

Gly Ala Glu Ser Ala Pro Pro Gly Gln Gln Ala Pro Pro Asn Thr Asp
                805             810             815

Trp Arg Phe Ser Gln Ala Gln Arg Pro Gly Thr Ser Gly Ser Gln Asn
            820             825             830

Gly Asp Asp Thr Gly Thr Trp Pro Asn Asn Gln Phe Asp Thr Glu Met
        835             840             845

Leu Gln Ala Met Ile Leu Ala Ser Ala Ser Glu Ala Ala Asp Gly Ser
    850             855             860

Ser Thr Leu Gly Gly Gly Ala Gly Thr Met Gly Leu Ser Ala Arg Tyr
865             870             875             880

Gly Pro Gln Phe Thr Leu Gln His Val Pro Asp Tyr Arg Gln Asn Val
            885             890             895

Tyr Ile Pro Gly Ser Asn Ala His
        900

( 2 ) INFORMATION FOR SEQ ID NO:98:

( i ) SEQUENCE CHARACTERISTICS:
        ( A ) LENGTH: 555 amino acids
        ( B ) TYPE: amino acid
        ( D ) TOPOLOGY: linear ( i i ) MOLECULE TYPE: protein ( x i ) SEQUENCE DESCRIPTION: SEQ ID NO:98:

Asp Trp Val Ile Pro Pro Ile Asn Leu Pro Glu Asn Ser Arg Gly Pro
1               5               10              15

Phe Pro Gln Glu Leu Val Arg Ile Arg Ser Asp Arg Asp Lys Asn Leu
            20              25              30

Ser Leu Arg Tyr Ser Val Thr Gly Pro Gly Ala Asp Gln Pro Pro Thr
        35              40              45

Gly Ile Phe Ile Ile Asn Pro Ile Ser Gly Gln Leu Ser Val Thr Lys
    50              55              60

Pro Leu Asp Arg Glu Leu Ile Ala Arg Phe His Leu Arg Ala His Ala
65              70              75              80

Val Asp Ile Asn Gly Asn Gln Val Glu Asn Pro Ile Asp Ile Val Ile
            85              90              95

Asn Val Ile Asp Met Asn Asp Asn Arg Pro Glu Phe Leu His Gln Val
        100             105             110

Trp Asn Gly Ser Val Pro Glu Gly Ser Lys Pro Gly Thr Tyr Val Met
    115             120             125

Thr Val Thr Ala Ile Asp Ala Asp Pro Asn Ala Leu Asn Gly Met
130             135             140

Leu Arg Tyr Arg Ile Leu Ser Gln Ala Pro Ser Thr Pro Ser Pro Asn
145             150             155             160

Met Phe Thr Ile Asn Asn Glu Thr Gly Asp Ile Ile Thr Val Ala Ala
            165             170             175

Gly Leu Asp Arg Glu Lys Val Gln Gln Tyr Thr Leu Ile Ile Gln Ala
        180             185             190

| | | | | | | | | | | | | | | |
|---|---|---|---|---|---|---|---|---|---|---|---|---|---|---|
| Thr | Asp | Met | Glu | Gly | Asn | Pro | Thr | Tyr | Gly | Leu | Ser | Asn | Thr | Ala | Thr |
| | | 195 | | | | 200 | | | | | 205 | | | | |
| Ala | Val | Ile | Thr | Val | Thr | Asp | Val | Asn | Asp | Asn | Pro | Pro | Glu | Phe | Thr |
| | 210 | | | | 215 | | | | | 220 | | | | | |
| Ala | Met | Thr | Phe | Tyr | Gly | Glu | Val | Pro | Glu | Asn | Arg | Val | Asp | Val | Ile |
| 225 | | | | | 230 | | | | | 235 | | | | | 240 |
| Val | Ala | Asn | Leu | Thr | Val | Thr | Asp | Lys | Asp | Gln | Pro | His | Thr | Pro | Ala |
| | | | | 245 | | | | | 250 | | | | | 255 | |
| Trp | Asn | Ala | Ala | Tyr | Arg | Ile | Ser | Gly | Gly | Asp | Pro | Thr | Gly | Arg | Phe |
| | | | 260 | | | | | 265 | | | | | 270 | | |
| Ala | Ile | Leu | Thr | Asp | Pro | Asn | Ser | Asn | Asp | Gly | Leu | Val | Thr | Val | Val |
| | | 275 | | | | | 280 | | | | | 285 | | | |
| Lys | Pro | Ile | Asp | Phe | Glu | Thr | Asn | Arg | Met | Phe | Val | Leu | Thr | Val | Ala |
| | 290 | | | | | 295 | | | | | 300 | | | | |
| Ala | Glu | Asn | Gln | Val | Pro | Leu | Ala | Lys | Gly | Ile | Gln | His | Pro | Pro | Gln |
| 305 | | | | | 310 | | | | | 315 | | | | | 320 |
| Ser | Thr | Ala | Thr | Val | Ser | Val | Thr | Val | Ile | Asp | Val | Asn | Glu | Asn | Pro |
| | | | | 325 | | | | | 330 | | | | | 335 | |
| Tyr | Phe | Ala | Pro | Asn | Pro | Lys | Ile | Ile | Arg | Gln | Glu | Glu | Gly | Leu | His |
| | | | 340 | | | | | 345 | | | | | 350 | | |
| Ala | Gly | Thr | Met | Leu | Thr | Thr | Leu | Thr | Ala | Gln | Asp | Pro | Asp | Arg | Tyr |
| | | 355 | | | | | 360 | | | | | 365 | | | |
| Met | Gln | Gln | Asn | Ile | Arg | Tyr | Thr | Lys | Leu | Ser | Asp | Pro | Ala | Asn | Trp |
| | 370 | | | | | 375 | | | | | 380 | | | | |
| Leu | Lys | Ile | Asp | Pro | Val | Asn | Gly | Gln | Ile | Thr | Thr | Ile | Ala | Val | Leu |
| 385 | | | | | 390 | | | | | 395 | | | | | 400 |
| Asp | Arg | Glu | Ser | Pro | Tyr | Val | Gln | Asn | Asn | Ile | Tyr | Asn | Ala | Thr | Phe |
| | | | | 405 | | | | | 410 | | | | | 415 | |
| Leu | Ala | Ser | Asp | Asn | Gly | Ile | Pro | Pro | Met | Ser | Gly | Thr | Gly | Thr | Leu |
| | | | 420 | | | | | 425 | | | | | 430 | | |
| Gln | Ile | Tyr | Leu | Leu | Asp | Ile | Asn | Asp | Asn | Ala | Pro | Gln | Val | Leu | Pro |
| | | 435 | | | | | 440 | | | | | 445 | | | |
| Gln | Glu | Ala | Glu | Thr | Cys | Glu | Thr | Pro | Glu | Pro | Asn | Ser | Ile | Asn | Ile |
| | 450 | | | | | 455 | | | | | 460 | | | | |
| Ala | Ala | Leu | Asp | Tyr | Asp | Ile | Asp | Pro | Asn | Ala | Gly | Pro | Phe | Ala | Phe |
| 465 | | | | | 470 | | | | | 475 | | | | | 480 |
| Asp | Leu | Pro | Leu | Ser | Pro | Val | Thr | Ile | Lys | Arg | Asn | Trp | Thr | Ile | Asn |
| | | | | 485 | | | | | 490 | | | | | 495 | |
| Arg | Leu | Asn | Gly | Asp | Phe | Ala | Gln | Leu | Asn | Leu | Lys | Ile | Lys | Phe | Leu |
| | | | 500 | | | | | 505 | | | | | 510 | | |
| Glu | Ala | Gly | Ile | Tyr | Glu | Val | Pro | Ile | Ile | Ile | Thr | Asp | Ser | Gly | Asn |
| | | 515 | | | | | 520 | | | | | 525 | | | |
| Pro | Pro | Lys | Ser | Asn | Ile | Ser | Ile | Leu | Arg | Val | Lys | Val | Cys | Gln | Cys |
| | 530 | | | | | 535 | | | | | 540 | | | | |
| Asp | Ser | Asn | Gly | Asp | Cys | Thr | Asp | Val | Asp | Arg | | | | | |
| 545 | | | | | 550 | | | | | 555 | | | | | |

( 2 ) INFORMATION FOR SEQ ID NO:99:

( i ) SEQUENCE CHARACTERISTICS:
        ( A ) LENGTH: 105 amino acids
        ( B ) TYPE: amino acid
        ( C ) STRANDEDNESS: single
        ( D ) TOPOLOGY: linear ( i i ) MOLECULE TYPE: protein -continued (x i) SEQUENCE DESCRIPTION: SEQ ID NO:99:

| Glu | Asp | Thr | Val | Tyr | Ser | Phe | Asp | Ile | Pro | Glu | Asn | Ala | Gln | Arg | Gly |
|---|---|---|---|---|---|---|---|---|---|---|---|---|---|---|---|
| 1 | | | | 5 | | | | | 10 | | | | | 15 | |

| Tyr | Gln | Val | Gly | Gln | Ile | Val | Ala | Arg | Asp | Ala | Asp | Leu | Gly | Gln | Asn |
|---|---|---|---|---|---|---|---|---|---|---|---|---|---|---|---|
| | | | 20 | | | | | 25 | | | | | 30 | | |

| Ala | Gln | Leu | Ser | Tyr | Gly | Val | Val | Ser | Asp | Trp | Ala | Asn | Asp | Val | Phe |
|---|---|---|---|---|---|---|---|---|---|---|---|---|---|---|---|
| | | 35 | | | | | 40 | | | | | 45 | | | |

| Ser | Leu | Asn | Pro | Gln | Thr | Gly | Met | Leu | Thr | Leu | Thr | Ala | Arg | Leu | Asp |
|---|---|---|---|---|---|---|---|---|---|---|---|---|---|---|---|
| | 50 | | | | | 55 | | | | | 60 | | | | |

| Tyr | Glu | Glu | Val | Gln | His | Tyr | Ile | Leu | Ile | Val | Gln | Ala | Gln | Asp | Asn |
|---|---|---|---|---|---|---|---|---|---|---|---|---|---|---|---|
| 65 | | | | | 70 | | | | | 75 | | | | | 80 |

| Gly | Gln | Pro | Ser | Leu | Ser | Thr | Thr | Ile | Thr | Val | Tyr | Cys | Asn | Val | Leu |
|---|---|---|---|---|---|---|---|---|---|---|---|---|---|---|---|
| | | | | 85 | | | | | 90 | | | | | 95 | |

| Asp | Leu | Asn | Asp | Asn | Ala | Pro | Ile | Phe |
|---|---|---|---|---|---|---|---|---|
| | | | 100 | | | | | 105 |

(2) INFORMATION FOR SEQ ID NO:100:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (x i) SEQUENCE DESCRIPTION: SEQ ID NO:100:

| Asp | Xaa | Asp | Xaa | Gly | Xaa | Asn |
|---|---|---|---|---|---|---|
| 1 | | | | 5 | | |

(2) INFORMATION FOR SEQ ID NO:101:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (x i) SEQUENCE DESCRIPTION: SEQ ID NO:101:

| Ala | Xaa | Asp | Xaa | Gly | Xaa | Pro |
|---|---|---|---|---|---|---|
| 1 | | | | 5 | | |

(2) INFORMATION FOR SEQ ID NO:102:

(i) SEQUENCE CHARACTERISTICS:
        (A) LENGTH: 4650 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 495..4103

(x i) SEQUENCE DESCRIPTION: SEQ ID NO:102:

| CCTCTATTCG | ACATTCTCTT | TGGATTGTTT | TGCTATAACT | TGAAATTTGG | GATGTCACAA | 60 |
| ACGAAACTGT | CATCTGTTTC | CGCCAAACTG | TGGTTCTGCT | AATCTCCCAG | GCTGGCAGCA | 120 |
| TTGGAGACTT | GCTGACTTCT | TTCATCCCCC | ACTCTTTTCA | CCTGAAATTC | CTTTCCTTGG | 180 |
| TTTTGCTCTA | AGTCCTATGC | TTCAGTCAGG | GGCCAACCAA | ATCTCACTGC | CTCCTTTTTA | 240 |

-continued

| | | | | |
|---|---|---|---|---|
| TCATGAAGCC | TTTGATCACT | GATAGTTCTT | TTTATATCTT | GAAAAATCAC CCTTCCCAGT | 300 |
| ACAGTTAATA | TTTAGTATCT | CTACTCATCT | TGGCACTTAC | TCACAGCTCC ATAATTCAGT | 360 |
| CGTTTTCGTA | CCTCTTCATG | GTGATGGGGA | GCCCTTTGGA | GGTGGTGACT GTGCTTTATA | 420 |
| CTCCTCATGA | TGCTTCACAT | GTGGCAGGCG | TGGAGTGCCC | GGAGGCGGCC CTCCTGATTC | 480 |

```
TGGGGCCTCC CAGG ATG GAG CCC CTG AGG CAC AGC CCA GGC CCT GGG GGG                530
              Met Glu Pro Leu Arg His Ser Pro Gly Pro Gly Gly
               1           5                  10

CAA CGG CTA CTG CTG CCC TCC ATG CTG CTA GCA CTG CTG CTC CTG CTG                578
Gln Arg Leu Leu Leu Pro Ser Met Leu Leu Ala Leu Leu Leu Leu Leu
         15              20                  25

GCT CCA TCC CCA GGC CAC GCC ACT CGG GTA GTG TAC AAG GTG CCG GAG                626
Ala Pro Ser Pro Gly His Ala Thr Arg Val Val Tyr Lys Val Pro Glu
     30              35                  40

GAA CAG CCA CCC AAC ACC CTC ATT GGG AGC CTC GCA GCC GAC TAT GGT                674
Glu Gln Pro Pro Asn Thr Leu Ile Gly Ser Leu Ala Ala Asp Tyr Gly
 45              50                  55                      60

TTT CCA GAT GTG GGG CAC CTG TAC AAG CTA GAG GTG GGT GCC CCG TAC                722
Phe Pro Asp Val Gly His Leu Tyr Lys Leu Glu Val Gly Ala Pro Tyr
                     65                  70                  75

CTT CGC GTG GAT GGC AAG ACA GGT GAC ATT TTC ACC ACC GAG ACC TCC                770
Leu Arg Val Asp Gly Lys Thr Gly Asp Ile Phe Thr Thr Glu Thr Ser
             80                  85                  90

ATC GAC CGT GAG GGG CTC CGT GAA TGC CAG AAC CAG CTC CCT GGT GAT                818
Ile Asp Arg Glu Gly Leu Arg Glu Cys Gln Asn Gln Leu Pro Gly Asp
         95                 100                 105

CCC TGC ATC CTG GAG TTT GAG GTA TCT ATC ACA GAC CTC GTG CAG AAT                866
Pro Cys Ile Leu Glu Phe Glu Val Ser Ile Thr Asp Leu Val Gln Asn
     110                 115                 120

GCG AGC CCC CGG CTG CTA GAG GGC CAG ATA GAA GTA CAA GAC ATC AAT                914
Ala Ser Pro Arg Leu Leu Glu Gly Gln Ile Glu Val Gln Asp Ile Asn
125                 130                 135                 140

GAC AAC ACA CCC AAC TTC GCC TCA CCA GTC ATC ACT CTG GCC ATC CCT                962
Asp Asn Thr Pro Asn Phe Ala Ser Pro Val Ile Thr Leu Ala Ile Pro
                 145                 150                 155

GAG AAC ACC AAC ATC GGC TCA CTC TTC CCC ATC CCG CTG GCT TCA GAC                1010
Glu Asn Thr Asn Ile Gly Ser Leu Phe Pro Ile Pro Leu Ala Ser Asp
             160                 165                 170

CGT GAT GCT GGT CCC AAC GGT GTG GCA TCC TAT GAG CTG CAG GTG GCA                1058
Arg Asp Ala Gly Pro Asn Gly Val Ala Ser Tyr Glu Leu Gln Val Ala
         175                 180                 185

GAG GAC CAG GAG GAG AAG CAA CCA CAG CTC ATT GTG ATG GGC AAC CTG                1106
Glu Asp Gln Glu Glu Lys Gln Pro Gln Leu Ile Val Met Gly Asn Leu
     190                 195                 200

GAC CGT GAG CGC TGG GAC TCC TAT GAC CTC ACC ATC AAG GTG CAG GAT                1154
Asp Arg Glu Arg Trp Asp Ser Tyr Asp Leu Thr Ile Lys Val Gln Asp
205                 210                 215                 220

GGC GGC AGC CCC CCA CGC GCC ACG AGT GCC CTG CTG CGT GTC ACC GTG                1202
Gly Gly Ser Pro Pro Arg Ala Thr Ser Ala Leu Leu Arg Val Thr Val
                 225                 230                 235

CTT GAC ACC AAT GAC AAC GCC CCC AAG TTT GAG CGG CCC TCC TAT GAG                1250
Leu Asp Thr Asn Asp Asn Ala Pro Lys Phe Glu Arg Pro Ser Tyr Glu
             240                 245                 250

GCC GAA CTA TCT GAG AAT AGC CCC ATA GGC CAC TCG GTC ATC CAG GTG                1298
Ala Glu Leu Ser Glu Asn Ser Pro Ile Gly His Ser Val Ile Gln Val
         255                 260                 265

AAG GCC AAT GAC TCA GAC CAA GGT GCC AAT GCA GAA ATC GAA TAC ACA                1346
Lys Ala Asn Asp Ser Asp Gln Gly Ala Asn Ala Glu Ile Glu Tyr Thr
     270                 275                 280
```

| | | | | | | | | | | | | | | | | |
|---|---|---|---|---|---|---|---|---|---|---|---|---|---|---|---|---|
| TTC | CAC | CAG | GCG | CCC | GAA | GTT | GTG | AGG | CGT | CTT | CTT | CGA | CTG | GAC | AGG | 1394 |
| Phe | His | Gln | Ala | Pro | Glu | Val | Val | Arg | Arg | Leu | Leu | Arg | Leu | Asp | Arg | |
| 285 | | | | 290 | | | | | 295 | | | | | | 300 | |
| AAC | ACT | GGA | CTT | ATC | ACT | GTT | CAG | GGC | CCG | GTG | GAC | CGT | GAG | GAC | CTA | 1442 |
| Asn | Thr | Gly | Leu | Ile | Thr | Val | Gln | Gly | Pro | Val | Asp | Arg | Glu | Asp | Leu | |
| | | | | 305 | | | | | 310 | | | | | 315 | | |
| AGC | ACC | CTG | CGC | TTC | TCA | GTG | CTT | GCT | AAG | GAC | CGA | GGC | ACC | AAC | CCC | 1490 |
| Ser | Thr | Leu | Arg | Phe | Ser | Val | Leu | Ala | Lys | Asp | Arg | Gly | Thr | Asn | Pro | |
| | | | 320 | | | | | 325 | | | | | 330 | | | |
| AAG | AGT | GCC | CGT | GCC | CAG | GTG | GTT | GTG | ACC | GTG | AAG | GAC | ATG | AAT | GAC | 1538 |
| Lys | Ser | Ala | Arg | Ala | Gln | Val | Val | Val | Thr | Val | Lys | Asp | Met | Asn | Asp | |
| | | 335 | | | | | 340 | | | | | 345 | | | | |
| AAT | GCC | CCC | ACC | ATT | GAG | ATC | CGG | GGC | ATA | GGG | CTA | GTG | ACT | CAT | CAA | 1586 |
| Asn | Ala | Pro | Thr | Ile | Glu | Ile | Arg | Gly | Ile | Gly | Leu | Val | Thr | His | Gln | |
| | 350 | | | | | 355 | | | | | 360 | | | | | |
| GAT | GGG | ATG | GCT | AAC | ATC | TCA | GAG | GAT | GTG | GCA | GAG | GAG | ACA | GCT | GTG | 1634 |
| Asp | Gly | Met | Ala | Asn | Ile | Ser | Glu | Asp | Val | Ala | Glu | Glu | Thr | Ala | Val | |
| 365 | | | | | 370 | | | | | 375 | | | | | 380 | |
| GCC | CTG | GTG | CAG | GTG | TCT | GAC | CGA | GAT | GAG | GGA | GAG | AAT | GCA | GCT | GTC | 1682 |
| Ala | Leu | Val | Gln | Val | Ser | Asp | Arg | Asp | Glu | Gly | Glu | Asn | Ala | Ala | Val | |
| | | | | 385 | | | | | 390 | | | | | 395 | | |
| ACC | TGT | GTG | GTG | GCA | GGT | GAT | GTG | CCC | TTC | CAG | CTG | CGC | CAG | GCC | AGT | 1730 |
| Thr | Cys | Val | Val | Ala | Gly | Asp | Val | Pro | Phe | Gln | Leu | Arg | Gln | Ala | Ser | |
| | | | 400 | | | | | 405 | | | | | 410 | | | |
| GAG | ACA | GGC | AGT | GAC | AGC | AAG | AAG | AAG | TAT | TTC | CTG | CAG | ACT | ACC | ACC | 1778 |
| Glu | Thr | Gly | Ser | Asp | Ser | Lys | Lys | Lys | Tyr | Phe | Leu | Gln | Thr | Thr | Thr | |
| | | 415 | | | | | 420 | | | | | 425 | | | | |
| CCG | CTA | GAC | TAC | GAG | AAG | GTC | AAA | GAC | TAC | ACC | ATT | GAG | ATT | GTG | GCT | 1826 |
| Pro | Leu | Asp | Tyr | Glu | Lys | Val | Lys | Asp | Tyr | Thr | Ile | Glu | Ile | Val | Ala | |
| | 430 | | | | | 435 | | | | | 440 | | | | | |
| GTG | GAC | TCT | GGC | AAC | CCC | CCA | CTC | TCC | AGC | ACT | AAC | TCC | CTC | AAG | GTG | 1874 |
| Val | Asp | Ser | Gly | Asn | Pro | Pro | Leu | Ser | Ser | Thr | Asn | Ser | Leu | Lys | Val | |
| 445 | | | | | 450 | | | | | 455 | | | | | 460 | |
| CAG | GTG | GTG | GAC | GTC | AAT | GAC | AAC | GCA | CCT | GTC | TTC | ACT | CAG | AGT | GTC | 1922 |
| Gln | Val | Val | Asp | Val | Asn | Asp | Asn | Ala | Pro | Val | Phe | Thr | Gln | Ser | Val | |
| | | | | 465 | | | | | 470 | | | | | 475 | | |
| ACT | GAG | GTC | GCC | TTC | CCG | GAA | AAC | AAC | AAG | CCT | GGT | GAA | GTG | ATT | GCT | 1970 |
| Thr | Glu | Val | Ala | Phe | Pro | Glu | Asn | Asn | Lys | Pro | Gly | Glu | Val | Ile | Ala | |
| | | | 480 | | | | | 485 | | | | | 490 | | | |
| GAG | ATC | ACT | GCC | AGT | GAT | GCT | GAC | TCT | GGC | TCT | AAT | GCT | GAG | CTG | GTT | 2018 |
| Glu | Ile | Thr | Ala | Ser | Asp | Ala | Asp | Ser | Gly | Ser | Asn | Ala | Glu | Leu | Val | |
| | | 495 | | | | | 500 | | | | | 505 | | | | |
| TAC | TCT | CTG | GAG | CCT | GAG | CCG | GCT | GCT | AAG | GGC | CTC | TTC | ACC | ATC | TCA | 2066 |
| Tyr | Ser | Leu | Glu | Pro | Glu | Pro | Ala | Ala | Lys | Gly | Leu | Phe | Thr | Ile | Ser | |
| | | 510 | | | | | 515 | | | | | 520 | | | | |
| CCC | GAG | ACT | GGA | GAG | ATC | CAG | GTG | AAG | ACA | TCT | CTG | GAT | CGG | GAA | CAG | 2114 |
| Pro | Glu | Thr | Gly | Glu | Ile | Gln | Val | Lys | Thr | Ser | Leu | Asp | Arg | Glu | Gln | |
| 525 | | | | | 530 | | | | | 535 | | | | | 540 | |
| CGG | GAG | AGC | TAT | GAG | TTG | AAG | GTG | GTG | GCA | GCT | GAC | CGG | GGC | AGT | CCT | 2162 |
| Arg | Glu | Ser | Tyr | Glu | Leu | Lys | Val | Val | Ala | Ala | Asp | Arg | Gly | Ser | Pro | |
| | | | | 545 | | | | | 550 | | | | | 555 | | |
| AGC | CTC | CAG | GGC | ACA | GCC | ACT | GTC | CTT | GTC | AAT | GTG | CTG | GAC | TGC | AAT | 2210 |
| Ser | Leu | Gln | Gly | Thr | Ala | Thr | Val | Leu | Val | Asn | Val | Leu | Asp | Cys | Asn | |
| | | | 560 | | | | | 565 | | | | | 570 | | | |
| GAC | AAT | GAC | CCC | AAA | TTT | ATG | CTG | AGT | GGC | TAC | AAC | TTC | TCA | GTG | ATG | 2258 |
| Asp | Asn | Asp | Pro | Lys | Phe | Met | Leu | Ser | Gly | Tyr | Asn | Phe | Ser | Val | Met | |
| | | 575 | | | | | 580 | | | | | 585 | | | | |
| GAG | AAC | ATG | CCA | GCA | CTG | AGT | CCA | GTG | GGC | ATG | GTG | ACT | GTC | ATT | GAT | 2306 |
| Glu | Asn | Met | Pro | Ala | Leu | Ser | Pro | Val | Gly | Met | Val | Thr | Val | Ile | Asp | |
| | | 590 | | | | | 595 | | | | | 600 | | | | |

| | | | | | | | | | | | | | | | | |
|---|---|---|---|---|---|---|---|---|---|---|---|---|---|---|---|---|
| GGA | GAC | AAG | GGG | GAG | AAT | GCC | CAG | GTG | CAG | CTC | TCA | GTG | GAG | CAG | GAC | 2354 |
| Gly | Asp | Lys | Gly | Glu | Asn | Ala | Gln | Val | Gln | Leu | Ser | Val | Glu | Gln | Asp | |
| 605 | | | | 610 | | | | | 615 | | | | | | 620 | |
| AAC | GGT | GAC | TTT | GTT | ATC | CAG | AAT | GGC | ACA | GGC | ACC | ATC | CTA | TCC | AGC | 2402 |
| Asn | Gly | Asp | Phe | Val | Ile | Gln | Asn | Gly | Thr | Gly | Thr | Ile | Leu | Ser | Ser | |
| | | | | 625 | | | | | 630 | | | | | 635 | | |
| CTG | AGC | TTT | GAT | CGA | GAG | CAA | CAA | AGC | ACC | TAC | ACC | TTC | CAG | CTG | AAG | 2450 |
| Leu | Ser | Phe | Asp | Arg | Glu | Gln | Gln | Ser | Thr | Tyr | Thr | Phe | Gln | Leu | Lys | |
| | | | 640 | | | | | 645 | | | | | | 650 | | |
| GCA | GTG | GAT | GGT | GGC | GTC | CCA | CCT | CGC | TCA | GCT | TAC | GTT | GGT | GTC | ACC | 2498 |
| Ala | Val | Asp | Gly | Gly | Val | Pro | Pro | Arg | Ser | Ala | Tyr | Val | Gly | Val | Thr | |
| | | 655 | | | | | 660 | | | | | 665 | | | | |
| ATC | AAT | GTG | CTG | GAC | GAG | AAT | GAC | AAC | GCA | CCC | TAT | ATC | ACT | GCC | CCT | 2546 |
| Ile | Asn | Val | Leu | Asp | Glu | Asn | Asp | Asn | Ala | Pro | Tyr | Ile | Thr | Ala | Pro | |
| | 670 | | | | | 675 | | | | | 680 | | | | | |
| TCT | AAC | ACC | TCT | CAC | AAG | CTG | CTG | ACC | CCC | CAG | ACA | CGT | CTT | GGT | GAG | 2594 |
| Ser | Asn | Thr | Ser | His | Lys | Leu | Leu | Thr | Pro | Gln | Thr | Arg | Leu | Gly | Glu | |
| 685 | | | | | 690 | | | | | 695 | | | | | 700 | |
| ACG | GTC | AGC | CAG | GTG | GCA | GCC | GAG | GAC | TTT | GAC | TCT | GGT | GTC | AAT | GCC | 2642 |
| Thr | Val | Ser | Gln | Val | Ala | Ala | Glu | Asp | Phe | Asp | Ser | Gly | Val | Asn | Ala | |
| | | | | 705 | | | | | 710 | | | | | 715 | | |
| GAG | CTG | ATC | TAC | AGC | ATT | GCA | GGT | GGC | AAC | CCT | TAT | GGA | CTC | TTC | CAG | 2690 |
| Glu | Leu | Ile | Tyr | Ser | Ile | Ala | Gly | Gly | Asn | Pro | Tyr | Gly | Leu | Phe | Gln | |
| | | | 720 | | | | | 725 | | | | | 730 | | | |
| ATT | GGG | TCA | CAT | TCA | GGT | GCC | ATC | ACC | CTG | GAG | AAG | GAG | ATT | GAG | CGG | 2738 |
| Ile | Gly | Ser | His | Ser | Gly | Ala | Ile | Thr | Leu | Glu | Lys | Glu | Ile | Glu | Arg | |
| | | 735 | | | | | 740 | | | | | 745 | | | | |
| CGC | CAC | CAT | GGG | CTA | CAC | CGC | CTG | GTG | GTG | AAG | GTC | AGT | GAC | CGC | GGC | 2786 |
| Arg | His | His | Gly | Leu | His | Arg | Leu | Val | Val | Lys | Val | Ser | Asp | Arg | Gly | |
| | 750 | | | | | 755 | | | | | 760 | | | | | |
| AAG | CCC | CCA | CGC | TAT | GGC | ACA | GCC | TTG | GTC | CAT | CTT | TAT | GTC | AAT | GAG | 2834 |
| Lys | Pro | Pro | Arg | Tyr | Gly | Thr | Ala | Leu | Val | His | Leu | Tyr | Val | Asn | Glu | |
| 765 | | | | | 770 | | | | | 775 | | | | | 780 | |
| ACT | CTG | GCC | AAC | CGC | ACG | CTG | CTG | GAG | ACC | CTC | CTG | GGC | CAC | AGC | CTG | 2882 |
| Thr | Leu | Ala | Asn | Arg | Thr | Leu | Leu | Glu | Thr | Leu | Leu | Gly | His | Ser | Leu | |
| | | | | 785 | | | | | 790 | | | | | 795 | | |
| GAC | ACG | CCG | CTG | GAT | ATT | GAC | ATT | GCT | GGG | GAT | CCA | GAA | TAT | GAG | CGC | 2930 |
| Asp | Thr | Pro | Leu | Asp | Ile | Asp | Ile | Ala | Gly | Asp | Pro | Glu | Tyr | Glu | Arg | |
| | | | 800 | | | | | 805 | | | | | 810 | | | |
| TCC | AAG | CAG | CGT | GGC | AAC | ATT | CTC | TTT | GGT | GTG | GTG | GCT | GGT | GTG | GTG | 2978 |
| Ser | Lys | Gln | Arg | Gly | Asn | Ile | Leu | Phe | Gly | Val | Val | Ala | Gly | Val | Val | |
| | | 815 | | | | | 820 | | | | | 825 | | | | |
| GCC | GTG | GCC | TTG | CTC | ATC | GCC | CTG | GCG | GTT | CTT | GTG | CGC | TAC | TGC | AGA | 3026 |
| Ala | Val | Ala | Leu | Leu | Ile | Ala | Leu | Ala | Val | Leu | Val | Arg | Tyr | Cys | Arg | |
| | 830 | | | | | 835 | | | | | 840 | | | | | |
| CAG | CGG | GAG | GCC | AAA | AGT | GGT | TAC | CAG | GCT | GGT | AAG | AAG | GAG | ACC | AAG | 3074 |
| Gln | Arg | Glu | Ala | Lys | Ser | Gly | Tyr | Gln | Ala | Gly | Lys | Lys | Glu | Thr | Lys | |
| 845 | | | | | 850 | | | | | 855 | | | | | 860 | |
| GAC | CTG | TAT | GCC | CCC | AAG | CCC | AGT | GGC | AAG | GCC | TCC | AAG | GGA | AAC | AAA | 3122 |
| Asp | Leu | Tyr | Ala | Pro | Lys | Pro | Ser | Gly | Lys | Ala | Ser | Lys | Gly | Asn | Lys | |
| | | | | 865 | | | | | 870 | | | | | 875 | | |
| AGC | AAA | GGC | AAG | AAG | AGC | AAG | TCC | CCA | AAG | CCC | GTG | AAG | CCA | GTG | GAG | 3170 |
| Ser | Lys | Gly | Lys | Lys | Ser | Lys | Ser | Pro | Lys | Pro | Val | Lys | Pro | Val | Glu | |
| | | | 880 | | | | | 885 | | | | | 890 | | | |
| GAC | GAG | GAT | GAG | GCC | GGG | CTG | CAG | AAG | TCC | CTC | AAG | TTC | AAC | CTG | ATG | 3218 |
| Asp | Glu | Asp | Glu | Ala | Gly | Leu | Gln | Lys | Ser | Leu | Lys | Phe | Asn | Leu | Met | |
| | | | 895 | | | | | 900 | | | | | 905 | | | |
| AGC | GAT | GCC | CCT | GGG | GAC | AGT | CCC | CGC | ATC | CAC | CTG | CCC | CTC | AAC | TAC | 3266 |
| Ser | Asp | Ala | Pro | Gly | Asp | Ser | Pro | Arg | Ile | His | Leu | Pro | Leu | Asn | Tyr | |
| | 910 | | | | | 915 | | | | | 920 | | | | | |

```
CCA CCA GGC AGC CCT GAC CTG GGC CGC CAC TAT CGC TCT AAC TCC CCA     3314
Pro Pro Gly Ser Pro Asp Leu Gly Arg His Tyr Arg Ser Asn Ser Pro
925             930                 935                 940

CTG CCT TCC ATC CAG CTG CAG CCC CAG TCA CCC TCA GCC TCC AAG AAG     3362
Leu Pro Ser Ile Gln Leu Gln Pro Gln Ser Pro Ser Ala Ser Lys Lys
                945                 950                 955

CAC CAG GTG GTA CAG GAC CTG CCA CCT GCA AAC ACA TTC GTG GGC ACC     3410
His Gln Val Val Gln Asp Leu Pro Pro Ala Asn Thr Phe Val Gly Thr
            960                 965                 970

GGG GAC ACC ACG TCC ACG GGC TCT GAG CAG TAC TCC GAC TAC AGC TAC     3458
Gly Asp Thr Thr Ser Thr Gly Ser Glu Gln Tyr Ser Asp Tyr Ser Tyr
        975                 980                 985

CGC ACC AAC CCC CCC AAA TAC CCC AGC AAG CAG TTA CCT CAC CGC CGC     3506
Arg Thr Asn Pro Pro Lys Tyr Pro Ser Lys Gln Leu Pro His Arg Arg
    990                 995                 1000

GTC ACC TTC TCG GCC ACC AGC CAG GCC CAG GAG CTG CAG GAC CCA TCC     3554
Val Thr Phe Ser Ala Thr Ser Gln Ala Gln Glu Leu Gln Asp Pro Ser
1005                1010                1015                1020

CAG CAC AGT TAC TAT GAC AGT GGC CTG GAG GAG TCT GAG ACG CCG TCC     3602
Gln His Ser Tyr Tyr Asp Ser Gly Leu Glu Glu Ser Glu Thr Pro Ser
                1025                1030                1035

AGC AAG TCA TCC TCA GGG CCT CGA CTC GGT CCC CTG GCC CTG CCT GAG     3650
Ser Lys Ser Ser Ser Gly Pro Arg Leu Gly Pro Leu Ala Leu Pro Glu
            1040                1045                1050

GAT CAC TAT GAG CGC ACC ACC CCT GAT GGC AGC ATA GGA GAG ATG GAG     3698
Asp His Tyr Glu Arg Thr Thr Pro Asp Gly Ser Ile Gly Glu Met Glu
        1055                1060                1065

CAC CCC GAG AAT GAC CTT CGC CCT TTG CCT GAT GTC GCC ATG ACA GGC     3746
His Pro Glu Asn Asp Leu Arg Pro Leu Pro Asp Val Ala Met Thr Gly
    1070                1075                1080

ACA TGT ACC CGG GAG TGC AGT GAG TTT GGC CAC TCT GAC ACA TGC TGG     3794
Thr Cys Thr Arg Glu Cys Ser Glu Phe Gly His Ser Asp Thr Cys Trp
1085                1090                1095                1100

ATG CCT GGC CAG TCA TCT CCC AGC CGC CGG ACC AAG AGC AGC GCC CTC     3842
Met Pro Gly Gln Ser Ser Pro Ser Arg Arg Thr Lys Ser Ser Ala Leu
                1105                1110                1115

AAA CTC TCC ACC TTC ATG CCT TAC CAG GAC CGA GGA GGG CAG GAG CCT     3890
Lys Leu Ser Thr Phe Met Pro Tyr Gln Asp Arg Gly Gly Gln Glu Pro
            1120                1125                1130

GCG GGC GCC GGC AGC CCC AGC CCC CCG GAA GAC CGG AAC ACC AAA ACG     3938
Ala Gly Ala Gly Ser Pro Ser Pro Pro Glu Asp Arg Asn Thr Lys Thr
        1135                1140                1145

GCC CCC GTG CGC CTC CTG CCC TCC TAC AGT GCC TTC TCC CAC AGT AGC     3986
Ala Pro Val Arg Leu Leu Pro Ser Tyr Ser Ala Phe Ser His Ser Ser
    1150                1155                1160

CAT GAT TCC TGC AAG GAC TCG GCC ACC TTG GAG GAA ATC CCC CTG ACC     4034
His Asp Ser Cys Lys Asp Ser Ala Thr Leu Glu Glu Ile Pro Leu Thr
1165                1170                1175                1180

CAG ACC TCG GAC TTC CCA CCC GCA GCC ACA CCG GCA TCT GCC CAG ACG     4082
Gln Thr Ser Asp Phe Pro Pro Ala Ala Thr Pro Ala Ser Ala Gln Thr
                1185                1190                1195

GCC AAG CGC GAG ATC TAC CTG TGAGCCCCCT ACTGGCCGGC CCCCCTCCCC        4133
Ala Lys Arg Glu Ile Tyr Leu
            1200

CAGCGCCGGC CAGCTCCCAA ATGCCCATTC CAGGGCCTCA CTCTCCACCC CTTCAGCGTG   4193

GACTTCCTGC CAGGGCCCAA GTGGGGGTAT CACTGACCTC ATGACCACGC TGGCCCTTCT   4253

CCCATGCAGG GTCCAGGTCC TCTCCCCTCA TTTCCATCTC CCAGCCCAGG GGCCCCTTCC   4313

CCTTTATGGG GCTTCCCCCA GCTGATGCCC AAGAGGGCTC CTCTGCAATG ACTGGGCTCC   4373
```

-continued

```
TTCCCTTGAC  TTCCAGGGAG  CACCCCCTCG  ATTTGGGCAG  ATGGTGGAGT  CAAGGGTGGG    4433

CAGCGTACTT  CTAACTCATT  GTTTCCCTCA  TGGCCGACCA  GGGCGGGGAT  AGCATGCCCA    4493

ATTTTAGCCC  TGAAGCAGGG  CTGAACTGGG  GAGCCCCTTT  CCCTGGGAGC  TCCCAGAGGA    4553

AACTCTTGAC  CACCAGTGGC  TCCCTGAAGG  GCTTTTGTTA  CCAAAGGTGG  GGTAGGGACG    4613

GGGGTGGGAG  TGGAGCGGAG  GCCTTGTTTT  CCCGTGG                               4650
```

( 2 ) INFORMATION FOR SEQ ID NO:103:

( i ) SEQUENCE CHARACTERISTICS:
        ( A ) LENGTH: 1203 amino acids
        ( B ) TYPE: amino acid
        ( D ) TOPOLOGY: linear ( i i ) MOLECULE TYPE: protein ( x i ) SEQUENCE DESCRIPTION: SEQ ID NO:103:

```
Met  Glu  Pro  Leu  Arg  His  Ser  Pro  Gly  Pro  Gly  Gly  Gln  Arg  Leu  Leu
  1                    5                        10                       15

Leu  Pro  Ser  Met  Leu  Leu  Ala  Leu  Leu  Leu  Leu  Ala  Pro  Ser  Pro
              20                        25                       30

Gly  His  Ala  Thr  Arg  Val  Val  Tyr  Lys  Val  Pro  Glu  Glu  Gln  Pro  Pro
              35                        40                       45

Asn  Thr  Leu  Ile  Gly  Ser  Leu  Ala  Ala  Asp  Tyr  Gly  Phe  Pro  Asp  Val
      50                        55                       60

Gly  His  Leu  Tyr  Lys  Leu  Glu  Val  Gly  Ala  Pro  Tyr  Leu  Arg  Val  Asp
 65                        70                       75                       80

Gly  Lys  Thr  Gly  Asp  Ile  Phe  Thr  Thr  Glu  Thr  Ser  Ile  Asp  Arg  Glu
              85                        90                       95

Gly  Leu  Arg  Glu  Cys  Gln  Asn  Gln  Leu  Pro  Gly  Asp  Pro  Cys  Ile  Leu
             100                       105                      110

Glu  Phe  Glu  Val  Ser  Ile  Thr  Asp  Leu  Val  Gln  Asn  Ala  Ser  Pro  Arg
             115                       120                      125

Leu  Leu  Glu  Gly  Gln  Ile  Glu  Val  Gln  Asp  Ile  Asn  Asp  Asn  Thr  Pro
      130                       135                      140

Asn  Phe  Ala  Ser  Pro  Val  Ile  Thr  Leu  Ala  Ile  Pro  Glu  Asn  Thr  Asn
145                       150                      155                      160

Ile  Gly  Ser  Leu  Phe  Pro  Ile  Pro  Leu  Ala  Ser  Asp  Arg  Asp  Ala  Gly
                     165                       170                      175

Pro  Asn  Gly  Val  Ala  Ser  Tyr  Glu  Leu  Gln  Val  Ala  Glu  Asp  Gln  Glu
             180                       185                      190

Glu  Lys  Gln  Pro  Gln  Leu  Ile  Val  Met  Gly  Asn  Leu  Asp  Arg  Glu  Arg
             195                       200                      205

Trp  Asp  Ser  Tyr  Asp  Leu  Thr  Ile  Lys  Val  Gln  Asp  Gly  Gly  Ser  Pro
      210                       215                      220

Pro  Arg  Ala  Thr  Ser  Ala  Leu  Leu  Arg  Val  Thr  Val  Leu  Asp  Thr  Asn
225                       230                      235                      240

Asp  Asn  Ala  Pro  Lys  Phe  Glu  Arg  Pro  Ser  Tyr  Glu  Ala  Glu  Leu  Ser
                     245                       250                      255

Glu  Asn  Ser  Pro  Ile  Gly  His  Ser  Val  Ile  Gln  Val  Lys  Ala  Asn  Asp
             260                       265                      270

Ser  Asp  Gln  Gly  Ala  Asn  Ala  Glu  Ile  Glu  Tyr  Thr  Phe  His  Gln  Ala
             275                       280                      285

Pro  Glu  Val  Val  Arg  Arg  Leu  Leu  Arg  Leu  Asp  Arg  Asn  Thr  Gly  Leu
             290                       295                      300

Ile  Thr  Val  Gln  Gly  Pro  Val  Asp  Arg  Glu  Asp  Leu  Ser  Thr  Leu  Arg
```

```
305                      310                      315                      320
Phe  Ser  Val  Leu  Ala  Lys  Asp  Arg  Gly  Thr  Asn  Pro  Lys  Ser  Ala  Arg
                    325                      330                      335
Ala  Gln  Val  Val  Val  Thr  Val  Lys  Asp  Met  Asn  Asp  Asn  Ala  Pro  Thr
                    340                      345                      350
Ile  Glu  Ile  Arg  Gly  Ile  Gly  Leu  Val  Thr  His  Gln  Asp  Gly  Met  Ala
                    355                      360                      365
Asn  Ile  Ser  Glu  Asp  Val  Ala  Glu  Glu  Thr  Ala  Val  Ala  Leu  Val  Gln
     370                      375                      380
Val  Ser  Asp  Arg  Asp  Glu  Gly  Glu  Asn  Ala  Ala  Val  Thr  Cys  Val  Val
385                      390                      395                      400
Ala  Gly  Asp  Val  Pro  Phe  Gln  Leu  Arg  Gln  Ala  Ser  Glu  Thr  Gly  Ser
                    405                      410                      415
Asp  Ser  Lys  Lys  Lys  Tyr  Phe  Leu  Gln  Thr  Thr  Thr  Pro  Leu  Asp  Tyr
                    420                      425                      430
Glu  Lys  Val  Lys  Asp  Tyr  Thr  Ile  Glu  Ile  Val  Ala  Val  Asp  Ser  Gly
               435                      440                      445
Asn  Pro  Pro  Leu  Ser  Ser  Thr  Asn  Ser  Leu  Lys  Val  Gln  Val  Val  Asp
     450                      455                      460
Val  Asn  Asp  Asn  Ala  Pro  Val  Phe  Thr  Gln  Ser  Val  Thr  Glu  Val  Ala
465                      470                      475                      480
Phe  Pro  Glu  Asn  Asn  Lys  Pro  Gly  Glu  Val  Ile  Ala  Glu  Ile  Thr  Ala
                    485                      490                      495
Ser  Asp  Ala  Asp  Ser  Gly  Ser  Asn  Ala  Glu  Leu  Val  Tyr  Ser  Leu  Glu
                    500                      505                      510
Pro  Glu  Pro  Ala  Ala  Lys  Gly  Leu  Phe  Thr  Ile  Ser  Pro  Glu  Thr  Gly
          515                      520                      525
Glu  Ile  Gln  Val  Lys  Thr  Ser  Leu  Asp  Arg  Glu  Gln  Arg  Glu  Ser  Tyr
     530                      535                      540
Glu  Leu  Lys  Val  Val  Ala  Ala  Asp  Arg  Gly  Ser  Pro  Ser  Leu  Gln  Gly
545                      550                      555                      560
Thr  Ala  Thr  Val  Leu  Val  Asn  Val  Leu  Asp  Cys  Asn  Asp  Asn  Asp  Pro
                    565                      570                      575
Lys  Phe  Met  Leu  Ser  Gly  Tyr  Asn  Phe  Ser  Val  Met  Glu  Asn  Met  Pro
                    580                      585                      590
Ala  Leu  Ser  Pro  Val  Gly  Met  Val  Thr  Val  Ile  Asp  Gly  Asp  Lys  Gly
                    595                      600                      605
Glu  Asn  Ala  Gln  Val  Gln  Leu  Ser  Val  Glu  Gln  Asp  Asn  Gly  Asp  Phe
     610                      615                      620
Val  Ile  Gln  Asn  Gly  Thr  Gly  Thr  Ile  Leu  Ser  Ser  Leu  Ser  Phe  Asp
625                      630                      635                      640
Arg  Glu  Gln  Gln  Ser  Thr  Tyr  Thr  Phe  Gln  Leu  Lys  Ala  Val  Asp  Gly
                    645                      650                      655
Gly  Val  Pro  Pro  Arg  Ser  Ala  Tyr  Val  Gly  Val  Thr  Ile  Asn  Val  Leu
                    660                      665                      670
Asp  Glu  Asn  Asp  Asn  Ala  Pro  Tyr  Ile  Thr  Ala  Pro  Ser  Asn  Thr  Ser
          675                      680                      685
His  Lys  Leu  Leu  Thr  Pro  Gln  Thr  Arg  Leu  Gly  Glu  Thr  Val  Ser  Gln
     690                      695                      700
Val  Ala  Ala  Glu  Asp  Phe  Asp  Ser  Gly  Val  Asn  Ala  Glu  Leu  Ile  Tyr
705                      710                      715                      720
Ser  Ile  Ala  Gly  Gly  Asn  Pro  Tyr  Gly  Leu  Phe  Gln  Ile  Gly  Ser  His
                    725                      730                      735
```

-continued

```
Ser  Gly  Ala  Ile  Thr  Leu  Glu  Lys  Glu  Ile  Glu  Arg  Arg  His  His  Gly
              740                 745                           750

Leu  His  Arg  Leu  Val  Val  Lys  Val  Ser  Asp  Arg  Gly  Lys  Pro  Pro  Arg
          755                 760                 765

Tyr  Gly  Thr  Ala  Leu  Val  His  Leu  Tyr  Val  Asn  Glu  Thr  Leu  Ala  Asn
     770                      775                 780

Arg  Thr  Leu  Leu  Glu  Thr  Leu  Leu  Gly  His  Ser  Leu  Asp  Thr  Pro  Leu
785                 790                      795                           800

Asp  Ile  Asp  Ile  Ala  Gly  Asp  Pro  Glu  Tyr  Glu  Arg  Ser  Lys  Gln  Arg
                    805                 810                      815

Gly  Asn  Ile  Leu  Phe  Gly  Val  Val  Ala  Gly  Val  Val  Ala  Val  Ala  Leu
               820                      825                 830

Leu  Ile  Ala  Leu  Ala  Val  Leu  Val  Arg  Tyr  Cys  Arg  Gln  Arg  Glu  Ala
               835                 840                      845

Lys  Ser  Gly  Tyr  Gln  Ala  Gly  Lys  Lys  Glu  Thr  Lys  Asp  Leu  Tyr  Ala
     850                      855                 860

Pro  Lys  Pro  Ser  Gly  Lys  Ala  Ser  Lys  Gly  Asn  Lys  Ser  Lys  Gly  Lys
865                      870                 875                           880

Lys  Ser  Lys  Ser  Pro  Lys  Pro  Val  Lys  Pro  Val  Glu  Asp  Glu  Asp  Glu
                    885                 890                      895

Ala  Gly  Leu  Gln  Lys  Ser  Leu  Lys  Phe  Asn  Leu  Met  Ser  Asp  Ala  Pro
               900                 905                      910

Gly  Asp  Ser  Pro  Arg  Ile  His  Leu  Pro  Leu  Asn  Tyr  Pro  Pro  Gly  Ser
               915                 920                      925

Pro  Asp  Leu  Gly  Arg  His  Tyr  Arg  Ser  Asn  Ser  Pro  Leu  Pro  Ser  Ile
     930                      935                 940

Gln  Leu  Gln  Pro  Gln  Ser  Pro  Ser  Ala  Ser  Lys  Lys  His  Gln  Val  Val
945                      950                 955                           960

Gln  Asp  Leu  Pro  Pro  Ala  Asn  Thr  Phe  Val  Gly  Thr  Gly  Asp  Thr  Thr
                    965                 970                      975

Ser  Thr  Gly  Ser  Glu  Gln  Tyr  Ser  Asp  Tyr  Ser  Tyr  Arg  Thr  Asn  Pro
               980                 985                      990

Pro  Lys  Tyr  Pro  Ser  Lys  Gln  Leu  Pro  His  Arg  Arg  Val  Thr  Phe  Ser
          995                      1000                     1005

Ala  Thr  Ser  Gln  Ala  Gln  Glu  Leu  Gln  Asp  Pro  Ser  Gln  His  Ser  Tyr
     1010                     1015                     1020

Tyr  Asp  Ser  Gly  Leu  Glu  Glu  Ser  Glu  Thr  Pro  Ser  Ser  Lys  Ser  Ser
1025                     1030                     1035                    1040

Ser  Gly  Pro  Arg  Leu  Gly  Pro  Leu  Ala  Leu  Pro  Glu  Asp  His  Tyr  Glu
                    1045                     1050                    1055

Arg  Thr  Thr  Pro  Asp  Gly  Ser  Ile  Gly  Glu  Met  Glu  His  Pro  Glu  Asn
               1060                     1065                    1070

Asp  Leu  Arg  Pro  Leu  Pro  Asp  Val  Ala  Met  Thr  Gly  Thr  Cys  Thr  Arg
          1075                     1080                    1085

Glu  Cys  Ser  Glu  Phe  Gly  His  Ser  Asp  Thr  Cys  Trp  Met  Pro  Gly  Gln
     1090                     1095                    1100

Ser  Ser  Pro  Ser  Arg  Arg  Thr  Lys  Ser  Ser  Ala  Leu  Lys  Leu  Ser  Thr
1105                     1110                     1115                    1120

Phe  Met  Pro  Tyr  Gln  Asp  Arg  Gly  Gly  Gln  Glu  Pro  Ala  Gly  Ala  Gly
                    1125                     1130                    1135

Ser  Pro  Ser  Pro  Pro  Glu  Asp  Arg  Asn  Thr  Lys  Thr  Ala  Pro  Val  Arg
                    1140                     1145                    1150

Leu  Leu  Pro  Ser  Tyr  Ser  Ala  Phe  Ser  His  Ser  Ser  His  Asp  Ser  Cys
          1155                     1160                    1165
```

| | | | | | | | | | | | | | | |
|---|---|---|---|---|---|---|---|---|---|---|---|---|---|---|
| Lys | Asp | Ser | Ala | Thr | Leu | Glu | Glu | Ile | Pro | Leu | Thr | Gln | Thr | Ser | Asp |
| | 1170 | | | | | 1175 | | | | | 1180 | | | | |
| Phe | Pro | Pro | Ala | Ala | Thr | Pro | Ala | Ser | Ala | Gln | Thr | Ala | Lys | Arg | Glu |
| 1185 | | | | | 1190 | | | | | 1195 | | | | | 1200 |
| Ile | Tyr | Leu | | | | | | | | | | | | | |

( 2 ) INFORMATION FOR SEQ ID NO:104:

( i ) SEQUENCE CHARACTERISTICS:
        ( A ) LENGTH: 2789 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 115..2622

( x i ) SEQUENCE DESCRIPTION: SEQ ID NO:104:

```
CGAAAGCCAT GTCGGACTCG TCGCCCAGCG CCCAAGCGCT AACCCGCTGA AAGTTTCTCA        60

GCGAAATCTC AGGGACGATC TGGACCCCGC TGAGAGGAAC TGCTTTTGAG TGAG ATG         117
                                                              Met
                                                              1

GTC CCA GAG GCC TGG AGG AGC GGA CTG GTA AGC ACC GGG AGG GTA GTG         165
Val Pro Glu Ala Trp Arg Ser Gly Leu Val Ser Thr Gly Arg Val Val
            5                   10                  15

GGA GTT TTG CTT CTG CTT GGT GCC TTG AAC AAG GCT TCC ACG GTC ATT         213
Gly Val Leu Leu Leu Leu Gly Ala Leu Asn Lys Ala Ser Thr Val Ile
        20                  25                  30

CAC TAT GAG ATC CCG GAG GAA AGA GAG AAG GGT TTC GCT GTG GGC AAC         261
His Tyr Glu Ile Pro Glu Glu Arg Glu Lys Gly Phe Ala Val Gly Asn
    35                  40                  45

GTG GTC GCG AAC CTT GGT TTG GAT CTC GGT AGC CTC TCA GCC CGC AGG         309
Val Val Ala Asn Leu Gly Leu Asp Leu Gly Ser Leu Ser Ala Arg Arg
50                  55                  60                  65

TTC CCG GTG GTG TCT GGA GCT AGC CGA AGA TTC TTT GAG GTG AAC CGG         357
Phe Pro Val Val Ser Gly Ala Ser Arg Arg Phe Phe Glu Val Asn Arg
                70                  75                  80

GAG ACC GGA GAG ATG TTT GTG AAC GAC CGT CTG GAT CGA GAG GAG CTG         405
Glu Thr Gly Glu Met Phe Val Asn Asp Arg Leu Asp Arg Glu Glu Leu
            85                  90                  95

TGT GGG ACA CTG CCC TCT TGC ACT GTA ACT CTG GAG TTG GTA GTG GAG         453
Cys Gly Thr Leu Pro Ser Cys Thr Val Thr Leu Glu Leu Val Val Glu
        100                 105                 110

AAC CCG CTG GAG CTG TTC AGC GTG GAA GTG GTG ATC CAG GAC ATC AAC         501
Asn Pro Leu Glu Leu Phe Ser Val Glu Val Val Ile Gln Asp Ile Asn
    115                 120                 125

GAC AAC AAT CCT GCT TTC CCT ACC CAG GAA ATG AAA TTG GAG ATT AGC         549
Asp Asn Asn Pro Ala Phe Pro Thr Gln Glu Met Lys Leu Glu Ile Ser
130                 135                 140                 145

GAG GCC GTG GCT CCG GGG ACG CGC TTT CCG CTC GAG AGC GCG CAC GAT         597
Glu Ala Val Ala Pro Gly Thr Arg Phe Pro Leu Glu Ser Ala His Asp
                150                 155                 160

CCC GAT CTG GGA AGC AAC TCT TTA CAA ACC TAT GAG CTG AGC CGA AAT         645
Pro Asp Leu Gly Ser Asn Ser Leu Gln Thr Tyr Glu Leu Ser Arg Asn
            165                 170                 175

GAA TAC TTT GCG CTT CGC GTG CAG ACG CGG GAG GAC AGC ACC AAG TAC         693
Glu Tyr Phe Ala Leu Arg Val Gln Thr Arg Glu Asp Ser Thr Lys Tyr
        180                 185                 190
```

| | | | | | | | | | | | | | | | | |
|---|---|---|---|---|---|---|---|---|---|---|---|---|---|---|---|---|
| GCG | GAG | CTG | GTG | TTG | GAG | CGC | GCC | CTG | GAC | CGA | GAA | CGG | GAG | CCT | AGT | 741 |
| Ala | Glu | Leu | Val | Leu | Glu | Arg | Ala | Leu | Asp | Arg | Glu | Arg | Glu | Pro | Ser | |
| | | 195 | | | | 200 | | | | 205 | | | | | | |
| CTC | CAG | TTA | GTG | CTG | ACG | GCG | TTG | GAC | GGA | GGG | ACC | CCA | GCT | CTC | TCC | 789 |
| Leu | Gln | Leu | Val | Leu | Thr | Ala | Leu | Asp | Gly | Gly | Thr | Pro | Ala | Leu | Ser | |
| 210 | | | | | 215 | | | | | 220 | | | | | 225 | |
| GCC | AGC | CTG | CCT | ATT | CAC | ATC | AAG | GTG | CTG | GAC | GCG | AAT | GAC | AAT | GCG | 837 |
| Ala | Ser | Leu | Pro | Ile | His | Ile | Lys | Val | Leu | Asp | Ala | Asn | Asp | Asn | Ala | |
| | | | | 230 | | | | 235 | | | | | 240 | | | |
| CCT | GTC | TTC | AAC | CAG | TCC | TTG | TAC | CGG | GCG | CGC | GTT | CCT | GGA | GGA | TGC | 885 |
| Pro | Val | Phe | Asn | Gln | Ser | Leu | Tyr | Arg | Ala | Arg | Val | Pro | Gly | Gly | Cys | |
| | | | 245 | | | | | 250 | | | | | 255 | | | |
| ACC | TCC | GGC | ACG | CGC | GTG | GTA | CAA | GTC | CTT | GCA | ACG | GAT | CTG | GAT | GAA | 933 |
| Thr | Ser | Gly | Thr | Arg | Val | Val | Gln | Val | Leu | Ala | Thr | Asp | Leu | Asp | Glu | |
| | | 260 | | | | | 265 | | | | | 270 | | | | |
| GGC | CCC | AAC | GGT | GAA | ATT | ATT | TAC | TCC | TTC | GGC | AGC | CAC | AAC | CGC | GCC | 981 |
| Gly | Pro | Asn | Gly | Glu | Ile | Ile | Tyr | Ser | Phe | Gly | Ser | His | Asn | Arg | Ala | |
| | 275 | | | | | 280 | | | | | 285 | | | | | |
| GGC | GTG | CGG | CAA | CTA | TTC | GCC | TTA | GAC | CTT | GTA | ACC | GGG | ATG | CTG | ACA | 1029 |
| Gly | Val | Arg | Gln | Leu | Phe | Ala | Leu | Asp | Leu | Val | Thr | Gly | Met | Leu | Thr | |
| 290 | | | | | 295 | | | | | 300 | | | | | 305 | |
| ATC | AAG | GGT | CGG | CTG | GAC | TTC | GAG | GAC | ACC | AAA | CTC | CAT | GAG | ATT | TAC | 1077 |
| Ile | Lys | Gly | Arg | Leu | Asp | Phe | Glu | Asp | Thr | Lys | Leu | His | Glu | Ile | Tyr | |
| | | | | 310 | | | | | 315 | | | | | 320 | | |
| ATC | CAG | GCC | AAA | GAC | AAG | GGC | GCC | AAT | CCC | GAA | GGA | GCA | CAT | TGC | AAA | 1125 |
| Ile | Gln | Ala | Lys | Asp | Lys | Gly | Ala | Asn | Pro | Glu | Gly | Ala | His | Cys | Lys | |
| | | | 325 | | | | | 330 | | | | | 335 | | | |
| GTG | TTG | GTG | GAG | GTT | GTG | GAT | GTG | AAT | GAC | AAC | GCC | CCG | GAG | ATC | ACA | 1173 |
| Val | Leu | Val | Glu | Val | Val | Asp | Val | Asn | Asp | Asn | Ala | Pro | Glu | Ile | Thr | |
| | | 340 | | | | | 345 | | | | | 350 | | | | |
| GTC | ACC | TCC | GTG | TAC | AGC | CCA | GTA | CCC | GAG | GAT | GCC | TCT | GGG | ACT | GTC | 1221 |
| Val | Thr | Ser | Val | Tyr | Ser | Pro | Val | Pro | Glu | Asp | Ala | Ser | Gly | Thr | Val | |
| | | 355 | | | | | 360 | | | | | 365 | | | | |
| ATC | GCT | TTG | CTC | AGT | GTG | ACT | GAC | CTG | GAT | GCT | GGC | GAG | AAC | GGG | CTG | 1269 |
| Ile | Ala | Leu | Leu | Ser | Val | Thr | Asp | Leu | Asp | Ala | Gly | Glu | Asn | Gly | Leu | |
| 370 | | | | | 375 | | | | | 380 | | | | | 385 | |
| GTG | ACC | TGC | GAA | GTT | CCA | CCG | GGT | CTC | CCT | TTC | AGC | CTT | ACT | TCT | TCC | 1317 |
| Val | Thr | Cys | Glu | Val | Pro | Pro | Gly | Leu | Pro | Phe | Ser | Leu | Thr | Ser | Ser | |
| | | | | 390 | | | | | 395 | | | | | 400 | | |
| CTC | AAG | AAT | TAC | TTC | ACT | TTG | AAA | ACC | AGT | GCA | GAC | CTG | GAT | CGG | GAG | 1365 |
| Leu | Lys | Asn | Tyr | Phe | Thr | Leu | Lys | Thr | Ser | Ala | Asp | Leu | Asp | Arg | Glu | |
| | | | 405 | | | | | 410 | | | | | 415 | | | |
| ACT | GTG | CCA | GAA | TAC | AAC | CTC | AGC | ATC | ACC | GCC | CGA | GAC | GCC | GGA | ACC | 1413 |
| Thr | Val | Pro | Glu | Tyr | Asn | Leu | Ser | Ile | Thr | Ala | Arg | Asp | Ala | Gly | Thr | |
| | | 420 | | | | | 425 | | | | | 430 | | | | |
| CCT | TCC | CTC | TCA | GCC | CTT | ACA | ATA | GTG | CGT | GTT | CAA | GTG | TCC | GAC | ATC | 1461 |
| Pro | Ser | Leu | Ser | Ala | Leu | Thr | Ile | Val | Arg | Val | Gln | Val | Ser | Asp | Ile | |
| | 435 | | | | | 440 | | | | | 445 | | | | | |
| AAT | GAC | AAC | CCT | CCA | CAA | TCT | TCT | CAA | TCT | TCC | TAC | GAC | GTT | TAC | ATT | 1509 |
| Asn | Asp | Asn | Pro | Pro | Gln | Ser | Ser | Gln | Ser | Ser | Tyr | Asp | Val | Tyr | Ile | |
| 450 | | | | | 455 | | | | | 460 | | | | | 465 | |
| GAA | GAA | AAC | AAC | CTC | CCC | GGG | GCT | CCA | ATA | CTA | AAC | CTA | AGT | GTC | TGG | 1557 |
| Glu | Glu | Asn | Asn | Leu | Pro | Gly | Ala | Pro | Ile | Leu | Asn | Leu | Ser | Val | Trp | |
| | | | | 470 | | | | | 475 | | | | | 480 | | |
| GAC | CCC | GAC | GCC | CCG | CAG | AAT | GCT | CGG | CTT | TCT | TTC | TTT | CTC | TTG | GAG | 1605 |
| Asp | Pro | Asp | Ala | Pro | Gln | Asn | Ala | Arg | Leu | Ser | Phe | Phe | Leu | Leu | Glu | |
| | | | 485 | | | | | 490 | | | | | 495 | | | |
| CAA | GGA | GCT | GAA | ACC | GGG | CTA | GTG | GGT | CGC | TAT | TTC | ACA | ATA | AAT | CGT | 1653 |
| Gln | Gly | Ala | Glu | Thr | Gly | Leu | Val | Gly | Arg | Tyr | Phe | Thr | Ile | Asn | Arg | |
| | | 500 | | | | | 505 | | | | | 510 | | | | |

| | | | | | | | | | | | | | | | | |
|---|---|---|---|---|---|---|---|---|---|---|---|---|---|---|---|---|
| GAC | AAT | GGC | ATA | GTG | TCA | TCC | TTA | GTG | CCC | CTA | GAC | TAT | GAG | GAT | CGG | 1701 |
| Asp | Asn | Gly | Ile | Val | Ser | Ser | Leu | Val | Pro | Leu | Asp | Tyr | Glu | Asp | Arg | |
| 515 | | | | | 520 | | | | | 525 | | | | | | |
| CGG | GAA | TTT | GAA | TTA | ACA | GCT | CAT | ATC | AGC | GAT | GGG | GGC | ACC | CCG | GTC | 1749 |
| Arg | Glu | Phe | Glu | Leu | Thr | Ala | His | Ile | Ser | Asp | Gly | Gly | Thr | Pro | Val | |
| 530 | | | | | 535 | | | | | 540 | | | | | 545 | |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile | Ser | Val | Asn | Ile | Phe | Val | Thr | Asp | Arg | Asn | Asp | |
| | | | | 550 | | | | | 555 | | | | | 560 | | |
| AAT | GCC | CCC | CAG | GTC | CTA | TAT | CCT | CGG | CCA | GGT | GGG | AGC | TCG | GTG | GAG | 1845 |
| Asn | Ala | Pro | Gln | Val | Leu | Tyr | Pro | Arg | Pro | Gly | Gly | Ser | Ser | Val | Glu | |
| | | | 565 | | | | | 570 | | | | | 575 | | | |
| ATG | CTG | CCT | CGA | GGT | ACC | TCA | GCT | GGC | CAC | CTA | GTG | TCA | CGG | GTG | GTA | 1893 |
| Met | Leu | Pro | Arg | Gly | Thr | Ser | Ala | Gly | His | Leu | Val | Ser | Arg | Val | Val | |
| | | | 580 | | | | | 585 | | | | | 590 | | | |
| GGC | TGG | GAC | GCG | GAT | GCA | GGG | CAC | AAT | GCC | TGG | CTC | TCC | TAC | AGT | CTC | 1941 |
| Gly | Trp | Asp | Ala | Asp | Ala | Gly | His | Asn | Ala | Trp | Leu | Ser | Tyr | Ser | Leu | |
| | | 595 | | | | | 600 | | | | | 605 | | | | |
| TTT | GGA | TCC | CCT | AAC | CAG | AGC | CTT | TTT | GCC | ATA | GGG | CTG | CAC | ACT | GGT | 1989 |
| Phe | Gly | Ser | Pro | Asn | Gln | Ser | Leu | Phe | Ala | Ile | Gly | Leu | His | Thr | Gly | |
| 610 | | | | | 615 | | | | | 620 | | | | | 625 | |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala | Arg | Pro | Val | Gln | Asp | Thr | Asp | Ser | Pro | Arg | Gln | |
| | | | | 630 | | | | | 635 | | | | | 640 | | |
| ACT | CTC | ACT | GTC | TTG | ATC | AAA | GAC | AAT | GGG | GAG | CCT | TCG | CTC | TCC | ACC | 2085 |
| Thr | Leu | Thr | Val | Leu | Ile | Lys | Asp | Asn | Gly | Glu | Pro | Ser | Leu | Ser | Thr | |
| | | | 645 | | | | | 650 | | | | | 655 | | | |
| ACT | GCT | ACC | CTC | ACT | GTG | TCA | GTA | ACC | GAG | GAC | TCT | CCT | GAA | GCC | CGA | 2133 |
| Thr | Ala | Thr | Leu | Thr | Val | Ser | Val | Thr | Glu | Asp | Ser | Pro | Glu | Ala | Arg | |
| | | 660 | | | | | 665 | | | | | 670 | | | | |
| GCC | GAG | TTC | CCC | TCT | GGC | TCT | GCC | CCC | CGG | GAG | CAG | AAA | AAA | AAT | CTC | 2181 |
| Ala | Glu | Phe | Pro | Ser | Gly | Ser | Ala | Pro | Arg | Glu | Gln | Lys | Lys | Asn | Leu | |
| 675 | | | | | 680 | | | | | 685 | | | | | | |
| ACC | TTT | TAT | CTA | CTT | CTT | TCT | CTA | ATC | CTG | GTT | TCT | GTG | GGC | TTC | GTG | 2229 |
| Thr | Phe | Tyr | Leu | Leu | Leu | Ser | Leu | Ile | Leu | Val | Ser | Val | Gly | Phe | Val | |
| 690 | | | | | 695 | | | | | 700 | | | | | 705 | |
| GTC | ACA | GTG | TTC | GGA | GTA | ATC | ATA | TTC | AAA | GTT | TAC | AAG | TGG | AAG | CAG | 2277 |
| Val | Thr | Val | Phe | Gly | Val | Ile | Ile | Phe | Lys | Val | Tyr | Lys | Trp | Lys | Gln | |
| | | | | 710 | | | | | 715 | | | | | 720 | | |
| TCT | AGA | GAC | CTA | TAC | CGA | GCC | CCG | GTG | AGC | TCA | CTG | TAC | CGA | ACA | CCA | 2325 |
| Ser | Arg | Asp | Leu | Tyr | Arg | Ala | Pro | Val | Ser | Ser | Leu | Tyr | Arg | Thr | Pro | |
| | | | 725 | | | | | 730 | | | | | 735 | | | |
| GGG | CCC | TCC | TTG | CAC | GCG | GAC | GCC | GTG | CGG | GGA | GGC | CTG | ATG | TCG | CCG | 2373 |
| Gly | Pro | Ser | Leu | His | Ala | Asp | Ala | Val | Arg | Gly | Gly | Leu | Met | Ser | Pro | |
| | | 740 | | | | | 745 | | | | | 750 | | | | |
| CAC | CTT | TAC | CAT | CAG | GTG | TAT | CTC | ACC | ACG | GAC | TCC | CGC | CGC | AGC | GAC | 2421 |
| His | Leu | Tyr | His | Gln | Val | Tyr | Leu | Thr | Thr | Asp | Ser | Arg | Arg | Ser | Asp | |
| | 755 | | | | | 760 | | | | | 765 | | | | | |
| CCG | CTG | CTG | AAG | AAA | CCT | GGT | GCA | GCC | AGT | CCA | CTG | GCC | AGC | CGC | CAG | 2469 |
| Pro | Leu | Leu | Lys | Lys | Pro | Gly | Ala | Ala | Ser | Pro | Leu | Ala | Ser | Arg | Gln | |
| 770 | | | | | 775 | | | | | 780 | | | | | 785 | |
| AAC | ACG | CTG | CGG | AGC | TGT | GAT | CCG | GTG | TTC | TAT | AGG | CAG | GTG | TTG | GGT | 2517 |
| Asn | Thr | Leu | Arg | Ser | Cys | Asp | Pro | Val | Phe | Tyr | Arg | Gln | Val | Leu | Gly | |
| | | | | 790 | | | | | 795 | | | | | 800 | | |
| GCA | GAG | AGC | GCC | CCT | CCC | GGA | CAG | GTA | AGG | TTT | AGC | AAG | TCA | TGC | TTG | 2565 |
| Ala | Glu | Ser | Ala | Pro | Pro | Gly | Gln | Val | Arg | Phe | Ser | Lys | Ser | Cys | Leu | |
| | | | 805 | | | | | 810 | | | | | 815 | | | |
| ACC | CTG | TTA | GTG | CCT | TTT | TAT | TCC | TAC | ATC | ATA | TTG | AGA | AGG | CTG | GAG | 2613 |
| Thr | Leu | Leu | Val | Pro | Phe | Tyr | Ser | Tyr | Ile | Ile | Leu | Arg | Arg | Leu | Glu | |
| | | 820 | | | | | 825 | | | | | 830 | | | | |

```
CTG TTT TTT TAGTGATGAA GATGTTTTCC TGGTGATGCA TTCACACTTT              2662
Leu Phe Phe
    835

CAACTGGCTC TTCCTAGATC AAAGTTAGTG CCTTTGTGAG ATGGTGGCCT GCCAGAGTGT    2722

GGTTTGTGGT CCCATTTCAG GGGGAAGATA CTTGACTCAT CTGTGGACCT AATTCACATC    2782

CTCAGCG                                                              2789
```

( 2 ) INFORMATION FOR SEQ ID NO:105:

( i ) SEQUENCE CHARACTERISTICS:
        ( A ) LENGTH: 836 amino acids
        ( B ) TYPE: amino acid
        ( D ) TOPOLOGY: linear ( i i ) MOLECULE TYPE: protein ( x i ) SEQUENCE DESCRIPTION: SEQ ID NO:105:

```
Met Val Pro Glu Ala Trp Arg Ser Gly Leu Val Ser Thr Gly Arg Val
  1               5                  10                  15

Val Gly Val Leu Leu Leu Leu Gly Ala Leu Asn Lys Ala Ser Thr Val
             20                  25                  30

Ile His Tyr Glu Ile Pro Glu Glu Arg Glu Lys Gly Phe Ala Val Gly
         35                  40                  45

Asn Val Val Ala Asn Leu Gly Leu Asp Leu Gly Ser Leu Ser Ala Arg
     50                  55                  60

Arg Phe Pro Val Val Ser Gly Ala Ser Arg Arg Phe Phe Glu Val Asn
 65                  70                  75                  80

Arg Glu Thr Gly Glu Met Phe Val Asn Asp Arg Leu Asp Arg Glu Glu
                 85                  90                  95

Leu Cys Gly Thr Leu Pro Ser Cys Thr Val Thr Leu Glu Leu Val Val
            100                 105                 110

Glu Asn Pro Leu Glu Leu Phe Ser Val Glu Val Val Ile Gln Asp Ile
        115                 120                 125

Asn Asp Asn Asn Pro Ala Phe Pro Thr Gln Glu Met Lys Leu Glu Ile
130                 135                 140

Ser Glu Ala Val Ala Pro Gly Thr Arg Phe Pro Leu Glu Ser Ala His
145                 150                 155                 160

Asp Pro Asp Leu Gly Ser Asn Ser Leu Gln Thr Tyr Glu Leu Ser Arg
                165                 170                 175

Asn Glu Tyr Phe Ala Leu Arg Val Gln Thr Arg Glu Asp Ser Thr Lys
                180                 185                 190

Tyr Ala Glu Leu Val Leu Glu Arg Ala Leu Asp Arg Glu Arg Glu Pro
            195                 200                 205

Ser Leu Gln Leu Val Leu Thr Ala Leu Asp Gly Gly Thr Pro Ala Leu
210                 215                 220

Ser Ala Ser Leu Pro Ile His Ile Lys Val Leu Asp Ala Asn Asp Asn
225                 230                 235                 240

Ala Pro Val Phe Asn Gln Ser Leu Tyr Arg Ala Arg Val Pro Gly Gly
                245                 250                 255

Cys Thr Ser Gly Thr Arg Val Val Gln Val Leu Ala Thr Asp Leu Asp
            260                 265                 270

Glu Gly Pro Asn Gly Glu Ile Ile Tyr Ser Phe Gly Ser His Asn Arg
            275                 280                 285

Ala Gly Val Arg Gln Leu Phe Ala Leu Asp Leu Val Thr Gly Met Leu
        290                 295                 300

Thr Ile Lys Gly Arg Leu Asp Phe Glu Asp Thr Lys Leu His Glu Ile
```

```
                    305                     310                     315                     320
Tyr  Ile  Gln  Ala  Lys  Asp  Lys  Gly  Ala  Asn  Pro  Glu  Gly  Ala  His  Cys
                    325                     330                     335

Lys  Val  Leu  Val  Glu  Val  Val  Asp  Val  Asn  Asp  Asn  Ala  Pro  Glu  Ile
                    340                     345                     350

Thr  Val  Thr  Ser  Val  Tyr  Ser  Pro  Val  Pro  Glu  Asp  Ala  Ser  Gly  Thr
                    355                     360                     365

Val  Ile  Ala  Leu  Leu  Ser  Val  Thr  Asp  Leu  Asp  Ala  Gly  Glu  Asn  Gly
                    370                     375                     380

Leu  Val  Thr  Cys  Glu  Val  Pro  Pro  Gly  Leu  Pro  Phe  Ser  Leu  Thr  Ser
385                 390                     395                                 400

Ser  Leu  Lys  Asn  Tyr  Phe  Thr  Leu  Lys  Thr  Ser  Ala  Asp  Leu  Asp  Arg
                    405                     410                     415

Glu  Thr  Val  Pro  Glu  Tyr  Asn  Leu  Ser  Ile  Thr  Ala  Arg  Asp  Ala  Gly
                    420                     425                     430

Thr  Pro  Ser  Leu  Ser  Ala  Leu  Thr  Ile  Val  Arg  Val  Gln  Val  Ser  Asp
                    435                     440                     445

Ile  Asn  Asp  Asn  Pro  Pro  Gln  Ser  Ser  Gln  Ser  Ser  Tyr  Asp  Val  Tyr
                    450                     455                     460

Ile  Glu  Glu  Asn  Asn  Leu  Pro  Gly  Ala  Pro  Ile  Leu  Asn  Leu  Ser  Val
465                 470                     475                                 480

Trp  Asp  Pro  Asp  Ala  Pro  Gln  Asn  Ala  Arg  Leu  Ser  Phe  Phe  Leu  Leu
                    485                     490                     495

Glu  Gln  Gly  Ala  Glu  Thr  Gly  Leu  Val  Gly  Arg  Tyr  Phe  Thr  Ile  Asn
                    500                     505                     510

Arg  Asp  Asn  Gly  Ile  Val  Ser  Ser  Leu  Val  Pro  Leu  Asp  Tyr  Glu  Asp
                    515                     520                     525

Arg  Arg  Glu  Phe  Glu  Leu  Thr  Ala  His  Ile  Ser  Asp  Gly  Gly  Thr  Pro
                    530                     535                     540

Val  Leu  Ala  Thr  Asn  Ile  Ser  Val  Asn  Ile  Phe  Val  Thr  Asp  Arg  Asn
545                 550                     555                                 560

Asp  Asn  Ala  Pro  Gln  Val  Leu  Tyr  Pro  Arg  Pro  Gly  Gly  Ser  Ser  Val
                    565                     570                     575

Glu  Met  Leu  Pro  Arg  Gly  Thr  Ser  Ala  Gly  His  Leu  Val  Ser  Arg  Val
                    580                     585                     590

Val  Gly  Trp  Asp  Ala  Asp  Ala  Gly  His  Asn  Ala  Trp  Leu  Ser  Tyr  Ser
                    595                     600                     605

Leu  Phe  Gly  Ser  Pro  Asn  Gln  Ser  Leu  Phe  Ala  Ile  Gly  Leu  His  Thr
                    610                     615                     620

Gly  Gln  Ile  Ser  Thr  Ala  Arg  Pro  Val  Gln  Asp  Thr  Asp  Ser  Pro  Arg
625                 630                     635                                 640

Gln  Thr  Leu  Thr  Val  Leu  Ile  Lys  Asp  Asn  Gly  Glu  Pro  Ser  Leu  Ser
                    645                     650                     655

Thr  Thr  Ala  Thr  Leu  Thr  Val  Ser  Val  Thr  Glu  Asp  Ser  Pro  Glu  Ala
                    660                     665                     670

Arg  Ala  Glu  Phe  Pro  Ser  Gly  Ser  Ala  Pro  Arg  Glu  Gln  Lys  Lys  Asn
                    675                     680                     685

Leu  Thr  Phe  Tyr  Leu  Leu  Leu  Ser  Leu  Ile  Leu  Val  Ser  Val  Gly  Phe
                    690                     695                     700

Val  Val  Thr  Val  Phe  Gly  Val  Ile  Ile  Phe  Lys  Val  Tyr  Lys  Trp  Lys
705                 710                     715                                 720

Gln  Ser  Arg  Asp  Leu  Tyr  Arg  Ala  Pro  Val  Ser  Ser  Leu  Tyr  Arg  Thr
                    725                     730                     735
```

| | | | | | | | | | | | | | | |
|---|---|---|---|---|---|---|---|---|---|---|---|---|---|---|
|Pro|Gly|Pro|Ser<br>740|Leu|His|Ala|Asp|Ala<br>745|Val|Arg|Gly|Gly|Leu<br>750|Met|Ser|
|Pro|His|Leu<br>755|Tyr|His|Gln|Val|Tyr<br>760|Leu|Thr|Thr|Asp|Ser<br>765|Arg|Arg|Ser|
|Asp|Pro<br>770|Leu|Leu|Lys|Lys|Pro<br>775|Gly|Ala|Ala|Ser|Pro<br>780|Leu|Ala|Ser|Arg|
|Gln<br>785|Asn|Thr|Leu|Arg|Ser<br>790|Cys|Asp|Pro|Val|Phe<br>795|Tyr|Arg|Gln|Val|Leu<br>800|
|Gly|Ala|Glu|Ser|Ala<br>805|Pro|Pro|Gly|Gln|Val<br>810|Arg|Phe|Ser|Lys|Ser<br>815|Cys|
|Leu|Thr|Leu|Leu<br>820|Val|Pro|Phe|Tyr|Ser<br>825|Tyr|Ile|Ile|Leu|Arg<br>830|Arg|Leu|
|Glu|Leu|Phe<br>835|Phe| | | | | | | | | | | | |

(2) INFORMATION FOR SEQ ID NO:106:

(i) SEQUENCE CHARACTERISTICS:
        (A) LENGTH: 2751 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 115..2160

(xi) SEQUENCE DESCRIPTION: SEQ ID NO:106:

```
CGAAAGCCAT  GTCGGACTCG  TCGCCCAGCG  CCCAAGCGCT  AACCCGCTGA  AAGTTTCTCA        60

GCGAAATCTC  AGGGACGATC  TGGACCCCGC  TGAGAGGAAC  TGCTTTTGAG  TGAG ATG         117
                                                               Met
                                                                 1
```

| | | | | | | | | | | | | | | | |
|---|---|---|---|---|---|---|---|---|---|---|---|---|---|---|---|
|GTC|CCA|GAG|GCC|TGG|AGG|AGC|GGA|CTG|GTA|AGC|ACC|GGG|AGG|GTA|GTG|165|
|Val|Pro|Glu|Ala<br>5|Trp|Arg|Ser|Gly|Leu<br>10|Val|Ser|Thr|Gly|Arg<br>15|Val|Val| |
|GGA|GTT|TTG|CTT|CTG|CTT|GGT|GCC|TTG|AAC|AAG|GCT|TCC|ACG|GTC|ATT|213|
|Gly|Val|Leu<br>20|Leu|Leu|Leu|Gly|Ala<br>25|Leu|Asn|Lys|Ala|Ser<br>30|Thr|Val|Ile| |
|CAC|TAT|GAG|ATC|CCG|GAG|GAA|AGA|GAG|AAG|GGT|TTC|GCT|GTG|GGC|AAC|261|
|His|Tyr|Glu|Ile|Pro|Glu|Glu|Arg|Glu|Lys|Gly|Phe|Ala|Val|Gly|Asn| |
| | |35| | | | |40| | | | |45| | | | |
|GTG|GTC|GCG|AAC|CTT|GGT|TTG|GAT|CTC|GGT|AGC|CTC|TCA|GCC|CGC|AGG|309|
|Val|Val|Ala|Asn|Leu|Gly|Leu|Asp|Leu|Gly|Ser|Leu|Ser|Ala|Arg|Arg| |
|50| | | | |55| | | | |60| | | | |65| |
|TTC|CCG|GTG|GTG|TCT|GGA|GCT|AGC|CGA|AGA|TTC|TTT|GAG|GTG|AAC|CGG|357|
|Phe|Pro|Val|Val|Ser|Gly|Ala|Ser|Arg|Arg|Phe|Phe|Glu|Val|Asn|Arg| |
| | | | |70| | | | |75| | | | |80| | |
|GAG|ACC|GGA|GAG|ATG|TTT|GTG|AAC|GAC|CGT|CTG|GAT|CGA|GAG|GAG|CTG|405|
|Glu|Thr|Gly|Glu|Met|Phe|Val|Asn|Asp|Arg|Leu|Asp|Arg|Glu|Glu|Leu| |
| | | | |85| | | | |90| | | | |95| | |
|TGT|GGG|ACA|CTG|CCC|TCT|TGC|ACT|GTA|ACT|CTG|GAG|TTG|GTA|GTG|GAG|453|
|Cys|Gly|Thr|Leu|Pro|Ser|Cys|Thr|Val|Thr|Leu|Glu|Leu|Val|Val|Glu| |
| | |100| | | | |105| | | | |110| | | | |
|AAC|CCG|CTG|GAG|CTG|TTC|AGC|GTG|GAA|GTG|GTG|ATC|CAG|GAC|ATC|AAC|501|
|Asn|Pro|Leu|Glu|Leu|Phe|Ser|Val|Glu|Val|Val|Ile|Gln|Asp|Ile|Asn| |
| |115| | | | |120| | | | |125| | | | |
|GAC|AAC|AAT|CCT|GCT|TTC|CCT|ACC|CAG|GAA|ATG|AAA|TTG|GAG|ATT|AGC|549|
|Asp|Asn|Asn|Pro|Ala|Phe|Pro|Thr|Gln|Glu|Met|Lys|Leu|Glu|Ile|Ser| |
|130| | | | |135| | | | |140| | | | |145| |

| | | | | | | | | | | | | | | | | |
|---|---|---|---|---|---|---|---|---|---|---|---|---|---|---|---|---|
| GAG | GCC | GTG | GCT | CCG | GGG | ACG | CGC | TTT | CCG | CTC | GAG | AGC | GCG | CAC | GAT | 597 |
| Glu | Ala | Val | Ala | Pro | Gly | Thr | Arg | Phe | Pro | Leu | Glu | Ser | Ala | His | Asp | |
| | | | | 150 | | | | 155 | | | | | | 160 | | |
| CCC | GAT | CTG | GGA | AGC | AAC | TCT | TTA | CAA | ACC | TAT | GAG | CTG | AGC | CGA | AAT | 645 |
| Pro | Asp | Leu | Gly | Ser | Asn | Ser | Leu | Gln | Thr | Tyr | Glu | Leu | Ser | Arg | Asn | |
| | | | | 165 | | | | 170 | | | | | 175 | | | |
| GAA | TAC | TTT | GCG | CTT | CGC | GTG | CAG | ACG | CGG | GAG | GAC | AGC | ACC | AAG | TAC | 693 |
| Glu | Tyr | Phe | Ala | Leu | Arg | Val | Gln | Thr | Arg | Glu | Asp | Ser | Thr | Lys | Tyr | |
| | | 180 | | | | | 185 | | | | | 190 | | | | |
| GCG | GAG | CTG | GTG | TTG | GAG | CGC | GCC | CTG | GAC | CGA | GAA | CGG | GAG | CCT | AGT | 741 |
| Ala | Glu | Leu | Val | Leu | Glu | Arg | Ala | Leu | Asp | Arg | Glu | Arg | Glu | Pro | Ser | |
| 195 | | | | | 200 | | | | | 205 | | | | | | |
| CTC | CAG | TTA | GTG | CTG | ACG | GCG | TTG | GAC | GGA | GGG | ACC | CCA | GCT | CTC | TCC | 789 |
| Leu | Gln | Leu | Val | Leu | Thr | Ala | Leu | Asp | Gly | Gly | Thr | Pro | Ala | Leu | Ser | |
| 210 | | | | | 215 | | | | | 220 | | | | | 225 | |
| GCC | AGC | CTG | CCT | ATT | CAC | ATC | AAG | GTG | CTG | GAC | GCG | AAT | GAC | AAT | GCG | 837 |
| Ala | Ser | Leu | Pro | Ile | His | Ile | Lys | Val | Leu | Asp | Ala | Asn | Asp | Asn | Ala | |
| | | | | 230 | | | | 235 | | | | | 240 | | | |
| CCT | GTC | TTC | AAC | CAG | TCC | TTG | TAC | CGG | GCG | CGC | GTT | CCT | GGA | GGA | TGC | 885 |
| Pro | Val | Phe | Asn | Gln | Ser | Leu | Tyr | Arg | Ala | Arg | Val | Pro | Gly | Gly | Cys | |
| | | | 245 | | | | 250 | | | | | 255 | | | | |
| ACC | TCC | GGC | ACG | CGC | GTG | GTA | CAA | GTC | CTT | GCA | ACG | GAT | CTG | GAT | GAA | 933 |
| Thr | Ser | Gly | Thr | Arg | Val | Val | Gln | Val | Leu | Ala | Thr | Asp | Leu | Asp | Glu | |
| | | 260 | | | | | 265 | | | | | 270 | | | | |
| GGC | CCC | AAC | GGT | GAA | ATT | ATT | TAC | TCC | TTC | GGC | AGC | CAC | AAC | CGC | GCC | 981 |
| Gly | Pro | Asn | Gly | Glu | Ile | Ile | Tyr | Ser | Phe | Gly | Ser | His | Asn | Arg | Ala | |
| | 275 | | | | | 280 | | | | | 285 | | | | | |
| GGC | GTG | CGG | CAA | CTA | TTC | GCC | TTA | GAC | CTT | GTA | ACC | GGG | ATG | CTG | ACA | 1029 |
| Gly | Val | Arg | Gln | Leu | Phe | Ala | Leu | Asp | Leu | Val | Thr | Gly | Met | Leu | Thr | |
| 290 | | | | | 295 | | | | | 300 | | | | | 305 | |
| ATC | AAG | GGT | CGG | CTG | GAC | TTC | GAG | GAC | ACC | AAA | CTC | CAT | GAG | ATT | TAC | 1077 |
| Ile | Lys | Gly | Arg | Leu | Asp | Phe | Glu | Asp | Thr | Lys | Leu | His | Glu | Ile | Tyr | |
| | | | | 310 | | | | | 315 | | | | | 320 | | |
| ATC | CAG | GCC | AAA | GAC | AAG | GGC | GCC | AAT | CCC | GAA | GGA | GCA | CAT | TGC | AAA | 1125 |
| Ile | Gln | Ala | Lys | Asp | Lys | Gly | Ala | Asn | Pro | Glu | Gly | Ala | His | Cys | Lys | |
| | | | 325 | | | | | 330 | | | | | 335 | | | |
| GTG | TTG | GTG | GAG | GTT | GTG | GAT | GTG | AAT | GAC | AAC | GCC | CCG | GAG | ATC | ACA | 1173 |
| Val | Leu | Val | Glu | Val | Val | Asp | Val | Asn | Asp | Asn | Ala | Pro | Glu | Ile | Thr | |
| | | | 340 | | | | | 345 | | | | | 350 | | | |
| GTC | ACC | TCC | GTG | TAC | AGC | CCA | GTA | CCC | GAG | GAT | GCC | TCT | GGG | ACT | GTC | 1221 |
| Val | Thr | Ser | Val | Tyr | Ser | Pro | Val | Pro | Glu | Asp | Ala | Ser | Gly | Thr | Val | |
| | | 355 | | | | | 360 | | | | | 365 | | | | |
| ATC | GCT | TTG | CTC | AGT | GTG | ACT | GAC | CTG | GAT | GCT | GGC | GAG | AAC | GGG | CTG | 1269 |
| Ile | Ala | Leu | Leu | Ser | Val | Thr | Asp | Leu | Asp | Ala | Gly | Glu | Asn | Gly | Leu | |
| 370 | | | | | 375 | | | | | 380 | | | | | 385 | |
| GTG | ACC | TGC | GAA | GTT | CCA | CCG | GGT | CTC | CCT | TTC | AGC | CTT | ACT | TCT | TCC | 1317 |
| Val | Thr | Cys | Glu | Val | Pro | Pro | Gly | Leu | Pro | Phe | Ser | Leu | Thr | Ser | Ser | |
| | | | | 390 | | | | | 395 | | | | | 400 | | |
| CTC | AAG | AAT | TAC | TTC | ACT | TTG | AAA | ACC | AGT | GCA | GAC | CTG | GAT | CGG | GAG | 1365 |
| Leu | Lys | Asn | Tyr | Phe | Thr | Leu | Lys | Thr | Ser | Ala | Asp | Leu | Asp | Arg | Glu | |
| | | | 405 | | | | | 410 | | | | | 415 | | | |
| ACT | GTG | CCA | GAA | TAC | AAC | CTC | AGC | ATC | ACC | GCC | CGA | GAC | GCC | GGA | ACC | 1413 |
| Thr | Val | Pro | Glu | Tyr | Asn | Leu | Ser | Ile | Thr | Ala | Arg | Asp | Ala | Gly | Thr | |
| | | 420 | | | | | 425 | | | | | 430 | | | | |
| CCT | TCC | CTC | TCA | GCC | CTT | ACA | ATA | GTG | CGT | GTT | CAA | GTG | TCC | GAC | ATC | 1461 |
| Pro | Ser | Leu | Ser | Ala | Leu | Thr | Ile | Val | Arg | Val | Gln | Val | Ser | Asp | Ile | |
| | 435 | | | | | 440 | | | | | 445 | | | | | |
| AAT | GAC | AAC | CCT | CCA | CAA | TCT | TCT | CAA | TCT | TCC | TAC | GAC | GTT | TAC | ATT | 1509 |
| Asn | Asp | Asn | Pro | Pro | Gln | Ser | Ser | Gln | Ser | Ser | Tyr | Asp | Val | Tyr | Ile | |
| 450 | | | | | 455 | | | | | 460 | | | | | 465 | |

| | | | | | | | | | | | | | | | | |
|---|---|---|---|---|---|---|---|---|---|---|---|---|---|---|---|---|
| GAA | GAA | AAC | AAC | CTC | CCC | GGG | GCT | CCA | ATA | CTA | AAC | CTA | AGT | GTC | TGG | 1557 |
| Glu | Glu | Asn | Asn | Leu | Pro | Gly | Ala | Pro | Ile | Leu | Asn | Leu | Ser | Val | Trp | |
| | | | | 470 | | | | | 475 | | | | | 480 | | |
| GAC | CCC | GAC | GCC | CCG | CAG | AAT | GCT | CGG | CTT | TCT | TTC | TTT | CTC | TTG | GAG | 1605 |
| Asp | Pro | Asp | Ala | Pro | Gln | Asn | Ala | Arg | Leu | Ser | Phe | Phe | Leu | Leu | Glu | |
| | | | 485 | | | | | 490 | | | | | 495 | | | |
| CAA | GGA | GCT | GAA | ACC | GGG | CTA | GTG | GGT | CGC | TAT | TTC | ACA | ATA | AAT | CGT | 1653 |
| Gln | Gly | Ala | Glu | Thr | Gly | Leu | Val | Gly | Arg | Tyr | Phe | Thr | Ile | Asn | Arg | |
| | | 500 | | | | | 505 | | | | | 510 | | | | |
| GAC | AAT | GGC | ATA | GTG | TCA | TCC | TTA | GTG | CCC | CTA | GAC | TAT | GAG | GAT | CGG | 1701 |
| Asp | Asn | Gly | Ile | Val | Ser | Ser | Leu | Val | Pro | Leu | Asp | Tyr | Glu | Asp | Arg | |
| | 515 | | | | | 520 | | | | | 525 | | | | | |
| CGG | GAA | TTT | GAA | TTA | ACA | GCT | CAT | ATC | AGC | GAT | GGG | GGC | ACC | CCG | GTC | 1749 |
| Arg | Glu | Phe | Glu | Leu | Thr | Ala | His | Ile | Ser | Asp | Gly | Gly | Thr | Pro | Val | |
| 530 | | | | | 535 | | | | | 540 | | | | | 545 | |
| CTA | GCC | ACC | AAC | ATC | AGC | GTG | AAC | ATA | TTT | GTC | ACT | GAT | CGC | AAT | GAC | 1797 |
| Leu | Ala | Thr | Asn | Ile | Ser | Val | Asn | Ile | Phe | Val | Thr | Asp | Arg | Asn | Asp | |
| | | | | 550 | | | | | 555 | | | | | 560 | | |
| AAT | GCC | CCC | CAG | GTC | CTA | TAT | CCT | CGG | CCA | GGT | GGG | AGC | TCG | GTG | GAG | 1845 |
| Asn | Ala | Pro | Gln | Val | Leu | Tyr | Pro | Arg | Pro | Gly | Gly | Ser | Ser | Val | Glu | |
| | | | 565 | | | | | 570 | | | | | 575 | | | |
| ATG | CTG | CCT | CGA | GGT | ACC | TCA | GCT | GGC | CAC | CTA | GTG | TCA | CGG | GTG | GTA | 1893 |
| Met | Leu | Pro | Arg | Gly | Thr | Ser | Ala | Gly | His | Leu | Val | Ser | Arg | Val | Val | |
| | | | 580 | | | | | 585 | | | | | 590 | | | |
| GGC | TGG | GAC | GCG | GAT | GCA | GGG | CAC | AAT | GCC | TGG | CTC | TCC | TAC | AGT | CTC | 1941 |
| Gly | Trp | Asp | Ala | Asp | Ala | Gly | His | Asn | Ala | Trp | Leu | Ser | Tyr | Ser | Leu | |
| | | 595 | | | | | 600 | | | | | 605 | | | | |
| TTT | GGA | TCC | CCT | AAC | CAG | AGC | CTT | TTT | GCC | ATA | GGG | CTG | CAC | ACT | GGT | 1989 |
| Phe | Gly | Ser | Pro | Asn | Gln | Ser | Leu | Phe | Ala | Ile | Gly | Leu | His | Thr | Gly | |
| 610 | | | | | 615 | | | | | 620 | | | | | 625 | |
| CAA | ATC | AGT | ACT | GCC | CGT | CCA | GTC | CAA | GAC | ACA | GAT | TCA | CCC | AGG | CAG | 2037 |
| Gln | Ile | Ser | Thr | Ala | Arg | Pro | Val | Gln | Asp | Thr | Asp | Ser | Pro | Arg | Gln | |
| | | | | 630 | | | | | 635 | | | | | 640 | | |
| ACT | CTC | ACT | GTC | TTG | ATC | AAA | GAC | AAT | GGG | GAG | CCT | TCG | CTC | TCC | ACC | 2085 |
| Thr | Leu | Thr | Val | Leu | Ile | Lys | Asp | Asn | Gly | Glu | Pro | Ser | Leu | Ser | Thr | |
| | | | 645 | | | | | 650 | | | | | 655 | | | |
| ACT | GCT | ACC | CTC | ACT | GTG | TCA | GTA | ACC | GAG | GAC | TCT | CCT | GAA | GCC | CGA | 2133 |
| Thr | Ala | Thr | Leu | Thr | Val | Ser | Val | Thr | Glu | Asp | Ser | Pro | Glu | Ala | Arg | |
| | | 660 | | | | | 665 | | | | | 670 | | | | |
| GCC | GAG | TTC | CCC | TCT | GGC | TCT | GCC | AGT | TAAACCTTCT | | TTAATTATGG | | | | | 2180 |
| Ala | Glu | Phe | Pro | Ser | Gly | Ser | Ala | Ser | | | | | | | | |
| | 675 | | | | | 680 | | | | | | | | | | |

| | | | | |
|---|---|---|---|---|
| ATTAGCCATT | AACATTTTTG | AAACGTGGAC | CATTTAACCT | CGGCCTACCC | CCTCCAACTG | 2240 |
| TCCTGGTGAT | GAGTTCATTA | GCTAAGTTAA | ATTAATTGAA | CTTTGATCTA | AACCAAAACA | 2300 |
| AATCAGGAAA | ATAAAGCTGT | AAAGGAACTT | ATCAAGCATT | CCAAAACCAA | CTAGAAATTA | 2360 |
| CTTGAAGTTT | CGAGTGAGCA | TTGCCTGTGC | CAGTATTCTT | CATTATAGGA | TTATAAACTC | 2420 |
| GTTTTTTTCC | CAAAGCGCAT | GTCTACGCCA | GGCAGAGGAG | TAATTATTCA | GCCAATTTCA | 2480 |
| TGGATGTAAC | GATGGATATA | AATAATTGAT | AGCACCTAGA | GGCTTCCAGT | TTGGGTGGAA | 2540 |
| GGCTAAAAGT | AGAGGGAAC | TCACTCACTT | GAGAAATGAT | ATTTAAGTGA | ATAAATAGTT | 2600 |
| CTCTTCTATG | AAACTATTAC | TATTTAGTTC | TCTGGAAAAC | TTAAGTGTAT | TAATGATTAG | 2660 |
| AACATCAAAT | CCTAAGTAAA | GAAATGACAT | TTTAAATATA | AAAAGCCAAA | CTTTAAATAA | 2720 |
| ATCATAGAGA | CCTCAGACAT | AATATAGGAA | A | | | 2751 |

( 2 ) INFORMATION FOR SEQ ID NO:107:

( i ) SEQUENCE CHARACTERISTICS:

(A) LENGTH: 682 amino acids
(B) TYPE: amino acid
(D) TOPOLOGY: linear (ii) MOLECULE TYPE: protein (xi) SEQUENCE DESCRIPTION: SEQ ID NO:107:

| Met | Val | Pro | Glu | Ala | Trp | Arg | Ser | Gly | Leu | Val | Ser | Thr | Gly | Arg | Val |
|---|---|---|---|---|---|---|---|---|---|---|---|---|---|---|---|
| 1 | | | | 5 | | | | | 10 | | | | | 15 | |
| Val | Gly | Val | Leu | Leu | Leu | Leu | Gly | Ala | Leu | Asn | Lys | Ala | Ser | Thr | Val |
| | | | 20 | | | | | 25 | | | | | 30 | | |
| Ile | His | Tyr | Glu | Ile | Pro | Glu | Glu | Arg | Glu | Lys | Gly | Phe | Ala | Val | Gly |
| | | 35 | | | | | 40 | | | | | 45 | | | |
| Asn | Val | Val | Ala | Asn | Leu | Gly | Leu | Asp | Leu | Gly | Ser | Leu | Ser | Ala | Arg |
| | 50 | | | | | 55 | | | | | 60 | | | | |
| Arg | Phe | Pro | Val | Val | Ser | Gly | Ala | Ser | Arg | Arg | Phe | Phe | Glu | Val | Asn |
| 65 | | | | | 70 | | | | | 75 | | | | | 80 |
| Arg | Glu | Thr | Gly | Glu | Met | Phe | Val | Asn | Asp | Arg | Leu | Asp | Arg | Glu | Glu |
| | | | | 85 | | | | | 90 | | | | | 95 | |
| Leu | Cys | Gly | Thr | Leu | Pro | Ser | Cys | Thr | Val | Thr | Leu | Glu | Leu | Val | Val |
| | | | 100 | | | | | 105 | | | | | 110 | | |
| Glu | Asn | Pro | Leu | Glu | Leu | Phe | Ser | Val | Glu | Val | Val | Ile | Gln | Asp | Ile |
| | | 115 | | | | | 120 | | | | | 125 | | | |
| Asn | Asp | Asn | Asn | Pro | Ala | Phe | Pro | Thr | Gln | Glu | Met | Lys | Leu | Glu | Ile |
| | 130 | | | | | 135 | | | | | 140 | | | | |
| Ser | Glu | Ala | Val | Ala | Pro | Gly | Thr | Arg | Phe | Pro | Leu | Glu | Ser | Ala | His |
| 145 | | | | | 150 | | | | | 155 | | | | | 160 |
| Asp | Pro | Asp | Leu | Gly | Ser | Asn | Ser | Leu | Gln | Thr | Tyr | Glu | Leu | Ser | Arg |
| | | | | 165 | | | | | 170 | | | | | 175 | |
| Asn | Glu | Tyr | Phe | Ala | Leu | Arg | Val | Gln | Thr | Arg | Glu | Asp | Ser | Thr | Lys |
| | | | 180 | | | | | 185 | | | | | 190 | | |
| Tyr | Ala | Glu | Leu | Val | Leu | Glu | Arg | Ala | Leu | Asp | Arg | Glu | Arg | Glu | Pro |
| | | | 195 | | | | | 200 | | | | | 205 | | |
| Ser | Leu | Gln | Leu | Val | Leu | Thr | Ala | Leu | Asp | Gly | Gly | Thr | Pro | Ala | Leu |
| | 210 | | | | | 215 | | | | | 220 | | | | |
| Ser | Ala | Ser | Leu | Pro | Ile | His | Ile | Lys | Val | Leu | Asp | Ala | Asn | Asp | Asn |
| 225 | | | | | 230 | | | | | 235 | | | | | 240 |
| Ala | Pro | Val | Phe | Asn | Gln | Ser | Leu | Tyr | Arg | Ala | Arg | Val | Pro | Gly | Gly |
| | | | | 245 | | | | | 250 | | | | | 255 | |
| Cys | Thr | Ser | Gly | Thr | Arg | Val | Val | Gln | Val | Leu | Ala | Thr | Asp | Leu | Asp |
| | | | 260 | | | | | 265 | | | | | 270 | | |
| Glu | Gly | Pro | Asn | Gly | Glu | Ile | Ile | Tyr | Ser | Phe | Gly | Ser | His | Asn | Arg |
| | | | 275 | | | | | 280 | | | | | 285 | | |
| Ala | Gly | Val | Arg | Gln | Leu | Phe | Ala | Leu | Asp | Leu | Val | Thr | Gly | Met | Leu |
| | | 290 | | | | | 295 | | | | | 300 | | | |
| Thr | Ile | Lys | Gly | Arg | Leu | Asp | Phe | Glu | Asp | Thr | Lys | Leu | His | Glu | Ile |
| 305 | | | | | 310 | | | | | 315 | | | | | 320 |
| Tyr | Ile | Gln | Ala | Lys | Asp | Lys | Gly | Ala | Asn | Pro | Glu | Gly | Ala | His | Cys |
| | | | | 325 | | | | | 330 | | | | | 335 | |
| Lys | Val | Leu | Val | Glu | Val | Val | Asp | Val | Asn | Asp | Asn | Ala | Pro | Glu | Ile |
| | | | 340 | | | | | 345 | | | | | 350 | | |
| Thr | Val | Thr | Ser | Val | Tyr | Ser | Pro | Val | Pro | Glu | Asp | Ala | Ser | Gly | Thr |
| | | 355 | | | | | 360 | | | | | 365 | | | |
| Val | Ile | Ala | Leu | Leu | Ser | Val | Thr | Asp | Leu | Asp | Ala | Gly | Glu | Asn | Gly |
| | | 370 | | | | | 375 | | | | | 380 | | | |

| | | | | | | | | | | | | | | |
|---|---|---|---|---|---|---|---|---|---|---|---|---|---|---|
| Leu | Val | Thr | Cys | Glu | Val | Pro | Pro | Gly | Leu | Pro | Phe | Ser | Leu | Thr | Ser |
| 385 | | | | 390 | | | | | 395 | | | | | | 400 |
| Ser | Leu | Lys | Asn | Tyr | Phe | Thr | Leu | Lys | Thr | Ser | Ala | Asp | Leu | Asp | Arg |
| | | | | 405 | | | | | 410 | | | | | 415 | |
| Glu | Thr | Val | Pro | Glu | Tyr | Asn | Leu | Ser | Ile | Thr | Ala | Arg | Asp | Ala | Gly |
| | | | 420 | | | | | 425 | | | | | 430 | | |
| Thr | Pro | Ser | Leu | Ser | Ala | Leu | Thr | Ile | Val | Arg | Val | Gln | Val | Ser | Asp |
| | | 435 | | | | | 440 | | | | | 445 | | | |
| Ile | Asn | Asp | Asn | Pro | Pro | Gln | Ser | Ser | Gln | Ser | Ser | Tyr | Asp | Val | Tyr |
| | 450 | | | | | 455 | | | | | 460 | | | | |
| Ile | Glu | Glu | Asn | Asn | Leu | Pro | Gly | Ala | Pro | Ile | Leu | Asn | Leu | Ser | Val |
| 465 | | | | | 470 | | | | | 475 | | | | | 480 |
| Trp | Asp | Pro | Asp | Ala | Pro | Gln | Asn | Ala | Arg | Leu | Ser | Phe | Phe | Leu | Leu |
| | | | | 485 | | | | | 490 | | | | | 495 | |
| Glu | Gln | Gly | Ala | Glu | Thr | Gly | Leu | Val | Gly | Arg | Tyr | Phe | Thr | Ile | Asn |
| | | | 500 | | | | | 505 | | | | | 510 | | |
| Arg | Asp | Asn | Gly | Ile | Val | Ser | Ser | Leu | Val | Pro | Leu | Asp | Tyr | Glu | Asp |
| | | 515 | | | | | 520 | | | | | 525 | | | |
| Arg | Arg | Glu | Phe | Glu | Leu | Thr | Ala | His | Ile | Ser | Asp | Gly | Gly | Thr | Pro |
| | 530 | | | | | 535 | | | | | 540 | | | | |
| Val | Leu | Ala | Thr | Asn | Ile | Ser | Val | Asn | Ile | Phe | Val | Thr | Asp | Arg | Asn |
| 545 | | | | | 550 | | | | | 555 | | | | | 560 |
| Asp | Asn | Ala | Pro | Gln | Val | Leu | Tyr | Pro | Arg | Pro | Gly | Gly | Ser | Ser | Val |
| | | | | 565 | | | | | 570 | | | | | 575 | |
| Glu | Met | Leu | Pro | Arg | Gly | Thr | Ser | Ala | Gly | His | Leu | Val | Ser | Arg | Val |
| | | | 580 | | | | | 585 | | | | | 590 | | |
| Val | Gly | Trp | Asp | Ala | Asp | Ala | Gly | His | Asn | Ala | Trp | Leu | Ser | Tyr | Ser |
| | | 595 | | | | | 600 | | | | | 605 | | | |
| Leu | Phe | Gly | Ser | Pro | Asn | Gln | Ser | Leu | Phe | Ala | Ile | Gly | Leu | His | Thr |
| | 610 | | | | | 615 | | | | | 620 | | | | |
| Gly | Gln | Ile | Ser | Thr | Ala | Arg | Pro | Val | Gln | Asp | Thr | Asp | Ser | Pro | Arg |
| 625 | | | | | 630 | | | | | 635 | | | | | 640 |
| Gln | Thr | Leu | Thr | Val | Leu | Ile | Lys | Asp | Asn | Gly | Glu | Pro | Ser | Leu | Ser |
| | | | | 645 | | | | | 650 | | | | | 655 | |
| Thr | Thr | Ala | Thr | Leu | Thr | Val | Ser | Val | Thr | Glu | Asp | Ser | Pro | Glu | Ala |
| | | | 660 | | | | | 665 | | | | | 670 | | |
| Arg | Ala | Glu | Phe | Pro | Ser | Gly | Ser | Ala | Ser | | | | | | |
| | | 675 | | | | | 680 | | | | | | | | |

(2) INFORMATION FOR SEQ ID NO:108:

(i) SEQUENCE CHARACTERISTICS:
        (A) LENGTH: 2831 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:108:

```
GAATTCGGCA CGAGGCTGAA CTGAGGGTGA CGGACATAAA CGACTATTCT CCAGTGTTCA      60
GTGAAAGAGA AATGATACTG AGGATACCAG AAAACAGTGC TCGGGGAAAT ACATTCCCTT     120
TAAACAATGC TCTGGACTCA GACGTAGATA TCAACAATAT CCAGACCTAT AGGCTCAGCT     180
CAAACTCTCA TTTCCTGGTT GTAACCCGCA ACCGCAGTGA TGGCAGGAAG TACCCAGAGC     240
TGGTGCTGGA GAAAGAACTG GATCGAGAGG AGGAACCTGA GCTGAGGTTA ACGCTGACAG     300
```

| | | | | | | |
|---|---|---|---|---|---|---|
| CTTTGGATGG | TGGCTCTCCT | CCCCGGTCTG | GGACGACACA | GGTCCTCATT | GAAGTAGTGG | 360 |
| ACACCAACGA | TAATGCACCC | GAGTTTCAGC | AGCCAACATA | CCAAGTGCAA | ACTCCCGAGA | 420 |
| ACAGTCCCAC | CGGCTCTCTG | GTACTCACAG | TCTCAGCCAA | TGACTTAGAC | AGTGGAGACT | 480 |
| ATGGGAAAGT | CTTGTACGCA | CTTTCGCAAC | CCTCAGAAGA | TATTAGCAAA | ACATTCGAGG | 540 |
| TAAACCCTGT | AACCGGGGAA | ATTCGCCTAC | GAAAAGAGGT | GAATTTGAA | ACTATTCCTT | 600 |
| CGTATGAAGT | GGTTATCAAG | GGGACGGACG | GGGGAGGTCT | CTCAGGAAAA | TGCACTCTGT | 660 |
| TACTGCAGGT | GGTGGACGTG | AATGACAATG | CCCCAGAAGT | GATGCTATCT | GCGCTAACCA | 720 |
| ACCCAGTCCC | AGAAAATTCC | CCCGATGAGG | TAGTGGCTGT | TTTCAGTGTT | AGAGATCCTG | 780 |
| ACTCTGGGAA | CAACGGAAAA | GTGATTGCAT | CCATCGAGGA | AGACCTGCCC | TTTCTTCTAA | 840 |
| AATCTTCAGG | AAAGAACTTT | TACACTTTAG | TAACCAAGGG | AGCACTTGAC | AGGGAAGAAA | 900 |
| GAGAGCAATT | GAACATCACC | ATCACAGTCA | CTGACCTGGG | CATACCCAGG | CTCACCACCC | 960 |
| AACACACCAT | AACAGTGCAG | GTGGCAGACA | TCAACGACAA | TGCCCCCTCC | TTCACCCAAA | 1020 |
| CCTCCTACAC | CATGTTTGTC | CGCGAGAACA | ACAGCCCGC | CCTGCACATA | GGCACCATCA | 1080 |
| GCGCCACAGA | CTCAGACTCA | GGATCCAATG | CCCACATCAC | CTACTCGCTG | CTACCGCCCC | 1140 |
| AAGACCCACA | GCTGGCCCTC | GACTCGCTCA | TCTCCATCAA | TGTAGACAAC | GGGCAGCTGT | 1200 |
| TCGCGCTCAG | GGCGCTAGAC | TATGAGGCTC | TGCAGGGCTT | CGAGTTCCAT | GTGGGCGCCA | 1260 |
| CAGACCAAGG | CTCGCCCGCG | CTCAGCAGCC | AGGCTCTGGT | GCACGTGGTG | GTGTTGGACG | 1320 |
| ACAATGACAA | TGCGCCCTTC | GTGCTCTACC | CGCTGCAAAA | CGCCTCTGCA | CCCTTCACTG | 1380 |
| AGCTGCTGCC | CAGGGCGGCA | GAGCCTGGAT | ACCTGGTTAC | CAAGGTGGTA | GCTGTGGACC | 1440 |
| GCGACTCTGG | CCAGAATGCC | TGGCTGTCAT | TCCAGCTGCT | CAAGGCCACG | GAGCCCGGGC | 1500 |
| TGTTCAACGT | ATGGGCGCAC | AATGGCGAGG | TACGCACCTC | CAGGCTGCTG | AGCGAGCGCG | 1560 |
| ACGCACCCAA | GCACAAGCTG | CTGCTGTTGG | TCAAGGACAA | TGGAGATCCT | CCACGCTCTG | 1620 |
| CCAGTGTTAC | TCTGCACGTG | CTAGTGGTGG | ATGCCTTCTC | TCAGCCCTAC | CTGCCTCTGC | 1680 |
| CAGAGGTGGC | GCACGACCCT | GCACAAGAAG | AAGATGCGCT | AACACTCTAC | CTGGTCATAG | 1740 |
| CTTTGGCATC | TGTGTCTTCT | CTCTTCCTCT | TGTCTGTGCT | GCTGTTCGTG | GGGGTGAGGC | 1800 |
| TCTGCAGGAG | GGCCAGGGCA | GCCTCTCTGA | GTGCCTATTC | TGTGCCTGAA | GGCCACTTTC | 1860 |
| CTGGCCAGCT | GGTGGATGTC | AGAGGTATGG | GGACCCTGTC | CCAGAGCTAC | CAGTATGATG | 1920 |
| TATGTCTGAT | GGGGGATTCT | TCTGGGACCA | GCGAATTTAA | CTTCTTAAAG | CCAGTTCTGC | 1980 |
| CTAGCTCTCT | GCACCAGTGC | TCTGGGAAAG | AAATAGAGGA | AAATTCCACA | CTCCAGAATA | 2040 |
| GTTTTGGGTT | TCATCATTAA | TAGAAAACTA | CTTTACAGAT | ATTTAATTCC | AAATATCATC | 2100 |
| TTGTTGATTA | ACTAAAGTCT | GTTCACATGT | AGCTAGCTAG | CAACGATTTT | AATGTTCACT | 2160 |
| TTACCCATCT | TTTTTCAGGG | TCATGTCTAA | AGCTACAAGT | TTGNCTTTAC | TTATACTTGT | 2220 |
| CGCACAGAAT | NNNNNNNNN | TGGTGTATAA | GTCACAGTCA | TGGGATACTG | GCACAAGATG | 2280 |
| GCAGCTTGAT | TGCTCAGTTA | TGGCTGCAAA | GGGGNGCTTG | AGTTTAGGGA | ATGTGTTAGA | 2340 |
| GCTGGAATAA | GTTTTCTGAG | AAATGTGTAA | GACAAATTTC | TTTTGCACAT | TCCCTGTGTT | 2400 |
| CCTGTACCCC | TGTTTCCAGA | ACTACGAAAT | GTGTCATCAG | AAGGCATGCT | CACATTTTCC | 2460 |
| CCTTTGTTTG | CGTGACCCGG | GTGCCAGAAA | TTAAATAAAA | TTAGCATGGA | GTTCAATGCA | 2520 |
| GCATTAAAAC | AAAGTTACTT | CTACAAACCT | TTTATTCGAC | GGTTAAAATT | GTAACTTCCC | 2580 |
| CACCCATGAG | GCTGGCTGTA | AGAACCAGTA | TGAATGGGTG | TCTATCGCAA | CCTTATTTTC | 2640 |
| AAAAATCAAA | CAAAAGGAGA | AATGAGAGAC | CAAACAACAC | GCTACAGGAA | AGATTTCATA | 2700 |

-continued

| | | | | | |
|---|---|---|---|---|---|
| AGGATGTATG | TATGGACACA | AAAACTGGGA | TACAGACATT | TTAAATCTGT | TGGTACCACA | 2760 |
| TGGTGGCGCT | GCAGGCTAAA | GAAATGCAAG | GGAAATTAAA | AAGAGGCTGA | GCTAGAAGTC | 2820 |
| AAAAAAAAA A | | | | | | 2831 |

( 2 ) INFORMATION FOR SEQ ID NO:109:

( i ) SEQUENCE CHARACTERISTICS:
        ( A ) LENGTH: 3353 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 763..3123

( x i ) SEQUENCE DESCRIPTION: SEQ ID NO:109:

| | | | | | |
|---|---|---|---|---|---|
| GTATTTTTCC | ACAGTTTAAA | ATTTTCATAA | AATCATAACT | CTCTGACTTT | ATGTAGAAAG | 60 |
| GATACCACAC | TGGAATTAAC | GTGTAGCTTT | TTCTTGATGT | AATCCAACCA | ATGGGAGCAC | 120 |
| AATTCTGGTA | CATAGGCTGT | CTAGAATTTG | AAAGAAATTA | AAGAATTCAT | TTTGTTTTGC | 180 |
| TGATAAATTT | TTAAGAAATC | ACGTGGCTTT | ATGTTATTAT | TATTACAAGA | TGACTGATCA | 240 |
| CTATTATGTC | TTCTTTCACT | TCTCAATTTC | CCTCAGAACA | CTACACCCAG | ACTACAGGCT | 300 |
| CTGGAGGGTG | GGGACCATGT | CTGGGTTGTT | TACTGATGTA | TTTCATAATT | TGGCACATAG | 360 |
| AGACCAATAA | TACTCCTTTA | AATGAAGAAA | TTAATAATTA | CCATTGCGTG | ATATTGTGAT | 420 |
| TACATCATTT | CCTCCCAATT | TCCAAACTCC | TAATAGAATA | GAGAATAGAT | CAATTGTAGC | 480 |
| AATTCGTTTC | GAAGCAAAGA | CAACGCATGG | TGGCGCTGCA | GGCTAAGGCT | TCAAAAAAG | 540 |
| GAAAGGAAA | AAGCCCATGA | AATGCTACTA | GCTACTTCAG | ACCTCTTTCA | GCCTAAGAGG | 600 |
| AAAGCCTGTT | AGCAGAGCAC | GGACCAGTGT | CTCCGGAGAA | TGCTATTCTC | CTACATTTCC | 660 |
| GAACAGGTTA | TCAACGCACA | GATCGATCAC | TGCCTCTGTC | CCATCGCTCC | CTGAAGTAGC | 720 |
| TCTGACTCCG | GTTCCTTGAA | AGGGGCGTGT | ACAGAAGTAA | AG ATG GAG CCT GCA | | 774 |
| | | | | Met Glu Pro Ala | | |
| | | | | 1 | | |

| | | | | | | | | | | | | | | | |
|---|---|---|---|---|---|---|---|---|---|---|---|---|---|---|---|
| GGG | GAG | CGC | TTT | CCC | GAA | CAA | AGG | CAA | GTC | CTG | ATT | CTC | CTT | CTT | TTA | 822 |
| Gly | Glu | Arg | Phe | Pro | Glu | Gln | Arg | Gln | Val | Leu | Ile | Leu | Leu | Leu | Leu | |
| 5 | | | | 10 | | | | | 15 | | | | | | 20 | |
| CTG | GAA | GTG | ACT | CTG | GCA | GGC | TGG | GAA | CCC | CGT | CGC | TAT | TCT | GTG | ATG | 870 |
| Leu | Glu | Val | Thr | Leu | Ala | Gly | Trp | Glu | Pro | Arg | Arg | Tyr | Ser | Val | Met | |
| | | | | 25 | | | | 30 | | | | | 35 | | | |
| GAG | GAA | ACA | GAG | AGA | GGT | TCT | TTT | GTA | GCC | AAC | CTG | GCC | AAT | GAC | CTA | 918 |
| Glu | Glu | Thr | Glu | Arg | Gly | Ser | Phe | Val | Ala | Asn | Leu | Ala | Asn | Asp | Leu | |
| | | | 40 | | | | | 45 | | | | | 50 | | | |
| GGG | CTG | GGA | GTG | GGG | GAG | CTA | GCC | GAG | CGG | GGA | GCC | CGG | GTA | GTT | TCT | 966 |
| Gly | Leu | Gly | Val | Gly | Glu | Leu | Ala | Glu | Arg | Gly | Ala | Arg | Val | Val | Ser | |
| | | 55 | | | | | 60 | | | | | 65 | | | | |
| GAG | GAT | AAC | GAA | CAA | GGC | TTG | CAG | CTT | GAT | CTG | CAG | ACC | GGG | CAG | TTG | 1014 |
| Glu | Asp | Asn | Glu | Gln | Gly | Leu | Gln | Leu | Asp | Leu | Gln | Thr | Gly | Gln | Leu | |
| | 70 | | | | | 75 | | | | | 80 | | | | | |
| ATA | TTA | AAT | GAG | AAG | CTG | GAC | CGG | GAG | AAG | CTG | TGT | GGC | CCT | ACT | GAG | 1062 |
| Ile | Leu | Asn | Glu | Lys | Leu | Asp | Arg | Glu | Lys | Leu | Cys | Gly | Pro | Thr | Glu | |
| 85 | | | | | 90 | | | | | 95 | | | | | 100 | |
| CCC | TGT | ATA | ATG | CAT | TTC | CAA | GTG | TTA | CTG | AAA | AAA | CCT | TTG | GAA | GTA | 1110 |
| Pro | Cys | Ile | Met | His | Phe | Gln | Val | Leu | Leu | Lys | Lys | Pro | Leu | Glu | Val | |
| | | | | 105 | | | | 110 | | | | | 115 | | | |
| TTT | CGA | GCT | GAA | CTA | CTA | GTG | ACA | GAC | ATA | AAC | GAT | CAT | TCT | CCT | GAG | 1158 |

```
Phe Arg Ala Glu Leu Leu Val Thr Asp Ile Asn Asp His Ser Pro Glu
            120                 125                 130

TTT CCT GAA AGA GAA ATG ACC CTG AAA ATC CCA GAA ACT AGC TCC CTT    1206
Phe Pro Glu Arg Glu Met Thr Leu Lys Ile Pro Glu Thr Ser Ser Leu
        135                 140                 145

GGG ACT GTG TTT CCT CTG AAA AAA GCT CGG GAC TTG GAC GTG GGC AGC    1254
Gly Thr Val Phe Pro Leu Lys Lys Ala Arg Asp Leu Asp Val Gly Ser
    150                 155                 160

AAT AAT GTT CAA AAC TAC AAT ATT TCT CCC AAT TCT CAT TTC CAT GTT    1302
Asn Asn Val Gln Asn Tyr Asn Ile Ser Pro Asn Ser His Phe His Val
165                 170                 175                 180

TCC ACT CGC ACC CGA GGG GAT GGC AGG AAA TAC CCA GAG CTG GTG CTG    1350
Ser Thr Arg Thr Arg Gly Asp Gly Arg Lys Tyr Pro Glu Leu Val Leu
                185                 190                 195

GAC ACA GAA CTG GAT CGC GAG GAG CAG GCC GAG CTC AGA TTA ACC TTG    1398
Asp Thr Glu Leu Asp Arg Glu Glu Gln Ala Glu Leu Arg Leu Thr Leu
            200                 205                 210

ACA GCG GTG GAC GGT GGC TCT CCA CCC CGA TCT GGC ACC GTC CAG ATC    1446
Thr Ala Val Asp Gly Gly Ser Pro Pro Arg Ser Gly Thr Val Gln Ile
        215                 220                 225

CTC ATC TTG GTC TTG GAC GCC AAT GAC AAT GCC CCG GAG TTT GTG CAG    1494
Leu Ile Leu Val Leu Asp Ala Asn Asp Asn Ala Pro Glu Phe Val Gln
    230                 235                 240

GCG CTC TAC GAG GTG CAG GTC CCA GAG AAC AGC CCA GTA GGC TCC CTA    1542
Ala Leu Tyr Glu Val Gln Val Pro Glu Asn Ser Pro Val Gly Ser Leu
245                 250                 255                 260

GTT GTC AAG GTC TCT GCT AGG GAT TTA GAC ACT GGG ACA AAT GGA GAG    1590
Val Val Lys Val Ser Ala Arg Asp Leu Asp Thr Gly Thr Asn Gly Glu
                265                 270                 275

ATA TCA TAC TCC CTT TAT TAC AGC TCT CAG GAG ATA GAC AAA CCT TTT    1638
Ile Ser Tyr Ser Leu Tyr Tyr Ser Ser Gln Glu Ile Asp Lys Pro Phe
            280                 285                 290

GAG CTA AGC AGC CTT TCA GGA GAA ATT CGA CTA ATT AAA AAA CTA GAT    1686
Glu Leu Ser Ser Leu Ser Gly Glu Ile Arg Leu Ile Lys Lys Leu Asp
        295                 300                 305

TTT GAG ACA ATG TCT TCA TAT GAT CTA GAT ATA GAG GCA TCT GAT GGC    1734
Phe Glu Thr Met Ser Ser Tyr Asp Leu Asp Ile Glu Ala Ser Asp Gly
    310                 315                 320

GGG GGA CTT TCT GGA AAA TGC TCT GTC TCT GTT AAG GTG CTG GAT GTT    1782
Gly Gly Leu Ser Gly Lys Cys Ser Val Ser Val Lys Val Leu Asp Val
325                 330                 335                 340

AAC GAT AAC TTC CCG GAA CTA AGT ATT TCA TCA CTT ACC AGC CCT ATT    1830
Asn Asp Asn Phe Pro Glu Leu Ser Ile Ser Ser Leu Thr Ser Pro Ile
                345                 350                 355

CCC GAG AAT TCT CCA GAG ACA GAA GTG GCC CTG TTT AGG ATT AGA GAC    1878
Pro Glu Asn Ser Pro Glu Thr Glu Val Ala Leu Phe Arg Ile Arg Asp
            360                 365                 370

CGA GAC TCT GGA GAA AAT GGA AAA ATG ATT TGC TCA ATT CAG GAT GAT    1926
Arg Asp Ser Gly Glu Asn Gly Lys Met Ile Cys Ser Ile Gln Asp Asp
        375                 380                 385

GTT CCT TTT AAG CTA AAA CCT TCT GTT GAG AAT TTC TAC AGG CTG GTA    1974
Val Pro Phe Lys Leu Lys Pro Ser Val Glu Asn Phe Tyr Arg Leu Val
    390                 395                 400

ACA GAA GGG GCG CTG GAC AGA GAG ACC AGA GCC GAG TAC AAC ATC ACC    2022
Thr Glu Gly Ala Leu Asp Arg Glu Thr Arg Ala Glu Tyr Asn Ile Thr
405                 410                 415                 420

ATC ACC ATC ACA GAC TTG GGG ACT CCA AGG CTG AAA ACC GAG CAG AGC    2070
Ile Thr Ile Thr Asp Leu Gly Thr Pro Arg Leu Lys Thr Glu Gln Ser
                425                 430                 435

ATA ACC GTG CTG GTG TCG GAC GTC AAT GAC AAC GCC CCC GCC TTC ACC    2118
```

```
Ile Thr Val Leu  Val Ser Asp Val  Asn Asp Asn Ala  Pro Ala Phe Thr
        440               445               450

CAA ACC TCC TAC  ACC CTG TTC GTC  CGC GAG AAC AAC  AGC CCC GCC CTG     2166
Gln Thr Ser Tyr  Thr Leu Phe Val  Arg Glu Asn Asn  Ser Pro Ala Leu
        455               460               465

CAC ATC GGC AGT  GTC AGC GCC ACA  GAC AGA GAC TCG  GGC ACC AAC GCC     2214
His Ile Gly Ser  Val Ser Ala Thr  Asp Arg Asp Ser  Gly Thr Asn Ala
        470               475               480

CAG GTC ACC TAC  TCG CTG CTG CCG  CCC CAG GAC CCG  CAC CTG CCC CTA     2262
Gln Val Thr Tyr  Ser Leu Leu Pro  Pro Gln Asp Pro  His Leu Pro Leu
485              490               495                            500

ACC TCC CTG GTC  TCC ATT AAC ACG  GAC AAC GGC CAC  CTG TTC GCT CTC     2310
Thr Ser Leu Val  Ser Ile Asn Thr  Asp Asn Gly His  Leu Phe Ala Leu
                 505               510               515

CAG TCG CTG GAC  TAC GAG GCC CTG  CAG GCT TTC GAG  TTC CGC GTG GGC     2358
Gln Ser Leu Asp  Tyr Glu Ala Leu  Gln Ala Phe Glu  Phe Arg Val Gly
        520               525               530

GCC ACA GAC CGC  GGC TTC CCG GCG  CTG AGC AGC GAG  GCG CTG GTG CGA     2406
Ala Thr Asp Arg  Gly Phe Pro Ala  Leu Ser Ser Glu  Ala Leu Val Arg
        535               540               545

GTG CTG GTG CTG  GAC GCC AAC GAC  AAC TCG CCC TTC  GTG CTG TAC CCG     2454
Val Leu Val Leu  Asp Ala Asn Asp  Asn Ser Pro Phe  Val Leu Tyr Pro
550               555               560

CTG CAG AAC GGC  TCC GCG CCC TGC  ACC GAG CTG GTG  CCC CGG GCG GCC     2502
Leu Gln Asn Gly  Ser Ala Pro Cys  Thr Glu Leu Val  Pro Arg Ala Ala
565              570               575                            580

GAG CCG GGC TAC  CTG GTG ACC AAG  GTG GTG GCG GTG  GAC GGC GAC TCG     2550
Glu Pro Gly Tyr  Leu Val Thr Lys  Val Val Ala Val  Asp Gly Asp Ser
                 585               590               595

GGC CAG AAC GCC  TGG CTG TCG TAC  CAG CTG CTC AAG  GCC ACG GAG CCC     2598
Gly Gln Asn Ala  Trp Leu Ser Tyr  Gln Leu Leu Lys  Ala Thr Glu Pro
        600               605               610

GGG CTG TTC GGC  GTG TGG GCG CAC  AAT GGC GAG GTG  CGC ACC GCC AGG     2646
Gly Leu Phe Gly  Val Trp Ala His  Asn Gly Glu Val  Arg Thr Ala Arg
        615               620               625

CTG CTG AGC GAG  CGC GAC GTG GCC  AAG CAC AGG CTA  GTG GTG CTG GTC     2694
Leu Leu Ser Glu  Arg Asp Val Ala  Lys His Arg Leu  Val Val Leu Val
        630               635               640

AAG GAC AAT GGC  GAG CCT CCG CGC  TCG GCC ACA GCC  ACG CTG CAA GTG     2742
Lys Asp Asn Gly  Glu Pro Pro Arg  Ser Ala Thr Ala  Thr Leu Gln Val
645              650               655                            660

CTC CTG GTG GAC  GGC TTC TCT CAG  CCC TAC CTG CCG  CTC CCA GAG GCG     2790
Leu Leu Val Asp  Gly Phe Ser Gln  Pro Tyr Leu Pro  Leu Pro Glu Ala
                 665               670               675

GCC CCG GCC CAA  GCC CAG GCC GAC  TCG CTT ACC GTC  TAC CTG GTG GTG     2838
Ala Pro Ala Gln  Ala Gln Ala Asp  Ser Leu Thr Val  Tyr Leu Val Val
        680               685               690

GCA TTG GCC TCG  GTG TCT TCG CTC  TTC CTC TTC TCG  GTG TTC CTG TTC     2886
Ala Leu Ala Ser  Val Ser Ser Leu  Phe Leu Phe Ser  Val Phe Leu Phe
        695               700               705

GTG GCA GTG CGG  CTG TGC AGG AGG  AGC AGG GCG GCC  TCA GTG GGT CGC     2934
Val Ala Val Arg  Leu Cys Arg Arg  Ser Arg Ala Ala  Ser Val Gly Arg
        710               715               720

TGC TCG GTG CCC  GAG GGC CCC TTT  CCA GGG CAT CTG  GTG GAC GTG AGC     2982
Cys Ser Val Pro  Glu Gly Pro Phe  Pro Gly His Leu  Val Asp Val Ser
725              730               735                            740

GGC ACC GGG ACC  CTT TCC CAG AGC  TAC CAG TAC GAG  GTG TGT CTG ACG     3030
Gly Thr Gly Thr  Leu Ser Gln Ser  Tyr Gln Tyr Glu  Val Cys Leu Thr
                 745               750               755

GGA GGC TCT GAA  AGT AAT GAT TTC  AAG TTC TTG AAG  CCT ATA TTC CCA     3078
```

-continued

| Gly | Gly | Ser | Glu | Ser | Asn | Asp | Phe | Lys | Phe | Leu | Lys | Pro | Ile | Phe | Pro |
|-----|-----|-----|-----|-----|-----|-----|-----|-----|-----|-----|-----|-----|-----|-----|-----|
|     |     |     | 760 |     |     |     |     | 765 |     |     |     |     | 770 |     |     |

```
AAT ATT GTA AGC CAG GAC TCT AGG AGG AAA TCA GAA TTT CTA GAA           3123
Asn Ile Val Ser Gln Asp Ser Arg Arg Lys Ser Glu Phe Leu Glu
        775             780                 785

TAATGTAGGT ATCTGTAGCT TTCCGACCGT CTGTTAATTT TGTCTTCCTC ACTTTTCACC    3183

TTAGTTTTTT TTAACCCTTT AGTAATCTTG AATTCTACTT TTTTTTAAAT TTCTACTGTT    3243

GTCTTTAGTA ATGTTACTCA TTTCCTTTGT CTGATTGTTA GTTTCAAAT TATTGTATTA     3303

TTATAAATAT TTTATATCAG GAAAGTTCAT ATTTCTGAAT AAATTAATAG              3353
```

( 2 ) INFORMATION FOR SEQ ID NO:110:

( i ) SEQUENCE CHARACTERISTICS:
        ( A ) LENGTH: 787 amino acids
        ( B ) TYPE: amino acid
        ( D ) TOPOLOGY: linear ( i i ) MOLECULE TYPE: protein ( x i ) SEQUENCE DESCRIPTION: SEQ ID NO:110:

```
Met Glu Pro Ala Gly Glu Arg Phe Pro Glu Gln Arg Gln Val Leu Ile
 1               5                  10                  15

Leu Leu Leu Leu Leu Glu Val Thr Leu Ala Gly Trp Glu Pro Arg Arg
                20                  25                  30

Tyr Ser Val Met Glu Glu Thr Glu Arg Gly Ser Phe Val Ala Asn Leu
                35                  40                  45

Ala Asn Asp Leu Gly Leu Gly Val Gly Glu Leu Ala Glu Arg Gly Ala
        50                  55                  60

Arg Val Val Ser Glu Asp Asn Glu Gln Gly Leu Gln Leu Asp Leu Gln
 65                  70                  75                  80

Thr Gly Gln Leu Ile Leu Asn Glu Lys Leu Asp Arg Glu Lys Leu Cys
                85                  90                  95

Gly Pro Thr Glu Pro Cys Ile Met His Phe Gln Val Leu Leu Lys Lys
                100                 105                 110

Pro Leu Glu Val Phe Arg Ala Glu Leu Leu Val Thr Asp Ile Asn Asp
                115                 120                 125

His Ser Pro Glu Phe Pro Glu Arg Glu Met Thr Leu Lys Ile Pro Glu
        130                 135                 140

Thr Ser Ser Leu Gly Thr Val Phe Pro Leu Lys Lys Ala Arg Asp Leu
145                 150                 155                 160

Asp Val Gly Ser Asn Asn Val Gln Asn Tyr Asn Ile Ser Pro Asn Ser
                165                 170                 175

His Phe His Val Ser Thr Arg Thr Arg Gly Asp Gly Arg Lys Tyr Pro
                180                 185                 190

Glu Leu Val Leu Asp Thr Glu Leu Asp Arg Glu Glu Gln Ala Glu Leu
                195                 200                 205

Arg Leu Thr Leu Thr Ala Val Asp Gly Gly Ser Pro Pro Arg Ser Gly
210                 215                 220

Thr Val Gln Ile Leu Ile Leu Val Leu Asp Ala Asn Asp Asn Ala Pro
225                 230                 235                 240

Glu Phe Val Gln Ala Leu Tyr Glu Val Gln Val Pro Glu Asn Ser Pro
                245                 250                 255

Val Gly Ser Leu Val Val Lys Val Ser Ala Arg Asp Leu Asp Thr Gly
                260                 265                 270

Thr Asn Gly Glu Ile Ser Tyr Ser Leu Tyr Tyr Ser Ser Gln Glu Ile
                275                 280                 285
```

```
Asp  Lys  Pro  Phe  Glu  Leu  Ser  Ser  Leu  Ser  Gly  Glu  Ile  Arg  Leu  Ile
     290                      295                     300

Lys  Lys  Leu  Asp  Phe  Glu  Thr  Met  Ser  Ser  Tyr  Asp  Leu  Asp  Ile  Glu
305                      310                     315                          320

Ala  Ser  Asp  Gly  Gly  Gly  Leu  Ser  Gly  Lys  Cys  Ser  Val  Ser  Val  Lys
               325                     330                          335

Val  Leu  Asp  Val  Asn  Asp  Asn  Phe  Pro  Glu  Leu  Ser  Ile  Ser  Ser  Leu
               340                     345                     350

Thr  Ser  Pro  Ile  Pro  Glu  Asn  Ser  Pro  Glu  Thr  Glu  Val  Ala  Leu  Phe
               355                     360                     365

Arg  Ile  Arg  Asp  Arg  Asp  Ser  Gly  Glu  Asn  Gly  Lys  Met  Ile  Cys  Ser
          370                     375                     380

Ile  Gln  Asp  Asp  Val  Pro  Phe  Lys  Leu  Lys  Pro  Ser  Val  Glu  Asn  Phe
385                      390                     395                          400

Tyr  Arg  Leu  Val  Thr  Glu  Gly  Ala  Leu  Asp  Arg  Glu  Thr  Arg  Ala  Glu
                    405                     410                     415

Tyr  Asn  Ile  Thr  Ile  Thr  Ile  Thr  Asp  Leu  Gly  Thr  Pro  Arg  Leu  Lys
                    420                     425                     430

Thr  Glu  Gln  Ser  Ile  Thr  Val  Leu  Val  Ser  Asp  Val  Asn  Asp  Asn  Ala
               435                     440                     445

Pro  Ala  Phe  Thr  Gln  Thr  Ser  Tyr  Thr  Leu  Phe  Val  Arg  Glu  Asn  Asn
     450                     455                     460

Ser  Pro  Ala  Leu  His  Ile  Gly  Ser  Val  Ser  Ala  Thr  Asp  Arg  Asp  Ser
465                      470                     475                          480

Gly  Thr  Asn  Ala  Gln  Val  Thr  Tyr  Ser  Leu  Leu  Pro  Pro  Gln  Asp  Pro
                    485                     490                     495

His  Leu  Pro  Leu  Thr  Ser  Leu  Val  Ser  Ile  Asn  Thr  Asp  Asn  Gly  His
               500                     505                     510

Leu  Phe  Ala  Leu  Gln  Ser  Leu  Asp  Tyr  Glu  Ala  Leu  Gln  Ala  Phe  Glu
               515                     520                     525

Phe  Arg  Val  Gly  Ala  Thr  Asp  Arg  Gly  Phe  Pro  Ala  Leu  Ser  Ser  Glu
     530                     535                     540

Ala  Leu  Val  Arg  Val  Leu  Val  Leu  Asp  Ala  Asn  Asp  Asn  Ser  Pro  Phe
545                      550                     555                          560

Val  Leu  Tyr  Pro  Leu  Gln  Asn  Gly  Ser  Ala  Pro  Cys  Thr  Glu  Leu  Val
               565                     570                     575

Pro  Arg  Ala  Ala  Glu  Pro  Gly  Tyr  Leu  Val  Thr  Lys  Val  Val  Ala  Val
               580                     585                     590

Asp  Gly  Asp  Ser  Gly  Gln  Asn  Ala  Trp  Leu  Ser  Tyr  Gln  Leu  Leu  Lys
          595                     600                     605

Ala  Thr  Glu  Pro  Gly  Leu  Phe  Gly  Val  Trp  Ala  His  Asn  Gly  Glu  Val
     610                     615                     620

Arg  Thr  Ala  Arg  Leu  Leu  Ser  Glu  Arg  Asp  Val  Ala  Lys  His  Arg  Leu
625                      630                     635                          640

Val  Val  Leu  Val  Lys  Asp  Asn  Gly  Glu  Pro  Pro  Arg  Ser  Ala  Thr  Ala
                    645                     650                     655

Thr  Leu  Gln  Val  Leu  Leu  Val  Asp  Gly  Phe  Ser  Gln  Pro  Tyr  Leu  Pro
               660                     665                     670

Leu  Pro  Glu  Ala  Ala  Pro  Ala  Gln  Ala  Gln  Ala  Asp  Ser  Leu  Thr  Val
          675                     680                     685

Tyr  Leu  Val  Val  Ala  Leu  Ala  Ser  Val  Ser  Ser  Leu  Phe  Leu  Phe  Ser
     690                     695                     700

Val  Phe  Leu  Phe  Val  Ala  Val  Arg  Leu  Cys  Arg  Arg  Ser  Arg  Ala  Ala
```

|     |     |     |     |     |     |     |     |     |     |     |     |     |     |     |
|-----|-----|-----|-----|-----|-----|-----|-----|-----|-----|-----|-----|-----|-----|-----|
| 705 |     |     |     |     |     | 710 |     |     |     | 715 |     |     |     | 720 |
| Ser | Val | Gly | Arg | Cys | Ser | Val | Pro | Glu | Gly | Pro | Phe | Pro | Gly | His | Leu |
|     |     |     |     | 725 |     |     |     | 730 |     |     |     |     | 735 |     |
| Val | Asp | Val | Ser | Gly | Thr | Gly | Thr | Leu | Ser | Gln | Ser | Tyr | Gln | Tyr | Glu |
|     |     |     | 740 |     |     |     | 745 |     |     |     |     | 750 |     |     |
| Val | Cys | Leu | Thr | Gly | Gly | Ser | Glu | Ser | Asn | Asp | Phe | Lys | Phe | Leu | Lys |
|     |     | 755 |     |     |     |     | 760 |     |     |     |     | 765 |     |     |
| Pro | Ile | Phe | Pro | Asn | Ile | Val | Ser | Gln | Asp | Ser | Arg | Arg | Lys | Ser | Glu |
|     | 770 |     |     |     |     | 775 |     |     |     |     | 780 |     |     |     |
| Phe | Leu | Glu |
| 785 |     |     |

( 2 ) INFORMATION FOR SEQ ID NO:111:

( i ) SEQUENCE CHARACTERISTICS:
        ( A ) LENGTH: 3033 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 138..2528

( x i ) SEQUENCE DESCRIPTION: SEQ ID NO:111:

| | | | | | | | | | | | | | | | |
|---|---|---|---|---|---|---|---|---|---|---|---|---|---|---|---|
| GTGATTGGAC | GTGTTTTTGT | GACTATTTGG | GAAGAAGACA | CCTTCCTAAT | CAGATTTACT | | | | | | | | | | 60 |
| CCAATATCTT | CCCGGACCCT | CATGAGTGGA | TTGCAATTGA | CTTGAAGAAG | CAGCACCCTC | | | | | | | | | | 120 |
| AGGACTGAAT | CTGAACA | ATG | GAG | ACA | GCA | CTA | GCA | AAA | ATA | CCA | CAG | CAA | | | 170 |
| | | Met | Glu | Thr | Ala | Leu | Ala | Lys | Ile | Pro | Gln | Gln | | | |
| | | 1 | | | 5 | | | | | | 10 | | | | |
| AGG | CAA | GTC | TTT | TTT | CTT | ACT | ATA | TTG | TCG | TTA | TTG | TGG | AAG | TCT | AGC | 218 |
| Arg | Gln | Val | Phe | Phe | Leu | Thr | Ile | Leu | Ser | Leu | Leu | Trp | Lys | Ser | Ser |
| | | | 15 | | | | 20 | | | | | 25 | | | |
| TCT | GAG | GCC | ATT | AGA | TAT | TCC | ATG | CCA | GAA | GAA | ACA | GAG | AGT | GGC | TAT | 266 |
| Ser | Glu | Ala | Ile | Arg | Tyr | Ser | Met | Pro | Glu | Glu | Thr | Glu | Ser | Gly | Tyr |
| | | 30 | | | | | 35 | | | | | 40 | | | |
| ATG | GTG | GCT | AAC | CTG | GCG | AAA | GAT | CTG | GGG | ATC | AGG | GTT | GGA | GAA | CTG | 314 |
| Met | Val | Ala | Asn | Leu | Ala | Lys | Asp | Leu | Gly | Ile | Arg | Val | Gly | Glu | Leu |
| | 45 | | | | 50 | | | | | 55 | | | | | |
| TCC | TCT | AGA | GGA | GCT | CAA | ATC | CAT | TAC | AAA | GGA | AAC | AAA | GAA | CTT | TTG | 362 |
| Ser | Ser | Arg | Gly | Ala | Gln | Ile | His | Tyr | Lys | Gly | Asn | Lys | Glu | Leu | Leu |
| 60 | | | | | 65 | | | | | 70 | | | | | 75 |
| CAG | CTG | GAT | GCA | GAG | ACT | GGG | AAT | TTG | TTC | TTA | AAG | GAA | AAA | CTA | GAC | 410 |
| Gln | Leu | Asp | Ala | Glu | Thr | Gly | Asn | Leu | Phe | Leu | Lys | Glu | Lys | Leu | Asp |
| | | | | 80 | | | | | 85 | | | | | 90 | |
| AGA | GAA | CTG | CTG | TGT | GGA | GAG | ACA | GAA | CCC | TGT | GTG | CTG | AAC | TTC | CAG | 458 |
| Arg | Glu | Leu | Leu | Cys | Gly | Glu | Thr | Glu | Pro | Cys | Val | Leu | Asn | Phe | Gln |
| | | | | 95 | | | | | 100 | | | | | 105 | |
| ATC | ATA | CTG | GAA | AAC | CCT | ATG | CAG | TTC | TTC | CAA | ACT | GAA | CTG | CAG | CTC | 506 |
| Ile | Ile | Leu | Glu | Asn | Pro | Met | Gln | Phe | Phe | Gln | Thr | Glu | Leu | Gln | Leu |
| | | 110 | | | | | 115 | | | | | 120 | | | |
| ACA | GAT | ATA | AAC | GAC | CAT | TCT | CCA | GAG | TTC | CCC | AAC | AAG | AAA | ATG | CTT | 554 |
| Thr | Asp | Ile | Asn | Asp | His | Ser | Pro | Glu | Phe | Pro | Asn | Lys | Lys | Met | Leu |
| | 125 | | | | 130 | | | | | 135 | | | | | |
| CTA | ACA | ATT | CCT | GAG | AGT | GCC | CAT | CCA | GGG | ACT | GTG | TTT | CCT | CTG | AAG | 602 |
| Leu | Thr | Ile | Pro | Glu | Ser | Ala | His | Pro | Gly | Thr | Val | Phe | Pro | Leu | Lys |
| 140 | | | | | 145 | | | | | 150 | | | | | 155 |
| GCA | GCT | CGG | GAC | TCT | GAC | ATA | GGG | AGC | AAC | GCT | GTT | CAG | AAC | TAC | ACA | 650 |
| Ala | Ala | Arg | Asp | Ser | Asp | Ile | Gly | Ser | Asn | Ala | Val | Gln | Asn | Tyr | Thr |

```
                               160                            165                              170
GTC  AAT  CCC  AAC  CTC  CAT  TTC  CAC  GTC  GTT  ACT  CAC  AGT  CGC  ACA  GAT        698
Val  Asn  Pro  Asn  Leu  His  Phe  His  Val  Val  Thr  His  Ser  Arg  Thr  Asp
               175                 180                      185

GGC  AGG  AAA  TAC  CCA  GAG  CTG  GTG  CTG  GAC  AGA  GCC  CTG  GAT  AGG  GAG        746
Gly  Arg  Lys  Tyr  Pro  Glu  Leu  Val  Leu  Asp  Arg  Ala  Leu  Asp  Arg  Glu
               190                 195                      200

GAG  CAG  CCT  GAG  CTC  ACT  TTA  ATC  CTC  ACT  GCT  CTG  GAT  GGT  GGA  GCT        794
Glu  Gln  Pro  Glu  Leu  Thr  Leu  Ile  Leu  Thr  Ala  Leu  Asp  Gly  Gly  Ala
     205                      210                 215

CCT  TCC  AGG  TCA  GGA  ACC  ACC  ACA  GTT  CAC  ATA  GAA  GTT  GTG  GAC  ATC        842
Pro  Ser  Arg  Ser  Gly  Thr  Thr  Thr  Val  His  Ile  Glu  Val  Val  Asp  Ile
220                      225                 230                           235

AAT  GAT  AAC  TCC  CCC  CAG  TTT  GTA  CAG  TCA  CTC  TAT  AAG  GTG  CAA  GTT        890
Asn  Asp  Asn  Ser  Pro  Gln  Phe  Val  Gln  Ser  Leu  Tyr  Lys  Val  Gln  Val
               240                 245                      250

CCT  GAG  AAT  AAT  CCC  CTC  AAT  GCC  TTT  GTT  GTC  ACG  GTC  TCT  GCC  ACG        938
Pro  Glu  Asn  Asn  Pro  Leu  Asn  Ala  Phe  Val  Val  Thr  Val  Ser  Ala  Thr
               255                 260                      265

GAT  TTA  GAT  GCT  GGG  GTA  TAT  GGC  AAT  GTG  ACC  TAT  TCT  CTG  TTT  CAA        986
Asp  Leu  Asp  Ala  Gly  Val  Tyr  Gly  Asn  Val  Thr  Tyr  Ser  Leu  Phe  Gln
               270                 275                      280

GGG  TAT  GGG  GTA  TTT  CAA  CCA  TTT  GTA  ATA  GAC  GAA  ATC  ACT  GGA  GAA       1034
Gly  Tyr  Gly  Val  Phe  Gln  Pro  Phe  Val  Ile  Asp  Glu  Ile  Thr  Gly  Glu
     285                      290                 295

ATC  CAT  CTG  AGC  AAA  GAG  CTG  GAT  TTT  GAG  GAA  ATT  AGC  AAT  CAT  AAC       1082
Ile  His  Leu  Ser  Lys  Glu  Leu  Asp  Phe  Glu  Glu  Ile  Ser  Asn  His  Asn
300                      305                 310                           315

ATA  GAA  ATC  GCA  GCC  ACA  GAT  GGA  GGA  GGC  CTT  TCA  GGA  AAA  TGC  ACT       1130
Ile  Glu  Ile  Ala  Ala  Thr  Asp  Gly  Gly  Gly  Leu  Ser  Gly  Lys  Cys  Thr
               320                 325                      330

GTG  GCT  GTA  CAG  GTG  TTG  GAT  GTG  AAT  GAC  AAC  GCC  CCA  GAG  TTG  ACA       1178
Val  Ala  Val  Gln  Val  Leu  Asp  Val  Asn  Asp  Asn  Ala  Pro  Glu  Leu  Thr
               335                 340                      345

ATT  AGG  AAG  CTC  ACA  GTC  CTG  GTC  CCA  GAA  AAT  TCC  GCA  GAG  ACT  GTA       1226
Ile  Arg  Lys  Leu  Thr  Val  Leu  Val  Pro  Glu  Asn  Ser  Ala  Glu  Thr  Val
               350                 355                      360

GTT  GCT  GTT  TTT  AGT  GTT  TCT  GAT  TCT  GAT  TCG  GGG  GAC  AAT  GGA  AGG       1274
Val  Ala  Val  Phe  Ser  Val  Ser  Asp  Ser  Asp  Ser  Gly  Asp  Asn  Gly  Arg
     365                      370                 375

ATG  GTG  TGT  TCT  ATT  CCG  AAC  AAT  ATC  CCA  TTT  CTC  CTG  AAA  CCC  ACA       1322
Met  Val  Cys  Ser  Ile  Pro  Asn  Asn  Ile  Pro  Phe  Leu  Leu  Lys  Pro  Thr
380                      385                 390                           395

TTT  GAG  AAT  TAT  TAC  ACG  TTA  GTG  ACT  GAG  GGG  CCA  CTT  GAT  AGA  GAG       1370
Phe  Glu  Asn  Tyr  Tyr  Thr  Leu  Val  Thr  Glu  Gly  Pro  Leu  Asp  Arg  Glu
               400                 405                      410

AAC  AGA  GCT  GAG  TAC  AAC  ATC  ACC  ATC  ACG  GTC  TCA  GAT  CTG  GGC  ACA       1418
Asn  Arg  Ala  Glu  Tyr  Asn  Ile  Thr  Ile  Thr  Val  Ser  Asp  Leu  Gly  Thr
               415                 420                      425

CCC  AGG  CTC  ACA  ACC  CAG  CAC  ACC  ATA  ACA  GTG  CAA  GTG  TCC  GAC  ATC       1466
Pro  Arg  Leu  Thr  Thr  Gln  His  Thr  Ile  Thr  Val  Gln  Val  Ser  Asp  Ile
               430                 435                      440

AAC  GAC  AAC  GCC  CCT  GCC  TTC  ACC  CAA  ACC  TCC  TAC  ACC  ATG  TTT  GTC       1514
Asn  Asp  Asn  Ala  Pro  Ala  Phe  Thr  Gln  Thr  Ser  Tyr  Thr  Met  Phe  Val
     445                      450                 455

CAC  GAG  AAC  AAC  AGC  CCC  GCC  CTG  CAC  ATA  GGC  ACC  ATC  AGT  GCC  ACA       1562
His  Glu  Asn  Asn  Ser  Pro  Ala  Leu  His  Ile  Gly  Thr  Ile  Ser  Ala  Thr
460                      465                 470                           475

GAC  TCA  GAC  TCA  GGC  TCC  AAT  GCC  CAC  ATC  ACC  TAC  TCG  CTG  CTG  CCG       1610
Asp  Ser  Asp  Ser  Gly  Ser  Asn  Ala  His  Ile  Thr  Tyr  Ser  Leu  Leu  Pro
```

-continued

```
                         480                           485                           490
CCT  GAT  GAC  CCG  CAG  CTG  GCC  CTC  GAC  TCA  CTC  ATC  TCC  ATC  AAT  GTT       1658
Pro  Asp  Asp  Pro  Gln  Leu  Ala  Leu  Asp  Ser  Leu  Ile  Ser  Ile  Asn  Val
          495                      500                      505

GAC  AAT  GGG  CAG  CTG  TTC  GCG  CTC  AGA  GCT  CTA  GAC  TAT  GAG  GCA  CTG       1706
Asp  Asn  Gly  Gln  Leu  Phe  Ala  Leu  Arg  Ala  Leu  Asp  Tyr  Glu  Ala  Leu
          510                      515                      520

CAG  TCC  TTC  GAG  TTC  TAC  GTG  GGC  GCT  ACA  GAT  GGA  GGC  TCA  CCC  GCG       1754
Gln  Ser  Phe  Glu  Phe  Tyr  Val  Gly  Ala  Thr  Asp  Gly  Gly  Ser  Pro  Ala
     525                      530                      535

CTC  AGC  AGC  CAG  ACT  CTG  GTG  CGG  ATG  GTG  GTG  CTG  GAT  GAC  AAT  GAC       1802
Leu  Ser  Ser  Gln  Thr  Leu  Val  Arg  Met  Val  Val  Leu  Asp  Asp  Asn  Asp
540                 545                      550                           555

AAT  GCC  CCC  TTC  GTG  CTC  TAC  CCA  CTG  CAG  AAT  GCC  TCA  GCA  CCC  TGT       1850
Asn  Ala  Pro  Phe  Val  Leu  Tyr  Pro  Leu  Gln  Asn  Ala  Ser  Ala  Pro  Cys
                         560                      565                      570

ACT  GAG  CTA  CTG  CCT  AGG  GCA  GCA  GAG  CCC  GGC  TAC  CTG  ATC  ACC  AAA       1898
Thr  Glu  Leu  Leu  Pro  Arg  Ala  Ala  Glu  Pro  Gly  Tyr  Leu  Ile  Thr  Lys
               575                      580                      585

GTG  GTG  GCT  GTG  GAT  CGC  GAC  TCT  GGA  CAG  AAT  GCT  TGG  CTG  TCG  TTC       1946
Val  Val  Ala  Val  Asp  Arg  Asp  Ser  Gly  Gln  Asn  Ala  Trp  Leu  Ser  Phe
          590                      595                      600

CAG  CTA  CTT  AAA  GCT  ACA  GAG  CCA  GGG  CTG  TTC  AGT  GTA  TGG  GCA  CAC       1994
Gln  Leu  Leu  Lys  Ala  Thr  Glu  Pro  Gly  Leu  Phe  Ser  Val  Trp  Ala  His
     605                      610                      615

AAT  GGT  GAA  GTG  CGC  ACC  ACT  AGG  CTG  CTG  AGT  GAG  CGA  GAT  GCT  CAG       2042
Asn  Gly  Glu  Val  Arg  Thr  Thr  Arg  Leu  Leu  Ser  Glu  Arg  Asp  Ala  Gln
620                      625                      630                      635

AAG  CAC  AAG  CTA  CTG  CTG  CTG  GTC  AAG  GAC  AAT  GGC  GAT  CCT  CTG  CGC       2090
Lys  His  Lys  Leu  Leu  Leu  Leu  Val  Lys  Asp  Asn  Gly  Asp  Pro  Leu  Arg
                    640                      645                      650

TCT  GCC  AAT  GTC  ACT  CTT  CAC  GTG  CTA  GTG  GTG  GAT  GGC  TTC  TCG  CAG       2138
Ser  Ala  Asn  Val  Thr  Leu  His  Val  Leu  Val  Val  Asp  Gly  Phe  Ser  Gln
               655                      660                      665

CCT  TAC  CTA  CCA  TTG  GCT  GAG  GTG  GCA  CAG  GAT  TCC  ATG  CAA  GAT  AAT       2186
Pro  Tyr  Leu  Pro  Leu  Ala  Glu  Val  Ala  Gln  Asp  Ser  Met  Gln  Asp  Asn
          670                      675                      680

TAC  GAC  GTT  CTC  ACA  CTG  TAC  CTA  GTC  ATT  GCC  TTG  GCA  TCT  GTA  TCT       2234
Tyr  Asp  Val  Leu  Thr  Leu  Tyr  Leu  Val  Ile  Ala  Leu  Ala  Ser  Val  Ser
     685                      690                      695

TCT  CTC  TTC  CTC  TTG  TCT  GTA  GTG  CTG  TTT  GTG  GGG  GTG  AGG  CTG  TGC       2282
Ser  Leu  Phe  Leu  Leu  Ser  Val  Val  Leu  Phe  Val  Gly  Val  Arg  Leu  Cys
700                      705                      710                      715

AGG  AGG  GCC  AGG  GAG  GCC  TCC  TTG  GGT  GAC  TAC  TCT  GTG  CCT  GAG  GGA       2330
Arg  Arg  Ala  Arg  Glu  Ala  Ser  Leu  Gly  Asp  Tyr  Ser  Val  Pro  Glu  Gly
                    720                      725                      730

CAC  TTT  CCT  AGC  CAC  TTG  GTG  GAT  GTC  AGC  GGT  GCC  GGG  ACC  CTG  TCC       2378
His  Phe  Pro  Ser  His  Leu  Val  Asp  Val  Ser  Gly  Ala  Gly  Thr  Leu  Ser
               735                      740                      745

CAG  AGT  TAT  CAA  TAT  GAG  GTG  TGT  CTT  AAT  GGA  GGT  ACT  AGA  ACA  AAT       2426
Gln  Ser  Tyr  Gln  Tyr  Glu  Val  Cys  Leu  Asn  Gly  Gly  Thr  Arg  Thr  Asn
          750                      755                      760

GAG  TTT  AAC  TTT  CTT  AAA  CCA  TTG  TTT  CCT  ATC  CTT  CCG  ACC  CAG  GCT       2474
Glu  Phe  Asn  Phe  Leu  Lys  Pro  Leu  Phe  Pro  Ile  Leu  Pro  Thr  Gln  Ala
     765                      770                      775

GCT  GCT  GCT  GAA  GAA  AGA  GAA  AAC  GCT  GTT  GTG  CAC  AAT  AGC  GTT  GGA       2522
Ala  Ala  Ala  Glu  Glu  Arg  Glu  Asn  Ala  Val  Val  His  Asn  Ser  Val  Gly
780                 785                      790                           795

TTC  TAT  TAGAGCACTG  ATTTTGAAGT  GGTGGTTACC  TCATTTTTCC  TTAACTATCC              2578
Phe  Tyr
```

```
CTGATGTAGA  ATGGTGTAGT  GCCGTGAATC  AACTCCTGAG  ATATATGTTC  ATTTTATCCT       2638

TTGTTTTGAA  TCAAACTATT  CAGATGTGAT  CCTACTCTAG  AGAATTTGGT  TCTACTCCAT       2698

TGTGTTTGTT  TAGATTTCTA  CGCCATACCA  GTGCATGCTG  GGTTGTTTTT  TTTTTTACAA       2758

TTATTATAAC  TTTGCTTTGG  AGGGGAACTC  ATATTCGCTG  TAACGAATTG  GAACCACTTT       2818

CATTGTTAGA  GATGCCTTGC  TTTGTTGTGT  TATTTCAGAC  AGGGTCTTAA  ATTGTAGCCC       2878

TGGGTGACCT  GAAATGACTA  TGTACAGACT  GACTTTGAAT  TTGTGGCAGT  CCATCTGCCT       2938

CTGTTGTCCT  ATGTTGGGAT  TGTGAGCATG  CATGAGTAGG  CTCAGCTGTG  GTGAGCGACC       2998

TTAATAAAAA  TCAAATACTA  AAAAAAAAAA  AAAAA                                   3033
```

( 2 ) INFORMATION FOR SEQ ID NO:112:

( i ) SEQUENCE CHARACTERISTICS:
        ( A ) LENGTH: 797 amino acids
        ( B ) TYPE: amino acid
        ( D ) TOPOLOGY: linear ( i i ) MOLECULE TYPE: protein ( x i ) SEQUENCE DESCRIPTION: SEQ ID NO:112:

```
Met  Glu  Thr  Ala  Leu  Ala  Lys  Ile  Pro  Gln  Gln  Arg  Gln  Val  Phe  Phe
 1                   5                  10                  15

Leu  Thr  Ile  Leu  Ser  Leu  Leu  Trp  Lys  Ser  Ser  Glu  Ala  Ile  Arg
               20                  25                  30

Tyr  Ser  Met  Pro  Glu  Glu  Thr  Glu  Ser  Gly  Tyr  Met  Val  Ala  Asn  Leu
          35                  40                       45

Ala  Lys  Asp  Leu  Gly  Ile  Arg  Val  Gly  Glu  Leu  Ser  Ser  Arg  Gly  Ala
     50                  55                       60

Gln  Ile  His  Tyr  Lys  Gly  Asn  Lys  Glu  Leu  Leu  Gln  Leu  Asp  Ala  Glu
65                   70                  75                       80

Thr  Gly  Asn  Leu  Phe  Leu  Lys  Glu  Lys  Leu  Asp  Arg  Glu  Leu  Leu  Cys
               85                  90                       95

Gly  Glu  Thr  Glu  Pro  Cys  Val  Leu  Asn  Phe  Gln  Ile  Ile  Leu  Glu  Asn
              100                 105                 110

Pro  Met  Gln  Phe  Phe  Gln  Thr  Glu  Leu  Gln  Leu  Thr  Asp  Ile  Asn  Asp
          115                 120                 125

His  Ser  Pro  Glu  Phe  Pro  Asn  Lys  Lys  Met  Leu  Leu  Thr  Ile  Pro  Glu
130                 135                 140

Ser  Ala  His  Pro  Gly  Thr  Val  Phe  Pro  Leu  Lys  Ala  Ala  Arg  Asp  Ser
145                 150                 155                 160

Asp  Ile  Gly  Ser  Asn  Ala  Val  Gln  Asn  Tyr  Thr  Val  Asn  Pro  Asn  Leu
               165                 170                 175

His  Phe  His  Val  Val  Thr  His  Ser  Arg  Thr  Asp  Gly  Arg  Lys  Tyr  Pro
              180                 185                 190

Glu  Leu  Val  Leu  Asp  Arg  Ala  Leu  Asp  Arg  Glu  Glu  Gln  Pro  Glu  Leu
          195                 200                 205

Thr  Leu  Ile  Leu  Thr  Ala  Leu  Asp  Gly  Gly  Ala  Pro  Ser  Arg  Ser  Gly
     210                 215                 220

Thr  Thr  Thr  Val  His  Ile  Glu  Val  Val  Asp  Ile  Asn  Asp  Asn  Ser  Pro
225                 230                 235                 240

Gln  Phe  Val  Gln  Ser  Leu  Tyr  Lys  Val  Gln  Val  Pro  Glu  Asn  Asn  Pro
               245                 250                 255

Leu  Asn  Ala  Phe  Val  Val  Thr  Val  Ser  Ala  Thr  Asp  Leu  Asp  Ala  Gly
              260                 265                 270
```

| | | | | | | | | | | | | | | |
|---|---|---|---|---|---|---|---|---|---|---|---|---|---|---|
|Val|Tyr|Gly|Asn|Val|Thr|Tyr|Ser|Leu|Phe|Gln|Gly|Tyr|Gly|Val|Phe|
| | |275| | | |280| | | | |285| | | |
|Gln|Pro|Phe|Val|Ile|Asp|Glu|Ile|Thr|Gly|Glu|Ile|His|Leu|Ser|Lys|
| |290| | | |295| | | |300| | | | | | |
|Glu|Leu|Asp|Phe|Glu|Ile|Ser|Asn|His|Asn|Ile|Glu|Ile|Ala|Ala|
|305| | | |310| | | |315| | | | |320| |
|Thr|Asp|Gly|Gly|Gly|Leu|Ser|Gly|Lys|Cys|Thr|Val|Ala|Val|Gln|Val|
| | | | |325| | | |330| | | | |335| |
|Leu|Asp|Val|Asn|Asp|Asn|Ala|Pro|Glu|Leu|Thr|Ile|Arg|Lys|Leu|Thr|
| | | |340| | | |345| | | | |350| | |
|Val|Leu|Val|Pro|Glu|Asn|Ser|Ala|Glu|Thr|Val|Val|Ala|Val|Phe|Ser|
| | |355| | | |360| | | | |365| | | |
|Val|Ser|Asp|Ser|Asp|Ser|Gly|Asp|Asn|Gly|Arg|Met|Val|Cys|Ser|Ile|
| |370| | | |375| | | |380| | | | | |
|Pro|Asn|Asn|Ile|Pro|Phe|Leu|Leu|Lys|Pro|Thr|Phe|Glu|Asn|Tyr|Tyr|
|385| | | |390| | | |395| | | | |400| |
|Thr|Leu|Val|Thr|Glu|Gly|Pro|Leu|Asp|Arg|Glu|Asn|Arg|Ala|Glu|Tyr|
| | | |405| | | |410| | | | |415| | |
|Asn|Ile|Thr|Ile|Thr|Val|Ser|Asp|Leu|Gly|Thr|Pro|Arg|Leu|Thr|Thr|
| | |420| | | |425| | | | |430| | | |
|Gln|His|Thr|Ile|Thr|Val|Gln|Val|Ser|Asp|Ile|Asn|Asp|Asn|Ala|Pro|
| |435| | | | |440| | | | |445| | | |
|Ala|Phe|Thr|Gln|Thr|Ser|Tyr|Thr|Met|Phe|Val|His|Glu|Asn|Asn|Ser|
|450| | | | |455| | | |460| | | | | |
|Pro|Ala|Leu|His|Ile|Gly|Thr|Ile|Ser|Ala|Thr|Asp|Ser|Asp|Ser|Gly|
|465| | | |470| | | |475| | | | |480| |
|Ser|Asn|Ala|His|Ile|Thr|Tyr|Ser|Leu|Leu|Pro|Pro|Asp|Asp|Pro|Gln|
| | | |485| | | |490| | | | |495| | |
|Leu|Ala|Leu|Asp|Ser|Leu|Ile|Ser|Ile|Asn|Val|Asp|Asn|Gly|Gln|Leu|
| | |500| | | |505| | | | |510| | | |
|Phe|Ala|Leu|Arg|Ala|Leu|Asp|Tyr|Glu|Ala|Leu|Gln|Ser|Phe|Glu|Phe|
| |515| | | |520| | | | |525| | | | |
|Tyr|Val|Gly|Ala|Thr|Asp|Gly|Gly|Ser|Pro|Ala|Leu|Ser|Ser|Gln|Thr|
|530| | | |535| | | | |540| | | | | |
|Leu|Val|Arg|Met|Val|Val|Leu|Asp|Asp|Asn|Asp|Asn|Ala|Pro|Phe|Val|
|545| | | |550| | | |555| | | | |560| |
|Leu|Tyr|Pro|Leu|Gln|Asn|Ala|Ser|Ala|Pro|Cys|Thr|Glu|Leu|Leu|Pro|
| | | |565| | | |570| | | | |575| | |
|Arg|Ala|Ala|Glu|Pro|Gly|Tyr|Leu|Ile|Thr|Lys|Val|Val|Ala|Val|Asp|
| | |580| | | |585| | | | |590| | | |
|Arg|Asp|Ser|Gly|Gln|Asn|Ala|Trp|Leu|Ser|Phe|Gln|Leu|Leu|Lys|Ala|
| |595| | | |600| | | | |605| | | | |
|Thr|Glu|Pro|Gly|Leu|Phe|Ser|Val|Trp|Ala|His|Asn|Gly|Glu|Val|Arg|
|610| | | |615| | | |620| | | | | | |
|Thr|Thr|Arg|Leu|Leu|Ser|Glu|Arg|Asp|Ala|Gln|Lys|His|Lys|Leu|Leu|
|625| | | |630| | | |635| | | | |640| |
|Leu|Leu|Val|Lys|Asp|Asn|Gly|Asp|Pro|Leu|Arg|Ser|Ala|Asn|Val|Thr|
| | | |645| | | |650| | | | |655| | |
|Leu|His|Val|Leu|Val|Val|Asp|Gly|Phe|Ser|Gln|Pro|Tyr|Leu|Pro|Leu|
| |660| | | |665| | | | |670| | | | |
|Ala|Glu|Val|Ala|Gln|Asp|Ser|Met|Gln|Asp|Asn|Tyr|Asp|Val|Leu|Thr|
| |675| | | |680| | | | |685| | | | |
|Leu|Tyr|Leu|Val|Ile|Ala|Leu|Ala|Ser|Val|Ser|Ser|Leu|Phe|Leu|Leu|
|690| | | |695| | | |700| | | | | | |

| Ser | Val | Val | Leu | Phe | Val | Gly | Val | Arg | Leu | Cys | Arg | Arg | Ala | Arg | Glu |
| 705 | | | | | 710 | | | | | 715 | | | | | 720 |

| Ala | Ser | Leu | Gly | Asp | Tyr | Ser | Val | Pro | Glu | Gly | His | Phe | Pro | Ser | His |
| | | | | 725 | | | | | 730 | | | | | 735 | |

| Leu | Val | Asp | Val | Ser | Gly | Ala | Gly | Thr | Leu | Ser | Gln | Ser | Tyr | Gln | Tyr |
| | | | 740 | | | | | 745 | | | | | 750 | | |

| Glu | Val | Cys | Leu | Asn | Gly | Gly | Thr | Arg | Thr | Asn | Glu | Phe | Asn | Phe | Leu |
| | | 755 | | | | | 760 | | | | | 765 | | | |

| Lys | Pro | Leu | Phe | Pro | Ile | Leu | Pro | Thr | Gln | Ala | Ala | Ala | Ala | Glu | Glu |
| | 770 | | | | | 775 | | | | | 780 | | | | |

| Arg | Glu | Asn | Ala | Val | Val | His | Asn | Ser | Val | Gly | Phe | Tyr | | | |
| 785 | | | | | 790 | | | | | 795 | | | | | |

( 2 ) INFORMATION FOR SEQ ID NO:113:

( i ) SEQUENCE CHARACTERISTICS:
        ( A ) LENGTH: 2347 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:113:

```
AAAACACGGG  GGAAATGACA  GTAGCAAAGA  ATCTGGACTA  TGAAGAATGC  TCATTGTATG      60
AAATGGAAAT  ACAGGCTGAA  GATGTGGGGG  CGCTTCTGGG  GAGGAGCAAA  GTGGTAATTA     120
TGGTAGAAGA  TGTAAATGAC  AATCGGCCAG  AAGTGACCAT  TACATCCTTG  TTTAACCCGG     180
TATTGGAAAA  TTCTCTTCCC  GGGACAGTAA  TTGCCTTCTT  GAATGTGCAT  GACCGAGACT     240
CTGGAAAGAA  CGGCCAAGTT  GTCTGTTACA  CGCATGATAA  CTTACCTTTT  AAATTAGAAA     300
AGTCAATAGA  TAATTATTAT  AGATTGGTGA  CATGGAAATA  TTTGGACCGA  GAAAAAGTCT     360
CCATCTACAA  TATCACAGTG  ATAGCCTCAG  ATCTAGGAGC  CCACTCTGTC  ACTGAAACTT     420
ACATTGCCCT  GATTGTGGCA  GACACTAATG  ACAACCCTCC  TCGTTTTCCT  CACACCTCCT     480
ACACAGCCTA  TATTCCAGAG  AACAACCTGA  GGGGCGCCTC  CATCTTCTCA  CTGACTGCAC     540
ATGATCCTGA  CAGTCAGGAA  AATGCACAGG  TCACTTACTC  TGTGTCTGAG  ACACCATAC      600
AGGGAGTGCC  TTTGTCCTCT  TATATCTCCA  TCAACTCAGA  TACTGGTGTC  CTGTATGCAC     660
TGCACTCTTT  TGACTTCGAG  AAGATACAAG  ACTTGCAGCT  ACTGGTTGTT  GCCACTGACA     720
GTGGAAGCCC  ACCTCTCAGC  AGCAATGTGT  CATTGAGCTT  GTTTGTGTTG  GACCAGAACG     780
ACAACGCACC  TGAGATTCTA  TATCCTAGCT  TCCCCACAGA  TGGCTCCACT  GGTGTGGAAC     840
TAGCACCCCG  CTCTGCAGAG  CCTGGATACC  TAGTGACCAA  AGTGGTGGCA  GTGGACAAAG     900
ACTCAGGACA  GAATGCTTGG  CTGTCCTACC  GTCTGCTGAA  GGCCAGCGAA  CCTGGGCTCT     960
TCTCTGTAGG  ACTTCACACG  GGTGAGGTGC  GTACAGCGAG  GGCCCTGCTG  ACAGAGATG    1020
CTCTCAAACA  GAATCTGGTG  ATGGCCGTGC  AGGACCATGG  CCAACCCCCT  CTCTCGGCCA    1080
CTGTAACTCT  CACTGTGGCA  GTGGCTAACA  GCATCCCTGA  GGTGTTGGCT  GACTTGAGCA    1140
GCATTAGGAC  CCCTGGGGTA  CCAGAGGATT  CTGATATCAC  GCTCCACCTG  GTGGTGGCAG    1200
TGGCTGTGGT  CTCCTGTGTC  TTCCTTGTCT  TTGTCATTGT  CCTCCTAGCT  CTCAGGCTTC    1260
AGCGCTGGCA  GAAGTCTCGC  CAGCTCCAGG  GCTCCAAAGG  TGGATTGGCT  CCTGCACCTC    1320
CATCACATTT  TGTGGGCATC  GACGGGGTAC  AGGCTTTTCT  ACAAACCTAT  TCTCATGAAG    1380
TCTCGCTCAC  TTCAGGCTCC  CAGACAAGCC  ACATTATCTT  TCCTCAGCCC  AACTATGCAG    1440
```

-continued

| | | | | | |
|---|---|---|---|---|---|
| ACATGCTCAT | TAACCAAGAA | GGCTGTGAGA | AAAATGATTC | CTTATTAACA | TCCATAGATT | 1500
| TTCATGAGAG | TAACCGTGAA | GATGCTTGCG | CCCCGCAAGC | CCCGCCCAAC | ACTGACTGGC | 1560
| GTTTCTCTCA | AGCCCAGAGA | CCCGGCACGA | GCGGATCCCA | AAATGGGGAT | GAAACCGGCA | 1620
| CCTGGCCCAA | CAACCAGTTC | GATACAGAGA | TGCTGCAAGC | CATGATCTTG | GCCTCTGCCA | 1680
| GTGAAGCCGC | TGATGGGAGC | TCCACTCTGG | GAGGGGCAC | TGGCACTATG | GGTTTGAGCG | 1740
| CTCGATATGG | ACCCCAGTTT | ACCCTGCAGC | ACGTGCCTGA | CTACCGCCAG | AACGTGTACA | 1800
| TCCCTGGCAG | CAATGCCACA | CTGACCAACG | CAGCTGGCAA | ACGAGATGGC | AAGGCTCCGG | 1860
| CAGGCGGCAA | TGGCAACAAC | AACAAGTCGG | GCAAGAAAGA | GAAGAAGTAA | TATGGAGGCC | 1920
| AGGCCTTGAG | CCACAGGGCA | GCCTCCCTCC | CCAGCCAGTC | CAGCTTGTCC | TTACTTGTAC | 1980
| CCAGGCCTCA | GAATTTCAGG | GCTCACCCCA | GGATTCTGGT | AGGAGCCACA | GCCAGGCCAT | 2040
| GCTCCCCGTT | GGGAAACAGA | AACAAGTGCC | CAAGCCAACA | CCCCCTCTTT | GTACCCTAGG | 2100
| GGGGTTGAAT | ATGCAAAGAG | AGTTCTGCTG | GGACCCCCTA | TCCAATCAGT | GATTGTACCC | 2160
| ACATAGGTAG | CAGGGTTAGT | GTGGATACAC | ACACACACAC | ACACACACAC | ACACACACAA | 2220
| CCCTTGTCCT | CCGCAGTGCC | TGCCACTTTC | TGGGACTTTC | TCATCCCCCT | ACGCCCTTCC | 2280
| TTTATCCTCT | CCCACCCAGA | CACAGCTGCT | GGAGAATAAA | TTTGGGGATG | CTGATGCTAA | 2340
| AAAAAAA | | | | | | 2347

(2) INFORMATION FOR SEQ ID NO:114:

(i) SEQUENCE CHARACTERISTICS:
        (A) LENGTH: 2972 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..1849

(xi) SEQUENCE DESCRIPTION: SEQ ID NO:114:

| | | | | | | | | | | | | | | | | |
|---|---|---|---|---|---|---|---|---|---|---|---|---|---|---|---|---|
| A | GAG | GCT | GCT | CAC | CAC | CTG | GTC | CTC | ACG | GCC | TCG | GAT | GGC | GGC | AAG | 46 |
| | Glu | Ala | Ala | His | His | Leu | Val | Leu | Thr | Ala | Ser | Asp | Gly | Gly | Lys | |
| | 1 | | | | 5 | | | | | 10 | | | | | 15 | |

| CCG | CCT | CGC | TCT | AGC | ACA | GTG | CGC | ATC | CAC | GTG | ACA | GTG | TTG | GAT | ACA | 94 |
|---|---|---|---|---|---|---|---|---|---|---|---|---|---|---|---|---|
| Pro | Pro | Arg | Ser | Ser | Thr | Val | Arg | Ile | His | Val | Thr | Val | Leu | Asp | Thr | |
| | | | | 20 | | | | | 25 | | | | | 30 | | |

| AAT | GAC | AAT | GCC | CCG | GTT | TTT | CCT | CAC | CCG | ATT | TAC | CGA | GTG | AAA | GTC | 142 |
|---|---|---|---|---|---|---|---|---|---|---|---|---|---|---|---|---|
| Asn | Asp | Asn | Ala | Pro | Val | Phe | Pro | His | Pro | Ile | Tyr | Arg | Val | Lys | Val | |
| | | | | 35 | | | | | 40 | | | | | 45 | | |

| CTT | GAG | AAC | ATG | CCC | CCA | GGC | ACG | CGG | CTG | CTT | ACT | GTA | ACA | GCC | AGC | 190 |
|---|---|---|---|---|---|---|---|---|---|---|---|---|---|---|---|---|
| Leu | Glu | Asn | Met | Pro | Pro | Gly | Thr | Arg | Leu | Leu | Thr | Val | Thr | Ala | Ser | |
| | | | 50 | | | | | 55 | | | | | 60 | | | |

| GAC | CCG | GAT | GAG | GGA | ATC | AAC | GGA | AAA | GTG | GCA | TAC | AAA | TTC | CGG | AAA | 238 |
|---|---|---|---|---|---|---|---|---|---|---|---|---|---|---|---|---|
| Asp | Pro | Asp | Glu | Gly | Ile | Asn | Gly | Lys | Val | Ala | Tyr | Lys | Phe | Arg | Lys | |
| | 65 | | | | | 70 | | | | | 75 | | | | | |

| ATT | AAT | GAA | AAA | CAA | ACT | CCG | TTA | TTC | CAG | CTT | AAT | GAA | AAT | ACT | GGG | 286 |
|---|---|---|---|---|---|---|---|---|---|---|---|---|---|---|---|---|
| Ile | Asn | Glu | Lys | Gln | Thr | Pro | Leu | Phe | Gln | Leu | Asn | Glu | Asn | Thr | Gly | |
| 80 | | | | | 85 | | | | | 90 | | | | | 95 | |

| GAA | ATA | TCA | ATA | GCA | AAA | AGT | CTA | GAT | TAT | GAA | GAA | TGT | TCA | TTT | TAT | 334 |
|---|---|---|---|---|---|---|---|---|---|---|---|---|---|---|---|---|
| Glu | Ile | Ser | Ile | Ala | Lys | Ser | Leu | Asp | Tyr | Glu | Glu | Cys | Ser | Phe | Tyr | |
| | | | | 100 | | | | | 105 | | | | | 110 | | |

| GAA | ATG | GAA | ATA | CAA | GCC | GAA | GAT | GTG | GGG | GCA | CTT | CTG | GGG | AGG | ACC | 382 |
|---|---|---|---|---|---|---|---|---|---|---|---|---|---|---|---|---|
| Glu | Met | Glu | Ile | Gln | Ala | Glu | Asp | Val | Gly | Ala | Leu | Leu | Gly | Arg | Thr | |
| | | | 115 | | | | | 120 | | | | | 125 | | | |

| | | | | | | | | | | | | | | | | |
|---|---|---|---|---|---|---|---|---|---|---|---|---|---|---|---|---|
| AAA | TTG | CTC | ATT | TCT | GTG | GAA | GAT | GTA | AAT | GAC | AAT | AGA | CCA | GAA | GTG | 430 |
| Lys | Leu | Leu | Ile | Ser | Val | Glu | Asp | Val | Asn | Asp | Asn | Arg | Pro | Glu | Val | |
| | | 130 | | | | 135 | | | | | 140 | | | | | |
| ATC | ATT | ACG | TCT | TTG | TTT | AGC | CCA | GTG | TTA | GAA | AAT | TCT | CTT | CCC | GGG | 478 |
| Ile | Ile | Thr | Ser | Leu | Phe | Ser | Pro | Val | Leu | Glu | Asn | Ser | Leu | Pro | Gly | |
| 145 | | | | | 150 | | | | | 155 | | | | | | |
| ACA | GTA | ATT | GCC | TTC | TTG | AGT | GTG | CAT | GAC | CAA | GAC | TCT | GGA | AAG | AAT | 526 |
| Thr | Val | Ile | Ala | Phe | Leu | Ser | Val | His | Asp | Gln | Asp | Ser | Gly | Lys | Asn | |
| 160 | | | | | 165 | | | | | 170 | | | | | 175 | |
| GGT | CAA | GTT | GTC | TGT | TAC | ACA | CGT | GAT | AAT | TTA | CCT | TTT | AAA | TTA | GAA | 574 |
| Gly | Gln | Val | Val | Cys | Tyr | Thr | Arg | Asp | Asn | Leu | Pro | Phe | Lys | Leu | Glu | |
| | | | | 180 | | | | | 185 | | | | | 190 | | |
| AAG | TCA | ATA | GGT | AAT | TAT | TAT | AGA | TTA | GTG | ACA | AGG | AAA | TAT | TTG | GAC | 622 |
| Lys | Ser | Ile | Gly | Asn | Tyr | Tyr | Arg | Leu | Val | Thr | Arg | Lys | Tyr | Leu | Asp | |
| | | | 195 | | | | | 200 | | | | | 205 | | | |
| CGA | GAA | AAT | GTC | TCT | ATC | TAC | AAT | ATC | ACA | GTG | ATG | GCC | TCA | GAT | CTA | 670 |
| Arg | Glu | Asn | Val | Ser | Ile | Tyr | Asn | Ile | Thr | Val | Met | Ala | Ser | Asp | Leu | |
| | | | 210 | | | | | 215 | | | | | 220 | | | |
| GGA | ACA | CCA | CCT | CTG | TCC | ACT | GAA | ACT | CAA | ATC | GCT | CTG | CAC | GTG | GCA | 718 |
| Gly | Thr | Pro | Pro | Leu | Ser | Thr | Glu | Thr | Gln | Ile | Ala | Leu | His | Val | Ala | |
| | 225 | | | | | 230 | | | | | 235 | | | | | |
| GAC | ATT | AAC | GAC | AAC | CCT | CCT | ACT | TTC | CCT | CAT | GCC | TCC | TAC | TCA | GCG | 766 |
| Asp | Ile | Asn | Asp | Asn | Pro | Pro | Thr | Phe | Pro | His | Ala | Ser | Tyr | Ser | Ala | |
| 240 | | | | | 245 | | | | | 250 | | | | | 255 | |
| TAT | ATC | CTA | GAG | AAC | AAC | CTG | AGA | GGA | GCC | TCC | ATC | TTT | TCC | TTG | ACT | 814 |
| Tyr | Ile | Leu | Glu | Asn | Asn | Leu | Arg | Gly | Ala | Ser | Ile | Phe | Ser | Leu | Thr | |
| | | | | 260 | | | | | 265 | | | | | 270 | | |
| GCA | CAC | GAC | CCC | GAC | AGC | CAG | GAG | AAT | GCC | CAG | GTC | ACT | TAC | TCT | GTG | 862 |
| Ala | His | Asp | Pro | Asp | Ser | Gln | Glu | Asn | Ala | Gln | Val | Thr | Tyr | Ser | Val | |
| | | | 275 | | | | | 280 | | | | | 285 | | | |
| ACC | GAG | GAC | ACG | CTG | CAG | GGG | GCG | CCC | CTG | TCC | TCG | TAT | ATC | TCC | ATC | 910 |
| Thr | Glu | Asp | Thr | Leu | Gln | Gly | Ala | Pro | Leu | Ser | Ser | Tyr | Ile | Ser | Ile | |
| | | 290 | | | | | 295 | | | | | 300 | | | | |
| AAC | TCT | GAC | ACC | GGT | GTC | CTG | TAT | GCG | CTG | CAA | TCT | TTC | GAC | TAT | GAG | 958 |
| Asn | Ser | Asp | Thr | Gly | Val | Leu | Tyr | Ala | Leu | Gln | Ser | Phe | Asp | Tyr | Glu | |
| | 305 | | | | | 310 | | | | | 315 | | | | | |
| CAG | ATC | CGA | GAC | CTG | CAG | CTA | CTG | GTA | ACA | GCC | AGC | GAC | AGC | GGG | GAC | 1006 |
| Gln | Ile | Arg | Asp | Leu | Gln | Leu | Leu | Val | Thr | Ala | Ser | Asp | Ser | Gly | Asp | |
| 320 | | | | | 325 | | | | | 330 | | | | | 335 | |
| CCG | CCC | CTC | AGC | AGC | AAC | ATG | TCA | CTG | AGC | CTG | TTC | GTG | CTG | GAC | CAG | 1054 |
| Pro | Pro | Leu | Ser | Ser | Asn | Met | Ser | Leu | Ser | Leu | Phe | Val | Leu | Asp | Gln | |
| | | | | 340 | | | | | 345 | | | | | 350 | | |
| AAT | GAC | AAC | GCG | CCC | GAG | ATC | CTG | TAC | CCC | GCC | CTC | CCC | ACA | GAC | GGT | 1102 |
| Asn | Asp | Asn | Ala | Pro | Glu | Ile | Leu | Tyr | Pro | Ala | Leu | Pro | Thr | Asp | Gly | |
| | | | | 355 | | | | | 360 | | | | | 365 | | |
| TCC | ACT | GGC | GTG | GAG | CTG | GCG | CCC | CGC | TCC | GCA | GAG | CGT | GGC | TAC | CTG | 1150 |
| Ser | Thr | Gly | Val | Glu | Leu | Ala | Pro | Arg | Ser | Ala | Glu | Arg | Gly | Tyr | Leu | |
| | | 370 | | | | | 375 | | | | | 380 | | | | |
| GTG | ACC | AAG | GTG | GTG | GCG | GTG | GAC | AGA | GAC | TCG | GGC | CAG | AAC | GCC | TGG | 1198 |
| Val | Thr | Lys | Val | Val | Ala | Val | Asp | Arg | Asp | Ser | Gly | Gln | Asn | Ala | Trp | |
| | 385 | | | | | 390 | | | | | 395 | | | | | |
| CTG | TCC | TAC | CGC | CTG | CTC | AAG | GCC | AGC | GAG | CCG | GGA | CTC | TTC | TCG | GTG | 1246 |
| Leu | Ser | Tyr | Arg | Leu | Leu | Lys | Ala | Ser | Glu | Pro | Gly | Leu | Phe | Ser | Val | |
| 400 | | | | | 405 | | | | | 410 | | | | | 415 | |
| GGT | CTG | CAC | ACG | GGC | GAG | GTG | CGC | ACG | GCG | CGA | GCC | CTG | CTG | GAC | AGA | 1294 |
| Gly | Leu | His | Thr | Gly | Glu | Val | Arg | Thr | Ala | Arg | Ala | Leu | Leu | Asp | Arg | |
| | | | | 420 | | | | | 425 | | | | | 430 | | |
| GAC | GCG | CTC | AAG | CAG | AGC | CTC | GTG | GTG | GCC | GTC | CAG | GAC | CAT | GGC | CAG | 1342 |
| Asp | Ala | Leu | Lys | Gln | Ser | Leu | Val | Val | Ala | Val | Gln | Asp | His | Gly | Gln | |
| | | | 435 | | | | | 440 | | | | | 445 | | | |

| | | | | | | | | | | | | | | | | |
|---|---|---|---|---|---|---|---|---|---|---|---|---|---|---|---|---|
| CCC | CCT | CTC | TCC | GCC | ACT | GTC | ACG | CTC | ACC | GTA | GCC | GTG | GCT | GAC | AGC | 1390 |
| Pro | Pro | Leu | Ser | Ala | Thr | Val | Thr | Leu | Thr | Val | Ala | Val | Ala | Asp | Ser | |
| | | 450 | | | | | 455 | | | | | 460 | | | | |
| ATC | CCC | GAA | GTC | CTG | ACC | GAG | TTG | GGC | AGT | CTG | AAG | CCT | TCG | GTC | GAC | 1438 |
| Ile | Pro | Glu | Val | Leu | Thr | Glu | Leu | Gly | Ser | Leu | Lys | Pro | Ser | Val | Asp | |
| | 465 | | | | | 470 | | | | | 475 | | | | | |
| CCG | AAC | GAT | TCG | AGC | CTT | ACA | CTC | TAT | CTC | GTG | GTG | GCA | GTG | GCT | GCC | 1486 |
| Pro | Asn | Asp | Ser | Ser | Leu | Thr | Leu | Tyr | Leu | Val | Val | Ala | Val | Ala | Ala | |
| 480 | | | | | 485 | | | | | 490 | | | | | 495 | |
| ATC | TCC | TGT | GTC | TTC | CTC | GCC | TTT | GTC | GCT | GTG | CTT | CTG | GGG | CTC | AGG | 1534 |
| Ile | Ser | Cys | Val | Phe | Leu | Ala | Phe | Val | Ala | Val | Leu | Leu | Gly | Leu | Arg | |
| | | | | 500 | | | | | 505 | | | | | 510 | | |
| CTG | AGG | CGC | TGG | CAC | AAG | TCA | CGC | CTG | CTC | CAG | GAT | TCC | GGT | GGC | AGA | 1582 |
| Leu | Arg | Arg | Trp | His | Lys | Ser | Arg | Leu | Leu | Gln | Asp | Ser | Gly | Gly | Arg | |
| | | | 515 | | | | | 520 | | | | | 525 | | | |
| TTG | GTA | GGC | GTG | CCT | GCC | TCA | CAT | TTT | GTG | GGT | GTT | GAG | GAG | GTA | CAG | 1630 |
| Leu | Val | Gly | Val | Pro | Ala | Ser | His | Phe | Val | Gly | Val | Glu | Glu | Val | Gln | |
| | | 530 | | | | | 535 | | | | | 540 | | | | |
| GCT | TTC | CTG | CAG | ACC | TAT | TCC | CAG | GAA | GTC | TCC | CTC | ACC | GCC | GAC | TCG | 1678 |
| Ala | Phe | Leu | Gln | Thr | Tyr | Ser | Gln | Glu | Val | Ser | Leu | Thr | Ala | Asp | Ser | |
| | 545 | | | | | 550 | | | | | 555 | | | | | |
| CGG | AAG | AGT | CAC | CTG | ATC | TTT | CCC | CAG | CCC | AAC | TAC | GCA | GAC | ATG | CTC | 1726 |
| Arg | Lys | Ser | His | Leu | Ile | Phe | Pro | Gln | Pro | Asn | Tyr | Ala | Asp | Met | Leu | |
| 560 | | | | | 565 | | | | | 570 | | | | | 575 | |
| ATC | AGT | CAG | GAG | GGC | TGT | GAG | AAA | AAT | GAT | TCT | TTG | TTA | ACA | TCC | GTA | 1774 |
| Ile | Ser | Gln | Glu | Gly | Cys | Glu | Lys | Asn | Asp | Ser | Leu | Leu | Thr | Ser | Val | |
| | | | | 580 | | | | | 585 | | | | | 590 | | |
| GAT | TTT | CAT | GAA | TAT | AAG | AAT | GAA | GCT | GAT | CAT | GGT | CAG | GTG | AGT | TTA | 1822 |
| Asp | Phe | His | Glu | Tyr | Lys | Asn | Glu | Ala | Asp | His | Gly | Gln | Val | Ser | Leu | |
| | | | 595 | | | | | 600 | | | | | 605 | | | |
| GTT | CTT | TGC | TTG | CTT | TTA | ATT | TCC | AGA | TGAATTTTAT | | TTGGCATAAA | | | | | 1869 |
| Val | Leu | Cys | Leu | Leu | Leu | Ile | Ser | Arg | | | | | | | | |
| | | 610 | | | | | 615 | | | | | | | | | |

| | | |
|---|---|---|
| TTATGTTTTG AAAAACATTG TGAAGATAGT TGAAAATAAT TTTTAAGGTG TATCACAGAG | 1929 |
| TTTTGGGTTT ATTTTGGTGG TGTTACCAAA AAATTGAACT CTAATAGTCA TAGGTTATTG | 1989 |
| TTTCATTTGC TTTTAAACGA CTTGGAAAAG ATTGTTCCAC CATTTTAAAC CTTCCAGTAT | 2049 |
| TTTATTCCTA TTATCACTCA TTCACTTAAG AAGTAGCTAC CCGTCCATAC TGGTAATTTT | 2109 |
| GCTATTGTTT GTTTGTGTGT GTGTGTGTGT GTGTGTGTGT GTGTGTGTAT CCCAAACTAG | 2169 |
| AACTTCAGAA AATTATCAAG AAGTCTAAAG CCTTGTTATT AGCTTAGCAA AAGTAAAATA | 2229 |
| TATCTCAGAA TTTTTAGGGT TATGTTTAGC ATTTGAACCT GTAACTAGGC TCTTGTATAT | 2289 |
| TTCTTCACTT TAAACCTCTT TTCTGAGCCC TGTTTCTGTA CCAGTGCCCT TCAAAACTTT | 2349 |
| AATACTTCTT ACCATCCTTC AAAACATGAA CAAACTTTAA AGATGGATCT TGGTGGGAGA | 2409 |
| TGAGACTGGT TACTAAATAT TAAGTATGTG AGTCAGTGGT CACCTGGGCT CCATCCCCAT | 2469 |
| GGAGACATGA AATCTAAAGC CTAGAATGTC CATTGCTCCC CCAAACAAAA AACAAAAGCA | 2529 |
| AAAACATTAG ATCTGAATTA AAATGTAATT TTAAACTGTT GAAAGTGACT TTTGTAAAAT | 2589 |
| ATGTAAGAAC ATATTTCAAT ACAATTCCAA TTAGCTGTTT CGGTTGTGCA TTGATGTGAA | 2649 |
| GTGGTGAGAA TGTTGATATT AAGAACCAAT GTTTCAGGTA CACAAGTTCT AAATAAGCTG | 2709 |
| ATCAATTCAA TTAAAGTTAT TCAGTCTTGG CTGGACACAG TGCCTCATGT CTGAAATCCC | 2769 |
| AGCACTTTGG GAGGCTGGGG CAGGAGGACC GCTTGAGCCC CGGGGGTTTG AAACTGCAGT | 2829 |
| GAGCTATGAT CATGCCACTG CACTCCAGCC TAGGTGGCAG AACTAGACCC TGTCTCTAAA | 2889 |
| AAAACTATTA TTAGGCCGCG TGCGGTGGCT CACGCCTGTA ATCCCAGCAC TTTGGGAGAC | 2949 |

TGAGGTGGGT GGATCACCTG AGC                                                    2972

(2) INFORMATION FOR SEQ ID NO:115:

(i) SEQUENCE CHARACTERISTICS:
        (A) LENGTH: 616 amino acids
        (B) TYPE: amino acid
        (D) TOPOLOGY: linear (ii) MOLECULE TYPE: protein (xi) SEQUENCE DESCRIPTION: SEQ ID NO:115:

```
Glu Ala Ala His His Leu Val Leu Thr Ala Ser Asp Gly Gly Lys Pro
  1               5                  10                  15
Pro Arg Ser Ser Thr Val Arg Ile His Val Thr Val Leu Asp Thr Asn
             20                  25                  30
Asp Asn Ala Pro Val Phe Pro His Pro Ile Tyr Arg Val Lys Val Leu
         35                  40                  45
Glu Asn Met Pro Pro Gly Thr Arg Leu Leu Thr Val Thr Ala Ser Asp
         50                  55                  60
Pro Asp Glu Gly Ile Asn Gly Lys Val Ala Tyr Lys Phe Arg Lys Ile
 65                  70                  75                  80
Asn Glu Lys Gln Thr Pro Leu Phe Gln Leu Asn Glu Asn Thr Gly Glu
                 85                  90                  95
Ile Ser Ile Ala Lys Ser Leu Asp Tyr Glu Glu Cys Ser Phe Tyr Glu
                100                 105                 110
Met Glu Ile Gln Ala Glu Asp Val Gly Ala Leu Leu Gly Arg Thr Lys
                115                 120                 125
Leu Leu Ile Ser Val Glu Asp Val Asn Asp Asn Arg Pro Glu Val Ile
        130                 135                 140
Ile Thr Ser Leu Phe Ser Pro Val Leu Glu Asn Ser Leu Pro Gly Thr
145                 150                 155                 160
Val Ile Ala Phe Leu Ser Val His Asp Gln Asp Ser Gly Lys Asn Gly
                165                 170                 175
Gln Val Val Cys Tyr Thr Arg Asp Asn Leu Pro Phe Lys Leu Glu Lys
                180                 185                 190
Ser Ile Gly Asn Tyr Tyr Arg Leu Val Thr Arg Lys Tyr Leu Asp Arg
                195                 200                 205
Glu Asn Val Ser Ile Tyr Asn Ile Thr Val Met Ala Ser Asp Leu Gly
        210                 215                 220
Thr Pro Pro Leu Ser Thr Glu Thr Gln Ile Ala Leu His Val Ala Asp
225                 230                 235                 240
Ile Asn Asp Asn Pro Pro Thr Phe Pro His Ala Ser Tyr Ser Ala Tyr
                245                 250                 255
Ile Leu Glu Asn Asn Leu Arg Gly Ala Ser Ile Phe Ser Leu Thr Ala
                260                 265                 270
His Asp Pro Asp Ser Gln Glu Asn Ala Gln Val Thr Tyr Ser Val Thr
        275                 280                 285
Glu Asp Thr Leu Gln Gly Ala Pro Leu Ser Ser Tyr Ile Ser Ile Asn
        290                 295                 300
Ser Asp Thr Gly Val Leu Tyr Ala Leu Gln Ser Phe Asp Tyr Glu Gln
305                 310                 315                 320
Ile Arg Asp Leu Gln Leu Leu Val Thr Ala Ser Asp Ser Gly Asp Pro
                325                 330                 335
Pro Leu Ser Ser Asn Met Ser Leu Ser Leu Phe Val Leu Asp Gln Asn
                340                 345                 350
```

```
Asp  Asn  Ala  Pro  Glu  Ile  Leu  Tyr  Pro  Ala  Leu  Pro  Thr  Asp  Gly  Ser
          355                      360                      365

Thr  Gly  Val  Glu  Leu  Ala  Pro  Arg  Ser  Ala  Glu  Arg  Gly  Tyr  Leu  Val
     370                 375                      380

Thr  Lys  Val  Val  Ala  Val  Asp  Arg  Asp  Ser  Gly  Gln  Asn  Ala  Trp  Leu
385                      390                      395                      400

Ser  Tyr  Arg  Leu  Leu  Lys  Ala  Ser  Glu  Pro  Gly  Leu  Phe  Ser  Val  Gly
               405                      410                           415

Leu  His  Thr  Gly  Glu  Val  Arg  Thr  Ala  Arg  Ala  Leu  Leu  Asp  Arg  Asp
               420                 425                      430

Ala  Leu  Lys  Gln  Ser  Leu  Val  Val  Ala  Val  Gln  Asp  His  Gly  Gln  Pro
          435                 440                      445

Pro  Leu  Ser  Ala  Thr  Val  Thr  Leu  Thr  Val  Ala  Val  Ala  Asp  Ser  Ile
     450                      455                      460

Pro  Glu  Val  Leu  Thr  Glu  Leu  Gly  Ser  Leu  Lys  Pro  Ser  Val  Asp  Pro
465                      470                 475                           480

Asn  Asp  Ser  Ser  Leu  Thr  Leu  Tyr  Leu  Val  Val  Ala  Val  Ala  Ala  Ile
               485                      490                      495

Ser  Cys  Val  Phe  Leu  Ala  Phe  Val  Ala  Val  Leu  Leu  Gly  Leu  Arg  Leu
               500                 505                      510

Arg  Arg  Trp  His  Lys  Ser  Arg  Leu  Gln  Asp  Ser  Gly  Gly  Arg  Leu
          515                 520                      525

Val  Gly  Val  Pro  Ala  Ser  His  Phe  Val  Gly  Val  Glu  Glu  Val  Gln  Ala
     530                 535                      540

Phe  Leu  Gln  Thr  Tyr  Ser  Gln  Glu  Val  Ser  Leu  Thr  Ala  Asp  Ser  Arg
545                      550                 555                           560

Lys  Ser  His  Leu  Ile  Phe  Pro  Gln  Pro  Asn  Tyr  Ala  Asp  Met  Leu  Ile
               565                      570                           575

Ser  Gln  Glu  Gly  Cys  Glu  Lys  Asn  Asp  Ser  Leu  Leu  Thr  Ser  Val  Asp
               580                      585                      590

Phe  His  Glu  Tyr  Lys  Asn  Glu  Ala  Asp  His  Gly  Gln  Val  Ser  Leu  Val
          595                      600                      605

Leu  Cys  Leu  Leu  Leu  Ile  Ser  Arg
     610                 615
```